United States Patent
Nicolaou et al.

(10) Patent No.: US 6,380,394 B1
(45) Date of Patent: Apr. 30, 2002

(54) EPOTHILONE ANALOGS

(75) Inventors: Kyriacos C. Nicolaou, La Jolla; N. Paul King, San Diego; M. Ray Finlay, San Diego; Yun He, San Diego, all of CA (US); Frank Roschangar, Durham, NC (US); Dionisios Vourloumis, San Diego, CA (US); Hans Vallberg, Huddinge (SE); Francisco Sarabia, Torre de Benagalbon (ES); Sacha Ninkovic, San Diego, CA (US); David Hepworth, San Diego, CA (US); Tianhu Li, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/102,602

(22) Filed: Jun. 22, 1998

Related U.S. Application Data

(63) Continuation-in-part of application No. 08/923,869, filed on Sep. 4, 1997, which is a continuation of application No. 08/856,533, filed on May 14, 1997, now abandoned.
(60) Provisional application No. 60/032,864, filed on Dec. 13, 1996.

(51) Int. Cl.[7] .................. C07D 271/00; C07D 263/34; C07D 261/06
(52) U.S. Cl. .................. 548/125; 548/131; 548/143; 548/236; 548/247
(58) Field of Search ................... 548/125, 131, 548/143, 236, 247

(56) References Cited

FOREIGN PATENT DOCUMENTS

| WO | 93/10121 | 5/1993 |
|----|----------|--------|
| WO | 97/19086 | 5/1997 |
| WO | 98/08849 | 3/1998 |
| WO | 98/22461 | 5/1998 |
| WO | 98/25929 | 6/1998 |
| WO | 98/38192 | 9/1998 |
| WO | 99/01124 | 1/1999 |
| WO | 99/02514 | 1/1999 |
| WO | 99/07692 | 2/1999 |

OTHER PUBLICATIONS

Schinzer, et al., "Total Synthesis of (−)-Epothilone A", *Ang. Chem. Int. Ed.. Engl. 36(5)*: 523–524 (1997).
Yang, et al., "Total Synthesis of Epothilone A: The Olefin Metathesis Approach", *Ang. Chem. Int. Ed. Engl. 36*: 166–168 (1997).
Bollag, et al., "Epothilones, a New Class of Microtubule-stabilizing Agents with a Taxol-like Mechanism of Action", *Cancer Res. 55*: 2325–2333 (1995).
Meng, et al., "Remote Effects in Macrolide Formation through Ring–Forming Olefin Metathesis: An Application to the Synthesis of Fully Active Epothilone Congeners", *Amer. Chem. Soc. 119*: 2733–2734 (1997).
Grever, et al., "The National Cancer Institute: Cancer Drug Discovery and Development Program", *Seminars Oncol. 19*: 622–638 (1992).
Mulzer, et al., "Synthesis of the C(1)–C(9) Segment of the Cytotoxic Macrolides Epothilon A and B", *Tetr. Lett. 37(51)*: 9179–9182 (1996).
Claus, et al., "Synthesis of the C1–C9 Segment of Epothilons", *Tetr. Lett. 38(8)*: 1359–1362 (1997).
Gabriel, et al., "The Chromium–Reformatsky Reaction: Asymmetric Synthesis of the Aldol Fragment of the Cytotoxic Epothilons from 3-(2–Bromoacyl)–2–oxazolidinones", *Tetr. Lett. 38(8)*: 1363–1366 (1997).
Meng, et al., "Studies toward a Synthesis of Epothilone A: Use of Hydropyran Templates for the Management of Acyclic Stereochemical Relationships", *Org. Chem. 61*: 7998–7999 (1996).
Bertinato, et al., "Studies toward a Synthesis of Epothilone A: Stereocontrolled Assembly of the Acyl Region and Models for Macrocyclization", *J. Org. Chem. 61*: 8000–8001 (1996).
Kowalski, et al., "Activities of the Microtubule–stabilizing Agents Epothilones A and B with Purified Tubulin and in Cells Resistant to Paclitaxel (Taxol)", *J. Biol. Chem. 272*: 2534–2541 (1997).
Schiff, et al., "Promotion of Microtubule Assembly in vitro by Taxols", *Nature 277*: 665–667 (1979).
Balog, et al., "Total Synthesis of (−)–Epothilone A", *Ang. Chem. Int. Ed. Engl.35 (23/24)*: 2801–2803 (1996).
Hofle, et al., "Epothilone A and B–Novel 16–Membered Macrolides with Cytotoxic Activity: Isolation, Crystal Structure, and Conformation in Solution", *Ang. Chem. Int. Ed. Engl. 35 (13/14)*: 1567–1568 (1996).
Nicolaou, et al., "An Approach to Epothilones Based on Olefin Metathesis", *Ang. Chem. Int. Ed. Engl. 35 (20)*: 2399–2401 (1996).
Nicolaou, et al., "Total Synthesis of Epothilone A: The Macrolactonization Approach", *Ang. Chem. Int. Ed. Engl. 36 (5)*: 525–527 (1997).
Nicolaou, et al., "Chemistry and Biology of Taxol", *Ang. Chem. Int. Ed. Engl. 33*: 15–44 (1994).
Winkler, et al., "A Model for the Taxol (Paclitaxel)/Epothilone Pharmacophore", *Bioorg. Med. Chem. Int. Ed. Engl. 33*: 2963–2966 (1996).

(List continued on next page.)

*Primary Examiner*—Brenda Coleman
(74) *Attorney, Agent, or Firm*—Donald G. Lewis

(57) ABSTRACT

Novel analogs of epothilone A, epothilone B, and epothilone C are synthesized by Stille coupling thazole-stannanes to macrolactone intermediates. The synthetic epothilone analogs selectively prevent mitosis in cancer cells through the induction and stabilization of microtubulin assembly. Selected synthetic epothilone analogs are demonstrated to have greater bioactivity than their corresponding native compound.

10 Claims, 19 Drawing Sheets

OTHER PUBLICATIONS

Nicolaou, et al., "Designed Epothilones: Combinatorial Synthesis, Tubulin Assembly Properties, and Cytotoxic Action against Taxol–Resistant Tumor Cells", *Ang. Chem. Int. Ed. Engl. 36* (*19*): 2097–2103 (1997).

Nicolaou, et al., "The Olefin Metathesis Approach to Epothilone A and its Analogues", *J. Amer. Chem. Soc. 119*: 7960–7973 (1997).

Nicolaou, et al., "Total Synthesis of 26–Hydroxy–Epothilone B and Related Analogs via a Macrolactonization Based Strategy", *Tetrahdron 54*: 7127–7166 (1998).

May, et al., "Total Synthesis of (–)–epothilone B", *Chem. Commun.*: 1597–1598 (1998).

Nicolaou, et al., "Total Synthesis of 26–hydroxyepothilone B and Related Analogues", *Chem. Commun.*: 2343–2344 (1997).

Su, et al., "Structure–Activity Relationships of the Epothilones and the First in vivo Comparison with Paclitaxel", *Angew. Chem. Int. Ed. Engl 36*: 2093–2096 (1997).

Meng, et al., "Total Syntheses of Epothilones A and B", *J. Amer. Chem. Soc. 119*: 10073–10092 (1997).

Nicolaou, et al., "Synthesis of Epotnilones A and B in Solid and Solution Phase", *Nature 387*: 268–272 (1997).

Nicolaou, et al., "Total Syntheses of Epothilones A and B via a Macrolactonization–Based Strategy", *J. Amer. Chem. Soc. 119*: 7974–7991 (1997).

Balog, et al., "Stereoselective Syntheses and Evaluation of Compounds in the 8–Desmethylepothilone A Series: Some Surprising Observations Regarding their Chemical and Biological Properties", *Tetr. Lett. 38*: 4529–4532 (1997).

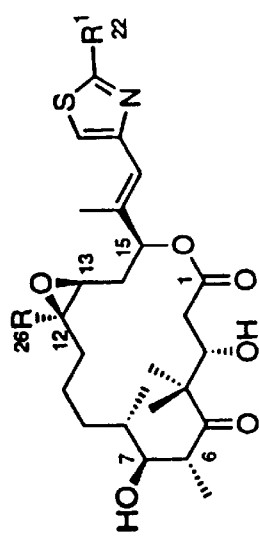
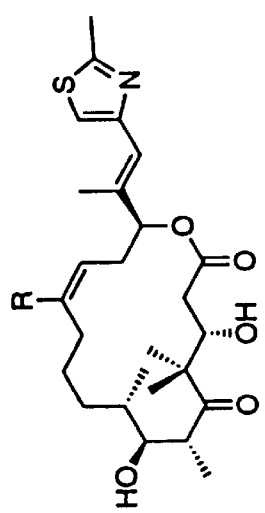
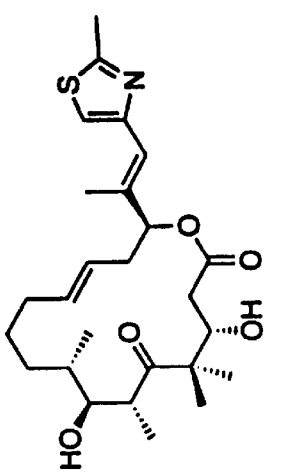
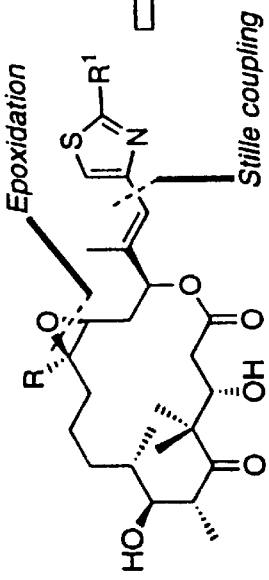
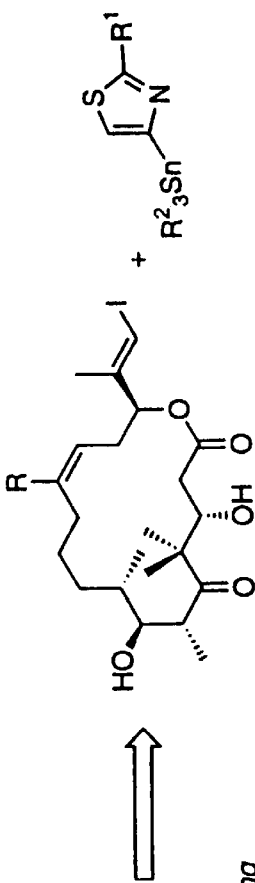
FIG. 1A
FIG. 1B

R = H; epothilone A (1)
R = OH; epothilone E (1a)

epothilone B (200)

C12,C13-cis-cyclopropyl-epothilone A (300)

C12,C13-trans-cyclopropyl-epothilone A (400)

| Entry | Compound | Induction of tubulin assembly (%) | IC$_{50}$/nm Parental 1A9 | Taxol resistant PTX10 | PTX22 |
|---|---|---|---|---|---|
| 1 | 1: X = O | 76 | 2.2 | 20 | 5.9 |
| 2 | 300: X = CH$_2$ | 2 | >100 | >100 | >100 |
| 3 | 1600: X = O | 92 | 2.0 | 18 | 3.0 |
| 4 | 400: X = CH$_2$ | 2 | >100 | >100 | >100 |
| 5 | 1a | 52 | >100 | 50 | 20 |
| 6 | 1700: X = OH | 34 | >100 | >100 | >100 |
| 7 | 1800: X = OAc | 3 | 50 | >100 | >100 |
| 8 | 1900: X = F | 57 | >100 | >100 | >100 |
| 9 | 2000: X = H | 50 | >100 | >100 | >100 |
| 10 | 2100: X = OEt | 3 | >100 | >100 | >100 |
| 11 | 2200: X = SMe | 92 | 9 | 22 | 28 |
| 12 | 2300: X = (CH$_2$)$_5$OAc | 2 | >100 | >100 | >100 |
| 13 | 2400: X = N(CH$_2$)$_5$ | 18 | >100 | >100 | >100 |
| 14 | 2500 | 2 | >100 | >100 | >100 |
| 15 | 2600 | 63 | 10 | 28 | 25 |
| 16 | 2700: X = O | 4 | >100 | >100 | >100 |
| 17 | 2800: X = S | 6 | >100 | >100 | >100 |
| 18 | 2900: X = CH | 16 | >100 | >100 | >100 |
| 19 | 3000: X = N | 13 | >100 | >100 | >100 |
| 20 | 3100 | 1 | >100 | >100 | >100 |

FIG. 13

| | | | IC$_{50}$ / nm | | |
|---|---|---|---|---|---|
| | | | Parental | Taxol resistant | |
| Entry | Compound | Induction of tubulin assembly (%) | 1A9 | PTX10 | PTX22 |
| 21 | 3200: X = OH | 40 | >100 | >100 | >100 |
| 22 | 3300: X = OAc | 2 | >100 | >100 | >100 |
| 23 | 3400: X = F | 55 | >100 | >100 | >100 |
| 24 | 3500: X = H | 41 | 20 | >100 | 45 |
| 25 | 3600: X = OEt | 2 | >100 | >100 | >100 |
| 26 | 3700: X = SMe | 71 | 15 | >100 | 20 |
| 27 | 3800: X = (CH$_2$)$_5$OAc | 0 | >100 | >100 | >100 |
| 28 | 3900: X = N(CH$_2$)$_5$ | 5 | >100 | >100 | >100 |
| 29 | 4000 | 2 | >100 | >100 | >100 |
| 30 | 4100 | 57 | >100 | 70 | >100 |
| 31 | 4200: X = O | 0 | >100 | >100 | >100 |
| 32 | 4300: X = S | 2 | >100 | >100 | >100 |
| 33 | 4400: X = CH | 26 | >100 | >100 | >100 |
| 34 | 4500: X = N | 2 | >100 | >100 | >100 |
| 35 | 4600 | 1 | >100 | >100 | >100 |

FIG. 14

| Entry | Compound | Induction of tubulin assembly (%) | IC$_{50}$/nm Parental 1A9 | Taxol resistant PTX10 | Taxol resistant PTX22 |
|---|---|---|---|---|---|
| |  | | | | |
| 36 | 4600: X = CH$_2$F | 11 | >100 | >100 | >100 |
| 37 | 4800: X = OMe | 25 | 75 | >100 | >100 |
| 38 | 4900: X = CHCH$_2$ | 48 | >100 | >100 | >100 |
| 39 | 5000: X = CH$_2$CH$_3$ | 58 | >100 | >100 | >100 |
| 40 | 5100: X = CH$_2$OH | 14 | >100 | >100 | >100 |
| |  | | | | |
| 41 | 5200: X = CH$_2$F | 80 | 80 | >100 | >100 |
| 42 | 5300: X = OMe | 80 | 10 | 90 | >100 |
| 43 | 5400: X = CHCH$_2$ | 92 | 1.2 | 11 | >100 |
| 44 | 5500: X = CH$_2$CH$_3$ | 97 | 2.0 | 15 | >100 |
| |  | | | | |
| 45 | 5600: X = CH$_2$F | 6 | >100 | >100 | >100 |
| 46 | 5700: X = OMe | 9 | >100 | >100 | >100 |
| 47 | 5800: X = CH$_2$CH$_3$ | 39 | >100 | >100 | >100 |
| |  | | | | |
| 48 | 5900: X = CH$_2$F | 92 | 0.54 | 2.8 | 1.5 |
| 49 | 6000: X = OMe | 91 | 0.40 | 1.2 | 2.5 |
| |  | | | | |
| 50 | 6100: X = CH$_2$F | 91 | 5.5 | 10 | 8.8 |
| 51 | 6200: X = OMe | 93 | 10 | 29 | 15 |
| 52 | 6300: X = CH$_2$CH$_3$ | 95 | 0.12 | 0.35 | 0.14 |

EPOTHILONE ANALOGS

CROSS-REFERENCE TO RELATED APPLICATION

This is a continuation-in-part application of U.S. patent application Ser. No. 08/923,869, filed Sep. 4, 1997, which is a continuation of U.S. patent application Ser. No. 08/856,533, filed May 14, 1997 now abandoned, which claims benefit of U.S. provisional application Ser. No. 06/032,864, filed Dec. 13, 1996.

GOVERNMENT RIGHTS

This invention was made with government support under Grant No. CA 46446 awarded by the National Institutes of Health. The U.S. government has certain rights in the invention.

TECHNICAL FIELD OF THE INVENTION

The present invention relates to epothilone analogs having side chain modifications and to methods for producing such compounds using solid phase and solution phase chemistries.

BACKGROUND OF THE INVENTION

The epothilones (1–5, FIG. 1) are natural substances which exhibit cytotoxicity against taxol-resistant tumor cells by promoting the polymerization of α- and β-tubulin subunits and stabilizing the resulting microtubule assemblies. Epothilones displace Taxol™ from its microtubul binding site and are reported to be about 2000–5000 times more potent than Taxol with respect to the stabilization of microtubules.

What is needed are analogs of epothilone A and B and libraries of analogs of epothilone A and B that exhibit superior pharmacological properties in the area of microtubule stabilizing agents.

Furthermore, what is needed are methods for producing synthetic epothilone A, epothilone B, analogs of epothilone A and B, and libraries of epothilone analogs, including epothilone analogs possessing both optimum levels of microtubule stabilizing effects and cytotoxicity.

BRIEF SUMMARY OF THE INVENTION

One aspect of the invention is directed to an epothilone analog represented by the following structure:

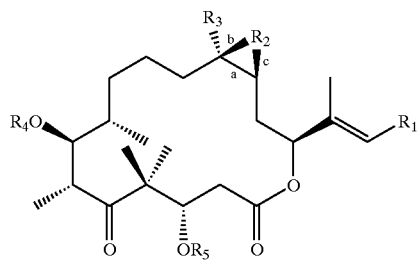

In the above structure, $R_2$ is absent or oxygen; "a" can be either a single or double bond; "b" can be either absent or a single bond; and "c" can be either absent or a single bond. However, the following provisos apply: if $R_2$ is oxygen, then "b" and "c" are both a single bonds and "a" is a single bond; if $R_2$ is absent, then "b" and "c" are absent and "a" is a double bond; and if "a" is a double bond, then $R_2$, "b", and "c" are absent. $R_3$ is a radical selected from the group consisting of hydrogen, methyl, —CHO, —COOH, —CO$_2$Me, —CO$_2$(tert-butyl), —CO$_2$(iso-propyl), —CO$_2$(phenyl), —CO$_2$(benzyl), —CONH(furfuryl), —CO$_2$(N-benzo-(2R,3S)-3-phenylisoserine), —CONH(methyl)$_2$, —CONH(ethyl)$_2$, —CONH(benzyl), —CH=CH$_2$, —C≡CH, and —CH$_2$R$_{11}$, wherein $R_{11}$ is a radical selected from the group consisting of —OH, —O-Trityl, —O—(C$_1$-C$_6$ alkyl), —(C$_1$-C$_6$ alkyl), —O-benzyl, —O-allyl, —O—COCH$_3$, —O—COCH$_2$Cl, —O—COCH$_2$CH$_3$, —O—COCF$_3$, —O—COCH(CH$_3$)$_2$, —O—COC(CH$_3$)$_3$, —O—CO(cyclopropane), —OCO(cyclohexane), —O—COCH=CH$_2$, —O—CO—Phenyl, —O-(2-furoyl), —O-(N-benzo-(2R,3S)-3-phenylisoserine), —O-cinnamoyl, —O-(acetyl-phenyl), —O-(2-thiophenesulfonyl), —S—(C$_1$-C$_6$ alkyl), —SH, —S-Phenyl, —S-Benzyl, —S-furfuryl, —NH$_2$, —N$_3$, —NHCOCH$_3$, —NHCOCH$_2$Cl, —NHCOCH$_2$CH$_3$, —NHCOCF$_3$, —NHCOCH(CH$_3$)$_2$, —NHCOC(CH$_3$)$_3$, —NHCO(cyclopropane), —NHCO(cyclohexane), —NHCOCH=CH$_2$, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, I, and —CH$_2$CO$_2$H. $R_4$ and $R_5$ are each independently selected from hydrogen, methyl or a protecting group. $R_1$ is a radical selected from the following structures:

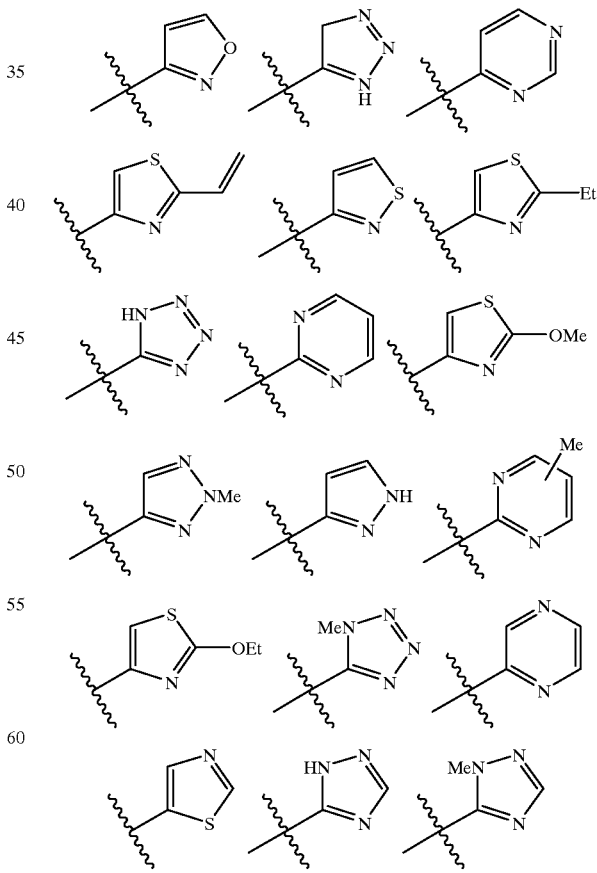

-continued

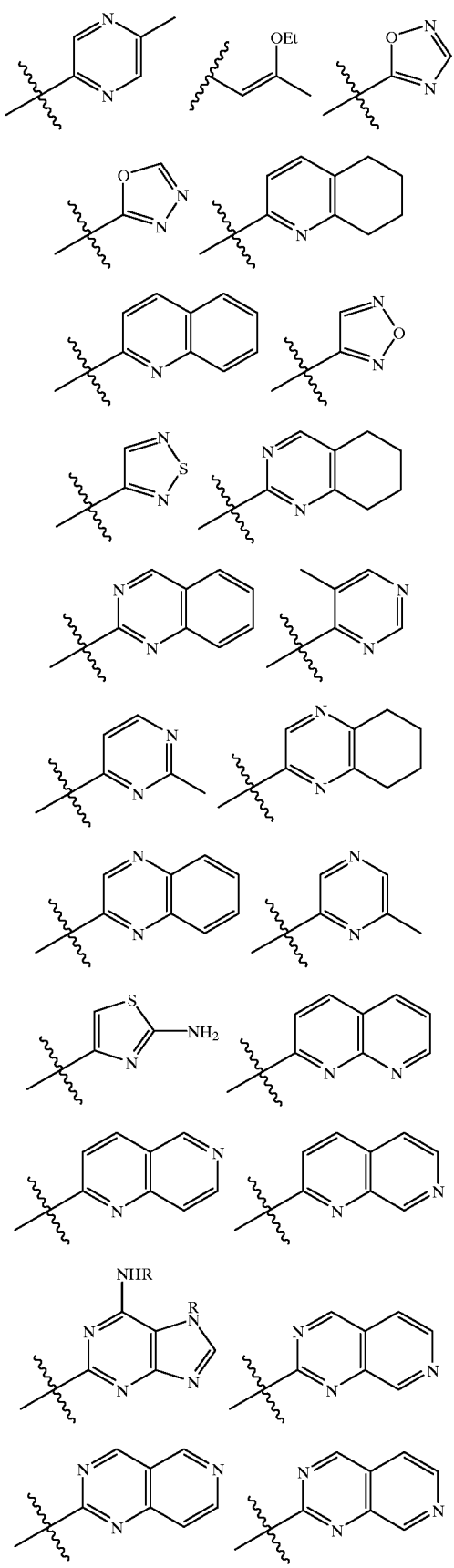

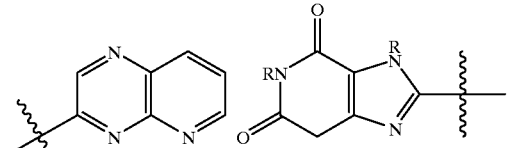

R = H, Me

In a preferred embodiment, $R_3$ is hydrogen or —$CH_2R_{11}$, $R_{11}$ is a radical selected from the group consisting of —OH and —F, and $R_1$ is a radical selected from the following structures:

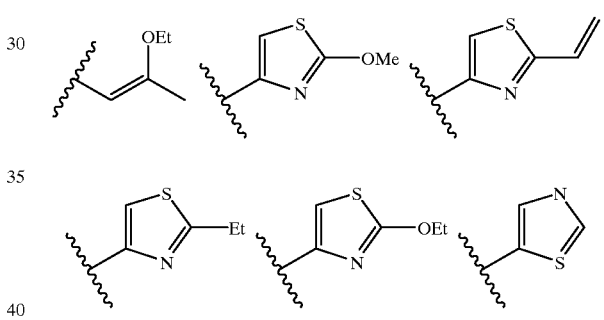

Another aspect of the invention is directed to a process for synthesizing an epothlone analog, or a salt thereof The process includes a coupling step wherein an epothilone intermediate and an aromatic stannane are coupled by means of a Stille coupling reaction for producing the epothilone analog. The epothilone is represented by the following structure:

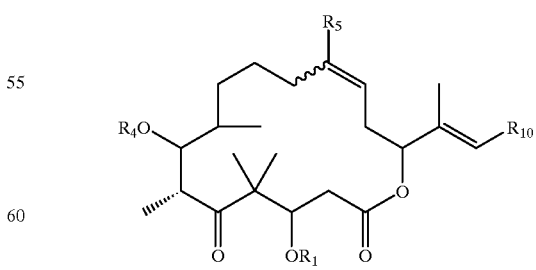

The epothilone intermediate is represented by the following structure:

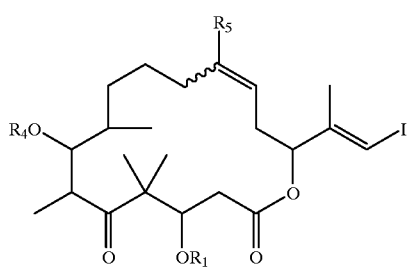

In the above structures, $R_1$ and $R_4$ are each independently selected from hydrogen, methyl or a protecting group; $R_5$ is —CH$_2$R$_x$ wherein R$_x$ is a radical selected from the group consisting of —OH, —O-Trityl, —O—(C$_1$-C$_6$ alkyl), —(C$_1$-C$_6$ alkyl), —O-benzyl, —O-allyl, —O—COCH$_3$, —O—COCH$_2$Cl, —O—COCH$_2$CH$_3$, —O—COCF$_3$, —O—COCH(CH$_3$)$_2$, —O—COC(CH$_3$)$_3$, —O—CO (cyclopropane), —OCO(cyclohexane), —O—COCH=CH$_2$, —O—CO-Phenyl, —O-(2-furoyl), —O-(N-benzo-(2R,3S)-3-phenylisoserine), —O-cinnamoyl, —O-(acetyl-phenyl), —O-(2-thiophenesulfonyl), —S—(C$_1$-C$_6$ alkyl), —SH, —S-Phenyl, —S-Benzyl, —S-furfuryl, —NH$_2$, —N$_3$, —NHCOCH$_3$, —NHCOCH$_2$Cl, —NHCOCH$_2$CH$_3$, —NHCOCF$_3$, —NHCOCH(CH$_3$)$_2$, —NHCOC(CH$_3$)$_3$, —NHCO(cyclopropane), —NHCO(cyclohexane), —NHCOCH=CH$_2$, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, —I, and —CH$_2$CO$_2$H and methyl; and the aromatic stannane is a compound represented as (R$_y$)$_3$Sn—R$_{10}$ wherein R$_y$ is either n-butyl or methyl; R$_{10}$ is a radical selected from a group consisting of one of the following structures:

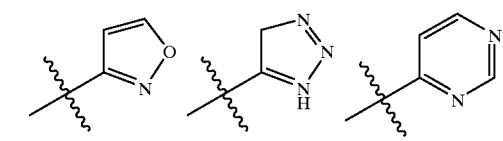

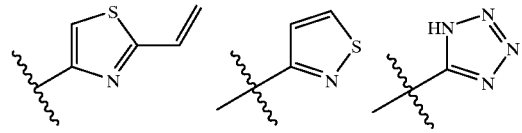

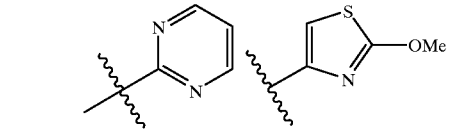

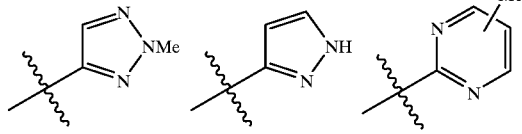

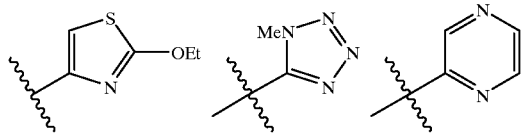

-continued

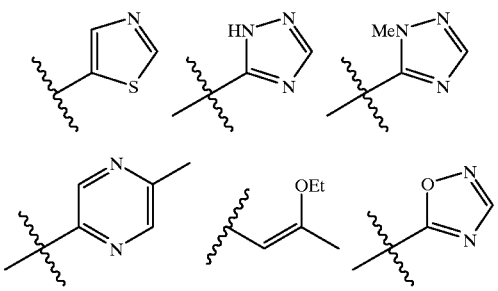

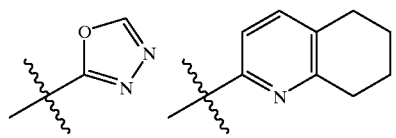

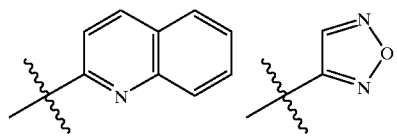

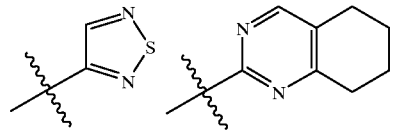

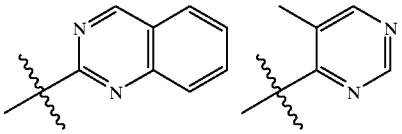

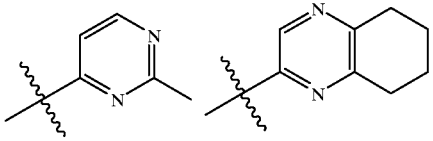

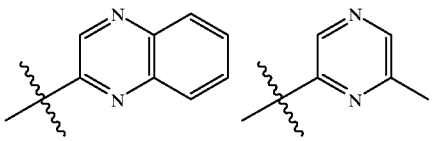

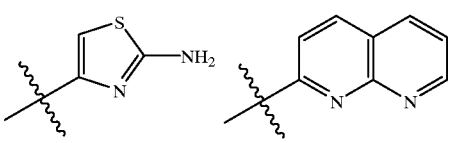

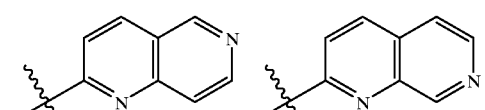

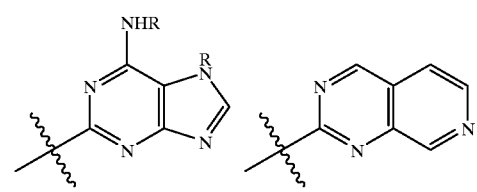

-continued

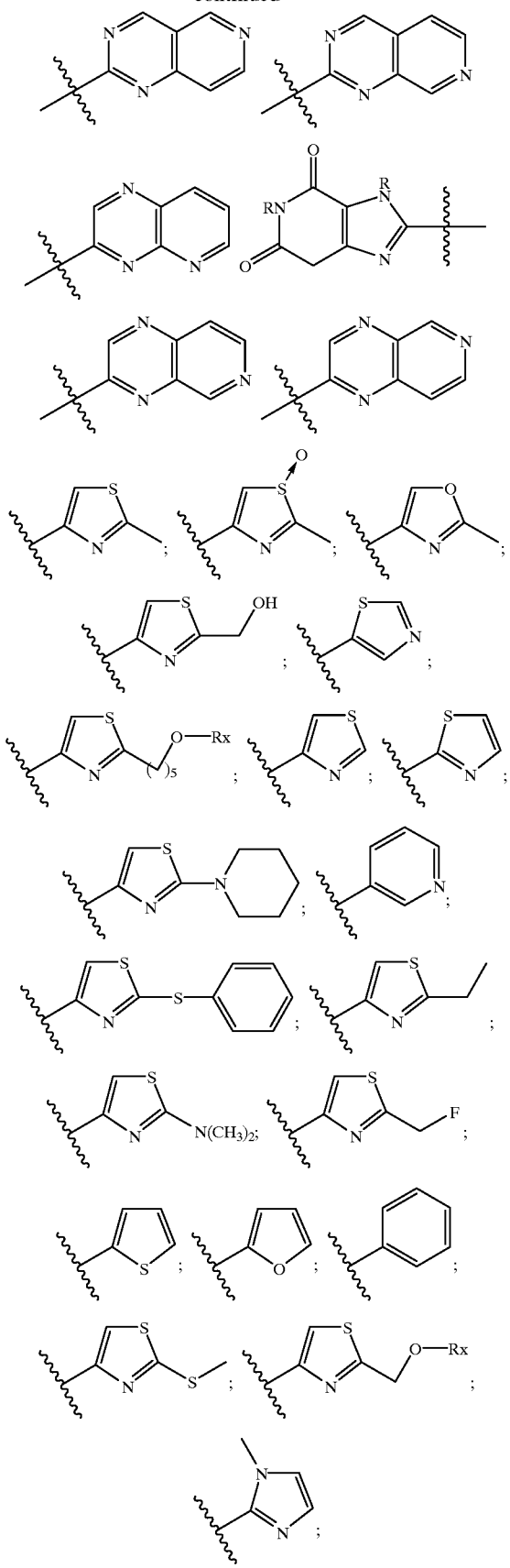

-continued

R = H, Me

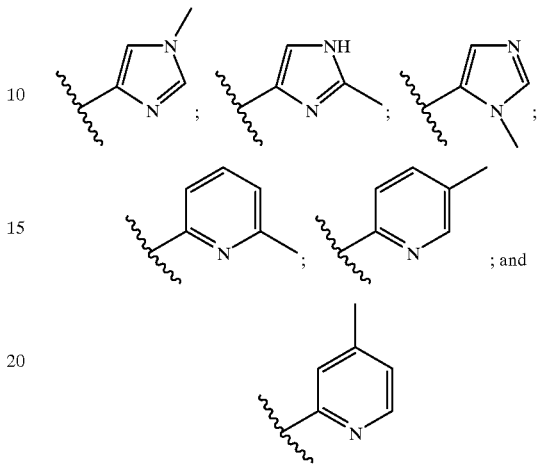

and (in a broader aspect of the invention)

wherein Rx is acyl, especially lower alkanoyl, such as acetyl.

DESCRIPTION OF FIGURES

FIG. 1(A) details the structures and numbering of epothilones A–E and C12,13-trans-epothilone C;

FIG. 1(B) details the chemical retrosynthesis of epothilone E.

FIG. 13 shows the biological activities of epothilones 1, 300–400, and 1600–3100.

FIG. 14 shows the biological activities of epothilones 3200–4600.

DETAILED DESCRIPTION OF THE INVENTION

Figure 2A:
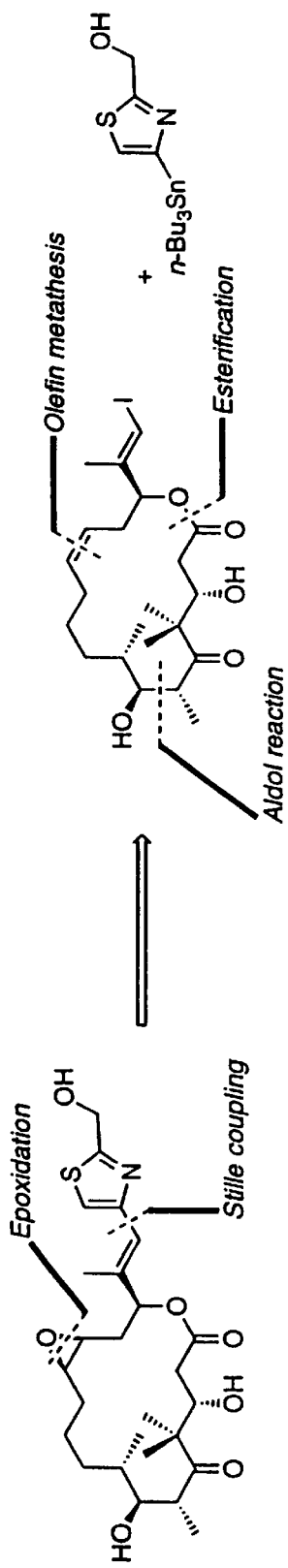
FIG. 2(A) details the retrosynthetic analysis and strategy for the total synthesis of epothilone E (3) and (B) shows side-chain analogs of epothilone C (9) and its $\Delta^{12,13}$ trans-isomer (10).

The invention is directed to epothilone analogs and methods for producing such analogs based on approaches used to synthesize epothilones A and B. One aspect of the invention relates to the use of an improved Stille coupling strategy to complete a total synthesis of epothilone E from vinyl iodide 7 and thiazole-stannane 8h. The central core fragment 7 and its trans-isomer 11 were prepared from triene 15 using ring-closing metathesis (RCM), and were subsequently coupled to a variety of alternative stannanes to provide a library of epothilone analogs 18a–o and 19a–o. The Stille coupling approach was then used to prepare epothilone B analogs from the key macrolactone intermediate 24 which was, itself, synthesized by a macrolactonization based strategy.

Another aspect of the invention is directed to the chemical synthesis of the C12,13-cyclopropyl analogs of the epothilones. These and several other epothilone analogs have been synthesized and then screened for their ability to induce tubulin polymerization and death of a number of tumor cells as described below.

The following examples illustrate methods for the total synthesis of the epithilone analogs. The examples represent exemplary conditions which demonstrate the versatility of the methodology and are not meant to be restrictive with the models disclosed.

Figure 2B:
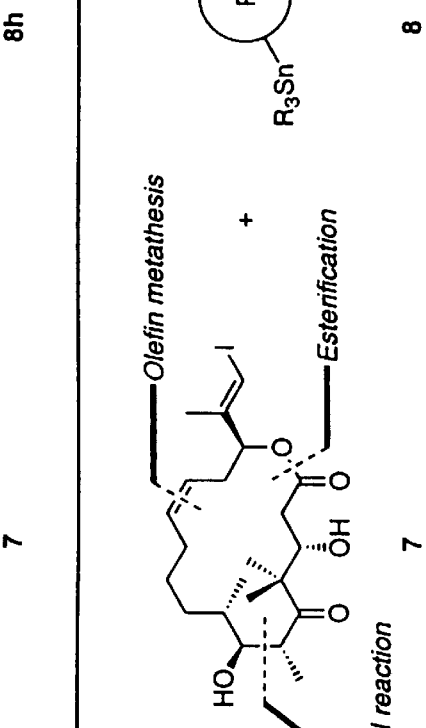

EXAMPLE 1
Total Synthesis of Epothilone E and Related Side-Chain Modified Analogs via a Stille Coupling Based Strategy As reported in a preliminary communication (Nicolaou et al. Angew. Chem. Int. Ed. 1998, 37, 84–87), the first total synthesis of epothilone E (3) has been accomplished by a strategy in which the key step was a Stille coupling (Stille et al. Angew. Chem. Int. Ed. Engl. 1986, 25, 508–524; Farina et al. J. Org. React. 1997, 50, 1–65) between vinyl iodide 7 and the thiazole moiety (8h, FIG. 2a). The macrolactone core fragment 7, which was prepared via ring-closing olefin metathesis (RCM), could subsequently be used to provide convenient and flexible access to a variety of side-chain modified epothilone analogs (9) for biological evaluation (FIG. 2b). The RCM reaction used to access 7 also provided frans-macrolactone (11, FIG. 2b) which could serve as an alternative template for the Stille coupling process and provide an additional array of analogs 10.

Figure 3:
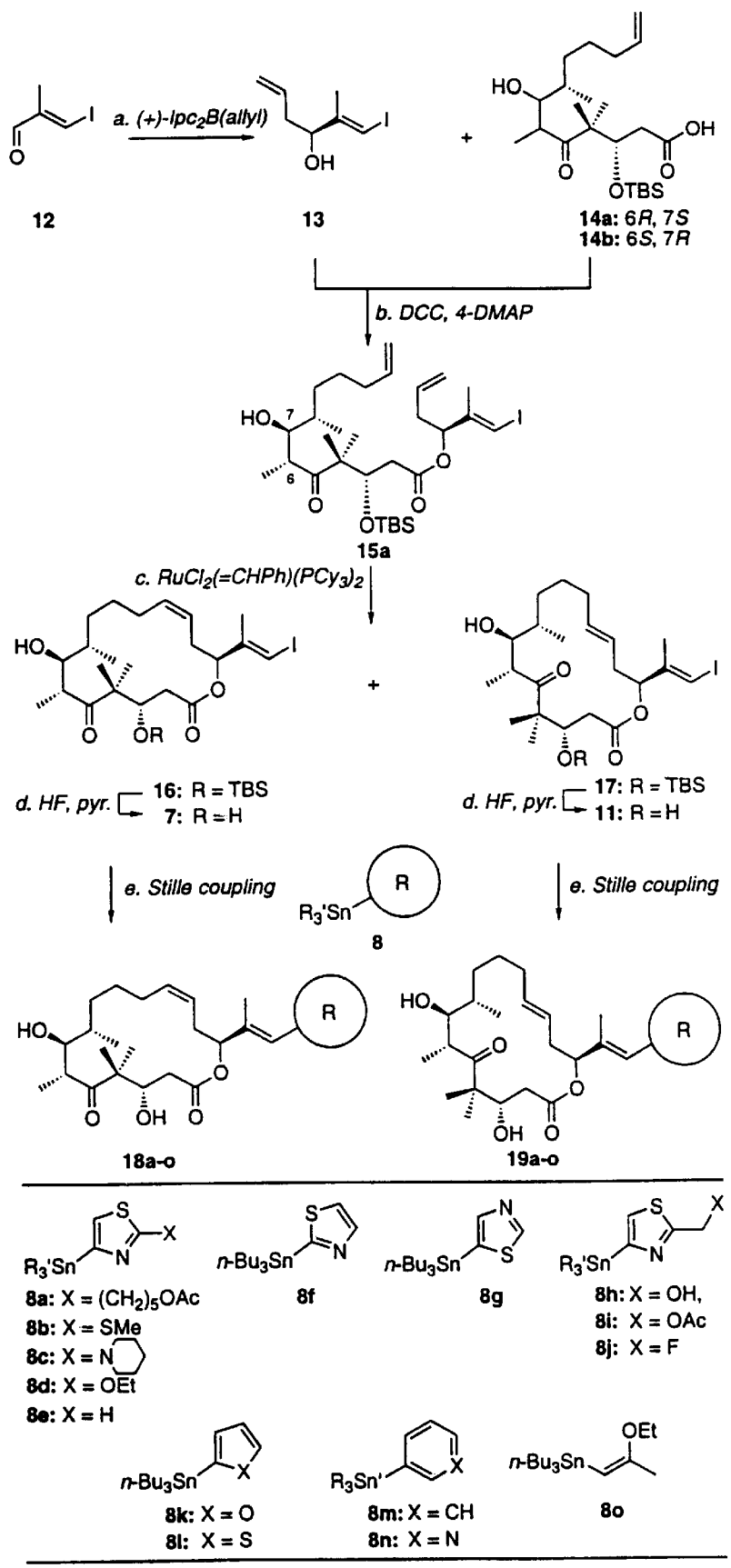
FIG. 3 illustrates the synthesis of common intermediates 7 and 11 and desoxyepothilones 18a–o and 19a–o. Reagents and conditions: (a) 1.3 equiv of (+)-Ipc$_2$B(allyl), Et$_2$O, −100° C., 0.5 h, 91%; (b) 2.0 equiv of 13, 1.5 equiv of DCC, 1.5 equiv of 4-DMAP, toluene, 0→25° C., 12 h, 49% of 15a plus 33% of its (6S,7R)-diastereoisomer 15b; (c) 10 mol % of RuCl$_2$(=CHPh)(PCy$_3$)$_2$, CH$_2$Cl$_2$, 25° C., 30 h, 35% of 16 plus 30% of 17; (d) 25% v/v HF.pyr. in THF, 25° C., 30 h, 84% of 7; 85% of 11; (e) procedure A: 2.0 equiv of 8, 5–10 mol % Pd(PPh$_3$)$_4$, toluene, 90–100° C., 15–40 min, 39–88%; procedure B: 2.0–2.2 equiv of 8, 20–30 mol % Pd(MeCN)$_2$Cl$_2$, DMF, 25° C., 12–33 h, 49–94%. TBS=tert-butyldimethylsilyl; DCC=dicyclohexylcarbodiimide; 4-DMAP=4-dimethylaminopyridine.

The chemical synthesis of the requisite vinyl iodides 7 and 11 is delineated in FIG. 3. Asymmetric allyboration of aldehyde 12 [(+)-$Ipc_2$B(allyl), $Et_2O$, -100° C.; Baker et al. J. Chem. Soc. Perkin Trans I 1990, 47–65; Racherla et al. J. Org. Chem. 1991, 56, 401–404] using Brown's methodology provided the enantiopure alcohol 13 in 91% yield. Subsequent coupling (DCC, 4-DMAP, toluene, 0 to 25° C.) with a 3:2 mixture of alcohols 14a and 14b used in our previous synthesis of epothilone A afforded metathesis precursor 15a (49% yield) and its readily separable 6S,7R diastereoisomer (15b, 33% yield, not shown). In an analogous fashion to our previous studies, RCM was achieved using the ruthenium initiator [$RuCl_2$(=CHPh)($PCy_3$)$_2$] ($CH_2Cl_2$, 25° C.) to provide the Z- and E-macrolactones 16 (35%) and 17 (30%). Separation and subsequent deprotection (HF,pyr., THF, 25° C.) of the individual isomers provided pure core structures 7 (84%) and 11 (85%), setting the stage for the all-important Stille coupling reaction.

The stannane coupling partners used in the Stille reaction are shown in FIG. 3. Thiazole stannanes 8k, 8l and 8o were obtained from commercial sources, whereas stannanes 8e–8g and 8m,n were prepared using established procedures. The remaining coupling partners 8a–d, 8h–j and additional stannanes 8p–r were prepared from readily accessible 2,4-dibromothiazole(20) via monobromides 21 as outlined in FIGS. 4 and 5. Thus, formation of thiazole 21a (FIG. 4) was achieved via a three-step process commencing with a Sonogashira coupling between dibromide 20 and pentyn-1-ol [Pd($PPh_3$)$_4$, CuI, i-PrNK 70° C.] to give an intermediate alkyne in 83% yield (Sonogashira et al. Tetrahedron Lett. 1975, 16, 4467–447). Catalytic hydrogenation ($H_2$, $PtO_2$, EtOH, 25° C.) and subsequent esterification ($Ac_2O$, pyr., $CH_2Cl_2$, 25° C.) afforded the desired monobromide (21a) in 83% yield for two steps. Sulfide 21b was obtained in 92% yield by replacing the 2-bromo substituent of 20 with the thiomethyl moiety using sodium thiomethoxide (EtOH, 25° C.). Alternatively, reaction of dibromide 20 with piperidine at 60° C., afforded thiazole 21c in quantitative yield. Finally, the ethoxy and methoxy thiazoles 21d and 21p were prepared by treating dibromide 20 with NaOH in ethanol and methanol, respectively. Bromides (21a–d) were then transformed to the desired trimethylstannanes (8a–c,p) with hexamethylditin under palladium catalyzed conditions [Pd($PPh_3$)$_4$, toluene, 80–100° C.], whereas tri-n-butylstannane 8d was obtained from ethoxybromide 21d by halogen-metal exchange (n-BuLi, $Et_2O$, -78° C.) and subsequent trapping with tri-n-butyltin chloride in 98% yield.

Figure 5:
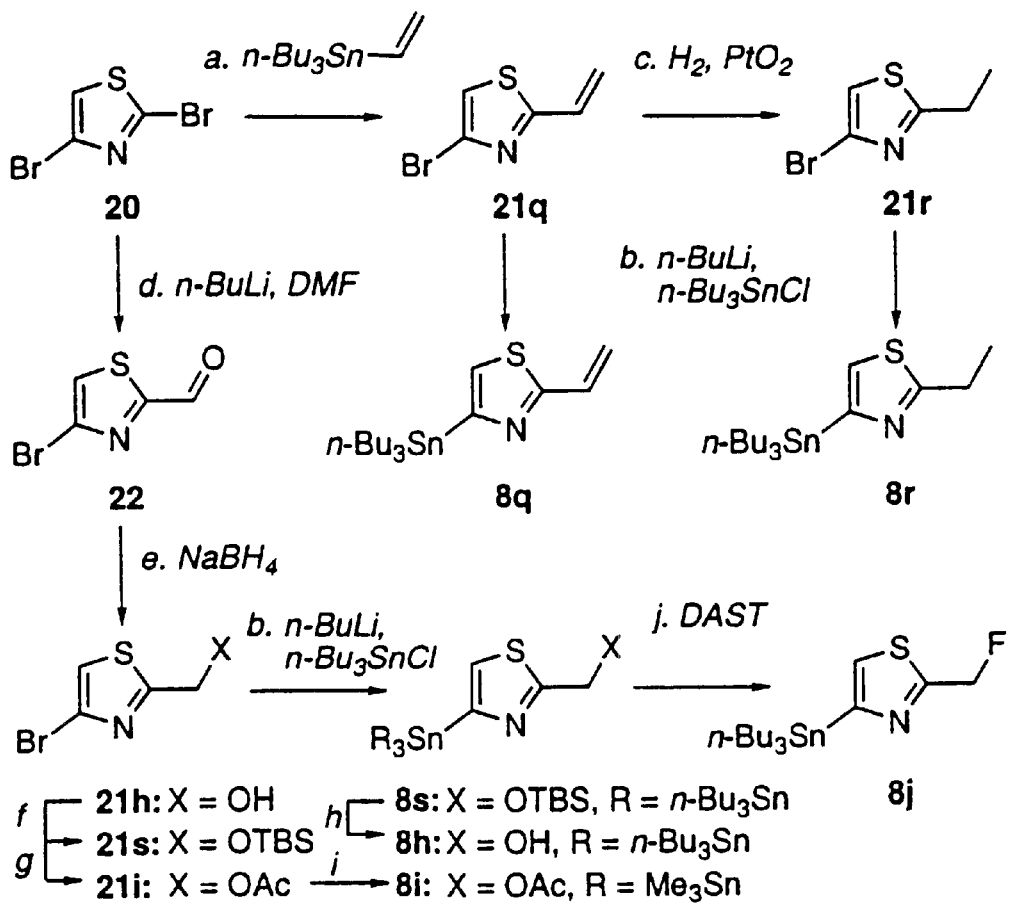
FIG. 5 illustrates the preparation of stannanes 8h–j and 8q–s. Reagents and conditions: (a) 1.05 equiv n-Bu$_3$SnCH=CH$_2$, toluene, 100° C., 21 h, 83%; (b) 1.1–1.2 equiv of n-BuLi, 1.2–1.25 equiv of n-Bu$_3$SnCl, −78→25° C., 1 h, 28–85%; (c) H$_2$, 0.15 equiv of PtO$_2$, EtOH, 25° C., 4 h; 84%; (d) 1.2 equiv of n-BuLi, 2.0 equiv of DMF, −78→25° C., 2 h; (e) 1.9 equiv of NaBH$_4$, MeOH, 25° C., 30 min, 63% for two steps; (f) 1.3 equiv of TBSCl, 2.0 equiv of imidazole, CH$_2$Cl$_2$, 25° C., 0.5 h, 96%; (g) 1.2 equiv of 4-DMAP, 3.2 equiv of Ac$_2$O, EtOAc, 25° C., 5 min, 91%; (h) 1.2 equiv of TBAF, THF, 25° C., 20 min, 95%; (i) 10 equiv of Me$_3$SnSnMe$_3$, 7 mol % of Pd(PPh$_3$)$_4$, toluene, 100° C., 25 min, 45%; (j) 1.1 equiv of DAST, CH$_2$Cl$_2$, −78→25° C., 10 min, 57%. DAST=diethylamino sulfurtrifluoride.

The synthesis of stannanes (8h–j and 8q–r) was also achieved from the common precursor 20 (FIG. 5). Thus, palladium catalyzed alkenylation [n-$Bu_3SnCH=CH_2$, Pd($PPh_3$)$_4$, toluene, 100° C.] of 2,4-dibromothiazole 20 afforded monobromide 21q, which underwent halogen-metal exchange (n-BuLi, $Et_2O$, -78° C.) and subsequent quenching with tri-n-butyltin chloride to furnish the desired stannane 8q. Reduction of the intermediate vinyl bromide 21q ($H_2$, $PtO_2$, EtOH, 25° C.) provided access to ethyl thiazole 21r, which was converted into stannane 8r in an identical manner to that described for 8q. The synthesis of stannanes 8h–j was achieved via the key hydroxymethyl thiazole 21h.

As shown in FIG. 5, this alcohol was, itself, obtained from dibromide 20 in a two-step process involving lithiation (n-BuLi, $Et_2O$, -78° C.) and subsequent quenching with DMF to give intermediate aldehyde 22, which was then reduced ($NaBH_4$, MeOH, 25° C.) to furnish the desired alcohol 21h in 63% overall yield. Conversion of 21h into stannane 8h required a three-step sequence involving protection of the hydroxyl group (TBSCl, imidazole, $CH_2Cl_2$, 96%), stannylation (i. n-BuLi, $Et_2O$, -78° C.; ii. n-$Bu_3SnCl$, 85%) and subsequent deprotection (TBAF, THF, 25° C., 95%). Fluorination of the resulting stannane 8h (DAST, $CH_2Cl_2$, -78° C.) provided direct access to stannane 8j in 57% yield. Esterification of the key alcohol 21h (4-DMAP, $Ac_2O$, EtOAc, 25° C.) afforded acetate 21i which was converted into stannane 8i with hexamethylditin [Pd($PPh_3$)$_4$, toluene, 100° C.] in 41% overall yield.

With the necessary components in hand, the critical Stille couplings could now be investigated. In the event, two alternative sets of reaction conditions proved adequate (FIG. 3). Procedure A involved heating a toluene solution of the desired vinyl iodide (7 or 11) with the appropriate stannane 8 in the presence of catalytic amounts of Pd(PPh$_3$)$_4$ at 80–100° C. for between 15 and 40 min. This protocol was used to couple stannanes 8a–c, 8e–i and 8n. The remaining stannanes, 8d, 8j–m and 8o (epothilones 18o and 19o, the products of coupling of stannane 8o with vinyl iodides 7 and 11, respectively, were isolated as C17-methyl ketones and not ethyl enol ethers) were coupled using an alternative, milder method, procedure B, in which a mixture of vinyl iodide (7 or 11) and stannane 8 in DMF was treated with PdCl$_2$(MeCN)$_2$ at 25° C.

Figure 6:
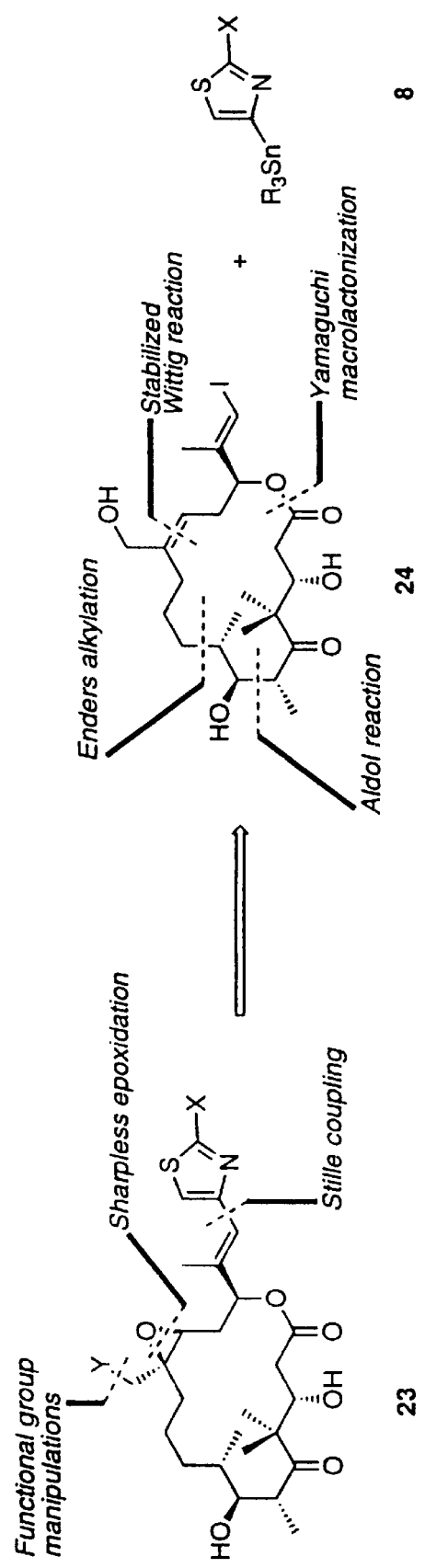
FIG. 6 illustrates a retrosynthetic analysis of epothilone analogs possessing modified C-26 and side-chain moieties.

The coupling of vinyl iodide 7 and stannane 8h provided macrolactone 18h which served as the precursor to the natural epothilone E (3) (FIG. 6a). The total synthesis was completed by epoxidation with in situ generated methylperoxycarboximidic acid (H$_2$O$_2$, KHCO$_3$, MeCN, MeOH, 25° C.; Chaudhuri et al. J. J. Org. Chem. 1982, 47, 5196–5198) furnishing epothilone E (3) (66% based on 50% conversion), which exhibited identical physical characteristics ($^1$H and $^{13}$C NMR, [α]$_D$) to those published in the art.

At this stage, we postulated that the Stille coupling approach could be extended to provide facile access to a variety of side-chain modified analogs of epothilone B (2). The impetus for this development was two-fold. Firstly, epothilone B is the most active of the epothilones and, therefore, warranted further investigation. Secondly, the C26 position of this compound has proved to be a fertile site for modification, and it was felt that analogs possessing a combination of these two variables could be interesting for further biological evaluation. The retrosynthetic analysis of epothilone analogs possessing these dual modifications is shown in FIG. 6b and requires the preparation of the crucial vinyl iodide core fragment 24. A macrolactonization strategy similar to that used in our synthesis of epothilone B and a variety of epothilone analogs was thought to be most suitable for this task.

The synthesis began from the vinyl iodide 13 (FIG. 7) which we had used in the preparation of epothilone E and related analogs (FIG. 3). Protection of the allylic hydroxyl group (TBSCl, imidazole, DMF, 0 to 25° C.) afforded silyl ether 25 (84%) which was transformed into aldehyde 26 by a two-step dihydroxylation-glycol-cleavage sequence (OsO$_4$, NMO, THF/t-BuOH/H$_2$O, 0 to 25° C.; then NaIO$_4$, MeOH/H$_2$O, 0° C., 82% for two steps). A stereocontrolled Wittig reaction with the stabilized ylide 27 (benzene, reflux; Marshall et al. J. Org. Chem. 1986, 51, 1735–1741; Bestmann et al. Angew. Chem. Int. Ed. Engl. 1965, 4, 645–660.) afforded ester 28 as a single geometrical isomer in 98% yield. Reduction of the latter compound (DIBAL, THF, −78° C.) afforded alcohol 29, which was protected as the triphenylmethyl (trityl) derivative 30 (TrCl, 4-DMAP, DMF, 70° C., 95%).

Elaboration of the terminal olefin was then achieved by selective hydroboration-oxidation to give alcohol 31 (9-BBN, THF, 0° C.; then NaOH H$_2$O$_2$, 0° C.) which was transformed further into dijodide 32 (I$_2$, imidazole, Ph$_3$P, 0° C.) in 92% overall yield. Introduction of the C8 stereocenter was then achieved using an Ender's alkylation protocol (SAMP hydrazone of propionaldehyde, LDA, THF, 0° C.; then −100° C. and add 32 in THF; Enders et al. Asymmetric Synthesis 1984; Morrison, J. D., Ed.; Academic Press, Orlando, Vol 3, p. 275–339; we thank Prof. Enders for a generous gift of SAMP) resulting in the formation of SAMP hydrazone 33 in 71% yield. Conversion to nitrile 34 (MMPP, MeOH/phosphate buffer pH 7, 0° C., 89%) and ensuing reduction (DIBAL, toluene, −78° C.) afforded the desired aldehyde 35 in 88% yield.

Figure 8:
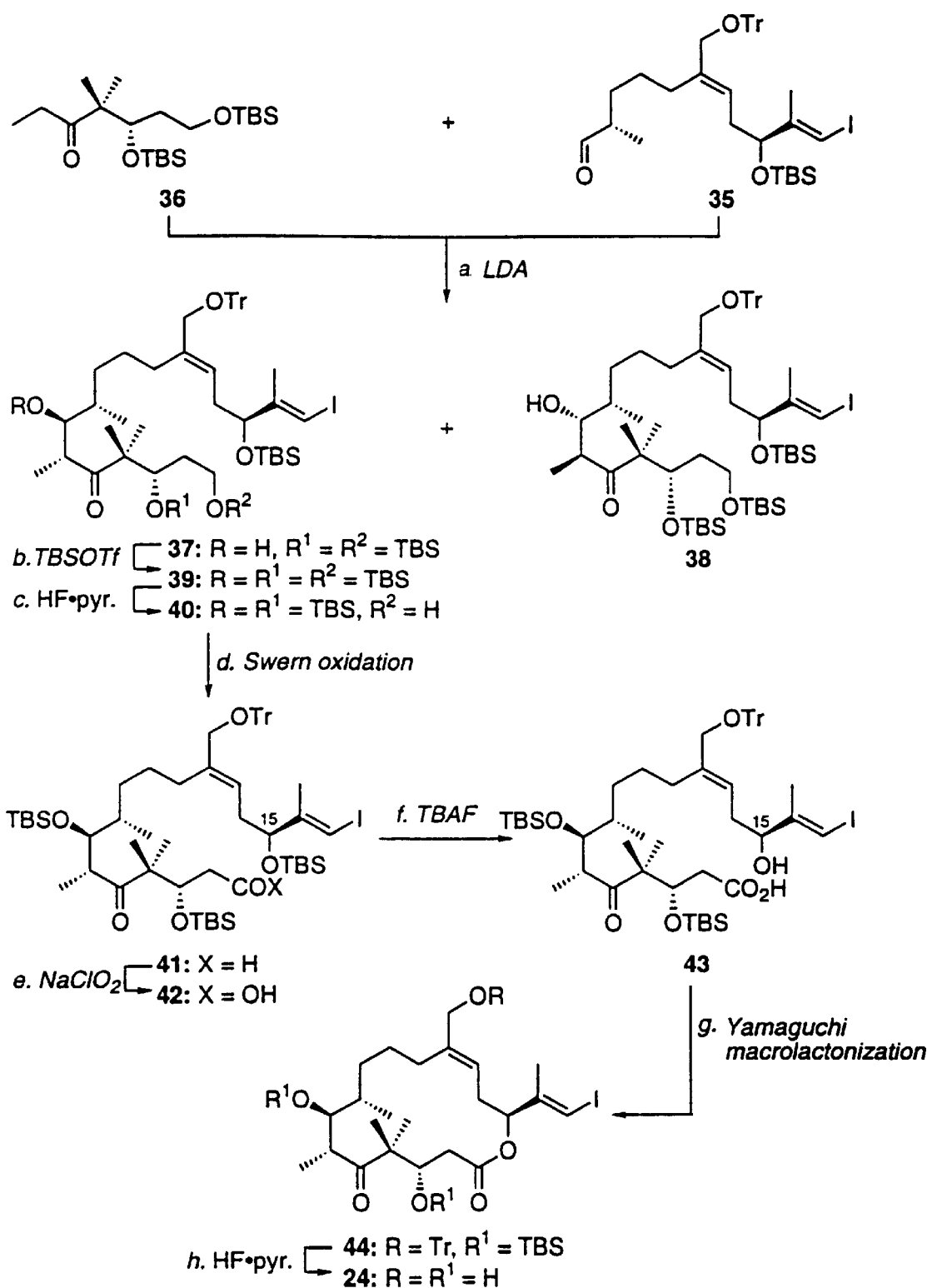
FIG. 8 illustrates the stereoselective synthesis of vinyl iodide 24. Reagents and conditions: (a) 1.45 equiv of LDA, THF, −78° C., then 1.4 equiv of 36 in THF, −78° C., 1.5 h then; −40° C., 0.5 h; then 1.0 equiv of 35 in THF at −78° C. (66% combined yield, ca. 1.5:1 ratio of 37:38); (b) 3.2 equiv of TBSOTf, 4.3 equiv of 2,6-lutidine, CH$_2$Cl$_2$, −20→0° C., 2.5 h, 90%; (c) HF.pyr. in pyridine, THF, 0° C., 3 h, 84%; (d) 2.0 equiv of (COCl)$_2$, 4.0 equiv of DMSO, 6.0 equiv of Et$_3$N, CH$_2$Cl$_2$, −78→0° C., 1.5 h, 98%; (e) 5.0 equiv of NaClO$_2$, 75 equiv of 2-methyl-2-butene, 2.5 equiv of NaH$_2$PO$_4$, t-BuOH:H$_2$O (4.5:1), 25° C., 40 min, 100%; (f) 6.0 equiv of TBAF, THF, 0→25° C., 19 h, 95%; (g) 6.0 equiv of Et$_3$N, 2.4 equiv of 2,4,6-trichlorobenzoylchloride, THF, 0° C., 1.5 h; then add to a solution of 2.2 equiv of 4-DMAP in toluene (0.005 M based on 43), 75° C., 2.5 h, 84%; (h) 25% v/v HF.pyr. in THF 0→25° C., 15 h, 86%. TBAF=tetra n-butylammonium fluoride.

The transformation of aldehyde 35 into the desired epothilone macrocyclic core 24 is summarized in FIG. 8. Aldol reaction of ketone 36, previously used in our synthesis of epothilone B and related analogs (LDA, THF, −78 to −40° C.) and aldehyde 35, afforded alcohols 37 and 38 in 66% overall yield, with modest selectivity for the desired 6R,7S diastereoisomer (37). Separation and silylation (TBSOTf, 2,6-lutidine, CH$_2$Cl$_2$, −20 to 0° C.) of the correct aldol product 37 provided tris-silyl ether 39 in 90% yield. Selective removal of the primary silyl ether protecting group (HFpyr. in pyridine/THF, 0° C.) afforded alcohol 40 (84%), which was oxidized to acid 42 via aldehyde 41 by a two-step procedure [Swern; then NaClO$_2$, 2-methyl-2-butene, NaH$_2$PO$_4$, t-BuOH/H$_2$O, 25° C., 98% for two steps). Removal of the C15 silicon protecting group (TBAF, THF, 0 to 25° C.) provided hydroxy-acid 43 (95%) and laid the foundation for the macrolactonization process. This key step was achieved under Yamaguchi conditions (2,4,6-trichlorobenzoylchloride, Et$_3$N, THF; then add to a solution of 4-DMAP in toluene, 0.005M, 75° C.; Inanaga et al. Bull. Chem. Soc. Jpn. 1979, 52, 1989; Mulzer et al. Synthesis 1992, 215–228; Nicolaou et al. Chem. Eur. J. 1996, 2, 847–868) to give the protected epothilone core 44 in 84% yield. Global deprotection (HFpyr., THF, 0 to 25° C., 86%) completed the synthesis of the key vinyl iodide intermediate 24.

With intermediate 24 in hand, the Stille coupling protocol could then be employed to attach the desired heterocyclic moiety. The mild procedure B, employing PdCl$_2$(MeCN)$_2$ was thought to be the most practical and efficient process and was utilized in the preparation of C26 hydroxy epothilones 45–48 (FIG. 9) from the vinyl iodide 24 and the appropriate stannanes 8 (see FIGS. 4 and 5). Unfortunately, these conditions were not suitable for the coupling of 24 and vinyl stannane 8q (see FIG. 5). Recourse to the alternative procedure A provided access to the desired epothilone 49, albeit, in poor yield.

Figure 9:
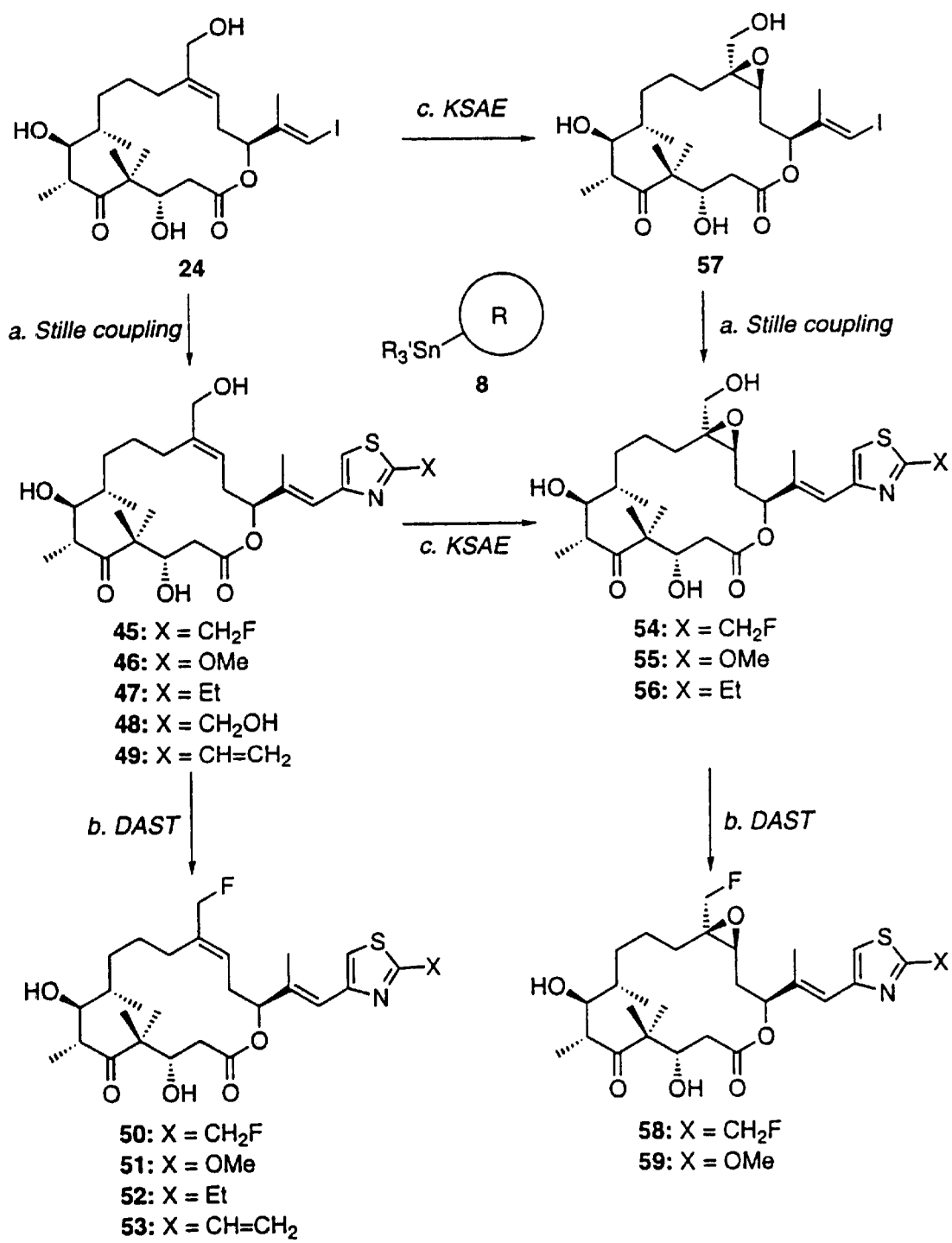
FIG. 9 illustrate the synthesis of epothilone analogs 54–56 and 58, 59 and desoxyepothilones 45–49 and 50–53. Reagents and conditions: (a) procedure A: 1.7 equiv of 8, 13 mol % Pd(PPh$_3$)$_4$, toluene, 100° C., 2 h, 15%; procedure B: 1.5–2.0 equiv of 8, 10–20 mol % Pd(MeCN)$_2$Cl$_2$, DMF, 25° C., 15–33 h, 41–56%; (b) 1.05–1.4 equiv of DAST, CH$_2$Cl$_2$, −78° C., 10 min, 26–58%; (c) 0.5 equiv (+)-DET, 0.5 equiv Ti(i-PrO)$_4$, 2.2 equiv of t-BuOOH, −40° C., CH$_2$Cl$_2$, 4 Å molecular sieves, 1–2 h, 52–89%. DET=diethyl tartrate.

The presence of the C26 hydroxy functionality provided a convenient handle for further elaboration of the epothilone products. For example, the C26 alcohols 45–47 and 49 were treated with DAST (CH$_2$Cl$_2$, −78° C.) to furnish fluorinated epothilone analogs 50–53 in moderate yields as shown in FIG. 9. Alternatively, asymmetric epoxidation of substrates 45 and 46 under Katsuki-Sharpless conditions [(+)-DET, Ti(i-PrO)$_4$, t-BuOOH, 4 Å molecular sieves, CH$_2$Cl$_2$, −40° C.; Katsuki, T.; Sharpless, K. B. J. Am. Chem. Soc. 1980, 102, 5976–5978] afforded epothilones 54 and 55, respectively. Subsequent treatment with DAST (CH$_2$Cl$_2$, −78° C.) provided additional analogs 58 and 59, again in moderate yield. At this juncture, a more efficient approach to epoxides such as 54 and 55 was envisaged in which asymmetric epoxidation of vinyl iodide 24 could be achieved to give a common intermediate, which could then serve as a substrate for the Stille coupling. Despite initial reservations concerning the compatibility of the epoxide functionality with the Stille conditions, the epoxide 57 required for this approach was prepared from olefin 24 in 81% yield as described for the synthesis of 45 and 46. To our pleasant surprise, application of the standard coupling procedure B, using stannane 8r, resulted in the successful preparation of epothilone analog 56 (73% yield based on 70% conversion).

Figure 10:
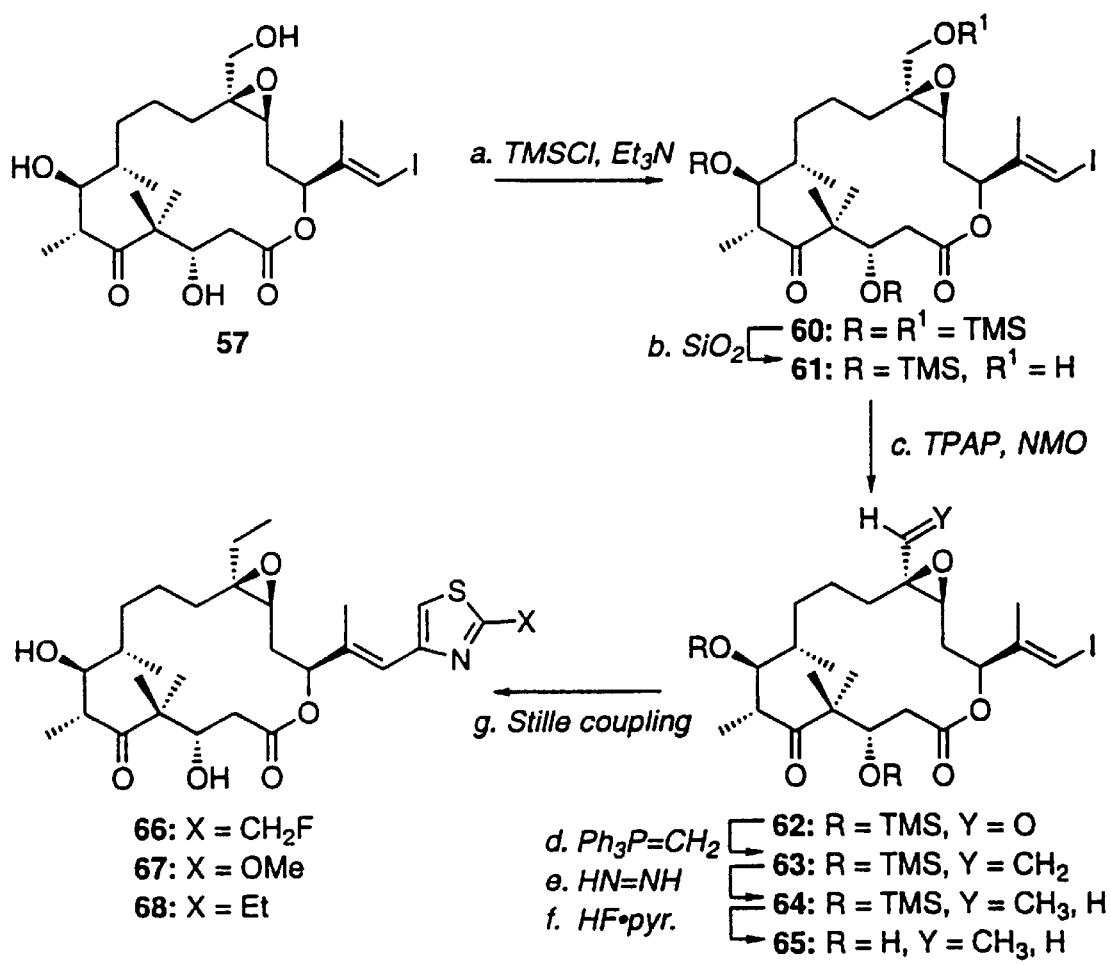
FIG. 10 illustrates the synthesis of C26-substituted epothilones 66–68. Reagents and conditions: (a) 15 equiv of Et$_3$N, 8.0 equiv TMSCl, DMF, 25° C., 12 h; (b) silica gel, CH2Cl2, 25° C., 12 h, 98% for two steps; (c) 3.0 equiv of NMO, 10 mol % TPAP, CH2Cl2, 25° C., 40 min, 90%; (d) 9.7 equiv of Ph$_3$P+CH$_3$Br— (mixture with NaNH2), THF, −5° C., 65% (e) 25 equiv of H2NNH2, 16 equiv of H2O2, EtOH, 0° C., 3 h; (f) HF.pyr. pyridine in THF, 0→25° C., 2 h, 75% for two steps; (g) 1.7–2.3 equiv of 8, 0.2–0.3 mol % Pd(MeCN)2Cl2, DMF, 25° C., 15–23 h, 52–79%. TPAP=tetrapropylammonium perrunthenate.

The success of the Stille coupling strategy on substrates possessing an epoxide moiety indicated that epothilones 66–68 could be accessed from a common intermediate 65 as outlined in FIG. 10. Preparation of the desired template (65) was achieved by a five-step sequence, which started with global protection of triol 57 (TMSCl, Et$_3$N, DMF, 25° C.). Selective deprotection, using silica gel (CH$_2$Cl$_2$, 25° C., 98% for two steps), revealed the C26 primary hydroxyl functionality which was then oxidized (TPAP, NMO, 4 Å molecular sieves, CH$_2$Cl$_2$, 25° C.) to furnish aldehyde 62 in 90% yield. Methylenation using methyl triphenylphosphonium bromide (Schlosser's "instant ylid" mix, THF, −5° C.; Schlosser, M.; Schaub, B. Chimia 1982, 36, 3965) furnished olefin 63 (65%) which underwent reduction with in situ generated diimide (H$_2$NNH$_2$, H$_2$O$_2$, EtOH, 0° C.) to give intermediate 64. Deprotection of the remaining silyl ethers (HFpyr. in pyridine/THF, 0° C.) afforded the desired vinyl iodide 65 in 75% yield for two steps. The Stille coupling procedure B described above was then used to access epothilones 66–68 in moderate yields (FIG. 10).

The chemistry described in this example relies on a Stille coupling approach to construct a series of epothilone analogs with diversity at the side-chain or at both the side-chain and C26 site from a common macrocyclic intermediate.

EXAMPLE 2

Synthesis and Biological Properties of C12,13-Cylopropyl-Epothilone A and Related Epothilones: Biological Evalation of Epothilone Candidates In this example, we disclose the biological properties of a series of new epothilone analogs, whose synthesis is described elsewhere (Nicolaou et al. *Angew. Chem. Int. Ed. Engl.*, 37, 84–87). In addition, we describe the chemical synthesis of the C12,13-cyclopropyl analog of epothilone A and its C12,13-trans-isomer and their biological evaluation in tubulin polymerization and certain cytotoxicity assays. The chemical synthesis of the C12,13-cyclopropyl analog of epothilone A and its C12,13-trans-diastereoisomer has been accomplished. These and several other epothilone analogs have been screened for their ability to induce tubulin polymerization and death of a number of tumor cells. Several interesting structure-activity trends within this family of compounds were identified.

The results of the biological tests conducted in this study have demonstrated that, while a number of positions on the epothilone skeleton are amenable to modification without significant loss of biological activity, the replacement of the epoxide moiety of epothilone A with a cyclopropyl group leads to total loss of activity.

Figure 11:
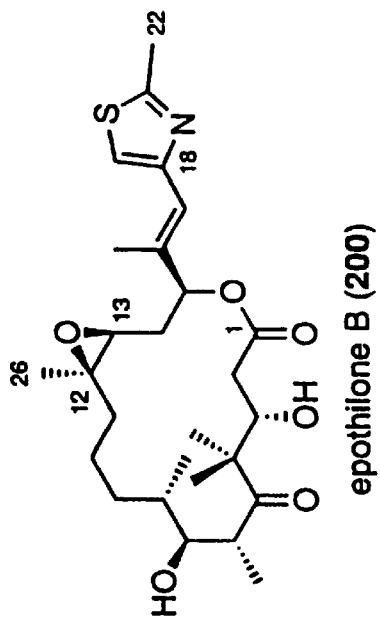
FIG. 11 illustrates structures of epothilones A (1), B (200), E (1a) and cylopropyl analogs 300 and 400.
Figure 11:
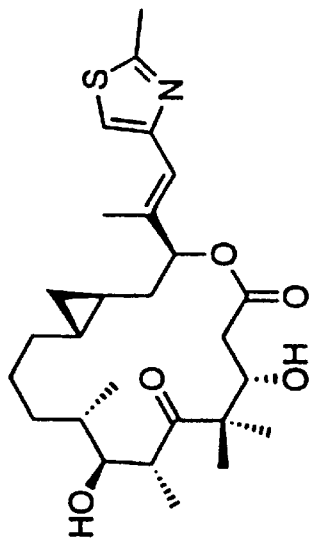
Figure 11:
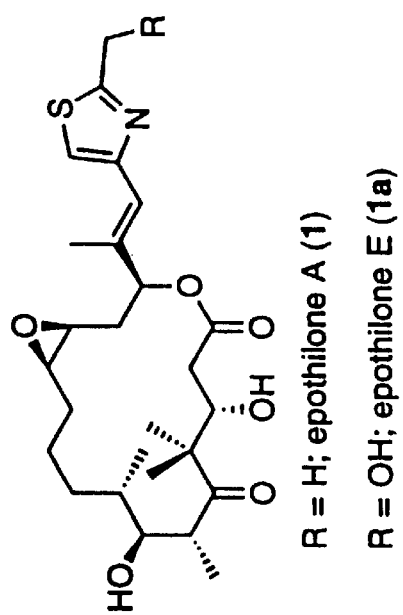
Figure 11:
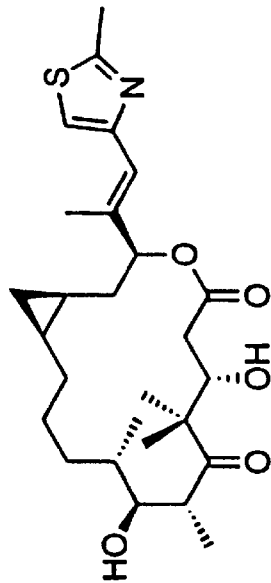

The synthesis of the cyclopropane analogs 300 and 400 (FIG. 11) required some rather unusual chemistry. A wide range of methods have been described in the literature for the transformation of allylic alcohols to the corresponding cyclopropyl systems, several in either diastereo- or enantioselective fashion (Kasdorf et al. *Chemtracts-Organic Chemistry*, 533–535). However, initial efforts employing either these methods or the classic Simmons-Smith procedure proved disappointing when attempted on the previously prepared (Nicolaou (1997) et al. *Chem. Commun.* 2343–2344). macrocyclic substrate 500 (FIG. 12).

In the light of these discouraging results, a new approach was devised. Previous studies (Isono et al. (1996) *J. Org. Chem.*, 61, 7867–7872; Hanessian et al. (1996) *Tetrahedron Lett.*, 37, 8971–8974) have shown that cyclopropanes may be prepared from γ-hydroxypropyl stannanes by elimination of the hydroxyl and stannyl moieties. We therefore, envisaged that if we could prepare the g-hydroxypropyl stannane systems 1000 and 1100 (FIG. 12) then alcohol derivatization and subsequent acid-catalyzed formation of a carbocation could trigger spontaneous cyclization to the required cyclopropanes 1200 and 1300 respectively (FIG. 12). It was further anticipated that the required stannanes could be prepared from allylic alcohol 900, which in turn would be derived from the macrocylic epoxide system 600 (FIG. 12).

Figure 12:
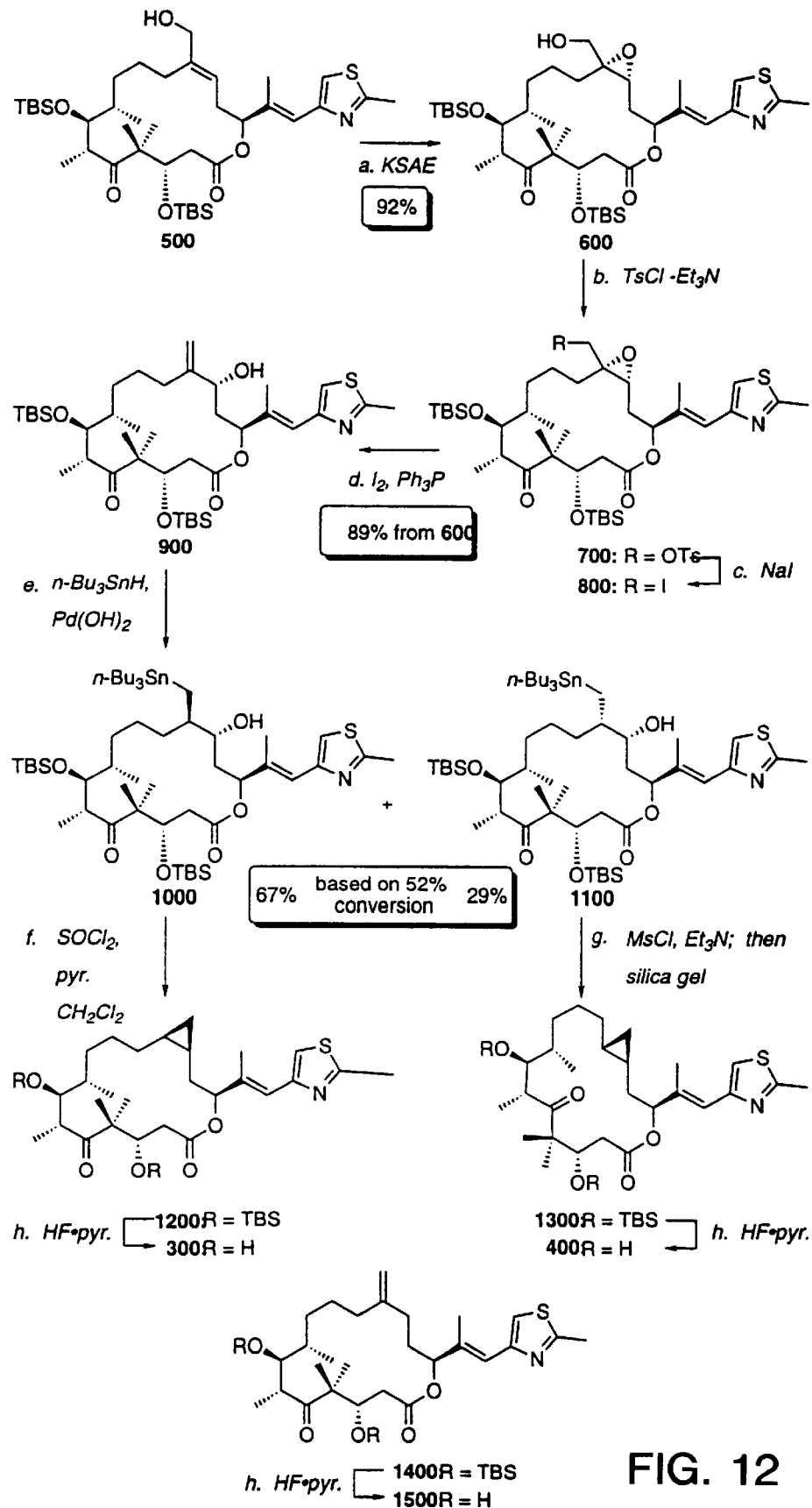
FIG. 12 illustrates the stereoselective synthesis of C12, 13-cyclopropyl-epothilone A (300) and C12,13-trans-cyclopropyl-epothilone A (400). Reagents and conditions: (a) 0.5 equiv. of (−)-diethyl-D-tartrate, 0.4 equiv. of Ti(i-OPr)$_4$, 2.0 equiv. of t-BuOOH, CH$_2$Cl$_2$, −30° C., 2 h, 92%; (b) 1.5 equiv. of tosyl chloride, 3.0 equiv. of Et$_3$N, 0.1 equiv. of 4-DMAP, CH$_2$Cl$_2$, 0→25° C.; (c) 5.0 equiv. of NaI, acetone, reflux, 2 h; (d) 0.1 equiv. of I$_2$, 1.5 equiv. of Ph$_3$P, acetone/DMF, 89% from 600; (e) 1.5 equiv. of n-Bu$_3$SnH, 0.1 equiv. of Pd(OH)$_2$, THF, 67% of 1000, 29% of 1100 based on 52% conversion; (f) 4.0 equiv of SOCl$_2$, 8.0 equiv. of pyridine, CH2Cl2, −78→25° C., 5 h; (g) 2.1 equiv. of mesyl chloride, 4.2 equiv. of Et$_3$N, CH$_2$Cl$_2$, 10 min, 89%; (h) 30% HF.pyr. (by volume) in THF, 0→25° C., 24 h, 20% of 300 (over 2 steps), 90% of 400, 62% of 1500 (over 2 steps). 4-DMAP=4-dimethylaminopyridine; DMF=N,N-dimethylformamide; THF=tetrahydrofuran.
Figure 15:
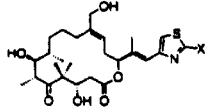
FIG. 15 illustrates biological activities of epothilones 4700–6300.
Figure 15:
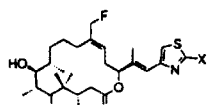
Figure 15:
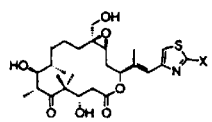
Figure 15:
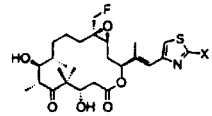
Figure 15:
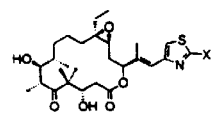

Thus, as shown in FIG. 12, subjecting allylic alcohol 500 (Nicolaou et al. (1997) *Chem. Commun.* 2343–2344) to Katsuki-Sharpless epoxidation conditions (Katsuki et al. *J. Am. Chem. Soc.*, 102, 5974–5976) provided epoxy alcohol 600 in 92% yield and as a single diastereoisomer (as judged by $^1$H NMR analysis). Tosylation of the primary alcohol also proceeded smoothly to afford tosylate 700. Subsequent treatment of 700 with sodium iodide in acetone gave the iodide 800 which, upon in situ treatment with triphenylphosphine and a catalytic amount of iodine, rapidly rearranged to allylic alcohol 900 (89% over three steps). The latter compound (900) was then exposed to tri-n-butyltin hydride in the presence of catalytic amounts of Pd(OH)$_2$ to afford the stannanes 1000 and 1100 (96% yield based on ca. 52% conversion) albeit, with modest diastereoselectivity (1000:1100; ca. 2:1). It was expected that, while elaboration of the C12-(R)-diastereoisomer 1000 would lead to the cis-cyclopropane 1200, the isomeric stannane 1100 could permit access to the equally interesting C12,13-trans-cyclopropane system 1300. Thus, treatment of 1000 with thionyl chloride and pyridine in dichloromethane at −78° C., followed by warming to room temperature over five hours, promoted the required elimination, leading to an inseparable mixture of 1200 and elimination product 1400. Desilylation (HF.pyr./THF) then allowed separation of the two components, providing C12,13-cis-cyclopropyl-epothilone A (300) (20% yield for two steps) and elimination product 1500 (62% yield for two steps)—FIG. 12.

In an analogous fashion, stannane 1100 was efficiently converted to cyclopropane system 400. Thus, following mesylation of the secondary hydroxyl group in 1100, exposure to silica gel facilitated ring closure, generating 1300 in excellent yield (89%). Finally, desilylation as before (HF.pyr./THF) afforded C12,13-trans-cyclopropyl-epqthilone A (400) in 90% yield. In both cases (300 and 400) the stereochemistry of the cyclopropane moiety was established by detailed 1H NMR experiments (1H-1H-COSY and NOESY).

The tubulin assembly and cytotoxicity data against certain tumor cell lines of cyclopropyl analogs 300 and 400, together with those of a number of other epothilone analogs recently prepared in these laboratories (Nicolaou et al. (1998) *Angew. Chem. Int. Ed. Engl.*, 37, 84–87) are shown in FIGS. 13–14. Examination of entries 1 and 2 clearly shows that replacement of the epoxide moiety with a cyclopropane system has a profound effect on both the tubulin polymerization and cytotoxic properties of the molecules. In order to more fully comprehend this drastic reduction in potency, we resorted to computational chemistry techniques to examine the conformations of 300 as compared to the parent epothilone A (1). We suspected that the partial sp2 character of the "banana bonds" of the cyclopropyl ring was possibly leading to distortion of the normal conformation of the epothilone framework, thereby preventing the molecule from adopting the required shape for binding to tubulin.

As shown in FIGS. 13–14, the substitution of an epoxide for a cylopropane moiety does indeed cause rather drastic changes to the minimum-energy conformation of epothilone A (1). The significant differences in the 1H NMR spectra of compounds 1 and 300 were also in support of the drastic conformational changes imposed on the epothilone A skeleton by the cyclopropane ring. Similarly, the C12,13-trans-cyclopropyl-epothilone analog 400 was found to be devoid of any tubulin polymerization and cytotoxicity properties as compared to its epoxide counterpart (1600) and epothilone A (1) itself (see FIG. 13, entries 1–4).

A number of additional trends are apparent from examination of the remaining data in FIG. 13. Although analogs without the epoxide moiety showed tubulin binding activity, for the most part they displayed very low levels of cytotoxic activity against the tumor cell lines examined. The trends discussed below, therefore, are based on levels of tubulin polymerization. As expected, epothilone B type analogs (entries 36–52) generally exhibited higher levels of activity than those of epothilone A (1, entry 1) and related analogs (entries 5–35). In comparing non-epoxidized substrates (entries 6–35), the C12,13-cis systems generally showed higher levels of tubulin polymerization than the corresponding C12,13-trans systems (compare entries 9–13 with 24–28).

Some more specific trends also became evident on comparing the C12,13-cis-olefins (entries 6–20). The presence and position of the nitrogen atom in the side chain heterocycle seems to be important. Compound 2600 (entry 15), in which the nitrogen atom is in its normal position adjacent to C18, but the sulfur of the thiazole has been relocated, still displayed good activity. However, compound 2500 (entry 14) where the nitrogen has been moved, was inactive. These trends were mirrored in the cases of the C12,13-trans-olefins (entries 29 and 30). A similar effect can be seen with the pyridine analogs 3000 and 4500 (entries 19 and 34). Previously synthesized pyridine-containing analogs in which the nitrogen atom was adjacent to C18 displayed good levels of activity (Nicolaou (1997) et al. *Angew. Chem. Int. Ed. Engl.*, 36, 2097–2102), whereas 3000 and 4500 showed low levels of tubulin polymerization. Clearly, altering the position of the nitrogen by one atom, has severe implications on activity.

Entries 16–17 and 31–32, where the thiazole of the epothilones had been replaced by either a furan or thiophene system, demonstrate that complete removal of the nitrogen leads to a considerable loss of tubulin polymerization activity. Substitution of the five-membered heterocycle with a six-membered carbocyclic moiety (entries 18 and 33), resulted in analogs with low activity. As can be seen from entries 20 and 35, removal of the heterocycle altogether resulted in essentially complete loss of activity.

Modification at C22 (entries 6–13) seems well tolerated, provided the substituent is not too sterically demanding. For example, hydroxymethylene (1700), fluoromethylene (1900) and thiomethylether (2200) compounds showed reasonable activity, whereas the larger acetate (1800), ethoxythiazole (2100), long-chain acetate (2300) and piperidine (2400) derivatives, were somewhat less active. A similar trend was seen in the C12,13-trans systems (entries 21–28). Alteration at C26 (entries 36–52) seemed to be fairly well tolerated with high levels of activity being displayed by the fluoromethylene-olefins 5200–5500, fluoromethylene-epoxides 5900 and 6000, and the ethyl-epoxides 6100–6300. However, the C26- hydroxy olefins 4600–5100 and C26-hydroxy epoxides 5600–5800 were somewhat less active.

The success of taxol as a therapeutic agent epitomizes the value of tubulin-polymerization-microtubule stabilizing agents in the fight against cancer. The similar mode of action and improved potency of the epothilones, particularly against taxol-resistant tumor cell lines, has made them of particular importance as potential anti-cancer drugs, especially in cases where taxol fails. A fuller understanding of the structural requirements of the epothilones for biological activity should facilitate their further development as potential anticancer agents.

In this study, the biological activities of a structurally diverse set of modified epothilones have been investigated and several useful trends noted. The biological action of the epothilones seems particularly sensitive to the location of basic heteroatoms in the side chain, and to the relative steric bulk of side-chain substituents. Furthermore, additional alterations at C26 may be tolerated resulting in analogs possessing varying degrees of activity. An important conclusion from this work was the finding that substitution of the epoxide moiety of epothilone A (1) by a cyclopropyl group leads to total loss of activity, presumably due to drastic conformational changes imposed by this substitution.

EXAMPLE 3

Figure 16:
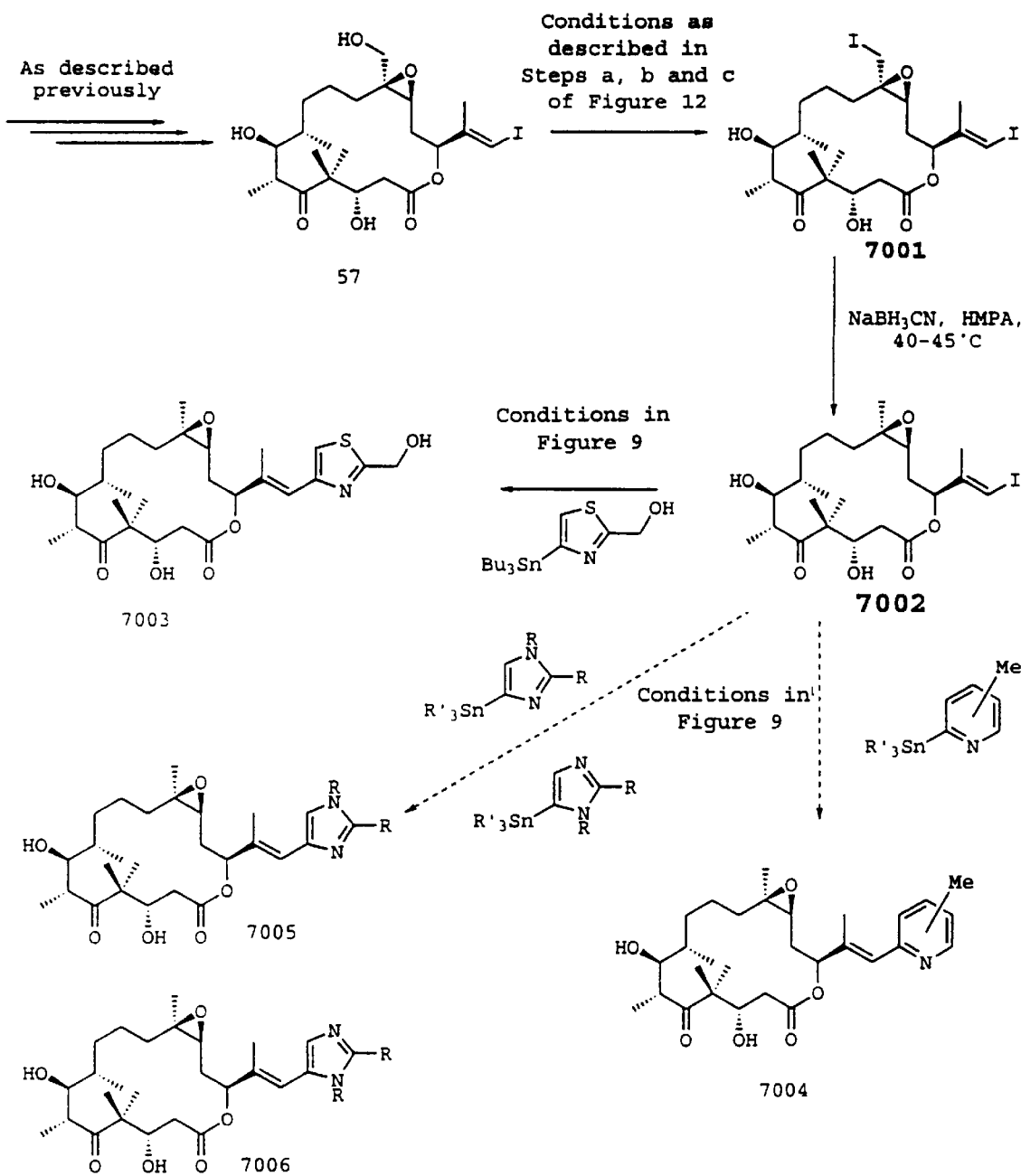
FIG. 16 illustrates the general route to synthesis various side-chain modified epothilone B analogs having pyridine and imidazole modifications. Some of the conditions in the figure are published as follows: Nicolaou et al. *Tetrahedron*, 1998, 54, 7127–7166.
Figure 19:
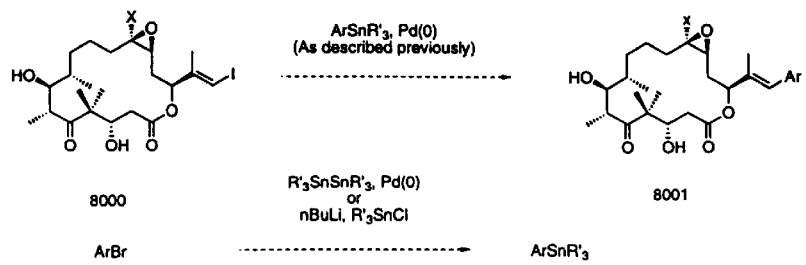
FIG. 19 illustrates various side chain modified epothilone analogs using indicated aryl stannanes (ArSnR'$_3$) from either the metathesis or macrocyclization approach wherein R' is from the group butyl or methyl; the stannanes are synthesized using standard conditions known in the art; X can be a radical selected from the group consisting of hydrogen, methyl, —CHO, —COOH, —CO$_2$Me, —CO$_2$(tert-butyl), —CO$_2$(iso-propyl), —CO$_2$(phenyl), —CO$_2$(benzyl), —CONH(furfuryl), —CO$_2$(N-Benzo-(2R,3S)-3-phenylisoserine), —CONH(methyl)$_2$, —COHN(ethyl)$_2$, —CONH(benzyl), —CH=CH$_2$, —C≡CH, and —CH$_2$R$_y$ wherein R$_{yy}$ is a radical selected from the group consisting of —OH, —O-Trityl, —O—(C$_1$–C$_6$ alkyl), -(C$_1$–C$_6$ alkyl), —O-benzyl, —O-allyl, —O—COCH$_3$, —O—COCH$_2$Cl, —O—COCH$_2$CH$_3$, —O—COCF$_3$, —O—COCH(CH$_3$)$_2$, —O—COC(CH$_3$)$_3$, —O—CO(cyclopropane), —OCO (cyclohexane), —O—COCH=CH$_2$, —O—CO-Phenyl, —O-(2-furoyl), —O-(N-benzo-(2R,3S)-3-phenylisoserine), —O-cinnamoyl, —O-(acetyl-phenyl), —O-(2-thiophenesulfonyl), —S—($C_1$-$C_6$ alkyl), —SH, —S-Phenyl, —S-Benzyl, —S-furfuryl, —$NH_2$, —$N_3$, —$NHCOCH_3$, —$NHCOCH_2Cl$, —$NHCOCH_2CH_3$, —$NHCOCF_3$, —$NHCOCH(CH_3)_2$, —$NHCOC(CH_3)_3$, —NHCO(cyclopropane), —NHCO(cyclohexane), —$NHCOCH=CH_2$, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, I, and —$CH_2CO_2H$ other related variations not included here can also be employed.
Figure 19:
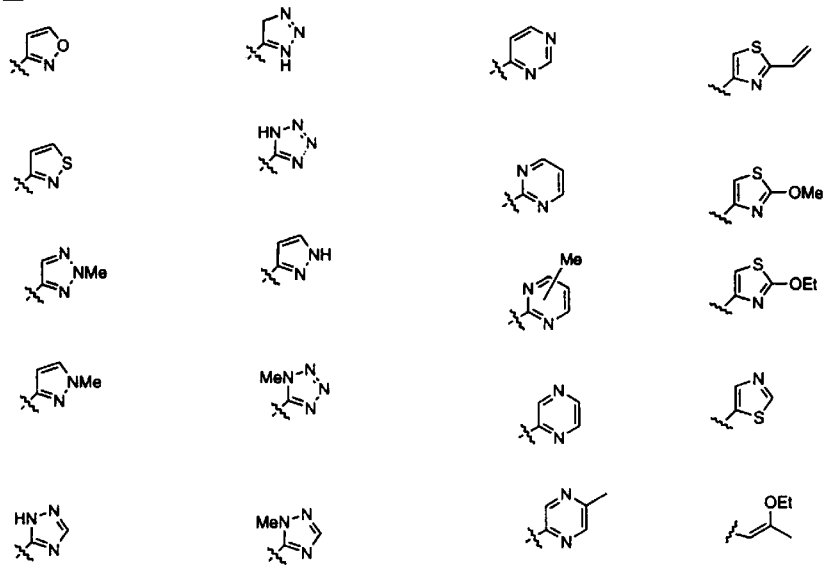
Figure 19:
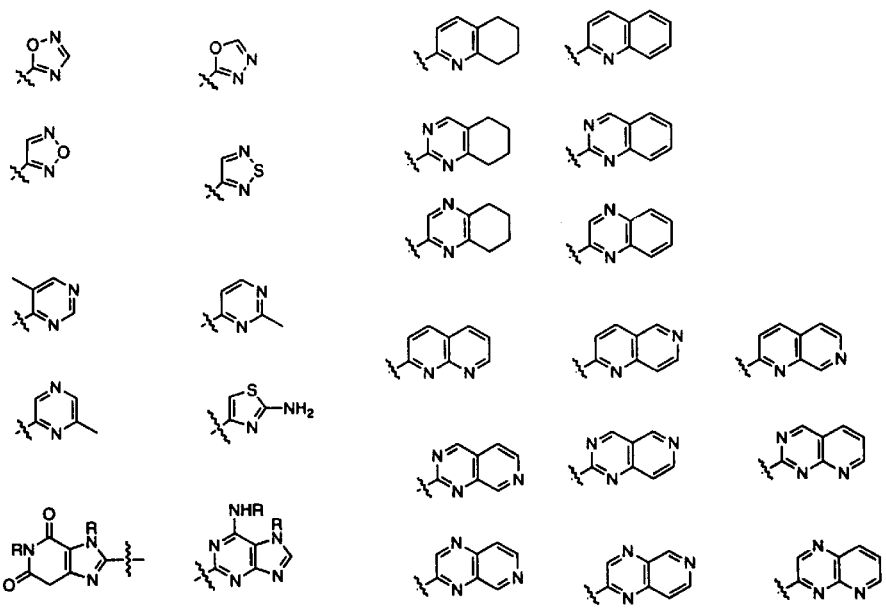

Use of Additional Stannanes to Synthesize Side Chain Modified Epothilone Analogs as Illustrated in FIGS. 16 and 19

Use of the Stille coupling procedure to prepare a number of side chain modified epothilone analogs from the common precursors 57, and 800 is described in FIGS. 16 and 19. Synthesis of vinyl iodide 7002 was achieved from the previously reported C26-hydroxy compound and involved conversion to diiodide 7001 and subsequent reduction using NaBH$_3$CN. Coupling to the epothilone E side chain has been achieved and the coupling of a number of pyridines and imidazoles is accomplished via coupling of numerous alternative side chains with the aromatic stannanes as shown in FIG. 16 and 19 using the standard methods outlined herein.

EXAMPLE 4

Figure 17:
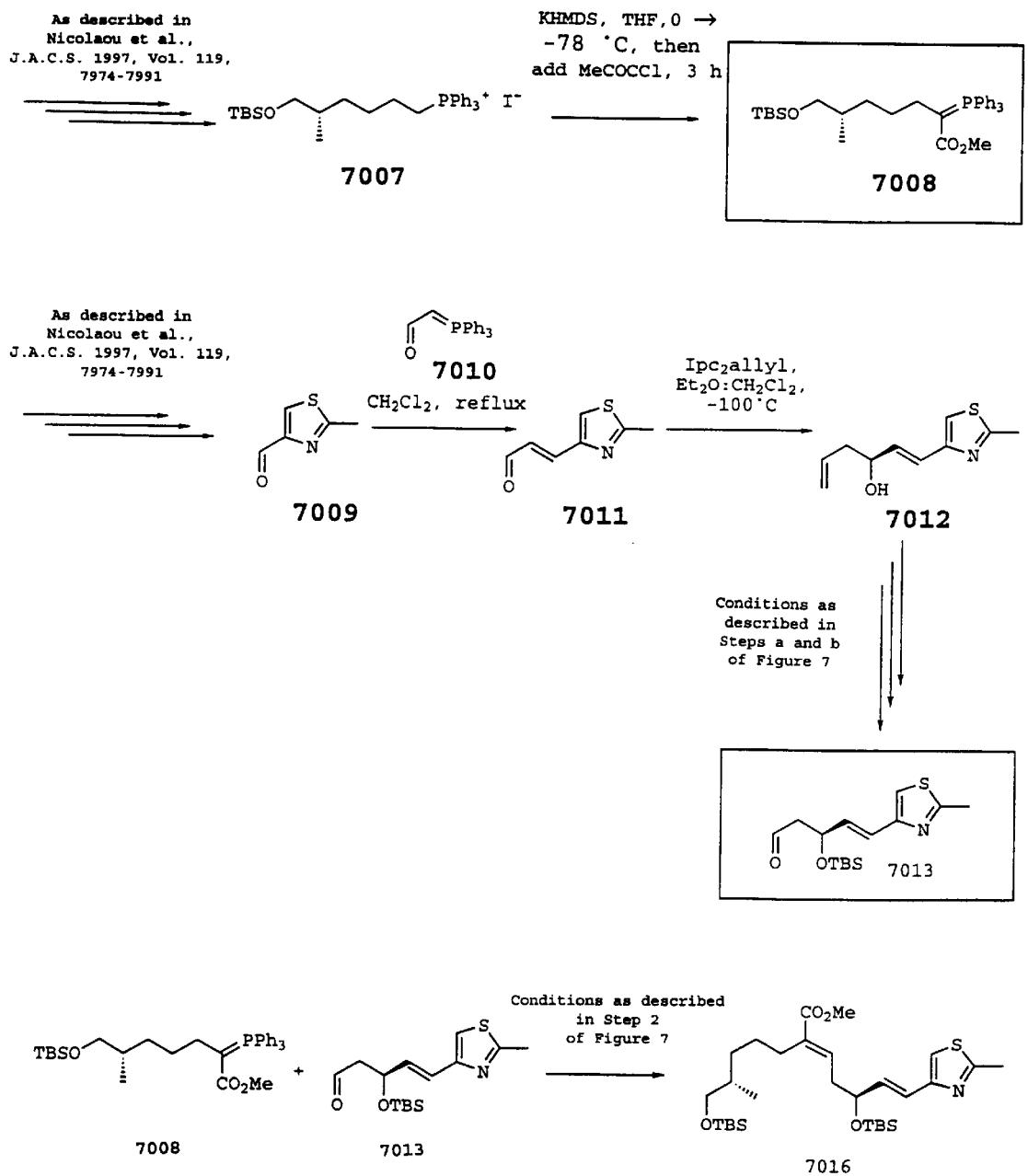
FIG. 17 illustrates the synthesis of C-17 desmethyl-epothilone B advanced intermediates 7008, 7012, and 7016, based upon intermediates described in Nicolaou et al. *J. Am. Chem. Soc.*, 1997, 119, 7974–7991.
Figure 18:
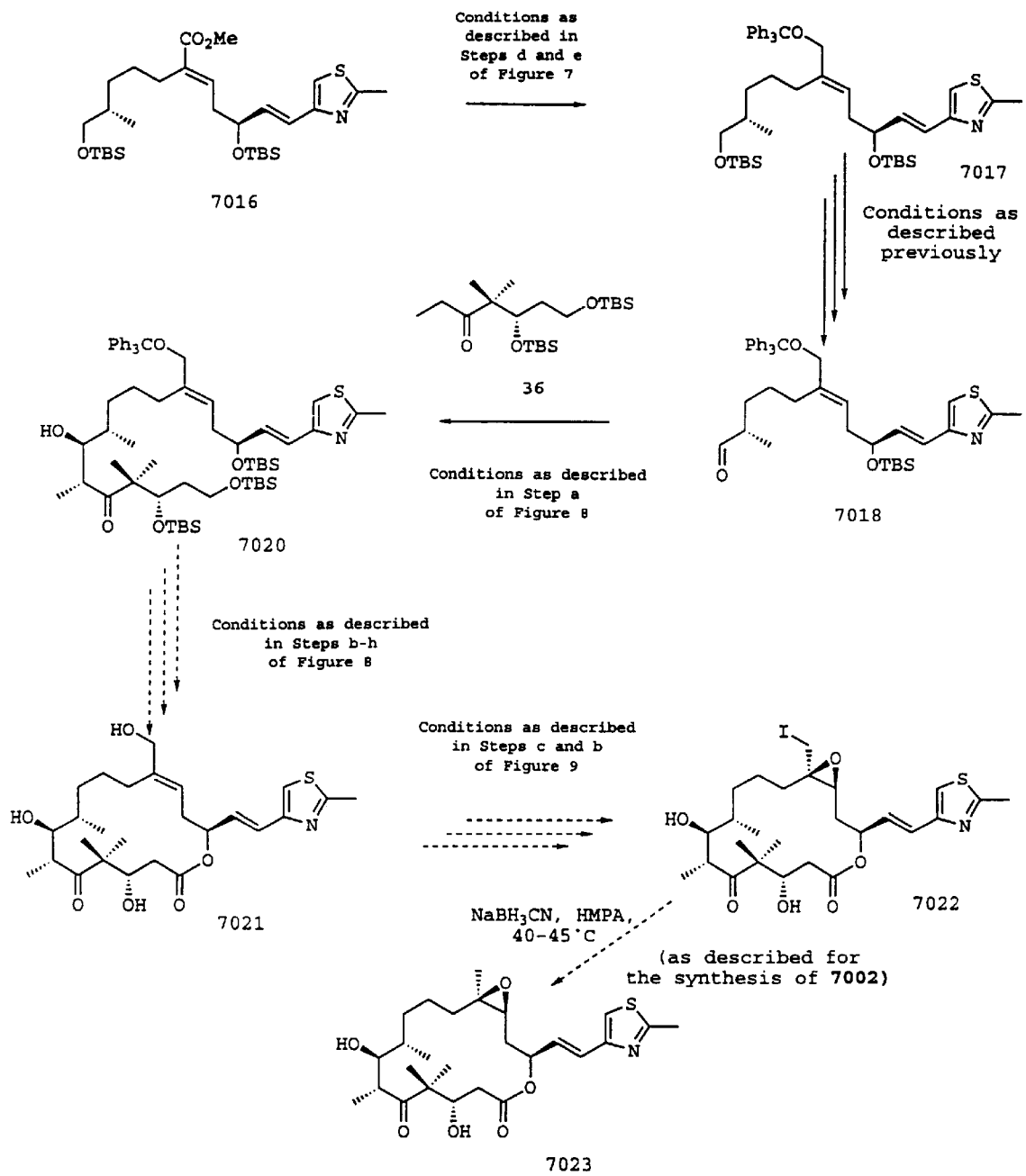
FIG. 18 illustrates the synthesis of C-17 desmethyl-epothilone B wherein some of the intermediates are synthesized according to the procedures outlined in Nicolaou et al. *J. Am. Chem. Soc.*, 1997, 119, 7974–7991; Nicolaou et al. *Tetrahedron*, 1998, 54, 7127–7166; Nicolaou et al. *Angew. Chem. Int. Ed.*, 1998, 37, 81–84.

Synthesis of C-17 Desmethylepothilone B as Illustrated in FIGS. 17–18

The synthesis of C17 desmethylepothilone B is described in FIGS. 17–18 using standard methods outlined herein. The synthetic route utilizes a macrolactonization reaction to prepare the core of the molecule and the strategy closely parallels that used in previous syntheses of epothilones A and B and related analogs. A new feature of the route is the removal of the C26 hydroxy substituent which is itself used to control the C12,13 Sharpless epoxidation reaction. Removal of this alcohol functionality is achieved by its conversion to the iodide and subsequent reduction using NaBH$_3$CN. The target compound is of interest since without the C17 methyl substituent the conformation of the thiazole side-chain will be altered and it is anticipated that this will place the important basic nitrogen of the thiazole in a preferential orientation (FIGS. 17–18).

Representative Procedures for Stannane Synthesis these Procedures are General and can be Used to Synthesize all Stannanes as shown in FIG. 19: All Reagents are Commercially Available from Aldrich, Sigma, Fluka or are Well Known in the Art General Procedure A: A solution of bromothiazole (1.0 equiv) in degassed toluene (0.1 M), was treated with hexamethylditin (10 equiv) and Pd(PPh$_3$)$_4$ (0.1 equiv) and the mixture was heated at 100° C. for 3 h. The reaction mixture was cooled to 25° C. and purified by flash column chromatography (silica gel; pre-treated with Et$_3$N, 50% ether in hexanes) to afford the desired stannane (93%)

General Procedure B: To a solution of bromothiazole (1.0 equiv) in ether (0.07M) at −78° C., was added n-BuLi (1.2 equiv) and the resulting mixture was stirred at −78° C. for 10 min. Tri-n-butyltin chloride (1.2 equiv) was then added, the solution stirred at −78° C. for 10 min, and then slowly warmed to 25° C. over a period of 1 h. The reaction mixture was diluted with hexane and passed through silica gel eluting with 20% EtOAc in hexanes. Flash column chromatography (silica gel; pre-treated with Et$_3$N, 5% ether in hexanes) furnished the desired stannane (85%).

Synthetic Protocals

General: All reactions were carried out under an argon atmosphere with dry, freshly distilled solvents under anhydrous conditions, unless otherwise noted. Tetrahydrofuran (THF) and diethyl ether (ether) were distilled from sodium-benzophenone, and dichloromethane ($CH_2Cl_2$), benzene (PhH), and toluene from calcium hydride. Anhydrous solvents were also obtained by passing them through commercially available activated alumina columns. Yields refer to chromatographically and spectroscopically ($^1H$ NMR) homogeneous materials, unless otherwise stated. All solutions used in workup procedures were saturated unless otherwise noted. All reagents were purchased at highest commercial quality and used without further purification unless otherwise stated.

All reactions were monitored by thin-layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography separations were carried out on 0.25, 0.50 or 1 mm E. Merck silica gel plates (60F-254). NMR spectra were recorded on Bruker DRX-600, AMX-500, AMX-400 or AC-250 instruments and calibrated using residual undeuterated solvent as an internal reference. The following abbreviations were used to explain the multiplicities: s, singlet; d, doublet; t, triplet; q, quartet; m, multiplet; band, several overlapping signals; b, broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE massspectrometer under fast atom bombardment (FAB) conditions.

Vinyl iodide 13 as illustrated in FIG. 3. Allylmagnesium bromide (183 mL, 1 M in ether, 183 mmol, 1.3 equiv) was added dropwise, over 45 min, to a solution of (−)-(Ipc)$_2$BOMe (58.0 g, 183 mmol, 1.3 equiv) in ether (800 mL) at 0° C., and the resulting pale gray slurry was allowed to warm to 25° C. over 1 h. The ether was removed under reduced pressure and pentane (800 mL) was added to the residual solid. The resulting slurry was stirred at 25° C. for 10 min and then the solids were allowed to settle over 30 min. The clear supernatant was then transferred carefully to a separate flask via cannula. This process was repeated four times (200 mL of pentane each) and the resulting solution was added dropwise, over 1 h, to a solution of aldehyde 12 at −100° C. After 1 h at −100° C., MeOH (10 mL) was added and the mixture was allowed to warm to ambient temperature over 40 min. Saturated $NaHCO_3$ (125 mL) and $H_2O_2$ (50 mL of a 50% aqueous solution) were then added and the mixture was left to warm to 25° C. over 12 h. The layers were separated and the aqueous phase was extracted with EtOAc (3×500 mL). The combined organic phases were washed with saturated aqueous $NH_4Cl$ (500 mL), dried ($Na_2SO_4$) and concentrated under reduced pressure. Flash column chromatography (silica gel, 25% ether in hexanes) furnished vinyl iodide 13 (26.7 g, 80% over two steps). $R_f$=0.31 (silica gel, 20% ether in hexanes); $[\alpha]^{22}D$ −18.4 (c 9.0, $CHCl_3$); IR (film) $n_{max}$ 3358 (br), 3077, 2977, 2914, 1642, 1619, 1433, 1379, 1279, 1048, 997, 918 cm$^{-1}$; $^1H$ NMR (500 MHz, $CDCl_3$) d 6.26 (s, 1 H, ICH=C($CH_3$)), 5.70 (dddd, J=17.0, 10.0, 7.0, 7.0 Hz, 1 H, $CH_2$=CH), 5.11 (dd, J=17.0, 1.5 Hz, 1 H, $CH_2$=CH), 5.10 (dd, J=10.0, 1.5 Hz, 1 H, $CH_2$=CH), 4.17 (dd, J=7.5, 5.5 Hz, 1 H, CHOH), 2.47 (bs, 1 H, OH), 2.33 (ddd, J=14.0, 7.0, 5.5 Hz, 1 H, $CH_2CH$=), 2.26 (ddd, J=14.0, 7.5, 7.0 Hz, 1 H, $CH_2CH$=), 1.79 (s, 3 H, $CH_3$); $^{13}C$ NMR (125.7 MHz, $CDCl_3$) d 148.9, 133.6, 118.4, 78.5, 75.3, 39.6, 20.0.

Triene 15a and its 6S,7R diastereoisomer 15b as illustrated in FIG. 3. A solution of ketoacids 14 (414 mg, 1.0 mmol, 1.0 equiv) (ca. 3:2 ratio 14a:14b), 4-(dimethylamino)pyridine (4-DMAP, 183 mg, 1.5 mmol, 1.5 equiv) and alcohol 13 (476 mg, 2.0 mmol, 2.0 equiv) in toluene (2.0 mL, 0.5 M) was cooled to 0° C. and then treated with 1,3-dicyclohexylcarbodiimide (DCC, 309 mg, 1.5 mmol, 1.5 equiv). The reaction mixture was stirred at 25° C. for 12 h, then concentrated under reduced pressure and the residue was partitioned between EtOAc (50 mL) and water (10 mL). The organic layer was separated, washed with saturated aqueous $NH_4Cl$ (5 mL) and water (5 mL) and dried ($MgSO_4$). Evaporation of the solvents followed by flash column chromatography of the residue (silica gel, 15% EtOAc in hexanes) furnished trienes 15a (318 mg, 49%) and 15b (214 mg, 33%). 15a: $R_f$=0.60 (silica gel, 18% EtOAc in hexanes); $[\alpha]^{22}D$ −16.1 (c 0.40, $CHCl_3$); IR (film) $n_{max}$ 3420, 2930, 2857, 1739, 1685, 1463, 1383, 1290, 1254, 1167, 1091, 995, 835 cm$^{-1}$; $^1H$ NMR (500 MHz, $CDCl_3$) d 6.33 (s, 1 H, ICH=C($CH_3$)), 5.86–5.78 (m, 1 H, $CH_2CH$=$CH_2$), 5.68–5.58 (m, 1 H, $CH_2CH$=$CH_2$), 5.31 (dd, J=7.0, 7.0 Hz, 1 H, CHOCO), 5.09 (dd, J=16.5, 2.0 Hz, 1 H, $CH_2CH$=$CH_2$), 5.06 (dd, J=9.5, 2.0 Hz, 1 H, $CH_2CH$=$CH_2$), 4.99 (dd, J=17.0, 2.0 Hz, 1 H, $CH_2CH$=$CH_2$), 4.92 (dd, J=10.5, 2.0 Hz, 1 H, $CH_2CH$=$CH_2$), 4.37 (dd, J=5.5, 4.0 Hz, 1 H, $(CH_3)_2CCH$(OTBS)), 3.37 (s, 1 H, CHOH), 3.30–3.26 (s, 1 H, CHOH), 3.28 (q, J=7.0 Hz, 1 H, $CH_3CH$(C=O)), 2.79 (dd, J=17.0, 5.5 Hz, 1 H, $CH_2COO$), 2.43 (dd, J=17.0, 4.0 Hz, 1 H, $CH_2COO$), 2.43–2.33 (m, 2 H), 2.11–1.98 (m, 2 H), 1.81 (s, 1 H, ICH=$CCH_3$), 1.81–1.72 (m, 1 H), 1.58–1.40 (m, 2 H), 1.37–1.27 (m, 1 H), 1.20–1.05 (m, 1 H), 1.19 (s, 3 H, C$(CH_3)_2$), 1.10 (s, 3 H, C$(CH_3)_2$), 1.03 (d, J=6.5 Hz, 3 H, $CH_3CH$(C=O)), 0.87 (s, 9 H, SiC$(CH_3)_3(CH_3)_2$), 0.83 (d, J=7.0 Hz, 3 H, $CH_3CHCH_2$), 0.10 (s, 3 H, SiC$(CH_3)_3(CH_3)_2$), 0.04 (s, 3 H, SiC$(CH_3)_3(CH_3)_2$); $^{13}C$ NMR (125.7 MHz, $CDCl_3$) d 221.8, 170.7, 144.7, 139.1, 132.4, 118.3, 114.2, 81.2, 77.0, 74.6, 73.4, 53.8, 41.3, 40.1, 37.1, 35.4, 34.2, 32.4, 26.1, 25.9, 22.0, 20.1, 19.8, 18.1, 15.3, 9.7, −4.4, −4.8; HRMS (FAB), calcd for $C_{30}H_{53}IO_5Si$ (M+Cs$^+$) 781.1761, found 781.1770. 15b: $R_f$=0.36 (silica gel, 17% EtOAc in hexanes); $[\alpha]^{22}D$ −20.4 (c 0.83, $CHCl_3$); IR (film) $n_{max}$ 3512, 3076, 2932, 2858, 1740, 1690, 1465, 1381, 1290, 1254, 1171, 1089, 986, 916, 835 cm$^{-1}$; $^1H$ NMR (500 MHz, $CDCl_3$) d 6.33 (s, 1 H, ICH=C($CH_3$)), 5.80 (dddd, J=17.0, 10.0, 6.5, 6.5 Hz, 1 H, $CH_2CH$=$CH_2$), 5.63 (dddd, J=17.0, 10.0, 7.0, 7.0 Hz, 1 H, $CH_2CH$=$CH_2$), 5.31 (dd, J=7.0, 7.0 Hz, 1 H, CHOCO), 5.11–5.06 (m, 2 H, $CH_2CH$=$CH_2$), 5.01 (dd, J=17.0, 2.0 Hz, 1 H, $CH_2CH$=$CH_2$), 4.96 (dd, J=10.0, 1.0 Hz, 1 H, $CH_2CH$=$CH_2$), 4.46 (dd, J=6.5, 4.0 Hz, 1 H, $(CH_3)_2CCH$(OTBS)), 3.41 (m, 1 H, CHOH) 3.33 (s, 1 H, OH), 3.21 (qd, J=7.0, 2.0 Hz, 1 H, $CH_3CH$(C=O)), 2.46–2.30 (m, 4 H), 2.12–1.98 (m, 2 H), 1.81 (s, 1 H, ICH=$CCH_3$), 1.60–1.33 (m, 5 H), 1.15 (s, 3 H, C$(CH_3)_2$), 1.11 (s, 3 H, C$(CH_3)_2$), 1.03 (d, J=7.0 Hz, 3 H, $CH_3CH$(C=O)), 0.99 (d, J=6.5 Hz, 3 H, $CH_3CHCH_2$) 0.86 (s, 9 H, SiC$(CH_3)_3(CH_3)_2$), 0.08 (s, 3 H, SiC$(CH_3)_3(CH_3)_2$), 0.04 (s, 3 H, SiC$(CH_3)_3(CH_3)_2$); $^{13}C$ NMR (125.7 MHz, $CDCl_3$) d 221.0, 170.8, 144.7, 138.7, 132.4, 118.3, 114.6, 81.2, 77.0, 74.8, 72.6, 53.9, 41.4, 40.1, 37.1, 35.3, 33.9, 32.1, 26.0, 25.9, 21.9, 20.1, 19.7, 18.2, 15.6, 10.7, −4.3, −4.7; HRMS (FAB), calcd for $C_{30}H_{53}IO_5Si$ (M+Cs$^+$) 781.1761, found 781.1735.

Macrolactones 16 and 17 as illustrated in FIG. 3. To a solution of triene 15a (649 mg, 1.0 mmol, 1.0 equiv) in CH$_2$Cl$_2$ (250 mL, 0.004 M) was added bis(tricyclohexylphosphine) benzylidine ruthenium dichloride (RuCl$_2$(=CHPh) (PCy$_3$)$_2$) (82 mg, 0.10 mmol, 0.1 equiv) and the reaction mixture was allowed to stir at 25° C. for 30 h. After completion of the reaction (established by TLC), the solvent was removed under reduced pressure and the crude products were purified by flash column chromatography (silica gel, 20% EtOAc in hexanes) to give cis-hydroxy lactone 16 (217 mg, 35%) and trans-hydroxy lactone 17 (186 mg, 30%). 16: R$_f$=0.47 (silica gel, 18% EtOAc in hexanes); [a]$^{22}$D −44.5 (c 0.40, CHCl$_3$); IR (thin film) n$_{max}$ 3416, 2929, 2856, 1745, 1694, 1463, 1384, 1254, 1158, 1096, 1067, 980, 828, 778 cm$^{-1}$; $^1$H NMR (500 MHz, CDCl$_3$) d 6.37 (s, 1 H, ICH=C(CH$_3$)), 5.45 (ddd, J=10.5, 10.5, 2.0 Hz, 1 H, CH=CHCH$_2$), 5.30 (ddd, J=10.5, 10.5, 4.0 Hz, 1 H, CH=CHCH$_2$), 5.08 (d, J=10.5 Hz, 1 H, CHOCO), 4.07 (dd, J=6.5, 6.5 Hz, 1 H, (CH$_3$)$_2$CCH(OTBS)), 3.94–3.90 (m, 1 H, CHOH(CHCH$_3$)), 3.03 (qd, J=6.5, 3.0 Hz, 1 H, CH$_3$CH(C=O)), 2.98 (bs, 1 H, OH), 2.77 (d, J=6.5 Hz, 1 H, CH$_2$COO), 2.76 (d, J=6.5 Hz, 1 H, CH$_2$COO), 2.69 (ddd, J=14.5, 11.0, 11.0 Hz, 1 H, =CHCH$_2$CHO), 2.33–2.24 (m, 1 H), 2.05–1.92 (m, 1 H), 1.86 (s, 3 H, ICH=CCH$_3$), 1.81–1.72 (m, 1 H), 1.68–1.58 (m, 1 H), 1.47–1.40 (m, 1 H), 1.28–1.08 (m, 2 H), 1.19 (s, 3 H, C(CH$_3$)$_2$), 1.18 (s, 3 H, C(CH$_3$)$_2$), 1.13 (d, J=6.5 Hz, 3 H, CH$_3$CH(C=O)), 1.01 (d, J=7.0 Hz, 3 H, CH$_3$CHCH$_2$), 0.82 (s, 9 H, SiC(CH$_3$)$_3$(CH$_3$)$_2$), 0.12 (s, 3 H, SiC(CH$_3$)$_3$(CH$_3$)$_2$), 0.07 (s, 3 H, SiC(CH$_3$)$_3$(CH$_3$)$_2$); $^{13}$C NMR (150.9 MHz, CDCl$_3$) d 217.6, 170.5, 145.8, 134.9, 123.3, 80.1, 77.4, 76.2, 73.2, 53.6, 43.1, 39.0, 38.8, 33.6, 31.6, 28.4, 27.9, 26.2, 24.8, 23.0, 20.6, 18.7, 16.5, 14.2, −3.5, −5.2; HRMS (FAB), calcd for C$_{28}$H$_{49}$IO$_5$Si (M+Cs$^+$) 753.1448, found 753.1458. 17: R$_f$=0.53 (silica gel, 18% EtOAc in hexanes); [a]$^{22}$D −21.0 (c 0.40, CHCl$_3$); IR (thin film) n$_{max}$ 3384, 2927, 2856, 1743, 1693, 1462, 1384, 1255, 1160, 1095, 836, 777 cm$^{-1}$; $^1$H NMR (500 MHz, CDCl$_3$) d 6.33 (s, 1 H, ICH=C(CH$_3$)), 5.42 (ddd, J=15.5, 7.5, 7.5 Hz, 1 H, CH=CHCH$_2$), 5.23 (ddd, J=15.5, 7.5, 7.5 Hz, 1 H, CH=CHCH$_2$), 5.23 (d, J=7.5 Hz, 1 H, CHOCO), 4.26 (dd, J=8.5, 3.5 Hz, 1 H, (CH$_3$)$_2$CCH(OTBS)), 3.81–3.77 (m, 1 H, CHOH(CHCH$_3$)), 3.07 (qd, J=7.0, 3.5 Hz, 1 H, CH$_3$CH(C=O)), 3.04 (bs, 1 H, OH), 2.71 (dd, J=16.5, 8.5 Hz, 1 H, CH$_2$COO), 2.65 (dd, J=16.5, 3.5 Hz, 1 H, CH$_2$COO), 2.43–2.30 (m, 2 H), 2.13–2.00 (m, 2 H), 1.87–1.78 (m, 1 H), 1.86 (s, 3 H, ICH=CCH$_3$), 1.76–1.66 (m, 1 H), 1.64–1.52 (m, 1 H), 1.40–1.30 (m, 2 H), 1.18 (s, 3 H, C(CH$_3$)$_2$), 1.17 (d, J=7.0 Hz, 3 H, CH$_3$CH(C=O)), 1.12 (s, 3 H, C(CH$_3$)$_2$), 0.99 (d, J=7.0 Hz, 3 H, CH$_3$CHCH$_2$), 0.85 (s, 9 H, SiC(CH$_3$)$_3$(CH$_3$)$_2$), 0.13 (s, 3 H, SiC(CH$_3$)$_3$(CH$_3$)$_2$), 0.01 (s, 3 H, SiC(CH$_3$)$_3$(CH$_3$)$_2$); $^{13}$C NMR (150.9 MHz, CDCl$_3$) d 218.8, 169.9, 145.0, 134.6, 124.5, 78.9, 76.4, 74.4, 74.0, 54.3, 42,5, 40.3, 38.7, 36.1, 32.8, 32.6, 26.3, 22.0, 21.4, 18.7, 16.2, 13.8, −3.7, −4.6; HRMS (FAB), calcd for C$_{28}$H$_{49}$IO$_5$Si (M+Cs$^+$) 753.1148, found 753.1456.

cis-Macrolactone diol 7 as illustrated in FIG. 3. To a solution of iodide 16 (305 mg, 0.491 mmol) in THF (8.2 mL, 0.06 M) at 25° C. was added HF.pyr. (2.7 mL) and the resulting solution was stirred at the same temperature for 27 h. The reaction was then quenched by careful addition to a mixture of saturated aqueous NaHCO$_3$ (100 mL) and EtOAc (100 mL), and the resulting two-phase mixture was stirred at 25° C. for 2 h. The extracts were then separated and the organic layer was washed with saturated aqueous NaHCO$_3$ (100 mL) and brine (100 mL), and then dried (MgSO$_4$). Purification by flash column chromatography (silica gel, 20 ® 50% EtOAc in hexanes) furnished diol 7 (208 mg, 84%). R$_f$=0.21 (silica gel, 25% EtOAc in hexanes); [a]$^{22}$D −53.1 (c 1.37, CHCl$_3$); IR (thin film) n$_{max}$ 3499 (br), 2930, 1732, 1688, 1469, 1379, 1259, 1149, 1093, 1048, 1006, 732 cm$^{-1}$; $^1$H NMR (500 MHz, CDCl$_3$) d 6.43 (s, 1 H, ICH=C(CH$_3$)), 5.44 (ddd, J=10.5, 10.5, 4.5 Hz, 1 H, CH=CHCH$_2$), 5.34 (dd, J 9.5, 2.0 Hz, 1 H, CHOCO), 5.32 (ddd, J=10.5, 10.5, 5.5 Hz, 1 H, CH=CHCH$_2$), 4.07 (ddd, J=11.0, 6.0, 3.0 Hz, 1 H, (CH$_3$)$_2$CCH(OH)), 3.73 (ddd, J=2.5, 2.5, 2.5 Hz, 1 H, CHOH(CHCH$_3$)), 3.10 (qd, J=7.0, 2.5 Hz, 1 H, CH$_3$CH(C=O)), 2.84 (d, J=2.5 Hz, 1 H, CH(CH$_3$)CHOHCH(CH$_3$)), 2.66 (ddd, J=15.0, 9.5, 9.5 Hz, 1 H, =CHCH$_2$CHO), 2.51 (dd, J=15.5, 11.0 Hz, 1 H, CH$_2$COO), 2.42 (dd, J=15.5, 3.0 Hz, 1 H, CH$_2$COO), 2.35 (d, J=6.0 Hz, 1 H, (CH$_3$)$_2$CHOH), 2.21–2.12 (m, 2 H), 2.05–1.97 (m, 1 H), 1.88 (s, 3 H, ICH=CCH$_3$), 1.76–1.70 (m, 1 H), 1.70–1.62 (m, 1 H), 1.32 (s, 3 H, C(CH$_3$)$_2$), 1.18 (d, J=7.0 Hz, 3 H, CH$_3$CH(C=O)), 1.10 (s, 3 H, C(CH$_3$)$_2$), 1.35–1.05 (m, 3 H), 0.99 (d, J=7.0 Hz, 3 H, CH$_3$CHCH$_2$); $^{13}$C NMR (125.7 MHz, CDCl$_3$) d 219.9, 170.0, 145.3, 133.8, 124.0, 80.2, 77.3, 74.1, 72.8, 52.7, 42.0, 38.8, 38.4, 32.5, 31.2, 27.5, 27.4, 22.2, 20.8, 19.7, 15.5, 13.6; HRMS (FAB), calcd for C$_{22}$H$_{35}$IO$_5$ (M+Cs$^+$) 639.0584, found 639.0557.

trans-Macrolactone diol 11 as illustrated in FIG. 3. A solution of iodide 17 (194 mg, 0,313 mmol) in THF (5.2 mL, 0.06 M) was treated with HF.pyr. (1.7 mL) according to the procedure described for the preparation of diol 7 to afford, after flash column chromatography (silica gel, 20 ® 50% EtOAc in hexanes), diol 11 (134 mg, 85%). R$_f$=0.16 (silica gel, 25% EtOAc in hexanes); [a]$^{22}$D −20.0 (c 1.15, CHCl$_3$); IR (film) n$_{max}$ 3478, 2930, 1732, 1693 cm$^{-1}$; $^1$H NMR (500 MHz, CDCl$_3$) d 6.37 (d, J=1.5 Hz, 1 H, ICH=CCH$_3$), 5.35 (ddd, J=14.5, 7.0, 7.0 Hz, 1 H, CH=CHCH$_2$), 5.24 (ddd, J=14.5, 7.0, 7.0 Hz, 1 H, CH=CHCH$_2$), 5.17 (dd, J=6.5, 3.5 Hz, 1 H, CHOCO), 4.41 (dd, J=8.0, 3.5 Hz, 1 H, (CH$_3$)$_2$CCH(OTBS)), 3.85 (bs, 1 H, CHOH (CHCH$_3$)), 3.38 (bs, 1 H, CHOH(CHCH$_3$)), 3.18 (qd, J=7.0, 6.5 Hz, 1 H, CH$_3$CH(C=O)), 2.68–2.34 (m, 4 H), 2.44 (s, 3 H, CH$_3$Ar), 2.19–2.11 (m, 1 H), 1.96 (s, 3 H, CH$_3$C=CH), 1.99–1.93 (m, 1 H), 1.67–1.52 (m, 2 H), 1.48–1.42 (m, 1 H), 1.31–0.99 (m, 2 H), 1.22 (d, J=7.0 Hz, 3 H, CH$_3$CH(C=O)), 1.14 (s, 3 H, C(CH$_3$)$_2$), 1.09 (s, 3 H, C(CH$_3$)$_2$), 1.02 (d, J=7.0 Hz, 3 H, CH$_3$CHCH$_2$), 0.84 (s, 9 H, SiC(CH$_3$)$_3$(CH$_3$)$_2$), 0.08 (s, 3 H, SiC(CH$_3$)$_3$(CH$_3$)$_2$), −0.01 (s, 3 H, SiC(CH$_3$)$_3$(CH$_3$)$_2$); $^{13}$C NMR (125.7 MHz, CDCl$_3$) d 218.3, 170.1, 160.9, 137.5, 136.3, 135.2, 134.6, 125.0, 115.8, 77.1, 75.1, 74.1, 54.0, 43.6, 40.7, 38.4, 35.3, 32.9, 30.9, 26.8, 26.1, 23.2, 21.8, 18.4, 16.8, 16.2,.14.6, 13.7, −3.9, −4.5; HRMS (FAB), calcd for C$_{22}$H$_{35}$IO$_5$ (M+Cs$^+$) 639.0584, found 639.0606.

Figure 4A:
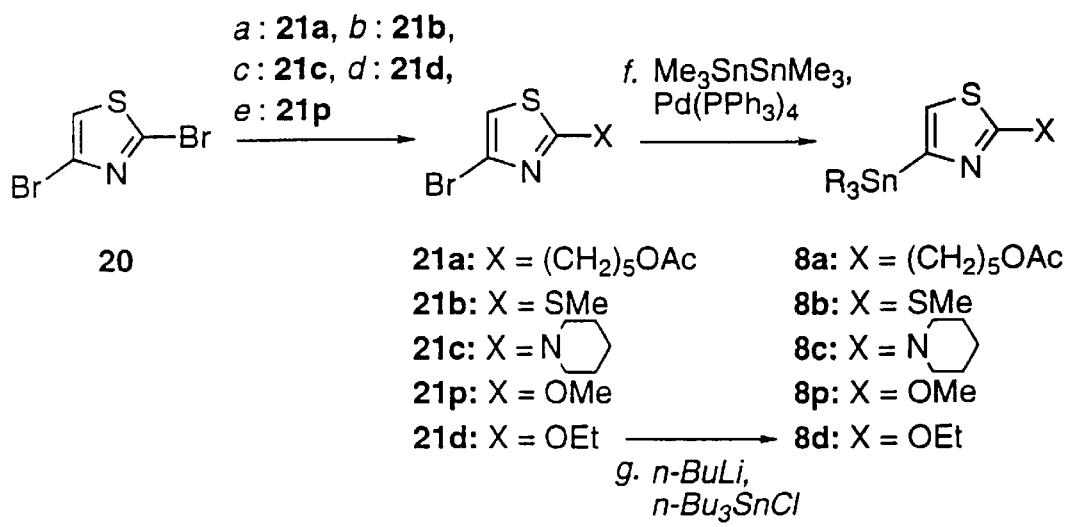
FIG. 4(A) shows the preparation of stannanes 8a–8d and 8p. Reagents and conditions: (a) i. 1.2 equiv of HCC(CH$_2$)$_3$OH, 0.05 equiv of Pd(PPh$_3$)$_4$, 0.1 equiv of CuI, i-Pr$_2$NH, 70° C., 2 h, 83%; ii. H2, 0.1 equiv of PtO$_2$, EtOH, 25° C., 4 h; 100%; iii. 2.0 equiv Ac$_2$O, 3.0 pyridine, CH$_2$Cl$_2$, 25° C., 83%; (b) 3.0 equiv of NaSMe, EtOH, 25° C., 2 h, 92%; (c) piperidine (0.1 M), 50° C., 8 h, 100%; (d) 13 equiv NaOH EtOH, 25° C., 30 h, 91%; (e) 13 equiv NaOH, MeOH, 25° C., 16 h, 82%; (f) 5–10 equiv of Me$_3$SnSnMe$_3$, 5–10 mol % of Pd(PPh$_3$)$_4$, toluene, 80–100° C., 0.5–3 h, 81–100%; (g) 1.1 equiv of n-BuLi, 1.2 equiv of n-Bu$_3$SnCl, −78→25° C., 30 min, 98%.
Figure 4B:
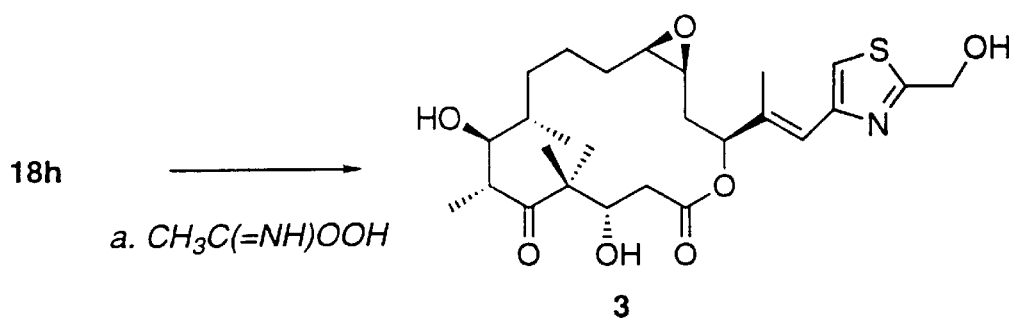
FIG. 4(B) illustrates the preparation of epoxide 3. Reagents and conditions: (a) 30 equiv of H2O2, 60 equiv of CH3CN, 10 equiv of KHCO3, MeOH, 25° C., 6 h, 66% (based on 50% conversion).

Bromothiazole 21a as illustrated in FIG. 4. To a solution of 2,4-dibromothiazole 20 (400 mg, 1.6 mmol, 1.0 equiv) in i-Pr$_2$NH (3.0 mL, 0.5 M) was added 4-pentyn-1-ol (270 mg, 3.2 mmol, 2.0 eq), Pd(PPh$_3$)$_4$ (95 mg, 0.082 mmol, 0.05 equiv) and CuI (30 mg, 0.16 mmol, 0.1 equiv). The reaction mixture was then heated at 70° C. for 2 h and, after cooling to 25° C., the solvents were removed under reduced pressure. Flash column chromatography (silica gel, 10 ® 75% EtOAc in hexanes) furnished alkyne 69 (326 mg, 83%). R$_f$=0.50 (silica gel, 100% ether); IR (film) n$_{max}$ 3377, 3118, 2933, 2876, 2230, 1458, 1258, 1206, 1075 cm$^{-1}$; $^1$H NMR (500 MHz, CDCl$_3$) d 7.16 (s, 1 H, ArH), 3.79 (t, J=6.0 Hz, 2 H, CH$_2$OH), 2.60 (t, J=7.0 Hz, 2 H, CH$_2$(CH$_2$)$_2$OH), 1.98 (bs, 1 H, OH), 1.87 (tt, J=7.0, 6.0 Hz, 2 H); $^{13}$C NMR (125.7 MHz, CDCl$_3$) d 150.0, 125.2, 117.7, 97.2, 73.5, 61.1, 30.4, 15.9; HRMS (FAB), calcd for C$_8$H$_8$NOS (M+H$^+$) 245.9588, found 245.9597.

A solution of alkyne 69 (70 mg, 0.280 mmol, 1.0 equiv) and PtO$_2$ (6.5 mg, 0.028 mmol, 0.1 equiv) in ethanol (2 mL) was stirred at 25° C. under an atmosphere of hydrogen for 4 h. Subsequent filtration through a short plug of silica gel, eluting with EtOAc, and removal of the solvents under reduced pressure furnished alcohol 70 (70 mg, 100%). $R_f$=0.40 (silica gel, 100% ether); IR (film) $n_{max}$ 3356, 3122, 2929, 2858, 1480, 1257, 1056 cm$^{-1}$; $^1$H NMR (500 MHz, CDCl$_3$) d 7.07 (s, 1 H, ArH), 3.64 (t, J=6.5 Hz, 2 H, CH$_2$OH), 3.00 (t, J=7.5 Hz, 2 H, CH$_2$(CH$_2$)$_4$OH), 1.81 (tt, J=8.0, 7.5 Hz, 2 H, CH$_2$(CH$_2$)$_3$OH), 1.74 (bs, 1 H, OH), 1.60 (tt, J=7.0, 6.5 Hz, 2 H, CH$_2$CH$_2$OH); $^{13}$C NMR (125.7 MHz, CDCl$_3$) d 142.1, 124.1, 115.7, 62.5, 33.4, 32.2, 29.4, 25.1; HRMS (FAB), calcd for C$_8$H$_{12}$BrNOS (M+H$^+$) 249.9901, found 249.9907.

A solution of alcohol 70 (25 mg, 0.100 mmol, 1.0 equiv) in CH$_2$Cl$_2$ (1.0 mL, 0.1 M), was treated with pyridine (16 mL, 0.200 mmol, 2.0 equiv) and Ac$_2$O (28 mL, 0.299 mmol, 3.0 equiv). The resulting mixture was stirred at 25° C. until the completion of the reaction was established by TLC. The mixture was then partitioned between water (10 mL) and CH$_2$Cl$_2$ (10 mL) and the layers were separated. The aqueous phase was extracted with CH$_2$Cl$_2$ (2×10 mL) and the combined extracts were concentrated under reduced pressure and purified by flash column chromatography (silica gel, 10 ⓑ 40% ether in hexanes) to furnish the desired bromothiazole 21a (24 mg, 83%). $R_f$=0.60 (silica gel, 50% ether in hexanes); IR (film) $n_{max}$ 3116, 2940, 2861, 1736, 1480, 1366, 1243, 1047, 888 cm$^{-1}$; $^1$H NMR (500 MHz, CDCl$_3$) d 7.08 (S, 1 H, ArH), 4.05 (t, J=6.5 Hz, 2 H, CH$_2$OH), 2.99 (t, J=7.5 Hz, 2 H, CH$_2$(CH$_2$)$_4$OH), 2.03 (s, 3 H, COCH$_3$), 1.81 (tt, J 8.0, 7.5 Hz, 2 H, CH$_2$(CH$_2$)$_3$OH), 1.66 (tt, J=8.0, 6.5 Hz, 2 H, CH$_2$CH$_2$OAc), 1.45 (tt, J=8.0, 7.5 Hz, 2 H, CH$_2$(CH$_2$)$_2$OAc); $^{13}$C NMR (125.7 MHz, CDCl$_3$) d 172.1, 137.1, 124.1, 115.7, 64.1, 33.3, 29.3, 28.2, 25.3, 20.9; HRMS (FAB), calcd for C$_{10}$H$_{14}$BrNO$_2$S (M+H$^+$) 292.0007, found 292.0016.

2-Thiomethyl-4-bromothiazole 21b as illustrated in FIG. 4. 2,4-Dibromothiazole 20 (82 mg, 0.34 mmol, 1.0 equiv) was dissolved in ethanol (2.3 mL, 0.15 M) and treated with sodium thiomethoxide (75 mg, 1.02 mmol, 3.0 equiv). The reaction mixture was stirred at 25° C. for 2 h, upon which time completion of the reaction was established by $^1$H NMR. The mixture was poured into water (5 mL) and extracted with ether (2×5 mL). The combined organic fractions were dried (MgSO$_4$), the solvents evaporated and the residue purified by flash column chromatography (silica gel, 5% EtOAc in hexanes) to furnish 2-thiomethyl-4-bromothiazole 21b (77 mg, 92%). $R_f$=0.58 (silica gel, 10% EtOAc in hexanes); IR (film) $n_{max}$ 3118, 2926, 1459, 1430, 1388, 1242, 1040, 966, 876, 818 cm$^{-1}$; $^1$H NMR (500 MHz, CDCl$_3$) d 7.07 (s, 1 H, ArH), 2.69 (s, 3 H, SCH$_3$); $^{13}$C NMR (125.7 MHz, CDCl$_3$) d 167.9, 124.2, 115.5, 16.6; GC/MS (EI), calcd for C$_4$H$_4$BrNS$_2$ (M$^+$) 209/211, found 209/211.

2-Piperidinyl-4-bromothiazole 21c as illustrated in FIG. 4. 2,4-Dibromothiazole 20 (184 mg, 0.76 mmol, 1.0 equiv) was dissolved in piperidine (1.5 mL, 0.5 M) and the reaction mixture heated at 50° C. for 8 h, upon which time completion of the reaction was indicated by TLC. The mixture was poured into water (5 mL) and extracted with ether (2×5 mL). After drying the combined organic fractions (MgSO$_4$), evaporation of the solvents and purification by flash column chromatography (silica gel, 5% EtOAc in hexanes) furnished 2-piperidinyl-4-bromothiazole 21c (188 mg, 100%). $R_f$=0.52 (silica gel, 10% EtOAc in hexanes); mp 66° C. (EtOAc-hexanes); IR (film) $n_{max}$ 3088, 2940, 2852, 1530, 1482, 1447, 1263 cm$^{-1}$; $^1$H NMR (500 MHz, CDCl$_3$) d 6.35 (s, 1 H, ArH), 3.42 (bt, J=5.5 Hz, 4 H, CH$_2$(CH$_2$CH$_2$)$_2$N), 1.66–1.62 (m, 6 H, CH$_2$(CH$_2$CH$_2$)$_2$N); $^{13}$C NMR (125.7 MHz, CDCl$_3$) d 170.8, 121.5, 102.8, 49.1, 24.9, 23.9; HRMS (FAB), calcd for C$_8$H$_{11}$BrN$_2$S (M+H$^+$) 246.9904, found 246.9910.

2-Ethoxy-4-bromothiazole 21d as illustrated in FIG. 4. To a solution of 2,4-dibromothiazole 20 (58 mg, 0.239 mmol, 1.0 equiv) in EtOH (2.4 mL, 0.1 M) was added NaOH (122 mg, 3.05 mmol, 12.8 equiv) and the resulting solution was stirred at 25° C. until TLC indicated the dissapearance of dibromide (ca. 30 h). The resulting yellow solution was then partitioned between ether (10 mL) and saturated aqueous NH$_4$Cl (10 mL) and the layers were separated. The aqueous layer was extracted with ether (10 mL) and the combined organic extracts were washed with brine (20 mL), dried (MgSO$_4$) and concentrated carefully under reduced pressure. Flash column chromatography (silica gel, 17% ether in hexanes) furnished 2-ethoxy-4-bromothiazole 21d as a volatile oil (45 mg, 91%). $R_f$=0.58 (silica gel, 17% ether in hexanes); IR (film) $n_{max}$ 3125, 2983, 2936, 2740, 1514, 1480, 1392, 1360, 1277, 1234, 1080, 1018, 897, 823 cm$^{-1}$; $^1$H NMR (500 MHz, CDCl$_3$) d 6.57 (s, 1 H, ArH), 4.48 (q, J=7.0 Hz, 2 H, CH$_3$CH$_2$), 1.43 (t, J=7.0 Hz, 3 H, CH$_3$CH$_2$); $^{13}$C NMR (125.7 MHz, CDCl$_3$) d 174.2, 118.5, 107.8, 68.3, 14.3; GC/MS (EI), calcd for C$_4$H$_4$BrNSO (M$^+$) 193/195, found 193/195.

2-Methoxy-4-bromothiazole 21p as illustrated in FIG. 4. To a solution of 2,4-dibromothiazole 20 (253 mg, 1.04 mmol, 1.0 equiv) in MeOH (10.5 mL, 0.1 M) was added NaOH (555 mg, 13.9 mmol, 13.3 equiv) and the resulting solution was stirred at 25° C. until TLC indicated the disappearance of dibromide (ca. 16 h). The resulting yellow solution was then partitioned between ether (10 mL) and saturated aqueous NH$_4$Cl (10 mL) and the layers were separated. The aqueous phase was extracted with ether (10 mL) and the combined organic extracts were dried (MgSO$_4$) and concentrated carefully under reduced pressure. Flash column chromatography (silica gel, 10% ether in hexanes) furnished 2-methoxy-4-bromothiazole 21p as a volatile oil (138 mg, 82%). $R_f$=0.56 (silica gel, 17% ether in hexanes); IR (film) $n_{max}$ 3125, 2952, 2752, 1524, 1520, 1481, 1417, 1277, 1238, 1081, 982, 884, 819 cm$^1$; $^1$H NMR (500 MHz, CDCl$_3$) d 6.58 (s, 1 H, ArH), 4.09 (q, 3 H, CH$_3$); $^{13}$C NMR (125.7 MHz, CDCl$_3$) d 174.8, 118.5, 108.4, 58.8; GC/MS (EI), calcd for C$_5$H$_6$BrNSO (M$^+$) 207/209, found 207/209.

2-Hydroxymethyl-4-bromothiazole 21h as illustrated in FIG. 4. To a solution of 2,4-dibromothiazole 20 (50 mg, 0.206 mmol, 1.0 equiv) in anhydrous ether (2.0 mL, 0.1 M) at −78° C., was added n-BuLi (154 mL, 1.6 M in hexanes, 0.247 mmol, 1.2 equiv), and the resulting solution was stirred at the same temperature for 30 min. DMF (32 mL, 0.412 mmol, 2.0 equiv) was then added at −78° C. and, after being stirred at −78° C. for 30 min, the reaction mixture was slowly warmed up to 25° C. over a period of 2 h. Hexane (2.0 mL) was added and the resulting mixture was passed through a short silica gel cake eluting with 30% EtOAc in hexanes. The solvents were evaporated to give the crude aldehyde 22 (50 mg), which was used directly in the next step.

To a solution of aldehyde 22 (50 mg) in methanol (2.0 mL) at 25° C., was added sodium borohydride (15 mg, 0.397 mmol, 1.9 equiv), and the resulting mixture was stirred at the same temperature for 30 min. EtOAc (1.0 mL) and hexane (2.0 mL) were added, and the mixture was passed through a short silica gel cake eluting with EtOAc. The solvents were then evaporated and the crude product was purified by flash column chromatography (silica gel, 20 ⓑ 50% EtOAc in hexanes) to furnish 2-hydroxymethyl-4-bromothiazole 21h (25 mg, 63% over two steps). $R_f$=0.16 (silica gel, 18% EtOAc in hexanes); IR (film) $n_{max}$ 3288, 3122, 2922, 2855, 1486, 1447, 1345, 1250, 1183, 1085, 1059, 967, 893 cm$^{-1}$; $^1$H NMR (500 MHz, CDCl$_3$) d 7.20 (s, 1 H, ArH), 4.93 (s, 2 H, CH$_2$); $^{13}$C NMR (125.7 MHz, CDCl$_3$) d 173.0, 124.4, 117.0, 61.8; HRMS (FAB), calcd for C$_4$H$_4$BrNOS (M+H$^+$) 193.9275, found 193.9283.

2-(tert-Butyldimethylsilyloxymethyl)-4-bromothiazole 21s as illustrated in FIG. 5. To a solution of alcohol 21h (59 mg, 0.304 mmol, 1.0 equiv) in CH$_2$Cl$_2$ (1.0 mL, 0.3 M) was added imidazole (62 mg, 0.608 mmol, 2.0 equiv), followed by tert-butyldimethylchlorosilane (69 mg, 0.456 mmol, 1.3 equiv) at 25° C. After 30 min at 25° C., the reaction mixture was quenched with methanol (100 mL) and then passed through silica gel eluting with CH$_2$Cl$_2$. Evaporation of solvents gave the desired silyl ether 21s (90 mg, 96%). R$_f$=60 (silica gel, 10% EtOAc in hexanes); IR (film) n$_{max}$ 2943, 2858, 1489, 1465, 1355, 1254, 1193, 1108, 887, 841, 780 cm$^{-1}$; $^1$H NMR (500 MHz, CDCl$_3$) d 7.16 (s, 1 H, ArH), 4.93 (s, 2 H, CH$_2$), 0,94 (s, 9 H, SiC(CH$_3$)$_3$(CH$_3$)$_2$), 0.12 (s, 6 H, SiC(CH$_3$)$_3$(CH$_3$)$_2$); $^{13}$C NMR (125.7 MHz, CDCl$_3$) d 174.5, 124.2, 116.4, 62.9, 25.7, −5.5; HRMS (FAB), calcd for C$_{10}$H$_{18}$BrNOSSi (M+H$^+$) 308.0140, found 308.0151.

2-Acetoxymethyl-4-bromothiazole 21i as illustrated in FIG. 5. To a solution of alcohol 21h (37 mg, 0.191 mmol, 1.0 equiv) in EtOAc (2.0 mL, 0.1 M) was added Ac$_2$O (58 mL, 0.618 mnmol, 3.2 equiv) followed by 4-DMAP (28 mg, 0.227 mmol, 1.2 equiv) and the resulting mixture was stirred for 5 min. The reaction mixture was then washed with brine (2.0 mL), dried (MgSO$_4$) and concentrated under reduced pressure. Flash column chromatography (silica gel, 17 ® 50% EtOAc in hexanes) furnished alcohol 2-acetoxymethyl-4-bromothiazole 21i (41 mg, 91%). R$_f$=0.27 (silica gel, 17% EtOAc in hexanes); IR (film) n$_{max}$ 3119, 2954, 1747, 1485, 1435, 1373, 1224, 1038, 890, 836 cm$^{-1}$; $^1$H NMR (500 MHz, CDCl$_3$) d 7.26 (s, 1 H, ArH), 5.35 (s, 2 H, CH$_2$OAc), 2.16 (s, 2 H, CH$_3$CO); $^{13}$C NMR (125.7 MHz, CDCl$_3$) d 170.0, 165.7, 125.0, 118.1, 62.1, 20.5; HRMS (FAB), calcd for C$_6$H$_6$BrNO$_2$S (M+H$^+$) 235.9381, found 235.9390.

2-Vinyl-4-bromothiazole 21q as illustrated in FIG. 5. To a solution of 2,4-dibromothiazole 20 (437 mg, 1.80 mmol, 1.0 equiv) in toluene was added tri-n-butyl(vinyl)tin (552 mL, 1.89 mmol, 1.05 equiv) followed by Pd(PPh$_3$)$_4$ (208 mg, 0.180 mmol, 0.1 equiv) and the resulting was heated at 100° C. After 21 h, the mixture was cooled and purified directly by flash column chromatography (silica gel, 0 ® 9% ether in hexanes) to afford 2-vinyl-4-bromothiazole 21q as an oil (285 mg, 83%). R$_f$=0.50 (silica gel, 17% ether in hexanes); IR (film) n$_{max}$ 3121, 1470, 1259, 1226, 1124, 1082, 975, 926, 887, 833 cm$^{-1}$; $^1$H NMR (500 MHz, CDCl$_3$) d 7.13 (s, 1 H, ArH), 6.86 (dd, J=17.5, 11.0 Hz, 1 H, CH=CH$_2$), 6.09 (d, J=17.5 Hz, 1 H, CHCH$_2$), 5.59 (d, J=10.5 Hz, 1 H, CHCH$_2$); $^{13}$C NMR (125.7 MHz, CDCl$_3$) d 167.7, 129.5, 125.6, 120.8, 116.2; GC/MS (EI), calcd for C$_5$H$_4$BrNS (M$^+$) 189/191, found 189/191.

2-Ethyl-4-bromothiazole 21r as illustrated in FIG. 5. A solution of 2-vinyl-4-bromothiazole 21q (279 mg, 1.47 mmol, 1.0 equiv) in ethanol (15 mL, 0.1 M) was added PtO$_2$ (50 mg, 0.220 mmol, 0.15 equiv) and the resulting mixture was stirred under an atmosphere of hydrogen at 25° C. for 4 h. Subsequent filtration through a short plug of silica gel, eluting with EtOAc, and careful concentration under reduced pressure furnished 2-ethyl-4-bromothiazole 21r (238 mg, 84%). R$_f$=0.63 (silica gel, CH$_2$Cl$_2$); IR (film) n$_{max}$ 3122, 2974, 2932, 1483, 1456, 1245, 1181, 1090, 1040, 956, 884, 831 cm$^{-1}$; $^1$H NMR (500 MHz, CDCl$_3$) d 7.08 (s, 1 H, ArH), 3.03 (q, J=7.5 Hz, 2 H, CH$_2$CH$_3$), 1.37 (t, J=7.5 Hz, 2 H, CH$_2$CH$_3$); $^{13}$C NMR (125.7 MHz, CDCl$_3$) d 174.1, 124.1, 115.6, 27.1, 13.8; GC/MS (EI), calcd for C$_5$H$_6$BrNS (M$^+$) 191/193, found 191/193.

Stannane 8a as illustrated in FIG. 3. A solution of bromothiazole 21a (7.5 mg, 0.026 mmol, 1.0 equiv) in degassed toluene (260 mL, 0.1 M), was treated with hexamethylditin (54 mL, 0.26 mamol, 10 equiv) and Pd(PPh$_3$)$_4$ (3.0 mg, 0.0026 mmol, 0.1 equiv) and the mixture was heated at 100° C. for 3 h. The reaction mixture was cooled to 25° C. and purified by flash column chromatography (silica gel; pre-treated with Et$_3$N, 50% ether in hexanes) to afford the desired stannane 8a (9.1 mg, 93%). R$_f$=0.60 (silica gel, 50% ether in hexanes); IR (film) n$_{max}$ 2922, 2851, 1737, 1461, 1381, 1238, 1043 cm$^{-1}$; $^1$H NMR (500 MHz, CDCl$_3$) d 7.23 (s, 1 H, ArH), 4.07 (t, J=6.5 Hz, 2 H, CH$_2$OH), 3.09 (t, J=8.0 Hz, 2 H, CH$_2$(CH$_2$)$_4$OH), 2.05 (s, 3 H, COCH$_3$), 1.83 (tt, J=8.0, 7.5 Hz, 2 H, CH$_2$(CH$_2$)$_3$OH), 1.67 (tt, J=8.0, 6.5 Hz, 2 H, CH$_2$CH$_2$OAc), 1.47 (tt, J=8.0, 7.5 Hz, 2 H, CH$_2$(CH$_2$)$_2$OAc), 0.34 (s, 9 H, Sn(CH$_3$)$_3$); $^{13}$C NMR (125.7 MHz, CDCl$_3$) d 172.2, 142.1, 124.7, 117.9, 64.2, 33.0, 30.0, 29.5, 28.2, 25.4, −9.1.

2-Thiomnethyl-4-trimethylstannylthiazole 8b as illustrated in FIG. 3. To a solution of bromothiazole 21b (51 mg, 0.24 mmol, 1.0 equiv) in degassed toluene (4.9 mL, 0.1 M) was added hexamethylditin (498 mL, 2.4 mmol, 10 equiv) and Pd(PPh$_3$)$_4$ (14 mg, 0.012 mmol, 0.05 equiv) and the reaction mixture was heated at 80° C. for 3 h according to the procedure described for the synthesis of stannane 8a to afford, after flash column chromatography (silica gel, 5% Et$_3$N in hexanes), stannane 8b (71 mg, 100%). R$_f$=0.67 (silica gel; pre-treated with Et$_3$N, 10% EtOAc); IR (film) n$_{max}$ 2981, 2924, 1382, 1030, 772 cm$^{-1}$; $^1$H NMR (500 MHz, CDCl$_3$) d 7.25 (s, 1 H, ArH), 2.70 (s, 3 H, SCH$_3$), 0.32 (s, 9 H, Sn(CH$_3$)$_3$);$^{13}$C NMR (125.7 MHz, CDCl$_3$) d 166.4, 160.2, 124.9, 17.2, −8.9; HRMS (FAIB), calcd for C$_7$H$_{13}$NS$_2$Sn (M+H$^+$) 295.9588, found 295.9576.

2-Piperidinyl-4-trimethylstannylthiazole 8c as illustrated in FIG. 3. A solution of bromothiazole 21c (64 mg, 26 mmol, 1.0 equiv) in degassed toluene (5.2 mL, 0.05 M) was treated with hexamethylditin (540 mL, 2.6 mmol, 10 equiv) and Pd(PPh$_3$)$_4$ (15 mg, 0.013 mmol, 0.05 equiv) and heated at 80° C. for 3 h according to the procedure described for the synthesis of stannane 8a to afford, after flash column chromatography (silica gel; pre-treated with Et$_3$N, hexanes), stannane 8c (86 mg, 100%). R$_f$=0.67 (silica gel, 10% EtOAc in hexanes containing Et$_3$N); IR (film) n$_{max}$ 2935, 2854, 1511, 1449, 1259, 771 cm$^{-1}$; $^1$H NMR (500 MHz, CDCl$_3$) d 6.58 (s, 1 H, ArH), 3.48 (bt, J=5.0 Hz, 4 H, CH$_2$(CH$_2$CH$_2$)$_2$N), 1.70–1.60 (m, 6 H, CH$_2$(CH$_2$CH$_2$)$_2$N), 0.29 (s, 9 H, Sn(CH$_3$)$_3$); $^{13}$C NMR (125.7 MHz, CDCl$_3$) d 173.4, 156.6, 113.9, 50.2, 25.3, 24.3, −9.0; HRMS (FAB), calcd for C$_{11}$H$_{20}$N$_2$SSn (M+H$^+$) 333.0447, found 333.0358.

2-Methoxy-4-trimethylstannylthiazole 8p as illustrated in FIG. 4. To a solution of bromothiazole 21p (147 mg, 0.758 mmol, 1.0 equiv) in degassed toluene (7.6 mL, 0.1 M) was added hexamethylditin (785 mL, 3.79 mmol, 5.0 equiv) and Pd(PPh$_3$)$_4$ (88 mg, 0.076 mmol, 0.1 equiv) and the reaction mixture was heated at 100° C. for 30 min according to the procedure described for the synthesis of stannane 8a to afford, after flash column chromatography (silica gel, 5% Et$_3$N in hexanes), stannane 8p (170 mg, 81%). R$_f$=0.49 (silica gel; pre-treated with Et$_3$N, 17% ether in hexanes); IR (film) n$_{max}$ 2985, 2948, 2915, 1512, 1414, 1259, 1234, 1219, 1087, 988 cm$^{-1}$; $^1$H NMR (500 MHz, CDCl$_3$) d 6.72 (s, 1 H, ArH), 4.07 (s, 3 H, OCH$_3$), 0.32 (s, 9 H, Sn(CH$_3$)$_3$); $^{13}$C NMR (125.7 MHz, CDCl$_3$) d 176.0, 154.5, 117.9, 58.5, −9.1; HRMS (FAB), calcd for C$_7$H$_{13}$NOSSn (M+H$^+$) 279.9818, found 279.9810.

2-Acetoxymethyl-4-trimethylstannylthiazole 8i as illustrated in FIG. 5. To a solution of bromothiazole 21i (41 mg, 0.174 mmol, 1.0 equiv) in degassed toluene (1.7 mL, 0.1 M) was added hexamethylditin (307 mL, 1.74 mmol, 10 equiv)

and Pd(PPh$_3$)$_4$ (15 mg, 0.013 mmol, 0.07 equiv) and the reaction mixture was heated at 100° C. for 25 min according to the procedure described for the synthesis of stannane 8a to afford, after flash column chromatography (silica gel, hexanes containing 5% Et$_3$N), stannane 8i (25 mg, 45%). R$_f$=0.33 (silica gel; pre-treated with Et$_3$N, 17% EtOAc in hexanes); IR (film) n$_{max}$ 2974, 2915, 1745, 1437, 1374, 1229, 1031 cm$^{-1}$; $^1$H NMR (500 MHz, CDCl$_3$) d 7.40 (s, 1 H, ArH), 5.45 (s, 2 H, CH$_2$OCOCH$_3$), 2.15 (s, 3 H, CH$_2$OCOCH$_3$) 0.37 (s, 9 H, Sn(CH$_3$)$_3$); $^{13}$C NMR (125.7 MHz, CDCl$_3$) d 170.3, 165.0, 160.1, 126.9, 62.5, 20.8, −8.9; HRMS (FAB), calcd for C$_9$H$_{15}$NO$_2$SSn (M+H$^+$) 321.9924, found 321.9939.

2-(tert-butyldimethylsilyloxymethyl)-4-tri-n-butylstannylthiazole 8s as illustrated in FIG. 5. To a solution of bromothiazole 21s (20 mg, 0.065 mmol, 1.0 equiv) in ether (1.0 mL, 0.07M) at −78° C., was added n-BuLi (49 mL, 1.6 M in hexanes, 0.078 mmol, 1.2 equiv) and the resulting mixture was stirred at −78° C. for 10 min. Tri-n-butyltin chloride (23 mL, 0.078 mmol, 1.2 equiv) was then added, the solution stirred at −78° C. for 10 min, and then slowly warmed to 25° C. over a period of 1 h. The reaction mixture was diluted with hexane (2.0 mL), and passed through silica gel eluting with 20% EtOAc in hexanes. Flash column chromatography (silica gel; pre-treated with Et$_3$N, 5% ether in hexanes) furnished the desired stannane 8s (35 mg, 85%). R$_f$=0.36 (silica gel, 5% EtOAc in hexanes); IR (film) n$_{max}$ 2955, 2928, 2856, 1464, 1353, 1255, 1185, 1103, 1081, 1006, 841 cm$^{-1}$; $^1$H NMR (500 MHz, C$_6$D$_6$) d 7.08 (s, 1 H, ArH), 4.98 (s, 2 H, CH$_2$), 1.75–1.57 (m, 6 H, CH$_3$CH$_2$), 1.44–1.31 (m, 6 H, CH$_3$CH$_2$CH$_2$), 1.26–1.09 (m, 6 H, CH$_3$CH$_2$CH$_2$CH$_2$), 0.94 (s, 9 H, SiC(CH$_3$)$_3$(CH$_3$)$_2$), 0.91 (t, J=7.0 Hz, 9 H, CH$_3$), −0.02 (s, 6 H, SiC(CH$_3$)$_3$(CH$_3$)$_2$); $^{13}$C NMR (125.7 MHz, CDCl$_3$) d 173.2, 159.1, 125.3, 63.5, 29.0, 27.3, 25.8, 18.3, 13.7, 10.1, −5.4; HRMS (FAB), calcd for C$_{22}$H$_{45}$NOSSiSn (M+H$^+$) 520.2093, found 520.2074.

2-Hydroxymethyl-4-tri-n-butylstannylthiazole 8h as illustrated in FIG. 5. To a solution of silyl ether 8s (20 mg, 0.039 mmol, 1.0 equiv) in THF (1.0 mL, 0.04 M) was added TBAF (46 mL, 1.0 M in THF, 0.046 mmol, 1.2 equiv) and the reaction mixture was stirred at 25° C. for 20 min. Hexane (2.0 mL) was added, and the mixture passed through silica gel eluting with EtOAc. Evaporation of solvents gave the desired alcohol 8h (15 mg, 95%). R$_f$=0.09 (silica gel, 20% ether in hexanes); IR (film) n$_{max}$ 3209, 2956, 2923, 2855, 1461, 1342, 1253, 1174, 1064, 962 cm$^{-1}$; $^1$H NMR (500 MHz, CDCl$_3$) d 7.30 (m, 1 H, ArH), 4.99 (s, 2 H, CH$_2$), 3.64 (bs, 1 H, OH), 1.62–1.45 (m, 6 H, CH$_3$CH$_2$), 1.38–1.27 (m, 6 H, CH$_3$CH$_2$CH$_2$), 1.19–1.02 (m, 6 H, CH$_3$CH$_2$CH$_2$CH$_2$), 0.88 (t, J=7.0 Hz, 9 H, CH$_3$); $^{13}$C NMR (125.7 MHz, CDCl$_3$) d 170.7, 159.1, 125.7, 61.7, 28.9, 27.1, 13.6, 10.1; HRMS (FAB), calcd for C$_{16}$H$_{31}$NOSSn (M+H$^+$) 406.1228, found 406.1237.

2-Fluoromethyl-4-tri-n-butylstannylthiazole 8j as illustrated in FIG. 5. To a solution of alcohol 8h (90 mg, 0.223 mmol, 1.0 equiv) in CH$_2$Cl$_2$ (2.2 mL, 0.1 M) at −78° C. was added DAST (32 mL, 0.242 mmol, 1.1 equiv) and the solution was stirred at this temperature for 10 min. After quenching with saturated aqueous NaHCO$_3$ (2 mL) the mixture was allowed to warm to 25° C., and then partitioned between CH$_2$Cl$_2$ (15 mL) and saturated aqueous NaHCO$_3$ (15 mL). The layers were separated and the aqueous phase was extracted with CH$_2$Cl$_2$ (2×15 mL). The combined organic extracts were washed with brine (40 mL), dried (MgSO$_4$) and concentrated under reduced pressure. Flash column chromatograpahy (silica gel; pre-treated with Et$_3$N, 17% ether in hexanes) furnished stannane 8j (52 mg, 57%). R$_f$=0.59 (silica gel, 17% ether in hexanes); IR (film) n$_{max}$ 2956, 2925, 2870, 2863, 1464, 1376, 1358, 1184, 1084, 1023, 874, 807 cm$^{-1}$; $^1$H NMR (500 MHz, CDCl$_3$) d 7.41 (s, 1 H, ArH), 5.69 (d, J=47.5 Hz, 2 H, CH$_2$F), 1.58–1.52 (m, 6 H, (CH$_3$CH$_2$(CH$_2$)$_2$)$_3$Sn), 1.36–1.29 (m, 6 H, (CH$_3$CH$_2$CH$_2$CH$_2$)$_3$Sn), 1.14–1.07 (m, 6 H, (CH$_3$CH$_2$CH$_2$CH$_2$)$_3$Sn), 0.88 (t, J=7.5 Hz, 9 H, (CH$_3$CH$_2$CH$_2$CH$_2$)$_3$Sn); $^{13}$C NMR (100.6 MHz, C$_6$D$_6$) d 165.0 (d, J=88 Hz), 160.1, 80.5 (d, J=676 Hz), 29.4, 27.6, 13.9, 10.5; HRMS (FAB), calcd for C$_{16}$H$_{30}$FNSSn (M+H$^+$) 408.1183, found 408.1169.

2-Ethoxy-4-tri-n-butylstannylthiazole 8d as illustrated in FIG. 4. A solution of bromothiazole 21d (82 mg, 0.394 mmol, 1.0 equiv) in ether (3.9 mL, 0.1 M) was treated with n-BuLi (289 mL, 1.5 M in hexanes, 0.433 mmol, 1.1 equiv) and tri-n-butylin chloride (128 mL, 0.473mmol, 1.2 equiv) according to the procedure described for the synthesis of stannane 8s, to yield, after column chromatography (silica gel; pre-treated with Et$_3$N, hexanes), stannane 8d (161 mg, 98%). IR (film) n$_{max}$ 2956, 2927, 2870, 2851, 1504, 1472, 1258, 1257, 1232, 1211, 1082, 1023, 960, 894, 872 cm$^{-1}$; $^1$H NMR (500 MHz, CDCl$_3$) d 6.65 (s, 1 H, ArH), 4.43 (q, J=7.0 Hz, 2 H, CH$_3$CH$_2$O), 1.61–1.53 (m, 6 H, (CH$_3$CH$_2$(CH$_2$)$_2$)$_3$Sn), 1.43 (t, J=7.0 Hz, 3 H, CH$_3$CH$_2$), 1.37–1.30 (m, 6 H, (CH$_3$CH$_2$CH$_2$CH$_2$)$_3$Sn), 1.08–1.04 (m, 6 H, (CH$_3$CH$_2$CH$_2$CH$_2$)$_3$Sn), 0.89 (t, J=7.5 Hz, 9 H, (CH$_3$CH$_2$CH$_2$CH$_2$)$_3$Sn); $^{13}$C NMR (125.7 MHz, CDCl$_3$) d 175.7, 155.3, 118.3, 68.5, 29.0, 27.2, 14.5, 13.7, 10.1; HRMS (FAB), calcd for C$_{17}$H$_{33}$NOSSn (M+H$^+$) 418.1380, found 418.1396.

2-Vinyl-4-tri-n-butylstannylthiazole 8q as illustrated in FIG. 5. A solution of bromothiazole 21q (191 mg, 1.00 mmol, 1.0 equiv) in ether (14.0 mL, 0.07 M), was treated with n-BuLi (804 mL, 1.5 M in hexanes, 1.20 mmol, 1.2 equiv) and tri-n-butylin chloride (341 mL, 1.26 mmol, 1.25 equiv) according to the procedure described for the synthesis of stannane 8s to yield, after column chromatography (silica gel; pre-treated with Et$_3$N, hexanes), stannane 8q (112 mg, 28%). R$_f$=0.63 (silica gel, 17% ether in hexanes); IR (film) n$_{max}$ 2956, 2925, 2870, 2850, 1459, 1377, 1205, 1080, 981, 913, 868 cm$^{-1}$; $^1$H NMR (500 MHz, CDCl$_3$) d 7.21 (s, 1 H, ArH), 7.02 (dd, J=17.5, 11.0 Hz, 1 H, CH=CH$_2$), 6.00 (d, J=17.5 Hz, 1 H, CHCH$_2$), 5.52 (d, J=11.0 Hz, 1 H, CH=CH$_2$), 1.61–1.53 (m, 6 H, (CH$_3$CH$_2$(CH$_2$)$_2$)$_3$Sn), 1.37–1.27 (m, 6 H, (CH$_3$CH$_2$CH$_2$CH$_2$)$_3$Sn), 1.13–1.10 (m, 6 H, (CH$_3$CH$_2$CH$_2$CH$_2$)$_3$Sn), 0.88 (t, J=7.5 Hz, 9 H, (CH$_3$CH$_2$CH$_2$CH$_2$)$_3$Sn); $^{13}$C NMR (100.6 MHz, CDCl$_3$) d 167.7, 160.3, 131.0, 124.7, 119.5, 29.0, 27.2, 13.6, 10.1; HRMS (FAB), calcd for C$_{17}$H$_{31}$NSSn (M+H$^+$) 402.1279, found 402.1290.

2-Ethyl-4-tri-n-butylstannylthiazole 8r as illustrated in FIG. 5. To a solution of bromothiazole 21r (238 mg, 1.24 mol, 1.0 equiv) in ether (12.0 mL, 0.1M) at −78° C., was treated with n-BuLi (909 mL, 1.5 M in hexanes, 1.36 mmol, 1.1 equiv) and tri-n-butyltin chloride (403 mL, 1.49 mmol, 1.2 equiv) according to the procedure described for the synthesis of stannane 8s to yield , after column chromatography (silica gel; pre-treated with Et$_3$N, hexanes), stannane 8r (357 mg, 72%). R$_f$=0.64 (silica gel, CH$_2$Cl$_2$); IR (film) n$_{max}$ 2956, 2925, 2870, 2852, 1464, 1376, 1292, 1174, 1072, 1033, 953, 875 cm$^{-1}$; $^1$H NMR (400MHz, CDCl$_3$) d 7.18 (s, 1 H, ArH), 3.10 (q, J=7.6 Hz, 2 H, CH$_3$CH$_2$Ar), 1.60–1.50 (m, 6 H, (CH$_3$CH$_2$(CH$_2$)$_2$)$_3$Sn), 1.39 (t, J=7.6 Hz, 3 H, CH$_3$CH$_2$Ar), 1.36–1.30 (m, 6 H, (CH$_3$CH$_2$CH$_2$CH$_2$)$_3$Sn), 1.13–1.08 (m, 6 H, (CH$_3$CH$_2$CH$_2$CH$_2$)$_3$Sn), 0.88 (t, J=7.3 Hz, 9 H, (CH$_3$CH$_2$CH$_2$CH$_2$)$_3$Sn); $^{13}$C NMR (100.6 MHz, CDCl$_3$) d 172.9, 158.9, 124.5, 29.1, 27.0, 26.6, 14.7, 13.7, 10.1; HRMS (FAB), calcd for $C_{17}H_{33}NSSn$ (M+H$^+$) 404.1434, found 404.1416.

cis-Macrolactone 18h as illustrated in FIG. 3. A solution of vinyl iodide 7 (10.0 mg, 0.020 mmol, 1.0 equiv), stannane 8h (16.0 mg, 0.040 mmol, 2.0 equiv) and Pd(PPh$_3$)$_4$ (2.1 mg, 0.002 mmol, 0.1 equiv) in degassed toluene (200 mL, 0.1 N) was heated at 100° C. for 20 min. The reaction mixture was poured into saturated aqueous NaHCO$_3$-NaCl (5 mL) and extracted with EtOAc (2×5 mL). After drying the combined organic fractions (Na$_2$SO$_4$), evaporation of the solvents and purification by preparative thin layer chromatography (500 mm silica gel plate, 50% EtOAc in hexanes), furnished macrolactone 18h (7.5 mg, 76%). R$_f$=0.29 (silica gel, 50% EtOAc in hexanes); [a]$^{22}$D −44.2 (c 0.60, CHCl$_3$); IR (thin film) n$_{max}$ 3387 (br), 2925, 2859, 1730, 1688, 1508, 1461, 1256, 1183, 1150, 1061, 980, 755 cm$^{-1}$; $^1$H NMR (500 MHz, CDCl$_3$) d 7.12 (s, 1 H, ArH), 6.61 (s, 1 H, CH=C(CH$_3$)), 5.45 (ddd, J=10.5, 10.5, 4.5 Hz, 1 H, CH=CHCH$_2$), 5.38 (ddd, J=10.5, 10.5, 5.0 Hz, 1 H, CH=CHCH$_2$), 5.31 (d, J=8.5 Hz, 1 H, CHOCO), 4.92 (d, J=4.0 Hz, 2 H, CH$_2$OH), 4.23 (ddd, J=11.5, 5.5, 2.5 Hz, 1 H, (CH$_3$)$_2$CCH(OH)), 3.75–3.71 (m, 1 H, CHOH(CHCH$_3$)), 3.32 (d, J=5.5 Hz, 1 H, C(CH$_3$)$_2$CHOH), 3.25 (t, J=4.0 Hz, 1 H, CH$_2$OH), 3.13 (qd, J=7.0, 2.0 Hz, 1 H, CH$_3$CH(C=O)), 3.03 (d, J=2.0 Hz, 1 H, CH$_3$CHCH(OH)CHCH$_3$), 2.68 (ddd, J=15.0, 9.5, 9.5 Hz, 1 H, =CHCH$_2$CHO), 2.50 (dd, J=15.0, 11.5 Hz, 1 H, CH$_2$COO), 2.35 (dd, J=15.0, 2.5 Hz, 1 H, CH$_2$COO), 2.31–2.24 (m, 1 H, =CHCH$_2$CHO), 2.24–2.16 (m, 1 H), 2.09 (s, 3 H, CH=CCH$_3$), 2.06–1.98 (m, 1 H), 1.82–1.73 (m, 1 H), 1.72–1.62 (m, 1 H), 1.39–1.17 (m, 3 H), 1.33 (s, 3 H, C(CH$_3$)$_2$), 1.19 (d, J=7.0 Hz, 3 H, CH$_3$CH(C=O)), 1.08 (s, 3 H, C(CH$_3$)$_2$), 1.00 (d, J=7.0 Hz, 3 H, CH$_3$CHCH$_2$); $^{13}$C NMR (125.7 MHz, CDCl$_3$) d 220.5, 170.3, 169.9, 152.3, 139.0, 133.5, 124.9, 118.9, 116.5, 78.4,.74.2, 72.2, 61.8, 53.4, 41.7, 39.3, 38.6, 32.4, 31.7, 27.5, 27.4, 22.8, 18.4, 16.0, 15.5, 13.5; HRMS (FAB), calcd for $C_{26}H_{39}NO_6S$ (M+Cs$^+$) 626.1552, found 626.1530.

Figure 2B:
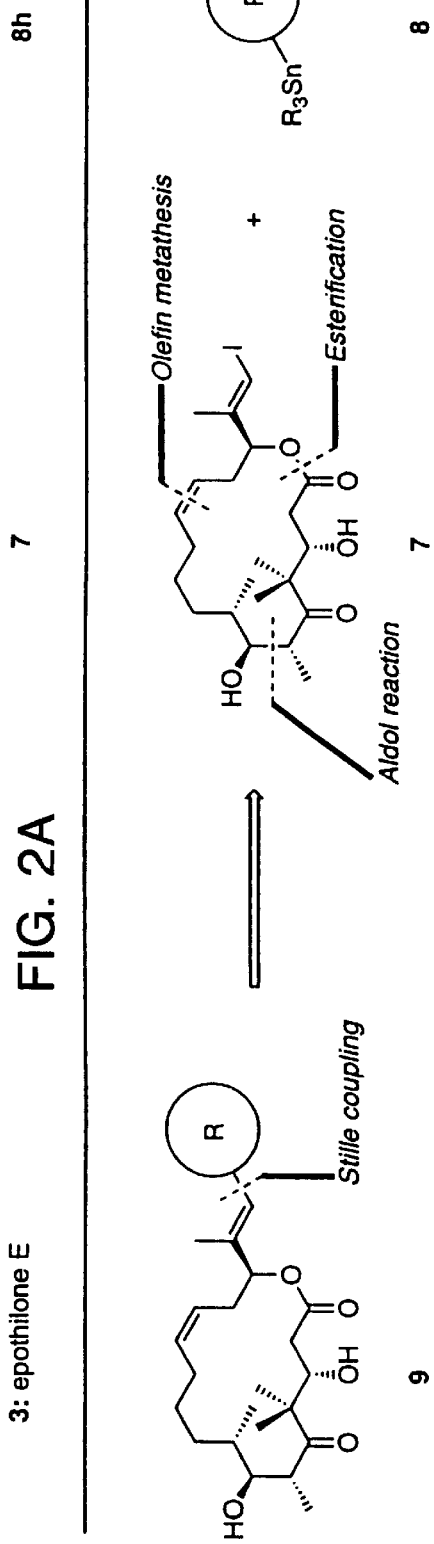

Epothilone E (3) as illustrated in FIGS. 2 and 3. To a solution of lactone 18h (10.0 mg, 0.020 mmol, 1.0 equiv) in methanol (600 mL, 0.03 M) was added acetonitrile (32 mL, 0.606 mmol, 30 equiv), KHCO$_3$ (10 mg, 0.102 mmol, 5 equiv) and hydrogen peroxide (27 mL, 35% w/w in water, 0.303 mmol, 15 equiv) and the reaction mixture stirred at 25° C. for 3 h. Additional acetonitrile (32 mL, 0.606 mmol, 30 equiv), KHCO$_3$ (10 mg, 0.102 mmol, 5 equiv) and hydrogen peroxide (27 mL, 35% w/w in water, 0.303 mmol, 15 equiv) were then added and stirring was continued for a further 3 h. The reaction mixture was then passed directly through a short plug of silica gel, eluting with ether, and the filtrate was concentrated under reduced pressure. Preparative thin layer chromatography (250 mm silica gel plate, 50% EtOAc in hexanes) furnished unreacted starting material 18h (5.0 mg, 50%) and epothilone E (3) (3.4 mg, 33%). R$_f$=0.56 (silica gel, 66% EtOAc in hexanes); [a]$^{22}$D =−27.5 (c 0.20, CDCl$_3$); IR (film) n$_{max}$ 3413, 2928, 2867, 1731, 1689, 1462, 1375, 1257, 1152, 1061, 978, 756 cm$^{-1}$; $^1$H NMR (600 MHz, CDCl$_3$) d 7.13 (s, 1 H, ArH), 6.61 (s, 1 H, CH=CCH$_3$), 5.46 (dd, J=8.1, 2.4 Hz, 1 H, CHOCO), 4.94 (d, J=5.2 Hz, 2 H, CH$_2$OH), 4.16–4.12 (m, 1 H, (CH$_3$)$_2$CCH (OH)), 3.82–3.78 (m, 1 H, CHOH(CHCH$_3$)), 3.66 (bs, 1 H, OH), 3.23 (qd, J=6.8, 5.2 Hz, 1 H, CH$_3$CH(C=O)), 3.04 (ddd, J=8.1, 4.5, 4.5 Hz, 1 H, CH$_2$CH(O)CHCH$_2$), 2.91 (ddd, J=7.3, 4.5, 4.1 Hz, 1 H, CH$_2$CH(O)CHCH$_2$), 2.61 (t, J=5.2 Hz, 1 H, CH$_2$OH), 2.55 (dd, J=14.7, 10.4 Hz, 1 H, CH$_2$COO), 2.48 (bs, 1 H, OH), 2.45 (dd, J=14.7, 3.2 Hz, 1 H, CH$_2$COO), 2.14–2.07 (m, 1 H, CH$_2$CH(O)CHCH$_2$), 2.11 (s, 3 H, CH=CCH$_3$), 1.91 (ddd, J=15.1, 8.1, 8.1 Hz, 1 H, CH$_2$CH(O)CHCH$_2$), 1.78–1.66 (m, 2 H, CH$_2$CH(O) CHCH$_2$), 1.52–1.38 (m, 5 H), 1.36 (s, 3 H C(CH$_3$)$_2$), 1.18 (d, 3 H, J=6.8 Hz, CH$_3$CH(C=O)), 1.10 (s, 3 H, C(CH$_3$)$_2$), 1.01 (d, J=7.0 Hz, 3 H, CH$_3$CHCH$_2$); $^{13}$C NMR (150.9 MHz, CDCl$_3$) d 220.0, 170.6, 169.9, 152.3, 137.6, 119.8, 117.0, 76.7, 74.8, 73.6, 62.3, 57.5, 54.4, 52.7, 43.6, 38.9, 36.2, 31.4, 30.4, 27.0, 23.7, 21.3, 21.0, 17.2, 15.6, 14.3; HRMS (FAB), calcd for $C_{26}H_{39}NO_7S$ (M+H$^+$) 510.2525, found 510.2539.

cis-Macrolactone 18a as illustrated in FIG. 3. A solution of vinyl iodide 7 (5.0 mg, 0.010 mmol, 1.0 equiv), stannane 8a (7.4 mg, 0.020 mmol, 2.0 equiv) and Pd(PPh$_3$)$_4$ (2.0 mg, 0.002 mmol, 0.1 equiv) in degassed toluene (200 mL, 0.1 M) was heated at 90° C. for 15 min according to the procedure described for the synthesis of macrolactone 18h, to yield, after preparative thin layer chromatography (250 mm silica gel plate, 75% ether in hexanes), macrolactone 18a (4.8 mg, 82%). R$_f$=0.30 (silica gel, 75% ether in hexanes); [a]$^{22}$D −34.0 (c 0.20, CHCl$_3$); IR (thin film) n$_{max}$ 3455 (br), 2921, 2852, 1733, 1688, 1461, 1370, 1245, 1046, 756 cm$^{-1}$; $^1$H NMR (500 MHz, CDCl$_3$) d 6.99 (s, 1 H, ArH), 6.61 (s, 1 H, CH=CCH$_3$), 5.45 (ddd, J=10.5, 10.5, 4.5 Hz, 1 H, CH=CHCH$_2$), 5.39 (ddd, J=10.5, 10.5, 4.5 Hz, 1 H, CH=CHCH$_2$), 5.29 (d, J=10.5, 2.5 Hz, 1 H, CHOCO), 4.26 (dd, J=10.5, 2.5 Hz, 1 H, (CH$_3$)$_2$CCHOH), 4.07 (t, J=6.5 Hz, 1 H, CH$_2$OAc), 3.75–3.72 (m, 1 H, CHOH(CHCH$_3$)), 3.42 (bs, 1 H, OH), 3.14 (qd, J=7.0, 2.5 Hz, 1 H, CH$_3$CH(C=O)), 2.99 (t, J=7.5 Hz, 2 H, ArCH$_2$), 2.70 (ddd, J=15.0, 10.0, 10.0 Hz, 1 H, CH=CHCH$_2$), 2.50 (dd, J=15.0, 11.5 Hz, 1 H, CH$_2$COO), 2.34 (dd, J=15.0, 2.5 Hz, 1 H, CH$_2$COO), 2.31–2.24 (m, 2 H), 2.25–2.18 (m, 2 H), 1.90–1.20 (m, 3 H), 2.10 (s, 3 H, CH=CCH$_3$), 1.85 (tt, J=8.0, 6.5 Hz, 2 H, CH$_2$CH$_2$O), 1.68 (tt, J=7.5, 7.0 Hz, 2 H, CH$_2$(CH$_2$)$_2$O), 1.48 (tt, J=8.0, 7.0 Hz, 2 H, CH$_2$(CH$_2$)$_2$O), 1.34 (s, 3 H, C(CH$_3$)$_2$), 1.19 (d, J=7.0 Hz, 3 H, CH$_3$CH(C=O)), 1.09 (s, 3 H, C(CH$_3$)$_2$), 1.01 (d, J=7.5 Hz, 3 H, CH$_3$CHCH$_2$); $^{13}$C NMR (125.7 MHz, CDCl$_3$) d 220.6, 171.2, 170.4, 152.0, 138.6, 133.4, 132.1, 125.1, 119.4, 115.4, 78.5, 74.1, 72.3, 64.2, 53.4, 41.6, 39.3, 38.6, 33.1, 32.4, 31.8, 29.7, 29.4, 28.2, 276, 27.5, 25.4, 22.7, 18.5, 15.9, 15.5, 13.5; HRMS (FAB), calcd for $C_{25}H_{37}NO_5S$ (M+Cs$^+$) 724.2284, found 724.2310.

trans-Macrolactone 19a as illustrated in FIG. 3. A solution of vinyl iodide 11 (5.0 mg, 0.010 mmol, 1.0 equiv), stannane 8a (7.4 mg, 0.020 mmol, 2.0 equiv) and Pd(PPh$_3$)$_4$ (2.0 mg, 0.001 mmol, 0.1 equiv) in degassed toluene (200 mL, 0.1 M) was heated at 100° C. for 15 min according to the procedure described for the synthesis of lactone 18h, to yield, after preparative thin layer chromatography (250 mm silica gel plate, 75% ether in hexanes), lactone 19a (4.9 mg, 84%). R$_f$=0.25 (silica gel, 75% ether in hexanes); [a]$^{22}$D −14.6 (c 0.50, CDCl$_3$); IR (thin film) n$_{max}$ 3483 (br), 2925, 2855, 1733, 1691, 1462, 1369, 1245, 1042, 976 cm$^{-1}$; $^1$H NMR (500 MHz, CDCl$_3$) d 7.00 (s, 1 H, ArH), 6.57 (s, 1 H, CH=C(CH$_3$)), 5.53 (ddd, J=15.0, 7.5, 7.5 Hz, 1 H, CH=CHCH$_2$), 5.40 (dd, J=6.0, 6.0 Hz, 1 H, CHOCO), 5.39 (ddd, J=15.0, 7.5, 7.5 Hz, 1 H, CH=CHCH$_2$), 4.18 (dd, J=10.5, 2.5, 2.5 Hz, 1 H, (CH$_3$)$_2$CCH(OH)), 4.07 (t, J=7.0 Hz, 2 H, CH$_2$OAc), 3.76–3.73 (m, 1 H, CHOH(CHCH$_3$)), 3.26–3.22 (m, 1 H), 3.24 (qd, J=7.0, 2.0 Hz, 1 H, CH$_3$CH (C=O)), 3.00 (t, J=8.0 Hz, 2 H, CH$_2$OAr), 2.70 (bs, 1 H, OH), 2.56 (dd, J=15.5, 10.5 Hz, 1 H, CH$_2$COO), 2.48–2.44 (m, 2 H), 2.47 (dd, J=15.5, 2.5 Hz, 1 H, CH$_2$COO), 2.22–2.14 (m, 1 H), 2.09 (s, 3 H, CH=CCH$_3$), 2.05 (s, 3 H, COCH$_3$), 2.02–1.94 (m, 1 H), 1.83 (tt, J=8.0, 7.5 Hz, 2 H, OCH$_2$CH$_2$), 1.70–1.20 (m, 4 H), 1.69 (tt, J=7.0, 6.5 Hz, 2 H, ArCH$_2$CH$_2$), 1.48 (tt, J=7.5, 6.5 Hz, 2 H, Ar(CH$_2$)$_2$CH$_2$), 1.30 (s, 3 H, C(CH$_3$)$_2$), 1.19 (d, J=7.0 Hz, 3 H, CH$_3$CH (C=O)), 1.08 (s, 3 H, C(CH$_3$)$_2$), 0.99 (d, J=7.0 Hz, 3 H, CH$_3$CHCH$_2$); $^{13}$C NMR (125.7 MHz, CDCl$_3$) d 220.0, 170.6, 169.9, 152.0, 137.1, 134.3, 127.8, 125.8, 119.9, 115.7, 77.8, 75.7, 72.4, 64.2, 52.6, 43.4, 38.8, 37.8, 36.3, 33.2, 32.4, 30.7, 28.3, 27.3, 25.4, 21.0, 20.7, 16.3, 16.1, 15.4, 14.8; HRMS (FAB), calcd for C$_{32}$H$_{49}$NO$_7$S (M+Cs$^+$) 724.2284, found 724.2308.

cis-Macrolactone 18b as illustrated in FIG. 3. A solution of vinyl iodide 7 (9.2 mg, 0.018 mmol, 1.0 equiv), stannane 8b (10.7 mg, 0.036 mmol, 2.0 equiv) and Pd(PPh$_3$)$_4$ (2.1 mg, 0.0018 mmol, 0.1 equiv) in degassed toluene (180 mL, 0.1 M) was heated at 100° C. for 40 min, according to the procedure described for the synthesis of lactone 18h, to yield, after preparative thin layer chromatography (250 mm silica gel plate, 75% ether in hexanes), macrolactone 18b (4.1 mg, 44%). R$_f$=0.50 (silica gel, 50% EtOAc in hexanes); [a]$^{22}$D −38.6 (c 0.21, CHCl$_3$); IR (thin film) n$_{max}$ 3444, 2925, 1732, 1682, 1259, 1037, 756 cm$^{-1}$; $^1$H NMR (500 MHz, CDCl$_3$) d 6.99 (s, 1 H, CH=C(CH$_3$)), 6.52 (bs, 1 H, ArH), 5.45 (ddd, J=10.5, 10.5, 4.0 Hz, 2 H, CH=CHCH$_2$), 5.39 (ddd, J=10.5, 10.5, 4.0 Hz, 1 H, CH=CHCH$_2$), 5.29 (d, J=8.0 Hz, 1 H, CHOCO), 4.20 (ddd, J=11.0, 5.5, 2.5 Hz, 1 H, (CH$_3$)$_2$CCH(OH)), 3.75–3.73 (m, 1 H, CHOH(CHCH$_3$)), 3.13 (qd, J=6.5, 2.0 Hz, 1 H, CH$_3$CH(C=O)), 2.98 (d, J=2.0 Hz, 1 H, CHOH(CHCH$_3$)), 2.93 (d, J=5.5 Hz, 1 H, (CH$_3$)$_2$CCH(OH)), 2.71 (ddd, J=15.0, 10.0, 10.0 Hz, 1 H, CH=CHCH$_2$), 2.70 (s, 3 H, SCH$_3$), 2.51 (dd, J=15.5, 11.5 Hz, 1 H, CH$_2$COO), 2.30 (dd, J=15.0, 2.5 Hz, 1 H, CH$_2$COO), 2.28–2.16 (m, 2 H), 2.13 (d, J=1.0 Hz, 3 H, CH=CCH$_3$), 2.06–1.98 (m, 1 H), 1.79–1.60 (m, 2 H), 1.40–1.06 (m, 3 H), 1.33 (s, 3 H, C(CH$_3$)$_2$), 1.19 (d, J=7.0 Hz, 3 H, CH$_3$CH(C=O)), 1.09 (s, 3 H, C(CH$_3$)$_2$), 1.00 (d, J=7.0 Hz, 3 H, CH$_3$CHCH$_2$); $^{13}$C NMR (125.7 MHz, CDCl$_3$) d 220.4, 170.4, 165.7, 152.7, 138.6, 133.5, 124.9, 119.1, 115.9, 78.8, 74.1, 72.6, 53.2, 41.8, 39.2, 38.6, 32.5, 31.7, 27.6, 27.5, 22.6, 19.0, 16.7, 15.6, 15.6, 13.5; HRMS (FAB), calcd for C$_{26}$H$_{39}$NO$_5$S$_2$ (M+Cs$^+$) 642.1324, found 642.1345.

trans-Macrolactone 19b as illustrated in FIG. 3. A solution of vinyl iodide 11 (6.9 mg, 0.014 mmol, 1.0 equiv), stannane 8b (8.2 mg, 0.028 mmol, 2.0 equiv) and Pd(PPh$_3$)$_4$ (1.6 mg, 0.0014 mmol, 0.1 equiv) in degassed toluene (140 mL, 0.1 M) was heated at 100° C. for 40 min, according to the procedure described for the synthesis of lactone 18h, to yield, after preparative thin layer chromatography (250 mm silica gel plate, 75% ether in hexanes), macrolactone 19b (5.0 mg, 72%). R$_f$=0.47 (silica gel, 50% EtOAc in hexanes); [a]$^{22}$D −32.9 (c 0.35, CDCl$_3$); IR (film) n$_{max}$ 3488, 2928, 1728, 1692, 1259, 1036, 800, 757 cm$^{-1}$; $^1$H NMR (500 MHz, CDCl$_3$) d 7.00 (s, 1 H, ArH), 6.48 (s, 1 H, CH=CCH$_3$), 5.53 (ddd, J=15.0, 7.5, 7.5 Hz, 1 H, CH=CHCH$_2$), 5.40 (d, J=8.0 Hz, 1 H, CHOCO), 5.39 (ddd, J=15.0, 7.5, 7.5 Hz, 1 H, CH=CHCH$_2$), 4.12 (ddd, J=11.0, 2.5, 2.5 Hz, 1 H, (CH$_3$)$_2$CCHOH), 3.77–3.74 (m, 1 H, CHOH(CHCH$_3$)), 3.24 (m, 1 H, CH=CHCH$_2$), 3.07 (m, 1 H, CH$_3$CH(C=O)), 2.70 (s, 3 H, SCH$_3$), 2.61 (d, J=3.5 Hz, 1 H, CHOH(CHCH$_3$)), 2.59–2.44 (m, 5 H), 2.19–2.12 (m, 1 H), 2.13 (s, 3 H, CH=CCH$_3$), 2.02–1.94 (m, 1 H), 1.70–1.55 (m, 2 H), 1.48–1.41 (m, 1 H), 1.29 (s, 3 H, C(CH$_3$)$_2$), 1.18 (d, J=7.0 Hz, 3 H, CH$_3$CH(C=O)), 1.08 (s, 3 H, C(CH$_3$)$_2$), 0.99 (d, J=7.0 Hz, 3 H, CH$_3$CHCH$_2$); $^{13}$C NMR (125.7 MHz, CDCl$_3$) d 220.0, 170.6, 165.6, 152.8, 137.5, 134.3, 125.9, 119.4, 116.2, 78.0, 75.6, 72.6, 52.5, 43.4, 38.7, 37.8, 36.5, 32.4, 30.6, 27.3, 21.4, 20.6, 16.7, 16.3, 15.5, 14.7; HRMS (FAB), calcd for C$_{26}$H$_{39}$NO$_5$S$_2$ (M+Cs$^+$) 642.1324, found 642.1298.

cis-Macrolactone 18c as illustrated in FIG. 3. A solution of vinyl iodide 7 (7.0 mg, 0.014 mmol, 1.0 equiv), stannane 8c (9.2 mg, 0.028 mmol, 2.0 equiv) and Pd(PPh$_3$)$_4$ (0.8 mg, 0.0007 mmol, 0.05 equiv) in degassed toluene (140 mL, 0.1 M) was heated at 100° C. for 40 min according to the procedure described for the synthesis of macrolactone 18h, to yield, after preparative thin layer chromatography (250 mm silica gel plate, 75% ether in hexanes) macrolactone 18c (5.4 mg, 72%). R$_f$=0.32 (silica gel, 50% EtOAc in hexanes); [a]$^{22}$D −48.5 (c 0.40, CHCl$_3$); IR (thin film) n$_{max}$ 3452, 2930, 2857, 1731, 1685, 1531, 1451, 1256 cm$^{-1}$; $^1$H NMR (500 MHz, CDCl$_3$) d 6.36 (bs, 1 H, ArH), 6.35 (s, 1 H, CH=C(CH$_3$)), 5.41 (ddd, J=11.0, 11.0, 5.0 Hz, 1 H, CH=CHCH$_2$), 5.39 (ddd, J=11.0, 11.0, 5.0 Hz, 1 H, CH=CHCH$_2$), 5.23 (d, J=9.5 Hz, 1 H, CHOCO), 4.27 (d, J=10.5 Hz, 1 H, (CH$_3$)$_2$CCH(OH)), 3.73–3.72 (m, 1 H, CHOH(CHCH$_3$)), 3.60 (bs, 1 H, OH), 3.45 (bt, 4 H, J=5.5 Hz, CH$_2$(CH$_2$CH$_2$)$_2$N), 3.14 (qd, J=7.0, 2.0 Hz, 1 H, CH$_3$CH (C=O)), 3.11 (bs, 1 H, OH), 2.67 (ddd, J=15.5, 10.0, 10.0 Hz, 1 H, CH=CHCH$_2$), 2.47 (dd, J=15.0, 2.5 Hz, 1 H, CH$_2$COO), 2.30 (dd, J=15.5, 2.5 Hz, 1 H, CH$_2$COO), 2.28–2.17 (m, 2 H), 2.10 (d, J=1.0 Hz, 3 H, CH=CCH$_3$), 2.06–1.97 (m, 1 H), 1.80–1.60 (m, 2 H), 1.70–1.56 (m, 6 H, CH$_2$(CH$_2$CH$_2$)$_2$N), 1.39–1.08 (m, 3 H), 1.32 (s, 3 H, C(CH$_3$)$_2$), 1.18 (d, J=6.5 Hz, 3 H, CH$_3$CH(C=O)), 1.07 (s, 3 H, C(CH$_3$)$_2$), 1.00 (d, J=7.5 Hz, 3 H, CH$_3$CHCH$_2$); $^{13}$C NMR (125.7 MHz, CDCl$_3$) d 220.7, 170.9, 170.4, 148.8, 137.8, 133.2, 125.3, 119.9, 105.0, 78.7, 74.0, 72.3, 55.6, 49.6, 41.5, 39.5, 38.5, 32.4, 31.9, 27.6, 27.4, 25.1, 24.1, 22.9, 18.3, 15.8, 15.5, 13.4; HRMS (FAB), calcd for C$_{30}$H$_{47}$N$_2$O$_5$S (M+H$^+$) 547.3206, found 547.3187.

trans-Macrolactone 19c as illustrated in FIG. 3. A solution of vinyl iodide 11 (6.0 mg, 0.012 mmol, 1.0 equiv), stannane 8c (7.9 mg, 0.024 mmol, 2.0 equiv) and Pd(PPh$_3$)$_4$ (0.7 mg, 0.0006 mmol, 0.05 equiv) in degassed toluene (120 mL, 0.1 M) was heated at 100° C. for 40 min, according to the procedure described for the synthesis of macrolactone 18h, to yield, after preparative thin layer chromatography (250 mm silica gel plate, 75% ether in hexanes), macrolactone 19c (2.9 mg, 44%). R$_f$=0.56 (silica gel, 50% EtOAc in hexanes); [a]$^{22}$D −23.8 (c 0.21, CHCl$_3$); IR (film) n$_{max}$ 3421, 2928, 2856, 1729, 1692, 1531, 1450, 1256 cm$^{-1}$; $^1$H NMR (500 MHz, CDCl$_3$) d 6.37 (s, 1 H, CH=CCH$_3$), 6.31 (s, 1 H, ArH), 5.51 (ddd, J=15.0, 7.0, 7.0 Hz, 1 H, CH=CHCH$_2$), 5.40 (ddd, J=15.0, 7.0, 7.0 Hz, 1 H, CH=CHCH$_2$), 5.38 (dd, J=8.0, 3.0 Hz, 1 H, CHOCO), 4.12 (ddd, J=6.0, 2.5, 2.5 Hz, 1 H, (CH$_3$)$_2$CCHOH), 3.76 (q, J=3.5 Hz, 1 H, CHOH (CHCH$_3$)), 3.45 (bt, 4 H, J=5.5 Hz, CH$_2$(CH$_2$CH$_2$)$_2$N), 3.30 (d, J=4.0 Hz, 1 H, CH$_3$CH(C=O)), 3.25–3.20 (m, 1 H, CH=CHCH$_2$), 2.61 (d, J=3.5 Hz, 1 H, CHOH(CHCH$_3$)), 2.54 (dd, J=15.0, 10.5 Hz, 1 H, CH$_2$COO), 2.49–2.41 (m, 4 H), 2.18–2.13 (m, 1 H), 2.13 (d, J=1.5 Hz, 3 H, CH=CCH$_3$), 2.02–1.93 (m, 2 H), 1.69–1.65 (m, 6 H, CH$_2$(CH$_2$CH$_2$)$_2$N), 1.48–1.43 (m, 3 H), 1.29 (s, 3 H, C(CH$_3$)$_2$), 1.18 (d, J=7.0 Hz, 3 H, CH$_3$CH(C=O)), 1.07 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 220.2, 170.6, 149.3, 135.9, 134.0, 126.1, 120.7, 105.9, 78.2, 75.4, 72.4, 55.7, 49.5, 43.2, 38.8, 38.0, 36.5, 32.4, 30.9, 29.9, 27.4, 25.1, 24.1, 20.8, 16.1, 15.2, 14.6; HRMS (FAB), calcd for C$_{30}$H$_{47}$N$_2$O$_5$S (M+H$^+$) 547.3206, found 547.3222.

cis-Macrolactone 18d as illustrated in FIG. 3. A solution of vinyl iodide 7 (14 mg, 0.028 mmol, 1.0 equiv), stannane 8d (14 mg, 0.055 mmol, 2.0 equiv) and PdCl$_2$(MeCN)$_2$ (2.0 mg, 0.008 mmol, 0.3 equiv) in degassed DMF (280 mL, 0.1 M) was stirred at 25° C. for 20 h. The resulting mixture was then concentrated under reduced pressure, filtered through silica, eluting with EtOAc, and purified by preparative thin layer chromatography (250 mm silica gel plate, 50% ether in hexanes) to furnish macrolactone 18d (12.5 mg, 89%). $R_f$=0.30 (silica gel, 66% ether in hexanes); $[a]^{22}D$ −70.2 (c 0.63, $CDCl_3$); IR (thin film) $n_{max}$ 3501 (br), 2934, 1732, 1688, 1526, 1472, 1386, 1232, 1150, 1091, 1007 cm$^{-1}$; $^1H$ NMR (500 MHz, $CDCl_3$) d 6.47 (s, 1 H, ArH), 6.33 (s, 1 H, CH=C($CH_3$)), 5.43 (ddd, J=10.5, 10.5, 3.5 Hz, 1 H, CH=CH$CH_2$), 5.37 (ddd, J=10.5, 10.5, 4.5 Hz, 1 H, CH=CH$CH_2$), 5.26 (dd, J=9.5, 1.5 Hz, 1 H, CHOCO), 4.44 (q, J=7.0 Hz, 2 H, $CH_3CH_2O$), 4.18 (ddd, J=11.0, 5.5, 2.5 Hz, 1 H, ($CH_3$)$_2$CCH(OH)), 3.73 (m, 1 H, CHOH(CH$CH_3$)), 3.12 (qd, J=7.0, 2.0 Hz, 1 H, $CH_3$CH(C=O)), 2.98 (d, J=1.5 Hz, 1 H, OH), 2.95 (d, J=5.5 Hz, 1 H, OH), 2.69 (ddd, J=15.0, 10.0, 10.0 Hz, 1 H, CH=CH$CH_2$CHO), 2.49 (dd, J=15.5, 11.5 Hz, 1 H, $CH_2$COO), 2.36 (dd, J=15.5, 2.5 Hz, 1 H, $CH_2$COO), 2.23–2.16 (m, 3 H), 2.11 (s, 3 H, CH=C($CH_3$)), 2.04–1.98 (m, 1 H), 1.77–1.71 (m, 1 H), 1.70–1.61 (m, 1 H), 1.42 (t, J=7.0 Hz, 3 H, $CH_3CH_2O$), 1.38–1.16 (m, 2 H), 1.31 (s, 3 H, C($CH_3$)$_2$), 1.17 (d, J=7.0 Hz, 3 H, $CH_3$CH(C=O)), 1.08 (s, 3 H, C($CH_3$)$_2$), 0.99 (d, J=7.0 Hz, 3 H, $CH_3$CH$CH_2$); $^{13}C$ NMR (100.6 MHz, $CDCl_3$) d 220.3, 173.4, 170.4, 146.7, 137.6, 133.4, 125.0, 119.8, 109.1, 79.0 74.1, 72.6, 67.7, 53.1, 41.8, 39.2, 38.5, 32.5, 31.7, 27.5, 27.5, 22.6, 19.1, 15.6, 15.3, 14.5, 13.5; HRMS (FAB), calcd for $C_{27}H_{41}NO_6S$ (M+Cs$^+$) 640.1709, found 640.1732.

trans-Macrolactone 19d as illustrated in FIG. 3. A solution of vinyl iodide 11 (14 mg, 0.028 mmol, 1.0 equiv), stannane 8d (23 mg, 0.055 mmol, 2.0 equiv) and $PdCl_2(MeCN)_2$ (2.0 mg, 0.008 mmol, 0.3 equiv) in degassed DMF (280 mL, 0.1 M) was stirred at 25° C. for 20 h, according to the procedure described for the synthesis of macrolactone 18d to yield, after preparative thin layer chromatography (250 mm silica gel plate, 50% EtOAc in hexanes), macrolactone 19d (12 mg, 86%). $R_f$=0.27 (silica gel, 66% ether in hexanes); $[a]^{22}D$ −28.0 (c 0.48, $CHCl_3$); IR (thin film) $n_{max}$ 3495 (br), 2930, 1732, 1690, 1526, 1472, 1233, 1017, 976 cm$^{-1}$; $^1H$ NMR (500 MHz, $CDCl_3$) d 6.50 (s, 1 H, ArH), 6.30 (s, 1 H, CH=C($CH_3$)), 5.57–5.51 (m, 1 H, CH=CH$CH_2$), 5.42–5.36 (m, 1 H, CH=CH$CH_2$), 5.37 (dd, J=9.0, 2.5 Hz, 1 H, CHOCO), 4.46 (q, J=7.0 Hz, 2 H, $CH_3CH_2O$), 4.10 (ddd, J=10.5, 3.5, 3.0 Hz, 1 H, ($CH_3$)$_2$CCH(OH)), 3.76–3.73 (m, 1 H, CHOH(CH$CH_3$)), 3.23 (qd, J=7.0, 4.5 Hz, 1 H, $CH_3$CH(C=O)), 3.07 (d, J=3.5 Hz, 1 H, OH), 2.57–2.38 (m, 3 H), 2.56 (dd, J=15.5, 10.5 Hz, 1 H, $CH_2$COO), 2.47 (dd, J=15.5, 2.5 Hz, 1 H, $CH_2$COO), 2.18–2.16 (m, 1 H), 2.13 (s, 3 H, CH=C($CH_3$)), 2.03–1.94 (m, 1 H), 1.70–1.55 (m, 2 H), 1.48–1.41 (m, 1 H), 1.44 (t, J=7.0 Hz, 3 H, $CH_3CH_2O$), 1.29 (s, 3 H, C($CH_3$)$_2$), 1.27–1.16 (m, 1 H), 1.18 (d, J=7.0 Hz, 3 H, $CH_3$CH(C=O)), 1.08 (s, 3 H, C($CH_3$)$_2$), 0.98 (d, J=7.0 Hz, 3 H, $CH_3$CH$CH_2$); $^{13}C$ NMR (100.6 MHz, $CDCl_3$) d 220.0, 173.3, 170.6, 146.8, 136.4, 134.1, 126.1, 120.2, 109.5, 78.3 75.5, 72.6, 67.7, 52.4, 43.4, 38.7, 37.8, 36.6, 32.4, 30.7, 27.4, 21.2, 20.5, 16.2, 15.0, 14.7, 14.5; HRMS (FAB), calcd for $C_{27}H_{41}NO_6S$ (M+Cs$^+$) 640.1709, found 640.1731.

cis-Macrolactone 18e as illustrated in FIG. 3. A solution of vinyl iodide 7 (5.1 mg, 0.010 mmol, 1.0 equiv), tri-n-butylstannane 8e$^{16}$ (7.5 mg, 0.020 mmol, 2.0 equiv) and $Pd(PPh_3)_4$ (1.1 mg, 0.001 mmol, 0.10 equiv) in degassed toluene (100 mL, 0.1 M) were heated at 100° C. for 20 min, according to the procedure described for the synthesis of macrolactone 18h, to yield, after preparative thin layer chromatography (500 mm silica gel plate, 50% EtOAc in hexanes), macrolactone 18e (3.2 mg, 70%). $R_f$=0.42 (silica gel, 50% EtOAc in hexanes); $[a]^{22}D$ −30.4 (c 0.35, $CHCl_3$); IR (thin film) $n_{max}$ 3438 (br), 2927, 2857, 1730, 1688, 1463, 1383, 1294, 1254, 1151, 1090, 1050, 980, 756 cm$^{-1}$; $^1H$ NMR (500 MHz, $CDCl_3$) d 8.79 (d, J=2.0 Hz, 1 H, NCHS), 7.20 (d, J=2.0 Hz, 1 H, NCHC), 6.70 (s, 1 H, CH=C($CH_3$)), 5.46 (ddd, J=10.5, 10.5, 4.0 Hz, 1 H, CH=CH$CH_2$), 5.39 (ddd, J=10.5, 10.5, 5.0 Hz, 1 H, CH=CH$CH_2$), 5.33 (dd, J=9.5, 1.5 Hz, 1 H, CHOCO), 4.22 (dd, J=11.5, 2.5 Hz, 1 H, ($CH_3$)$_2$CCH(OH)), 3.75–3.73 (m, 1 H, CHOH(CH$CH_3$)), 3.14 (qd, J=7.0, 2.0 Hz, 1 H, $CH_3$CH(C=O)), 3.05 (d, J=5.5 Hz, 1 H, $CH_3$CHCH(OH)CH$CH_3$), 3.00 (s, 1 H, C($CH_3$)$_2$CHOH), 2.73 (ddd, J=15.0, 9.5, 9.5 Hz, 1 H, =CHCH$_2$CHO), 2.51 (dd, J=15.5, 11.5 Hz, 1 H, $CH_2$COO), 2.38 (dd, J=15.5, 2.5 Hz, 1 H, $CH_2$COO), 2.31–2.24 (m, 1 H, =CHCH$_2$CHO), 2.24–2.16 (m, 1 H), 2.13 (s, 3 H, CH=C$CH_3$), 2.07–1.99 (m, 1 H), 1.81–1.73 (m, 1 H), 1.71–1.61 (m, 1 H), 1.41–1.16 (m, 3 H), 1.33 (s, 3 H, C($CH_3$)$_2$), 1.19 (d, J=7.0 Hz, 3 H, $CH_3$CH(C=O)), 1.09 (s, 3 H, C($CH_3$)$_2$), 1.00 (d, J=7.0 Hz, 3 H, $CH_3$CH$CH_2$); $^{13}C$ NMR (125.7 MHz, $CDCl_3$) d 220.5, 170.4, 153.4, 152.0, 138.8, 133.5, 124.9, 119.2, 116.2, 78.6, 74.1, 72.6, 53.2, 41.8, 39.2, 38.6, 32.5, 31.7, 27.6, 27.5, 22.6, 18.9, 15.7, 15.5, 13.5; HRMS (FAB), calcd for $C_{25}H_{37}NO_5S$ (M+Cs$^+$) 596.1447, found 596.1430.

trans-Macrolactone 19e as illustrated in FIG. 3. A solution of vinyl iodide 11 (5.1 mg, 0.010 mmol, 1.0 equiv), tri-n-butylstannane 8e$^{16}$ (7.5 mg, 0.020 mmol, 2.0 equiv) and $Pd(PPh_3)_4$ (1.1 mg, 0.002 mmol, 0.10 equiv) in degassed toluene (100 mL, 0.1 M) was heated at 100° C. for 20 min, according to the procedure described for the synthesis of macrolactone 18h, to yield, after preparative thin layer chromatography (500 mm silica gel plate, 50% EtOAc in hexanes), macrolactone 19e (3.4 mg, 74%). $R_f$=0.47 (silica gel, 50% EtOAc in hexanes); $[a]^{22}D$ −34.9 (c 0.35, $CDCl_3$); IR (thin film) $n_{max}$ 3437 (br), 2928, 2858, 1728, 1692, 1464, 1379, 1253, 1151, 1045, 975, 756 cm$^{-1}$; $^1H$ NMR (500 MHz, $CDCl_3$) d 8.80 (d, J=1.5 Hz, 1 H, NCHS), 7.21 (d, J=1.5 Hz, 1 H, NCHC), 6.66 (s, 1 H, CH=C($CH_3$)), 5.53 (ddd, J=14.5, 7.0, 7.0 Hz, 1 H, CH=CH$CH_2$), 5.42 (dd, J=5.5, 5.5 Hz, 1 H, CHOCO), 5.39 (ddd, J=14.5, 7.0, 7.0 Hz, 1 H, CH=CH$CH_2$), 4.19 (ddd, J=10.0, 3.5, 2.5 Hz, 1 H, ($CH_3$)$_2$CCH(OH)), 3.74 (dd, J=6.5, 3.5 Hz, 1 H, CHOH (CH$CH_3$)), 3.26 (qd, J=7.0, 6.5 Hz, 1 H, $CH_3$CH(C=O)), 3.08 (d, J=3.5 Hz, 1 H, OH), 2.71 (d, J=3.5 Hz, 1 H, OH), 2.57 (dd, J=15.0, 10.0 Hz, 1 H, $CH_2$COO), 2.52–2.44 (m, 2 H, =CHCH$_2$CHO), 2.50 (dd, J=15.0, 2.5 Hz, 1 H, $CH_2$COO), 2.22–2.14 (m, 1 H), 2.12 (s, 3 H, CH=CC$H_3$), 2.02–1.92 (m, 1 H), 1.69–1.56 (m, 2 H), 1.51–1.43 (m, 1 H), 1.36–1.16 (m, 2 H), 1.29 (s, 3 H, C($CH_3$)$_2$), 1.18 (d, J=7.0 Hz, 3 H, $CH_3$CH(C=O)), 1.07 (s, 3 H, C($CH_3$)$_2$), 0.98 (d, J=7.0 Hz, 3 H, $CH_3$CH$CH_2$); $^{13}C$ NMR (125.7 MHz, $CDCl_3$) d 220.0, 170.4, 153.4, 151.9, 137.7, 134.4, 125.7, 119.5, 116.3, 77.7, 75.8, 72.5, 52.5, 43.6, 38.8, 37.8, 36.3, 32.5, 30.6, 27.3, 21.2, 20.6, 16.4, 15.6, 14.8; HRMS (FAB), calcd for $C_{25}H_{37}NO_5S$ (M+Cs$^+$) 596.1447, found 596.1431.

cis-Macrolactone 18f as illustrated in FIG. 3. A solution of vinyl iodide 7 (5.1 mg, 0.010 mmol, 1.0 equiv), stannane 8f$^{16}$ (7.5 mg, 0.020 mnmol, 2.0 equiv) and $Pd(PPh_3)_4$ (1.1 mg, 0.001 mmol, 0.10 equiv) in degassed toluene (100 mL, 0.1 M) was heated at 100° C. for 20 min, according to the procedure described for the synthesis of macrolactone 18h, to yield, after preparative thin layer chromatography (500 mm silica gel plate, 50% EtOAc in hexanes), macrolactone 18f (3.9 mg, 84%). $R_f$=0.18 (silica gel, 33% EtOAc in hexanes); $[a]^{22}D$ −78.9 (c 0.35, $CHCl_3$); IR (thin film) $n_{max}$ 3380 (br), 2930, 1734, 1687, 1464, 1374, 1297, 1251, 1146, 1054, 1008, 979, 755 cm$^{-1}$; $^1H$ NMR (500 MHz, $CDCl_3$) d 7.80 (d, J=3.5 Hz, 1 H, NCHCHS), 7.34 (d, J=3.5 Hz, 1 H, NCHCHS), 6.90 (s, 1 H, CH=C ($CH_3$)), 5.46 (ddd, J=10.5, 10.0, 4.5 Hz, 1 H, CH=CH$CH_2$), 5.38 (ddd, J=10.5, 10.0, 5.0 Hz, 1 H, CH=CH$CH_2$), 5.32 (d, J=9.5, Hz, 1 H, CHOCO), 4.25 (dd, J=11.0, 2.5 Hz, 1 H, (CH$_3$)$_2$CCH(OH)), 3.73 (d, J=2 Hz, 1 H, CHOH(CHCH$_3$)), 3.23 (bs, 1 H, OH), 3.13 (qd, J=6.5, 2.0 Hz, 1 H, CH$_3$CH(C=O)), 3.01 (bs, 1 H, OH), 2.66 (ddd, J=15.0, 10.0, 10.0 Hz, 1 H, =CHCH$_2$CHO), 2.52 (dd, J=15.5, 11.0 Hz, 1 H, CH$_2$COO), 2.37 (dd, J=15.5, 2.5 Hz, 1 H, CH$_2$COO), 2.34–2.27 (m, 1 H, =CHCH$_2$CHO), 2.25–2.15 (m, 1 H), 2.18 (s, 3 H, CH=CCH$_3$), 2.07–2.00 (m, 1 H), 1.95–1.85 (m, 1 H), 1.80–1.73 (m, 1 H), 1.73–1.63 (m, 1 H), 1.40–1.10 (m, 2 H), 1.34 (s, 3 H, C(CH$_3$)$_2$), 1.19 (d, J=6.5 Hz, 3 H, CH$_3$CH (C=O)), 1.08 (s, 3 H, C(CH$_3$)$_2$), 0.99 (d, J=7.5 Hz, 3 H, CH$_3$CH$_2$); $^{13}$C NMR (125.7 MHz, CDCl$_3$) d 220.5, 170.2, 164.8, 142.6, 142.2, 133.8, 124.6, 119.2, 119.1, 78.0, 74.2, 72.4, 53.3, 41.8, 39.1, 38.6, 32.5, 31.6, 27.5, 27.5, 22.7, 18.7, 16.7, 15.4, 13.6; HRMS (FAB), calcd for C$_{25}$H$_{37}$NO$_5$S (M+Cs$^+$) 596.1447, found 596.1468.

trans-Macrolactone 19f as illustrated in FIG. 3. A solution of vinyl iodide 11 (5.1 mg, 0.010 mmol, 1.0 equiv), stannane 8f[16] (7.1 mg, 0.020 mmol, 2.0 equiv) and Pd(PPh$_3$)$_4$ (1.1 mg, 0.001 mmol, 0.1 equiv) in degassed toluene (100 mL, 0.1 M) was heated at 100° C. for 40 min, according to the procedure described for the synthesis of macrolactone 18h, to yield, after preparative thin layer chromatography (250 mm silica gel plate, 50% EtOAc in hexanes), macrolactone 19f (4.1 mg, 88%). R$_f$=0.42 (silica gel, 50% EtOAc in hexanes); [a]$^{22}$D −53.7 (c 0.35, CDCl$_3$); IR (thin film) n$_{max}$ 3380 (br), 2928, 1732, 1690, 1463, 1373, 1250, 1135, 1053, 1017, 974, 754 cm$^{-1}$; $^1$H NMR (500 MHz, CDCl$_3$) d 7.83 (d, J=3.5 Hz, 1 H, NCHCHS), 7.34 (d, J=3.5 Hz, 1 H, NCHCHS), 6.86 (s, 1 H, CH=C(CH$_3$)), 5.51 (ddd, J=15.0, 7.0, 7.0 Hz, 1 H, CH=CHCH$_2$), 5.41 (dd, J=7.5, 3.5 Hz, 1 H, CHOCO), 5.34 (ddd, J=15.0, 7.0, 7.0 Hz, 1 H, CH=CHCH$_2$), 4.24 (dd, J=10.0, 2.5 Hz, 1 H, (CH$_3$)$_2$CCH (OH)), 3.74 (d, J=4.5 Hz, 1 H, CHOH(CHCH$_3$)), 3.26 (qd, J=7.0, 4.5 Hz, 1 H, CH$_3$CH(C=O)), 3.11 (bs, 1 H, OH), 2.95 (bs, 1 H, OH), 2.57 (dd, J=15.5, 10.0 Hz, 1 H, CH$_2$COO), 2.52–2.40 (m, 2 H, =CHCH$_2$CHO), 2.50 (dd, J=15.5, 2.5 Hz, 1 H, CH$_2$COO), 2.23–2.15 (m, 1 H), 2.17 (s, 3 H, CH=CCH$_3$), 2.00–1.92 (m, 1 H), 1.66–1.58 (m, 2 H), 1.53–1.44 (m, 1 H), 1.38–1.15 (m, 2 H), 1.29 (s, 3 H, C(CH$_3$)$_2$), 1.19 (d, J=7.0 Hz, 3 H, CH$_3$CH(C=O)), 1.07 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 219.9, 170.5, 164.5, 142.7, 141.1, 134.9, 125.1, 119.5, 119.1, 76.9, 76.1, 72.4, 52.5, 43.7, 38.8, 37.6, 35.9, 32.5, 30.5, 27.1, 21.0, 20.8, 16.6, 16.6, 14.9; HRMS (FAB), calcd for C$_{25}$H$_{37}$NO$_5$S (M+Cs$^+$) 596.1447, found 596.1430.

cis-Macrolactone 18g as illustrated in FIG. 3. A solution of vinyl iodide 7 (10 mg, 0.020 mmol, 1.0 equiv), stannane 8g (10 mg, 0.040 mmol, 2.0 equiv) and Pd(PPh$_3$)$_4$ (2.5 mg, 0.002 mmol, 0.1 equiv) in degassed toluene (200 mL, 0.1 M) was heated at 100° C. for 40 min, according to the procedure described for the synthesis of macrolactone 18h, to yield, after preparative thin layer chromatography (250 mm silica gel plate, 50% EtOAc in hexanes), macrolactone 18g (6.5 mg, 73%). R$_f$=0.24 (silica gel, 50% EtOAc in hexanes); [a]$^{22}$D −29.3 (c 0.15, CHCl$_3$); IR (thin film) n$_{max}$ 3224 (br), 2922, 2853, 1721, 1682, 1460, 1254, 1089, 1050, 991, 884, 807, 702 cm$^{-1}$; $^1$H NMR (400 MHz, CDCl$_3$) d 8.74 (s, 1 H, NCHS), 7.82 (s, 1 H, NCHC), 6.75 (s, 1 H, CH=C(CH$_3$)), 5.46 (ddd, J=10.5, 10.5, 3.5 Hz, 1 H, CH=CHCH$_2$), 5.39 (ddd, J=10.5, 10.5, 4.5 Hz, 1 H, CH=CHCH$_2$), 5.34 (dd, J=8.5, 3.5 Hz, 1 H, CHOCO), 4.14–4.08 (m, 1 H, (CH$_3$)$_2$CCH(OH)), 3.76–3.72 (m, 1 H, CHOH(CHCH$_3$)), 3.12 (qd, J=7.0, 2.0 Hz, 1 H, CH$_3$CH(C=O)), 2.87 (bs, OH), 2.73 (ddd, J=15.0, 10.5, 8.5 Hz, 1 H, =CHCH$_2$CHO), 2.52 (dd, J=15.5, 10.5 Hz, 1 H, CH$_2$COO), 2.44 (dd, J=15.5, 3.0 Hz, 1 H, CH$_2$COO), 2.39–2.34 (m, 1 H), 2.26–2.13 (m, 2 H), 2.08–1.95 (m, 2 H), 2.00 (s, 3 H, CH=CCH$_3$), 1.77–1.15 (m, 3 H),1.33 (s, 3 H, C(CH$_3$)$_2$), 1.18 (d, J=7.0 Hz, 3 H, CH$_3$CH(C=O)), 1.09 (s, 3 H, C(CH$_3$)$_2$), 0.99 (d, J=7.0 Hz, 3 H, CH$_3$CHCH$_2$); $^{13}$C NMR (125.7 MHz, CDCl$_3$) d 220.0, 170.2, 152.3, 143.3, 137.0, 133.6, 124.4, 121.4, 116.6, 78.6, 74.1, 72.6, 53.2, 41.8, 39.2, 38.6, 32.5, 31.7, 27.6, 27.5, 22.6, 18.9, 15.7, 15.5, 13.5; HRMS (FAB), calcd for C$_{25}$H$_{37}$NaNO$_5$S (M+Na$^+$) 486.2290, found 486.2278.

trans-Macrolactone 19g as illustrated in FIG. 3. A solution of vinyl iodide 11 (12 mg, 0.024 mmol, 1.0 equiv), stannane 8g (12 mg, 0.047 mmol, 2.0 equiv) and Pd(PPh$_3$)$_4$ (3.0 mg, 0.002 mmol, 0.1 equiv) in degassed toluene (250 mL, 0.1 M) was heated at 100° C. for 40 min, according to the procedure described for the synthesis of macrolactone 18h, to yield, after preparative thin layer chromatography (250 mm silica gel plate, 50% EtOAc in hexanes), macrolactone 19g (8.5 mg, 76%). R$_f$=0.25 (silica gel, 66% EtOAc in hexanes); [a]$^{22}$D −15.9 (c 0.33, CDCl$_3$); IR (film) n$_{max}$ 3419 (br), 2932, 1734, 1728, 1691, 1466, 1375, 1252, 1149, 1043, 1008, 975, 881 cm$^{-1}$; $^1$H NMR (500 MHz, CDCl$_3$) d 8.80 (s, 1 H, NCHS), 7.83 (s, 1 H, NCHC), 6.72 (s, 1 H, CH=CCH$_3$), 5.57 (ddd, J=15.0, 7.5, 6.0 Hz, 1 H, CH=CHCH$_2$), 5.42 (dd, J=9.0, 3.5 Hz, 1 H, CHOCO), 5.38 (ddd, J=15.0, 8.0, 7.0 Hz, 1 H, CH=CHCH$_2$), 4.09 (ddd, J=10.5, 3.5, 3.0 Hz, 1 H, (CH$_3$)$_2$CCHOH), 3.78–3.72 (m, 1 H, CHOH(CHCH$_3$)), 3.23 (qd, J=6.5, 4.5 Hz, 1 H, CH$_3$CH (C=O)), 2.90 (d, J=4.0 Hz, 1 H, OH), 2.58 (dd, J=15.0, 10.5 Hz, 1 H, CH$_2$COO), 2.52 (dd, J=15.0, 3.0 Hz, 1 H, CH$_2$COO), 2.20 (m, 2 H), 2.05–1.94 (m, 1 H), 1.72–1.64 (m, 1 H), 1.64–1.55 (m, 1 H), 1.48–1.37 (m, 1 H), 1.35–1.16 (m, 3 H), 1.30 (s, 3 H, C(CH$_3$)$_2$), 1.19 (d, J=6.5 Hz, 3 H, CH$_3$CH(C=O)), 1.09 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 219.8, 170.5, 152.4, 143.3, 136.7, 134.4, 133.9, 125.7, 116.6, 77.9, 75.3, 72.7, 52.2, 43.4, 38.5, 37.6, 36.7, 32.2, 30.6, 27.2, 21.5, 20.3, 16.1, 15.3, 14.5; HRMS (FAB), calcd for C$_{25}$H$_{37}$NaNO$_5$S (M+Cs$^+$) 486.2290, found 486.2487.

trans-Macrolactone 19h as illustrated in FIG. 3. A solution of vinyl iodide 11 (5.1 mg, 0.010 mmol, 1.0 equiv), stannane 8h (8.0 mg, 0.020 mmol, 2.0 equiv) and Pd(PPh$_3$)$_4$ (1.1 mg, 0.001 mmol, 0.1 equiv) in degassed toluene (100 mL, 0.1 M) was heated at 100° C. for 20 min according to the procedure described for the synthesis of macrolactone 18h, to yield, after preparative thin layer chromatography (500 mm silica gel plate, 50% EtOAc in hexanes), macrolactone 19h (4.3 mg, 88%). R$_f$=0.20 (silica gel, 50% EtOAc in hexanes); [a]$^{22}$D −31.5 (c 0.60, CHCl$_3$); IR (thin film) n$_{max}$ 3410 (br), 2930, 1726, 1692, 1463, 1374, 1255, 1180, 1064, 973 cm$^{-1}$; $^1$H NMR (500 MHz, CDCl$_3$) d 7.13 (s, 1 H, ArH), 6.60 (s, 1 H, CH=C(CH$_3$)), 5.48 (ddd, J=15.0, 7.5, 7.5 Hz, 1 H, CH=CHCH$_2$), 5.40 (dd, J=5.5, 5.5 Hz, 1 H, CHOCO), 5.35 (ddd, J=15.0, 7.5, 7.5 Hz, 1 H, CH=CHCH$_2$), 4.91 (d, J=7.0 Hz, 2 H, CH$_2$OH), 4.23 (ddd, J=9.5, 3.5, 3.0 Hz, 1 H, (CH$_3$)$_2$CCH(OH)), 3.74 (ddd, J=7.0, 5.0, 2.5 Hz, 1 H, CHOH(CHCH$_3$)), 3.34 (t, J=7.0 Hz, 1 H, CH$_2$OH), 3.26 (qd, J=7.0, 7.0 Hz, 1 H, CH$_3$CH(C=O)), 3.05 (d, J=3.5 Hz, 1 H, C(CH$_3$)$_2$CHOH), 3.00 (d, J=5.0 Hz, 1 H, CH$_3$CHCH(OH) CHCH$_3$), 2.56 (dd, J=15.5, 9.5 Hz, 1 H, CH$_2$COO), 2.47 (dd, J=15.5, 3.0 Hz, 1 H, CH$_2$COO), 2.58–2.45 (m, 1 H, =CHCH$_2$CH), 2.24–2.16 (m, 1 H, =CHCH$_2$CH), 2.08 (s, 3 H, CH=CCH$_3$), 1.98–1.90 (m, 1 H), 1.63–1.56 (m, 2 H), 1.54–1.46 (m, 1 H), 1.41–1.30 (m, 1 H), 1.27 (s, 3 H, C(CH$_3$)$_2$), 1.20 (d, J=7.0 Hz, 3 H, CH$_3$CH(C=O)), 1.07 (s, 3 H, C(CH$_3$)$_2$), 0.99 (d, J=7.0 Hz, 3 H, CH$_3$CHCH$_2$); $^{13}$C NMR (125.7 MHz, CDCl$_3$) d 219.6, 170.4, 169.7, 158.1, 152.4, 137.5, 134.7, 125.3, 116.3, 76.8, 76.3, 72.2, 61.8, 53.5, 44.0, 39.1, 37.6, 35.8, 32.6, 30.2, 27.1, 21.0, 20.9, 16.7, 15.9, 15.1; HEMS (FAB), calcd for $C_{26}H_{39}NO_6S$ (M+Cs$^+$) 626.1552, found 626.1536.

cis-Macrolactone 18i as illustrated in FIG. 3. A solution of vinyl iodide 7 (7.9 mg, 0.016 mmol, 1.0 equiv), stannane 8i (10.0 mg, 0.031 mmol, 2.0 equiv) and Pd(PPh$_3$)$_4$ (1.8 mg, 0.002 mmol, 0.1 equiv) in degassed toluene (150 mL, 0.1 M) was heated at 100° C. for 40 min according to the procedure described for the synthesis of macrolactone 18h, to yield, after preparative thin layer chromatography (250 mm silica gel plate, 50% EtOAc in hexanes), macrolactone 18i (5.0 mg, 60%). R$_f$=0.33 (silica gel, 50% EtOAc in hexanes); [a]$^{22}$D −58.6 (c 0.14, CHCl$_3$); IR (thin film) n$_{max}$ 3466 (br), 2927, 1740, 1687, 1464, 1375, 1224, 1047, 1008, 977 cm$^{-1}$; $^1$H NMR (500 MHz, CDCl$_3$) d 7.15 (m, 1 H, ArH), 6.61 (s, 1 H, CH=C(CH$_3$)), 5.45 (ddd, J=10.5, 10.5, 4.0 Hz, 1 H, CH=CHCH$_2$), 5.41–5.35 (m, 1 H, CH=CHCH$_2$), 5.31–5.29 (m, 1 H, CHOCO), 4.20 (m, 1 H, (CH$_3$)$_2$CCH(OH)), 3.74 (m, 1 H, CHOH(CHCH$_3$)), 3.13 (qd, J=6.5, 2.0 Hz, 1 H, CH$_3$CH(C=O)), 3.03–2.96 (m, 2 H, OH), 2.70 (ddd, J=15.0, 10.0, 10.0 Hz, 1 H, CH=CHCH$_2$CHO), 2.51 (dd, J=15.0, 11.5 Hz, 1 H, CH$_2$COO), 2.38 (dd, J=15.0, 2.5 Hz, 1 H, CH$_2$COO), 2.28–2.23 (m, 1 H), 2.22–2.14 (m, 2 H), 2.16 (s, 3 H, COCH$_3$), 2.11 (s, 3 H, CH=C(CH$_3$)), 2.05–1.98 (m, 1 H), 1.79–1.72 (m, 1 H), 1.71–1.64 (m, 1 H), 1.39–1.15 (m, 2 H), 1.33 (s, 3 H, C(CH$_3$)$_2$), 1.19 (d, J=7.0 Hz, 3 H, CH$_3$CH (C=O)), 1.09 (s, 3 H, C(CH$_3$)$_2$), 1.00 (d, J=7.0 Hz, 3 H, CH$_3$CHCH$_2$); $^{13}$C NMR (100.6 MHz, CDCl$_3$) d 220.5, 170.4, 163.6, 152.7, 139.2, 133.6, 124.9, 119.1, 117.6, 116.5, 78.5, 74.1, 72.5, 62.4, 53.2, 41.8, 39.2, 38.6, 32.5, 31.7, 29.7, 27.5, 27.5, 22.6, 18.8, 15.7, 15.5, 13.5; HRMS (FAB), calcd for $C_{28}H_{41}NO_7S$ (M+Cs$^+$) 668.1658, found 668.1679.

trans-Macrolactone 19i as illustrated in FIG. 3. A solution of vinyl iodide 11 (11.0 mg, 0.022 mmol, 1.0 equiv), stannane 8i (14.0 mg, 0.044 mmol, 2.0 equiv) and Pd(PPh$_3$)$_4$ (2.5 mg, 0.002 mmol, 0.1 equiv) in degassed toluene (210 mL, 0.1 M) was heated at 100° C. for 40 min according to the procedure described for the synthesis of macrolactone 18h, to yield, after preparative thin layer chromatography (250 mm silica gel plate, 50% EtOAc in hexanes), unreacted vinyl iodide 11 (2.5 mg, 36%) and macrolactone 19i (4.5 mg, 39%). R$_f$=0.30 (silica gel, 50% EtOAc in hexanes); [a]$^{22}$D −33.7 (c 0.18, CDCl$_3$); IR (thin film) n$_{max}$ 3497 (br), 2933, 1739, 1694, 1506, 1456, 1374, 1225, 1046, 976 cm$^{-1}$; $^1$H NMR (500 MHz, CDCl$_3$) d 7.16 (s, 1 H, ArH), 6.58 (s, 1 H, CH=C(CH$_3$)), 5.56–5.50 (m, 1 H, CH=CHCH$_2$), 5.41–5.35 (m, 2 H, CH=CHCH$_2$ and CHOCO), 5.36 (s, 1 H, CH$_2$COCH$_3$), 4.15 (dd, J=10.5, 2.5 Hz, 1 H, (CH$_3$)$_2$CCH (OH)), 3.75–3.73 (m, 1 H, CHOH(CHCH$_3$)), 3.24 (qd, J=7.0, 4.5 Hz, 1 H, CH$_3$CH(C=O)), 3.10 (m, 1 H, OH), 2.62 (m, 1 H, OH), 2.56 (dd, J=15.0, 10.5 Hz, 1 H, CH$_2$COO), 2.48 (dd, J=15.0, 3.0 Hz, 1 H, CH$_2$COO), 2.47–2.43 (m, 2 H), 2.20–2.14 (m, 1 H), 2.16 (s, 3 H, COCH$_3$), 2.10 (d, J=1.5 Hz, 3 H, CH=C(CH$_3$)), 2.01–1.94 (m, 1 H), 1.69–1.55 (m, 2 H), 1.49–1.41 (m, 1 H), 1.30–1.15 (m, 2 H), 1.29 (s, 3 H, C(CH$_3$)$_2$), 1.18 (d, J=7.0 Hz, 3 H, CH$_3$CH(C=O)), 1.07 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 220.0, 170.6, 163.6, 152.7, 138.0, 134.4, 125.8, 119.4, 117.7, 116.5, 77.8, 75.7, 72.5, 62.5, 52.5, 43.5, 38.7, 37.8, 36.4, 32.4, 30.7, 29.7, 27.3, 21.1, 20.6, 16.3, 15.6, 14.7; HRMS (FAB), calcd for $C_{28}H_{41}NO_7S$ (M+Cs$^+$) 668.1658, found 668.1681.

cis-Macrolactone 18j as illustrated in FIG. 3. A solution of vinyl iodide 7 (12.5 mg, 0.025 mmol, 1.0 equiv), stannane 8j (20 mg, 0.049 mmol, 2.0 equiv) and PdCl$_2$(MeCN)$_2$ (1.5 mg, 0.006 mmol, 0.2 equiv) in degassed DMF (250 mL, 0.1 M) was stirred at 25° C. for 20 h, according to the procedure described for the synthesis of macrolactone 18d, to yield, after preparative thin layer chromatography (250 mm silica gel plate, 67% ether in hexanes) macrolactone 18j (9 mg, 74%). R$_f$=0.32 (silica gel, 50% EtOA cin hexanes); [a]$^{22}$D −65.3 (c 0.45, CDCl$_3$); IR (thin film) n$_{max}$ 3406 (br), 2924, 2852, 1732, 1682, 1455, 1366, 1263, 1192, 1148, 1096, 1043, 983, 881 cm$^{-1}$; $^1$H NMR (500 MHz, CDCl$_3$) d 7.21 (s, 1 H, ArH), 6.62 (s, 1 H, CH=C(CH$_3$)), 5.60 (d, J=47.0 Hz, 2 H, CH$_2$F), 5.45 (ddd, J=10.5, 10.5, 4.0 Hz, 1 H, CH=CHCH$_2$), 5.38 (ddd, J=10.0, 10.0, 5.0 Hz, 1 H, CH=CHCH$_2$), 5.31 (dd, J=10.0, 1.5 Hz, 1 H, CHOCO), 4.19 (ddd, 1 H, J=11.0, 5.0, 2.5 Hz, 1 H, (CH$_3$)$_2$CCH(OH)), 3.73 (m, 1 H, CHOH(CHCH$_3$)), 3.13 (qd, J=7.0, 2.0 Hz, 1 H, CH$_3$CH(C=O)), 2.97 (d, J=2.0 Hz, 1 H, OH), 2.93 (d, J=5.5 Hz, 1 H, OH), 2.71 (ddd, J=15.0, 10.0, 10.0 Hz, 1 H, CH=CHCH$_2$CHO), 2.51 (dd, J=15.5, 11.5 Hz, 1 H, CH$_2$COO), 2.39 (dd, J=15.5, 2.0 Hz, 1 H, CH$_2$COO), 2.29–2.22 (m, 1 H), 2.22–2.16 (m, 1 H), 2.11 (d, J=1.0 Hz, 3 H, CH=C(CH$_3$)), 2.06–1.99 (m, 1 H), 1.77–1.71 (m, 1 H), 1.69–1.62 (m, 1 H), 1.38–1.16 (m, 3 H), 1.32 (s, 3 H, C(CH$_3$)$_2$), 1.18 (d, J=7.0 Hz, 3 H, CH$_3$CH(C=O)), 1.08 (s, 3 H, C(CH$_3$)$_2$), 1.00 (d, J=7.0 Hz, 3 H, CH$_3$CHCH$_2$); $^{13}$C NMR (100.6 MHz, CDCl$_3$) d 220.4, 160.3, 170.4, 153.0, 139.3, 133.6, 124.8, 119.1, 117.9, 80.5 (d, J=676 Hz) 78.6, 74.1, 72.6, 53.1, 41.9, 39.2, 38.6, 32.5, 31.7, 27.5, 27.5, 22.6, 19.0, 15.6, 15.5, 13.6; HRMS (FAB), calcd for $C_{26}H_{38}FNO_5S$ (M+Cs$^+$) 628.1509, found 628.1530.

trans-Macrolactone 19j as illustrated in FIG. 3. A solution of vinyl iodide 11 (15 mg, 0.030 mmol, 1.0 equiv), stannane 8j (27 mg, 0.066 mmol, 2.2 equiv) and PdCl$_2$(MeCN)$_2$ (1.5 mg, 0.006 mmol, 0.2 equiv) in degassed DMF (300 mL, 0.1 M) was stirred at 25° C. for 20 h, according to the procedure described for the synthesis of macrolactone 18d, to yield, after preparative thin layer chromatography (250 mm silica gel plate, 50% EtOAc in hexanes) macrolactone 19j (11 mg, 75%). R$_f$=0.17 (silica gel, 33% ether in hexanes); [a]$^{22}$D −37.1 (c 0.55, CHCl$_3$); IR (thin film) n$_{max}$ 3508 (br), 2934, 1730, 1690, 1505, 1461, 1428, 1366, 1251, 1196, 1150, 1041, 977 cm$^{-1}$; $^1$H NMR (500 MHz, CDCl$_3$) d 7.22 (s, 1 H, ArH), 6.58 (s, 1 H, CH=C(CH$_3$)), 5.61 (d, J=47.0 Hz, 2 H, CH$_2$F), 5.55–5.50 (m, 1 H, CH=CHCH$_2$), 5.41–5.35 (m, 2 H, CH=CHCH$_2$ and CHOCO), 4.15 (ddd, J=10.0, 3.5, 3.0 Hz, 1 H, (CH$_3$)$_2$CCH(OH)), 3.75–3.73 (m, 1 H, CHOH (CHCH$_3$)), 3.24 (qd, J=7.0, 4.5 Hz, 1 H, CH$_3$CH(C=O)), 3.05 (d, J=4.0 Hz, 1 H, OH), 2.62 (d, J=4.0 Hz, 1 H, OH), 2.56 (dd, J=15.0, 10.5 Hz, 1 H, CH$_2$COO), 2.49 (dd, J=15.5, 2.5 Hz, 1 H, CH$_2$COO), 2.49–2.44 (m, 2 H), 2.20–2.13 (m, 1 H), 2.10 (s, 3 H, CH=C(CH$_3$)), 2.01–1.93 (m, 1 H), 1.67–1.56 (m, 2 H), 1.49–1.43 (m, 1 H), 1.31–1.17 (m, 2 H), 1.28 (s, 3 H, C(CH$_3$)$_2$), 1.18 (d, J=6.5 Hz, 3 H, CH$_3$CH (C=O)), 1.07 (s, 3 H, C(CH$_3$)$_2$), 0.98 (d, J=7.0 Hz, 3 H, CH$_3$CHCH$_2$); $^{13}$C NMR (100.6 MHz, CDCl$_3$) d 219.9, 170.5, 163.5, 153.0, 138.2, 134.4, 125.7, 119.3, 118.0, 80.6 (d, J=675 Hz), 77.7, 75.7, 72.5, 52.4, 43.6, 38.7, 37.7, 36.4, 32.4, 30.6, 27.3, 21.2, 20.6, 16.4, 15.5, 14.8; HRMS (FAB), calcd for $C_{26}H_{38}FNO_5S$ (M+Cs$^+$) 628.1509, found 628.1487.

cis-Macrolactone 18k as illustrated in FIG. 3. A solution of vinyl iodide 7 (5.1 mg, 0.010 mmol, 1.0 equiv), stannane 8k (7.1 mg, 0.020 mmol, 2.0 equiv) and PdCl$_2$(MeCN)$_2$ (0.5 mg, 0.002 mmol, 0.2 equiv) in degassed DMF (100 mL, 0.1 M) was stirred at 25° C. for 12 h according to the procedure described for the synthesis of macrolactone 18d, to yield, after preparative thin layer chromatography (500 mm silica gel plate, 33% EtOAc in hexanes) to furnish macrolactone 18k (3.9 mg, 87%). R$_f$=0.53 (silica gel, 33% EtOAc in hexanes); [a]$^{22}$D −45.8 (c 0.45, CDCl$_3$); IR (thin film) n$_{max}$ 3500 (br), 2929, 1730, 1689, 1463, 1378, 1296, 1253, 1154, 1088, 1047, 1013, 980, 753 cm$^{-1}$; $^1$H NMR (500 MHz, CDCl$_3$) d 7.39, (d, J=2.0 Hz, 1 H, ArH), 6.41 (dd, J=3.0, 2.0 Hz, 1 H, COCHCH), 6.37 (s, 1 H, CH=C(CH$_3$)), 6.30 (d, 1 H, J=3.0 Hz, ArH), 5.44 (ddd, J=10.5, 10.5, 3.5 Hz, 1 H, CH=CHCH$_2$), 5.38 (ddd, J=10.5, 10.5, 5.0 Hz, 1 H, CH=CHCH$_2$), 5.32 (dd, J=9.5, 1.5 Hz, 1 H, CHOCO), 4.14–4.07 (m, 1 H, (CH$_3$)$_2$CCH(OH)), 3.76–3.74 (m, 1 H, CHOH(CHCH$_3$)), 3.13 (qd, J=6.5, 2.5 Hz, 1 H, CH$_3$CH(C=O)), 2.87 (bs, 1 H, OH), 2.72 (ddd, J=15.0, 10.0, 10.0 Hz, 1 H, =CHCH$_2$CHO), 2.53 (dd, J=15.5, 11.0 Hz, 1 H, CH$_2$COO), 2.50 (bs, 1 H, OH), 2.44 (dd, J=15.5, 3.0 Hz, 1 H, CH$_2$COO), 2.25–2.15 (m, 1 H), 2.07–1.98 (m, 1 H), 2.04 (s, 3 H, CH=CCH$_3$), 1.78–1.71 (m, 1 H), 1.70–1.61 (m, 1 H), 1.39–1.16 (m, 3 H), 1.32 (s, 3 H, C(CH$_3$)$_2$), 1.18 (d, J=6.5 Hz, 3 H, CH$_3$CH(C=O)), 1.10 (s, 3 H, C(CH$_3$)$_2$), 1.00 (d, J=7.0 Hz, 3 H, CH$_3$CHCH$_2$); $^{13}$C NMR (125.7 MHz, CDCl$_3$) d 220.2, 170.3, 152.4, 141.6, 134.2, 133.6, 124.7, 115.7, 111.3, 109.8, 79.1, 74.1, 20 72.9, 52.8, 42.2, 39.0, 38.6, 32.6, 31.7, 27.7, 27.6, 22.3, 19.9, 15.6, 15.1, 13.7; HRMS (FAB), calcd for C$_{26}$H$_{38}$O$_6$ (M+Cs$^+$) 579.1723, found 579.1705.

trans-Macrolactone 19k as illustrated in FIG. 3. A solution of vinyl iodide 11 (5.1 mg, 0.010 mmol, 1.0 equiv), stannane 8k (7.1 mg, 0.020 mmol, 2.0 equiv) and PdCl$_2$(MeCN)$_2$ (0.5 mg, 0.002 mmol, 0.2 equiv) in degassed DMF (100 mL, 0.1 M) was stirred at 25° C. for 12 h, according to the procedure described for the synthesis of macrolactone 18d, to yield, after preparative thin layer chromatography (500 mm silica gel plate, 33% EtOAc in hexanes) macrolactone 19k (4.1 mg, 92%). R$_f$=0.44 (silica gel, 33% EtOAc in hexanes); [a]$^{22}$D −18.8 (c 0.44, CHCl$_3$); IR (thin film) n$_{max}$ 3518 (br), 2929, 1728, 1692, 1463, 1375, 1255, 1153, 1075, 1016, 975, 754 cm$^{-1}$; $^1$H NMR (500 MHz, CDCl$_3$) d 7.40 (s, 1 H, ArH), 6.41 (dd, J=3.0, 1.5 Hz, 1 H, COCHCH), 6.33 (s, 1 H, CH=C(CH$_3$)), 6.31 (d, J=3.0 Hz, 1 H, ArH), 5.55 (ddd, J=14.5, 7.0, 7.0 Hz, 1 H, CH=CHCH$_2$), 5.38 (dd, J=9.0, 4.0 Hz, 1 H, CHOCO), 5.43–5.34 (m, 1 H, CH=CHCH$_2$), 4.10–4.05 (m, 1 H, (CH$_3$)$_2$CCH(OH)), 3.78–3.72 (m, 1 H, CHOH(CHCH$_3$)), 3.24 (qd, J=7.0, 6.5 Hz, 1 H, CH$_3$CH(C=O)), 2.93 (d, J=3.5 Hz, 1 H, OH), 2.57 (dd, J=15.5, 10.5 Hz, 1 H, CH$_2$COO), 2.50 (dd, J=15.5, 2.5 Hz, 1 H, CH$_2$COO), 2.47–2.37 (m, 2 H), 2.19–2.0 (m, 1 H), 2.04–1.95 (m, 1 H), 2.03 (s, 3 H, CH=CCH$_3$), 1.71–1.61 (m, 2 H), 1.48–1.39 (m, 1 H), 1.38–1.32 (m, 1 H), 1.29 (s, 3 H, C(CH$_3$)$_2$), 1.27–1.20 (m, 3 H), 1.18 (d, J=7.0 Hz, 3 H, CH$_3$CH(C=O)), 1.08 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 220.2, 170.6, 152.3, 141.7, 134.3, 133.8, 126.1, 115.6, 111.3, 109.8, 78.2, 75.4, 72.7, 52.3, 43.5, 38.6, 37.8, 36.8, 32.4, 30.8, 27.4, 21.5, 20.4, 16.3, 15.2, 14.7; HRMS (FAB), calcd for C$_{26}$H$_{38}$O$_6$ (M+Cs$^+$) 579.1723, found 579.1707.

cis-Macrolactone 18l as illustrated in FIG. 3. A solution of vinyl iodide 7 (5.1 mg, 0.010 mmol, 1.0 equiv), stannane 8l (7.5 mg, 0.020 mmol, 2.0 equiv) and PdCl$_2$(MeCN)$_2$ (0.5 mg, 0.002 mmol, 0.2 equiv) in degassed DMF (100 mL, 0.1 M) was stirred at 25° C. for 12 h, according to the procedure described for the synthesis of macrolactone 18d, to yield, after preparative thin layer chromatography (500 mm silica gel plate, 33% EtOAc in hexanes) macrolactone 18l (4.1 mg, 88%). R$_f$=0.49 (silica gel, 33% EtOAc in hexanes); [a]$^{22}$D −34.0 (c 0.40, CHCl$_3$); IR (thin film) n$_{max}$ 3498 (br), 2928, 2858, 1729, 1688, 1462, 1377, 1251, 1152, 1089, 1048, 1008, 978, 756 cm$^{-1}$; $^1$H NMR (500 MHz, CDCl$_3$) d 7.29, (dd, J=3.5, 3.5 Hz, 1 H, SCHCHCH), 7.03 (d, J=3.5 Hz, 1 H, ArH), 6.73 (s, 1 H, CH=C(CH$_3$)), 5.45 (ddd, J=10.5, 10.5, 3.0 Hz, 1 H, CH=CHCH$_2$), 5.39 (ddd, J=10.5, 10.5, 5.0 Hz, 1 H, CH=CHCH$_2$), 5.37 (dd, J=10.5, 2.5 Hz, 1 H, CHOCO), 4.10 (ddd, J=10.5, 5.5, 2.5 Hz, 1 H, (CH$_3$)$_2$CCH(OH)), 3.77–3.74 (m, 1 H, CHOH(CHCH$_3$)), 3.14 (qd, J=7.0, 2.5 Hz, 1 H, CH$_3$CH(C=O)),), 2.88 (bs, 1 H, OH), 2.76 (ddd, J=14.0, 10.5, 10.5 Hz, 1 H, =CHCH$_2$CHO), 2.53 (dd, J=16.0, 10.5 Hz, 1 H, CH$_2$COO), 2.46 (bs, 1 H, OH), 2.45 (dd, J=16.0, 2.5 Hz, 1 H, CH$_2$COO), 2.25–2.15 (m, 2 H), 2.04–1.97 (m, 1 H), 2.04 (s, 3 H, CH=CCH$_3$), 1.78–1.70 (m, 1 H), 1.70–1.55 (m, 1 H), 1.42–1.15 (m, 3 H), 1.32 (s, 3 H, C(CH$_3$)$_2$), 1.18 (d, J=7.0 Hz, 3 H, CH$_3$CH(C=O)), 1.10 (s, 3 H, C(CH$_3$)$_2$), 1.00 (d, J=7.0 Hz, 3 H, CH$_3$CHCH$_2$); $^{13}$C NMR (125.7 MHz, CDCl$_3$) d 220.2, 170.4, 139.9, 133.8, 133.6, 127.9, 126.9, 125.6, 124.8, 120.6, 79.4, 74.1, 73.0, 52.8, 42.1, 39.1, 38.6, 32.6, 31.8, 27.7, 27.6, 22.3, 19.9, 15.6, 15.1, 13.7; HRMS (FAB), calcd for C$_{26}$H$_{38}$NaO$_5$S (M+Na$^+$) 485.2338, found 485.2321.

trans-Macrolactone 19l as illustrated in FIG. 3. A solution of vinyl iodide 11 (5.1 mg, 0.010 mmol, 1.0 equiv), stannane 8l (7.5 mg, 0.020 mmol, 2.0 equiv) and PdCl$_2$(MeCN)$_2$ (0.5 mg, 0.002 mmol, 0.2 equiv) in degassed DMF (100 mL, 0.1 M) was stirred at 25° C. for 12 h, according to the procedure described for the synthesis of macrolactone 8d, to yield, after preparative thin layer chromatography (500 mm silica gel plate, 18% EtOAc in hexanes) macrolactone 19l (4.4 mg, 94%). R$_f$=0.31 (silica gel, 18% EtOAc in hexanes); [a]$^{22}$D −12.9 (c 0.45, CHCl$_3$); IR (thin film) n$_{max}$ 3495 (br), 2928, 2928, 1727, 1692, 1462, 1374, 1251, 1150, 1044, 1012, 975, 697 cm$^{-1}$; $^1$H NMR (500 MHz, CDCl$_3$) d 7.29 (dd, J=4.0, 2.5 Hz, 1 H, SCHCHCH), 7.04 (d, J=4.0 Hz, 1 H, ArH), 7.03 (d, J=2.5 Hz, 1 H, ArH), 6.70 (s, 1 H, CH=C(CH$_3$)), 5.56 (ddd, J=14.5, 7.0, 7.0 Hz, 1 H, CH=CHCH$_2$), 5.43 (dd, J=9.5, 2.5 Hz, 1 H, CHOCO), 5.40 (ddd, J=14.5, 8.5, 5.0 Hz, 1 H, CH=CHCH$_2$), 4.07 (ddd, J=10.5, 3.0, 2.5 Hz, 1 H, (CH$_3$)$_2$CCH(OH)), 3.78–3.74 (m, 1 H, CHOH(CHCH$_3$)), 3.23 (qd, J=7.0, 4.5 Hz, 1 H, CH$_3$CH(C=O)), 2.93 (d, J=3.5 Hz, 1 H, OH), 2.57 (dd, J=15.5, 10.5 Hz, 1 H, CH$_2$COO), 2.50 (dd, J=15.5, 2.5 Hz, 1 H, CH$_2$COO), 2.52–2.37 (m, 2 H), 2.19–2.10 (m, 1 H), 2.05–1.97 (m, 1 H), 2.02 (s, 3 H, CH=CCH$_3$), 1.70–1.63 (m, 1 H), 1.63–1.57 (m, 1 H), 1.16–1.15 (m, 3 H), 1.29 (s, 3 H, C(CH$_3$)$_2$), 1.18 (d, J=7.0 Hz, 3 H, CH$_3$CH(C=O)), 1.08 (s, 3 H, C(CH$_3$)$_2$), 0.98 (d, J=7.0 Hz, 3 H, CH$_3$CHCH$_2$); $^{13}$C NMR (125.7 MHz, CDCl$_3$) d 20.0, 170.6, 139.8, 134.2, 133.4, 127.9, 126.9, 126.1, 125.6, 20.7, 78.6, 75.4, 72.8, 52.3, 43.4, 38.6, 37.8, 37.0, 32.4, 0.7, 27.4, 21.6, 20.4, 16.3, 15.1, 14.7; HRMS (FAB), calcd for C$_{26}$H$_{38}$O$_5$S (M+Cs$^+$) 595.1494, found 595.1511.

cis-Macrolactone 18m as illustrated in FIG. 3. A solution of vinyl iodide 7 (5.1 mg, 0.010 mmol, 1.0 equiv), stannane 8m (4.8 mg, 0.020 mmol, 2.0 equiv) and PdCl$_2$(MeCN)$_2$ (0.5 mg, 0.002 mmol, 0.2 equiv) in degassed DMF (100 mL, 0.1 M) was stirred at 25° C. for 12 h, according to the procedure described for the synthesis of macrolactone 18d, to yield, after preparative thin layer chromatography (500 mm silica gel plate, 33% EtOAc in hexanes), macrolactone 18m (3.9 mg, 86%). R$_f$=0.49 (silica gel, 33% EtOAc in hexanes); [a]$^{22}$D −28.8 (c 0.40, CDCl$_3$); IR (thin film) n$_{max}$ 3498 (br), 2930, 1729, 1688, 1462, 1379, 1298, 1254, 1152, 1089, 1047, 1008, 754 cm$^{-1}$; $^1$H NMR (500 MHz, CDCl$_3$) d 7.39–7.31 (m, 2 H, ArH), 7.30–7.21 (m, 3 H, ArH), 6.58 (s, 1 H, CH=C(CH$_3$)), 5.46 (ddd, J=10.5, 10.5, 4.0 Hz, 1 H, CH=CHCH$_2$), 5.42 (ddd, J=10.5, 10.5, 4.5 Hz, 1H, CH=CHCH$_2$), 5.38 (dd, J=9.5, 1.5 Hz, 1 H, CHOCO), 4.12 (ddd, J=11.0, 5.5, 3.0 Hz, 1 H, (CH$_3$)$_2$CCH(OH)), 3.79–3.74 (m, 1 H, CHOH(CHCH$_3$)), 3.13 (qd, J=7.0, 2.5 Hz, 1 H, CH$_3$CH(C=O)), 2.89 (d, J=2.5 Hz, 1 H, CHOH(CHCH$_3$)), 2.77 (ddd, J=15.5, 10.0, 10.0 Hz, 1 H, =CHCH₂CHO), 2.54 (dd, J=15.5, 11.0 Hz, 1 H, CH₂COO), 2.50 (d, J=5.5 Hz, 1 H, (CH₃)₂CCH(OH)), 2.45 (dd, J=15.5, 3.0 Hz, 1 H, CH₂COO), 2.28–2.17 (m, 2 H), 2.08–1.98 (m, 1 H), 1.93 (s, 3 H, CH=CCH₃), 1.81–1.71 (m, 1 H), 1.71–1.67 (m, 1 H), 1.42–1.16 (m, 3 H), 1.31 (s, 3 H, C(CH₃)₂), 1.18 (d, J=7.0 Hz, 3 H, CH₃CH(C=O)), 1.10 (s, 3 H, C(CH₃)₂), 1.00 (d, J=7.0 Hz, 3 H, CH₃CHCH₂); $^{13}$C NMR (125.7 MHz, CDCl₃) d 220.2, 170.4, 136.9, 136.0, 133.5, 129.0, 128.2, 127.1, 126.8, 124.9, 79.3, 74.1, 72.9, 52.8, 42.1, 39.1, 38.6, 32.6, 31.7, 27.7, 27.6, 22.3, 19.9, 15.6, 14.5, 13.7; HRMS (FAB), calcd for C₂₈H₄₀O₅ (M+Cs⁺) 589.1930, found 589.1944.

trans-Macrolactone 19m as illustrated in FIG. 3. A solution of vinyl iodide 11 (5.1 mg, 0.010 mmol, 1.0 equiv), stannane 8m (4.8 mg, 0.020 mmol, 2.0 equiv) and PdCl₂(MeCN)₂ (0.5 mg, 0.002 mmol, 0.2 equiv) in degassed DMF (100 mL, 0.1 M) was stirred at 25° C. for 12 h, according to the procedure described for the synthesis of macrolactone 18d, to yield, after preparative thin layer chromatography (500 mm silica gel plate, 18% EtOAc in hexanes) macrolactone 19m (4.1 mg, 89%). $R_f$=0.32 (silica gel, 18% EtOAc in hexanes); [a]$^{22}$D −3.8 (c 0.40, CHCl₃); IR (thin film) n$_{max}$ 3518 (br), 2930, 1728, 1692, 1461, 1374, 1256, 1174, 1073, 1043, 1012, 975, 755 cm⁻¹; ¹H NMR (500 MHz, CDCl₃) d 7.36–7.31 (m, 2 H, ArH), 7.27–7.21 (m, 3 H, ArH), 6.55 (s, 1 H, CH=C(CH₃)), 5.51 (ddd, J=14.5, 7.0, 7.0 Hz, 1 H, CH=CHCH₂), 5.44 (dd, J=9.0, 3.0 Hz, 1 H, CHOCO), 5.42 (ddd, J=14.5, 7.0, 7.0 Hz, 1 H, CH=CHCH₂), 4.08 (ddd, J=10.0, 3.0, 2.5 Hz, 1 H, (CH₃)₂CCH(OH)), 3.78–3.73 (m, 1 H, CHOH(CHCH₃)), 3.24 (qd, J=7.0, 4.5 Hz, 1 H, CH₃CH(C=O)), 2.96 (d, J=3.0 Hz, 1 H, OH), 2.59 (dd, J=15.0, 10.0 Hz, 1 H, CH₂COO), 2.51 (dd, J=15.0, 2.5 Hz, 1 H, CH₂COO), 2.50–2.42 (m, 2 H), 2.20–2.12 (m, 1 H), 2.05–1.94 (m, 1 H), 1.90 (s, 3 H, CH=CCH₃), 1.70–1.64 (m, 1 H), 1.65–1.55 (m, 1 H), 1.48–1.40 (m, 1 H), 1.30–1.10 (m, 1 H), 1.29 (s, 3 H, C(CH₃)₂), 1.17 (d, J=7.0 Hz, 3 H, CH₃CH(C=O)), 1.08 (s, 3 H, C(CH₃)₂), 0.97 (d, J=7.0 Hz, 3 H, CH₃CHCH₂); $^{13}$C NMR (125.7 MHz, CDCl₃) d 220.0, 170.7, 136.8, 135.6, 134.1, 129.0, 128.2, 127.1, 126.8, 126.3, 78.4, 75.4, 72.7, 52.4, 43.4, 38.6, 37.8, 36.9, 32.4, 30.8, 27.5, 21.5, 20.4, 16.3, 14.7, 14.5; HRMS (FAB), calcd for C₂₈H₄₀O₅ (M+Cs⁺) 589.1930, found 589.1948.

cis-Macrolactone 18n as illustrated in FIG. 3. A solution of vinyl iodide 7 (5.1 mg, 0.010 mmol, 1.0 equiv), stannane 8n (4.8 mg, 0.020 mmol, 2.0 equiv) and Pd(PPh₃)₄ (1.1 mg, 0.001 mmol, 0.10 equiv) in degassed toluene (100 mL, 0.1 M) was heated at 100° C. for 20 min, according to the procedure described for the synthesis of macrolactone 18h, to yield, after preparative thin layer chromatography (500 mm silica gel plate, 66% EtOAc in hexanes), macrolactone 18n (1.9 mg, 42%). $R_f$=0.24 (silica gel, 3% MeOH in CDCl₃); [a]$^{22}$D −20.0 (c 0.08, CHCl₃); IR (thin film) n$_{max}$ 3417 (br), 2926, 1730, 1687, 1463, 1414, 1377, 1252, 1148, 1011, 979, 754 cm⁻¹; ¹H NMR (500 MHz, CDCl₃) d 8.55–8.50 (m, 1 H, ArH), 8.50–8.44 (m, 1 H, ArH), 7.58 (d, J=8.0 Hz, 1 H, ArH), 7.31–7.23 (m, 1 H, ArH), 6.54 (s, 1 H, CH=C(CH₃)), 5.47 (ddd, J=10.5, 10.5, 3.5 Hz, 1 H, CH=CHCH₂), 5.41 (ddd, J=10.5, 10.5, 5.0 Hz, 1 H, CH=CHCH₂), 5.36 (dd, J=10.0, 2.0 Hz, 1 H, CHOCO), 4.16 (m, 1 H, (CH₃)₂CCH(OH)), 3.78–3.74 (m, 1 H, CHOH(CHCH₃)), 3.13 (qd, J=7.0, 2.5 Hz, 1 H, CH₃CH(C=O)), 2.89 (d, J=2.5 Hz, 1 H, OH), 2.76 (ddd, J=15.0, 10.0, 10.0 Hz, 1 H, =CHCH₂CHO), 2.53 (dd, J=15.5, 11.0 Hz, 1 H, CH₂COO), 2.45 (dd, J=15.5, 2.5 Hz, 1 H, CH₂COO), 2.28–2.17 (m, 2 H), 2.08–2.00 (m, 1 H), 1.93 (s, 3 H, CH=CCH₃), 1.79–1.73 (m, 1 H), 1.71–1.63 (m, 1 H), 1.40–1.15 (m, 3 H), 1.33 (s, 3 H, C(CH₃)₂), 1.18 (d, J=7.0 Hz, 3 H, CH₃CH(C=O)), 1.10 (s, 3 H, C(CH₃)₂), 1.00 (d, J=7.0 Hz, 3 H, CH₃CHCH₂); $^{13}$C NMR (125.7 MHz, CDCl₃) d 220.1, 170.3, 150.1, 147.8, 138.6, 136.0, 133.6, 124.7, 123.3, 123.1, 78.9, 74.1, 73.0, 52.9, 42.1, 39.2, 38.6, 32.6, 31.6, 27.6, 27.6, 22.4, 19.7, 15.6, 14.6, 13.7; HRMS (FAB), calcd for C₂₇H₄₀NO₅ (M+H⁺) 458.2906, found 458.2923.

trans-Macrolactone 19n as illustrated in FIG. 3. A solution of vinyl iodide 11 (5.1 mg, 0.010 mmol, 1.0 equiv), stannane 8n (4.8 mg, 0.020 mmol, 2.0 equiv) and Pd(PPh₃)₄ (1.1 mg, 0.002 mmol, 0.10 equiv) in degassed toluene (100 mL, 0.1 M) was heated at 100° C. for 20 min, according to the procedure described for the synthesis of macrolactone 18h, to yield, after preparative thin layer chromatography (500 mm silica gel plate, 66% EtOAc in hexanes), macrolactone 19n (2.1 mg, 46%). $R_f$=0.11 (silica gel, 50% EtOAc in hexanes); [a]$^{22}$D −12.9 (c 0.07, CDCl₃); IR (film) n$_{max}$ 3418 (br), 2924, 2855, 1729, 1693, 1461, 1375, 1251, 1153, 1048, 975, 756 cm⁻¹; ¹H NMR (500 MHz, CDCl₃) d 8.56–8.43 (m, 2 H, ArH), 8.50–8.44 (m, 1 H, ArH), 7.58 (d, J=7.5 Hz, 1 H, ArH), 7.35–7.25 (m, 1 H, ArH), 6.50 (s, 1 H, CH=CCH₃), 5.58 (ddd, J=15.0, 7.5, 7.5 Hz, 1 H, CH=CHCH₂), 5.43 (dd, J=7.5, 3.5 Hz, 1 H, CHOCO), 5.41 (ddd, J=15.0, 7.5, 7.5 Hz, 1 H, CH=CHCH₂), 4.09 (ddd, J=10.5, 3.5, 3.5 Hz, 1 H, (CH₃)₂CCHOH), 3.77–3.74 (m, 1 H, CHOH(CHCH₃)), 3.23 (qd, J=7.0, 4.5 Hz, 1 H, CH₃CH(C=O)), 2.89 (d, 1 H, OH), 2.60 (dd, J=15.5, 10.5 Hz, 1 H, CH₂COO), 2.52 (dd, J=15.5, 3.0 Hz, 1 H, CH₂COO), 2.52–2.45 (m, 2 H), 2.20–2.13 (m, 1 H), 2.05–1.97 (m, 1 H), 1.91 (s, 3 H, CH=CCH₃), 1.71–1.52 (m, 2 H), 1.48–1.40 (m, 1 H), 1.30 (s, 3 H, C(CH₃)₂), 1.18 (d, J=7.0 Hz, 3 H, CH₃CH(C=O)), 1.09 (s, 3 H, C(CH₃)₂), 0.97 (d, J=7.0 Hz, 3 H, CH₃CHCH₂); $^{13}$C NMR (125.7 MHz, CDCl₃) d 219.9, 170.6, 150.1, 147.8, 139.2, 138.3, 135.9, 134.4, 125.9, 123.3, 123.0, 78.0, 75.4, 72.8, 52.4, 43.4, 38.6, 37.8, 36.8, 32.4, 30.8, 27.4, 26.4, 21.5, 20.4, 16.2, 14.6; HRMS (FAB), calcd for C₂₇H₄₀NO₅ (M+H⁺) 458.2906, found 458.2927.

cis-Macrolactone 18o as illustrated in FIG. 3. A solution of vinyl iodide 7 (16.5 mg, 0.033 mmol, 1.0 equiv), stannane 8o (22 mL, 0.065 mmol, 2.0 equiv) and PdCl₂(MeCN)₂ (1.0 mg, 0.004 mmol, 0.1 equiv) in degassed DMF (330 mL, 0.1 M) was stirred at 25° C. for 33 h, according to the procedure described for the synthesis of macrolactone 18d, to yield, after preparative thin layer chromatography (250 mm silica gel plate, 50% EtOAc in hexanes) unreacted vinyl iodide 7 (3.4 mg, 21%) and macrolactone 18o²⁰ (7 mg, 51%). $R_f$=0.33 (silica gel, 50% EtOAc in hexanes); [a]$^{22}$D −48.4 (c 0.64, CDCl₃); IR (thin film) n$_{max}$ 3494 (br), 2932, 1737, 1688, 1622, 1464, 1364, 1300, 1249, 1226, 1150, 1090, 1049, 1006, 976 cm⁻¹; ¹H NMR (500 MHz, CDCl₃) d 6.29 (s, 1 H, CH=C(CH₃)), 5.47 (ddd, J=10.5, 10.5, 5.0 Hz, 1 H, CH=CHCH₂), 5.32 (ddd, J=10.0, 10.0, 5.0 Hz, 1 H, CH=CHCH₂), 5.15 (dd, J=9.5, 1.5 Hz, 1 H, CHOCO), 4.13 (m, 1 H, (CH₃)₂CCH(OH)), 3.72 (m, 1 H, CHOH(CHCH₃)), 3.12 (qd, J=7.0, 2.5 Hz, 1 H, CH₃CH(C=O)), 2.87 (bs, 1 H, OH), 2.61 (ddd, J=15.0, 10.0, 10.0 Hz, 1 H, CH=CHCH₂CHO), 2.50 (dd, J=15.5, 11.0 Hz, 1 H, CH₂COO), 2.42 (dd, J=15.5, 3.0 Hz, 1 H, CH₂COO), 2.36 (m, 1 H), 2.23–2.12 (m, 2 H), 2.22 (s, 3 H, COCH₃), 2.14 (d, J=1.0 Hz, 3 H, CH=C(CH₃)), 2.05–2.00 (m, 1 H), 1.76–1.72 (m, 1 H), 1.69–1.61 (m, 2 H), 1.38–1.15 (m, 2 H), 1.34 (s, 3 H, C(CH₃)₂), 1.19 (d, J=7.0 Hz, 3 H, CH₃CH(C=O)), 1.09 (s, 3 H, C(CH₃)₂), 0.99 (d, J=7.0 Hz, 3 H, CH₃CHCH₂); $^{13}$C NMR (125.7 MHz, CDCl₃) d 219.9, 198.8, 170.0, 152.9, 134.0, 124.0, 123.1, 78.0, 74.1, 72.8, 52.9, 42.0, 39.1, 38.4, 32.3, 31.9, 31.1, 27.4, 22.3, 19.2, 17.4, 15.7, 15.4, 13.5; HRMS (FAB), calcd for $C_{24}H_{38}O_6$ (M+Cs$^+$) 555.1723, found 555.1729.

trans-Macrolactone 19o as illustrated in FIG. 3. A solution of vinyl iodide 11 (17 mg, 0.034 mmol, 1.0 equiv), stannane 8o (23 mL, 0.068 mmol, 2.0 equiv) and $PdCl_2(MeCN)_2$ (1.1 mg, 0.004 nmmol, 0.1 equiv) in degassed DMF (340 mL, 0.1 M) was stirred at 25° C. for 20 h, according to the procedure described for the synthesis of macrolactone 18d, to yield, after preparative thin layer chromatography (250 mm silica gel plate, 50% EtOAc in hexanes) unreacted vinyl iodide 11 (2.3 mg, 14%) and macrolactone 19o[20] (7 mg, 49%). $R_f$=0.31 (silica gel, 50% EtOAc in hexanes); [a]$^{22}$D −15.5 (c 0.64, $CHCl_3$); IR (thin film) $n_{max}$ 3500 (br), 2937, 1732, 1688, 1622, 1472, 1428, 1361, 1250, 1220, 1164, 1043, 1011, 974 cm$^{-1}$; $^1$H NMR (500 MHz, $CDCl_3$) d 6.24 (s, 1 H, CH=C(CH$_3$)), 5.56–5.50 (m, 1 H, CH=CHCH$_2$), 5.35–5.29 (m, 1 H, CH=CHCH$_2$), 5.23 (dd, J=9.0, 2.5 Hz, 1 H, CHOCO), 4.14–4.09 (m, 1 H, (CH$_3$)$_2$CCH(OH)), 3.74–3.72 (m, 1 H, CHOH(CHCH$_3$)), 3.22 (qd, J=7.0, 4.5 Hz, 1 H, CH$_3$CH(C=O)), 2.74 (d, J=4.5 Hz, 1 H, OH), 2.56 (dd, J=15.0, 10.0 Hz, 1 H, CH$_2$COO), 2.51 (dd, J=15.0, 3.0 Hz, 1 H, CH$_2$COO), 2.46 (m, 1 H), 2.46–2.31 (m, 2 H), 2.22 (s, 3 H, COCH$_3$), 2.20–2.12 (m, 1 H), 2.13 (s, 3 H, CH=C(CH$_3$)), 2.02–1.95 (m, 1 H), 1.69–1.56 (m, 2 H), 1.46–1.22 (m, 2 H), 1.30 (s, 3 H, C(CH$_3$)$_2$), 1.17 (d, J=7.5 Hz, 3 H, CH$_3$CH(C=O)), 1.08 (s, 3 H, C(CH$_3$)$_2$), 0.97 (d, J=7.0 Hz, 3 H, CH$_3$CHCH$_2$); $^{13}$C NMR (125.7 MHz, $CDCl_3$) d 219.9, 198.7, 170.3, 52.8, 134.9, 125.2, 123.0, 77.1, 75.5, 72.8, 52.4, 43.4, 38.6, 7.6, 36.4, 32.2, 32.0, 30.7, 27.1, 21.4, 20.3, 16.2, 15.9, 14.6; HRMS (FAB), calcd for $C_{24}H_{38}O_6$ (M+Cs$^+$) 555.1723, found 555.1703.

Figure 7:
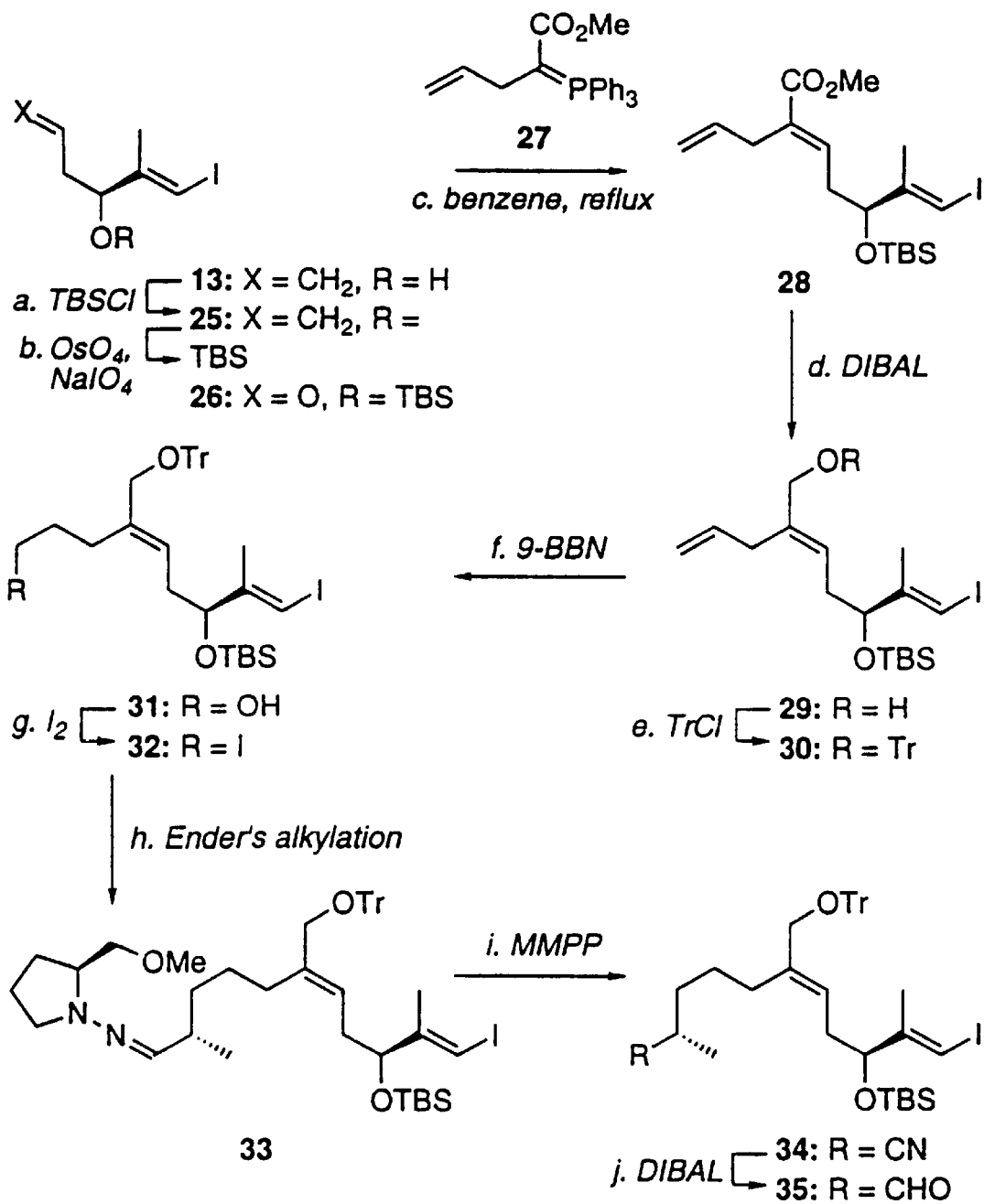
FIG. 7 illustrates the stereoselective synthesis of aldehyde 35. Reagents and conditions: (a) 1.7 equiv TBSCl, 2.8 equiv imidazole, DMF, 0→25° C., 7 h, 84%; (b) i. 1.0 mol % OsO$_4$, 1.1 equiv NMO, THF:t-BuOH:H$_2$O (5:5:1), 0→25° C., 13 h, 89%; ii. 6.0 equiv NaIO$_4$, MeOH:H$_2$O (2:1), 0° C., 30 min, 92%; (c) 2.4 equiv 27, benzene, reflux, 1.2 h, 98%; (d) 3.0 equiv DIBAL, THF, −78° C., 2.5 h, 100%. (e) 1.4 equiv of TrCl, 1.7 equiv of 4-DMAP, DMF, 80° C., 21 h, 95%; (f) 1.4 equiv of 9-BBN, THF, 0° C., 9 h; then 3 N aqueous NaOH and 30% H$_2$O$_2$, 0° C., 1 h, 95%; (g) 2.6 equiv of I$_2$, 5.0 equiv of imidazole, 2.5 equiv of Ph$_3$P, Et$_2$O:MeCN (3:1), 0° C., 45 min, 97%; (h) 1.3 equiv of the SAMP hydrazone of propionaldehyde, 1.4 equiv of LDA, THF, 0° C., 16 h; then −100° C. and add 1.0 equiv of 32 in THF, −100→−20° C., 20 h, 71%; (i) 2.5 equiv of MMPP, MeOH:phosphate buffer pH 7 (1:1), 0° C., 3.5 h, 89%; (j) 3.0 equiv of DIBAL, toluene, −78° C., 1 h, 88%. 9-BBN=9-borabicyclo[3.3.1]nonane; DIBAL=diisobutylaluminium hydride; 4-DMAP=4-dimethylaminopyridine; LDA=lithium diisopropylamide; NMO=4-methylmorpholine N-oxide; SAMP=(S)-(−)-1-amino-2-(methoxymethyl)pyrrolidine; MMPP=monoperoxyphthalic acid, magnesium salt.

Silyl ether 25 as illustrated in FIG. 7. To a solution of alcohol 13 (12.96 g, 54.4 mmol, 1.0 equiv), in DMF (180 mL, 0.3 M) at 0° C., was added imidazole (10.2 g, 150.0 mmol, 2.8 equiv) followed by tert-butyldimethylchlorosilane (13.5 g, 89.8 mmol, 1.7 equiv). After warming to 25° C. over 7 h, the solvent was removed under reduced pressure and the resulting oil was partitioned between ether (200 mL) and saturated aqueous NH$_4$Cl (200 mL). The aqueous layer was extracted with ether (200 mL) and the combined organic extracts were washed with brine (550 mL), dried (MgSO$_4$) and concentrated under reduced pressure. Flash column chromatography (silica gel, 0 ® 5% EtOAc in hexanes) furnished silyl ether 25 as an oil (16.03 g, 84%). $R_f$=0.48 (hexanes); [a]$^{22}$D −17.5 (c 1.65, CDCl$_3$); IR (thin film) $n_{max}$ 2954, 2928, 2857, 1472, 1361, 1278, 1252, 1082, 914, 836, 776, 677 cm$^{-1}$; $^1$H NMR (500 MHz, CDCl$_3$) d 6.15 (s, 1 H, CH=CCH$_3$), 5.74–5.66 (m, 1 H, CH=CH$_2$), 5.03 (bm, 1 H, CH=CH$_2$), 5.01 (s, 1 H, CH=CH$_2$), 4.16 (dd, J=6.5, 6.5 Hz, 1 H, CHOH), 2.25 (m, 1 H, CH$_2$=CHCH$_2$), 1.77 (s, 3 H, CH=CCH$_3$), 0.88 (s, 9 H, SiC(CH$_3$)$_3$), 0.04 (s, 3 H, Si(CH$_3$)$_2$), −0.01 (s, 3 H, Si(CH$_3$)$_2$); $^{13}$C NMR (125.7 MHz, CDCl$_3$) d 149.9, 134.4, 117.0, 77.5, 77.2, 41.0, 25.7, 19.6, 18.2,−4.8,−5.1.

Aldehyde 26 as illustrated in FIG. 7. To a solution of olefin 25 (16.0 g, 45.3 mmol, 1.0 equiv) in a mixture of THF (206 mL), t-BuOH (206 mL) and H$_2$O (41 mL) at 0° C. was added 4-methylmorpholine N-oxide (NMO) (5.84 g, 49.8 mmol, 1.1 equiv) followed by OsO$_4$ (5.2 mL, 2.5% w/v in t-BuOH, 0.453 mmol, 0.01 equiv). The mixture was vigorously stirred 13 h at 25° C. and then quenched with saturated aqueous Na$_2$SO$_3$ (125 mL). The resulting solution was stirred for 2 h and then partitioned between EtOAc (150 mL) and water (150 mL). The organic phase was separated and the aqueous phase was extracted with EtOAc (2×200 mL). The combined organic extracts were dried (MgSO$_4$), filtered, and the solvents were removed under reduced pressure. Flash column chromatography (silica gel, 50 ® 90% ether in hexanes) provided unreacted starting material (1.0 g, 6%) and the desired diols as a ca. 1:1 mixture of diastereoisomers (15.5 g, 89%). $R_f$=0.44 (silica gel, 50% EtOAc in hexanes); IR (thin film) $n_{max}$ 3387, 2952, 2928, 1252, 1080, 837, 777 cm$^{-1}$; $^1$H NMR (500 MHz, CDCl$_3$) d 6.28 and 6.26 (singlets, 1 H total, CH=CCH$_3$), 4.47–4.42 (m, 1 H, CHOSi), 3.86–3.76 (m, 1 H, CHOH), 3.61–3.55 and 3.49–3.39 (m, 2 H total, CH$_2$OH), 3.33 and 3.15 (2 doublets, J=2.0 and 3.5 Hz, 1 H total, CHOH), 2.46 and 2.45 (triplets, J=5.5 and 5.5 Hz, CH$_2$OH), 1.78 and 1.76 (singlets, 3 H total), 1.63–1.60 and 1.58–1.53 (m, 2 H total, CH$_2$), 0.88 and 0.87 (singlets, 9 H total, SiC(CH$_3$)$_3$), 0.08 and 0.07 (singlets, 3 H total, Si(CH$_3$)$_2$), 0.01 and 0.00 (singlets, 3 H total, Si(CH$_3$)$_2$); $^{13}$C NMR (125.7 MHz, CDCl$_3$) d 149.5, 149.1, 78.7, 77.8, 77.1, 76.6, 74.6, 70.5, 68.6, 66.8, 66.5, 38.6, 38.1, 25.6, 20.5, 19.2, 18.0, 17.9, −4.9, −5.1, −5.4, −5.5; HRMS (FAB), calcd for $C_{13}H_{27}IO_3Si$ (M+Na$^+$) 409.0672 found 409.0662.

The diols (obtained as described above) (23.3 g, 60.2 mmol, 1.0 equiv) were dissolved in a mixture of MeOH (400 mL) and water (200 mL) and the solution was cooled to 0° C. NaIO$_4$ (77.2 g, 361.1 mmol, 6.0 equiv) was then added portionwise over 5 min, and the resulting slurry was stirred vigorously for 30 min at 25° C. After completion of the reaction, the mixture was partitioned between CH$_2$Cl$_2$ (500 mL) and water (500 mL) and the organic phase was separated. The aqueous layer was extracted with CH$_2$Cl$_2$ (500 mL) and the combined organic extracts were washed with brine (1 L), dried (MgSO$_4$) and concentrated under reduced pressure. Flash column chromatography (silica gel, 17® 50% ether in hexanes) provided aldehyde 26 as an oil (19.6 g, 92%). $R_f$=0.35 (silica gel, 20% ether in hexanes); [a]$^{22}$D −34.1 (c 2.8, CHCl$_3$); IR (thin film) $n_{max}$ 2954, 2928, 2885, 2856, 1728, 1471, 1279, 1254, 1091, 838, 777, 677 cm$^{-1}$; $^1$H NMR (500 MHz, CDCl$_3$) d 9.73 (dd, J=2.5, 2.5 Hz, 1 H, CHO), 6.34 (s, 1 H, CH=CCH$_3$), 4.70 (dd, J=8.0, 4.0 Hz, 1 H, CHOSi), 2.68 (ddd, J=16.0, 8.3, 2.5 Hz, 1 H, (CHO)CH$_2$), 2.44 (ddd, J=16.0, 4.0, 2.5 Hz, 1 H, (CHO)CH$_2$), 1.80 (s, 3 H, CH=CCH$_3$), 0.85 (s, 9 H, SiC(CH$_3$)$_3$), 0.05 (s, 3 H, Si(CH$_3$)$_2$), 0.01 (s, 3 H, Si(CH$_3$)$_2$); $^{13}$C NMR (125.7 MHz, CDCl$_3$) d 200.5, 148.7, 78.9, 72.5, 49.6, 25.7, 19.8, 18.0, −4.9, −5.3; HRMS (FAB), calcd for $C_{12}H_{23}IO_2Si$ (M+Na$^+$) 377.0410 found 377.0402.

Methyl ester 28 as illustrated in FIG. 7. A mixture of aldehyde 26 (19.6 g, 55.2 mmol, 1.0 equiv) and stabilized ylide 27 (50.2 g, 134.0 mmol, 2.4 equiv) [prepared from 4-bromo-1-butene by: (i) phosphonium salt formation; (ii) anion formation with KHMDS; and (iii) quenching with MeOC(O)Cl)][22] in benzene (550 mL, 0.1 M) was heated at reflux for 1.5 h. After cooling to 25° C., the mixture was filtered and the solvent was removed under reduced pressure. Flash column chromatography (silica gel, 9® 17% ether in hexanes) furnished methyl ester 28 (24.5 g, 98%). $R_f$=0.37 (silica gel, 20% ether in hexanes); [a]$^{22}$D −7.25 (c 1.6, CHCl$_3$); IR (thin film) $n_{max}$ 3078, 2952, 2920, 2856, 1720, 1462, 1434, 1276, 1253, 1208, 1084, 836, 776, 672 cm$^{-1}$; $^1$H NMR (600 MHz, CDCl$_3$) d 6.81 (dd, J=7.4, 7.4 Hz, 1 H, CH=CCOOCH$_3$), 6.22 (s, 1 H, CH=CCH$_3$), 5.83–5.75 (m, 1 H, CH=CH$_2$), 4.99–4.98 (m, 1 H, CH=CH$_2$), 4.96 (m, 1 H, CH=CH$_2$), 4.22 (dd, J=7.5, 5.1 Hz, 1 H, CHOSi), 3.72 (s, 3 H, COOCH$_3$), 3.05 (d, J=6.0 Hz, 2 H, CH$_2$C(CO$_2$Me)), 2.40 (ddd, J=15.0, 7.5, 7.5 Hz, 1 H, CH$_2$CHOSi), 2.33 (ddd, J=15.0, 7.5, 5.1 Hz, 1 H, CH$_2$CHOSi), 1.77 (s, 3 H, CH=CCH$_3$), 0.85 (s, 9 H, SiC(CH$_3$)$_3$), 0.02 (s, 3 H, Si(CH$_3$)$_2$), −0.02 (s, 3 H, Si(CH$_3$)$_2$); $^{13}$C NMR (150.9 MHz, CDCl$_3$) d 167.6, 149.6, 139.5, 135.2, 131.1, 115.2, 78.1, 76.3, 51.7, 35.6, 31.0, 25.6, 19.6, 18.1, −5.0, −5.2; HRMS (FAB), calcd for $C_{18}H_{31}IO_3Si$ (M+Cs$^+$), 583.0142 found 583.0159.

Allylic alcohol 29 as illustrated in FIG. 7. Methyl ester 28 (24.5 g, 54.3 mmol, 1.0 equiv) was dissolved in THF (280 mL) and the solution was cooled to −78° C. DIBAL (163.0 mL, 1 M in $CH_2Cl_2$, 163.0 mmol, 3.0 equiv) was added dropwise at −78° C. over 50 min, and the reaction mixture was stirred for a further 80 min. The reaction mixture was quenched with saturated aqueous sodium-potassium tartrate (150 mL) and the resulting mixture was allowed to warm up to 25° C. over 16 h. The organic layer was separated and the aqueous phase was extracted with ether (3×250 mL). The combined organic extracts were washed with brine (650 mL), dried (MgSO$_4$) and concentrated under reduced pressure. Flash column chromatography (silica gel, 17 ⓑ 50% ether in hexanes) furnished alcohol 29 (22.9 g, 100%). R$_f$=0.11 (silica gel, 20% ether in hexanes); [a]$^{22}$D −7.25 (c 1.6, CDCl$_3$); IR (thin film) n$_{max}$ 3346, 3078, 2954, 2928, 2857, 1637, 1471, 1361, 1276, 1252, 1078, 1005, 836, 775, 674, 558 cm$^{-1}$; $^1$H NMR (500 MHz, CDCl$_3$) d 6.16 (s, 1 H, CH=CCH$_3$), 5.81–5.73 (m, 1 H, CH=CH$_2$), 5.45 (dd, J=6.5, 6.5 Hz, 1 H, CH=CCH$_2$OH), 5.03 (m, 2 H, CH=CH$_2$), 4.16 (dd, J=6.5, 6.5 Hz, 1 H, CHOSi), 4.02 (d, J=4.5 Hz, 2 H, CH$_2$OH), 2.85 (dd, J 15.0, 5.1 Hz, 1 H, CH$_2$CH=CH$_2$), 2.84 (dd, J=15.0, 5.0 Hz, 1 H, CH$_2$CH=CH$_2$), 2.27 (ddd, J=15.0, 6.5, 6.5 Hz, 1 H, CH$_2$CHOSi), 2.25 (ddd, J=15.0, 6.5, 6.5 Hz, 1 H, CH$_2$CHOSi), 1.78 (s, 3 H, CH=CCH$_3$), 0.88 (s, 9 H, SiC(CH$_3$)$_3$), 0.02 (s, 3 H, Si(CH$_3$)$_2$), −0.02 (s, 3 H, Si(CH$_3$)$_2$); $^{13}$C NMR (125.7 MHz, CDCl$_3$) d 149.9, 138.3, 135.5, 123.3, 115.5, 77.5, 76.6, 66.9, 34.4, 32.5, 25.6, 19.5, 18.0, −5.0, −5.2; HRMS (FAB), calcd for $C_{17}H_{31}IO_2Si$ (M+Cs$^+$), 555.0192 found 555.0177.

Triphenylmethyl ether 30 as illustrated in FIG. 7. Alcohol 29 (23.5 g, 55.7 mmol, 1.0 equiv) was dissolved in DMF (300 mL, 0.15 M) and 4-DMAP (11.3 g, 92.5 mmol, 1.7 equiv) and trityl chloride (22.1 g, 79.3 mmol, 1.4 equiv) were added. The reaction mixture was stirred at 80° C. for 21 h, cooled to room temperature and the solvent was removed under reduced pressure. The resulting residue was purified by flash column chromatography to afford the required ether 30 as an oil (35.3 g, 95%). R$_f$=0.88 (silica gel, 20% ether in hexanes); [a]$^{22}$D −0.74 (c 0.3, CHCl$_3$); IR (thin film) n$_{max}$ 3058, 2927, 2854, 1488, 1470, 1448, 1250, 1082, 836, 702, 632 cm$^{-1}$; $^1$H NMR (600 MHz, CDCl$_3$) d 7.45–7.43 (m, 5 H, Ph), 7.32–7.21 (m, 10 H, Ph), 6.19 (s, 1 H, CH=CCH$_3$), 5.61 (m, 2 H, CH=CH$_2$, CH=CH$_2$), 4.87 (m, 2 H, CH=CH$_2$, CH(C)CH$_2$OTr), 4.19 (dd, J=6.8, 6.8 Hz, 1 H, CHOSi), 3.46 (s, 2 H, CH$_2$OTr), 2.78 (dd, J=15.4, 6.7 Hz, 1 H, CH$_2$CH=CH$_2$), 2.73 (dd, J=15.4, 6.3 Hz, 1 H, CH$_2$CH=CH$_2$), 2.33 (ddd, J=14.5, 6.8, 6.8 Hz, 1 H, CH$_2$CHOSi), 2.31 (ddd, J=14.5, 6.8, 6.8 Hz, 1 H, CH$_2$CHOSi), 1.80 (s, 3 H, CH=CCH$_3$), 0.87 (s, 9 H, SiC(CH$_3$)$_3$), 0.04 (s, 3 H, Si(CH$_3$)$_2$), 0.00 (s, 3 H, Si(CH$_3$)$_2$); $^{13}$C NMR (150.9 MHz, CDCl$_3$) d 150.2, 144.3, 136.1, 135.6, 128.7, 127.7, 126.8, 122.5, 115.2, 86.6, 77.4, 67.0, 34.6, 33.0, 25.8, 19.7, 18.0, −4.9, −5.0; HRMS (FAB), calcd for $C_{36}H_{45}IO_2Si$ (M+Cs$^+$), 797.1288 found 797.1309.

Alcohol 31 as illustrated in FIG. 7. Olefin 30 (35.3 g, 53.1 mmol, 1.0 equiv) was dissolved in THF (53 mL, 1.0 M) and the solution was cooled to 0° C. 9-BBN (149 mL, 0.5 M in THF, 74.5 mmol, 1.4 equiv) was added dropwise over 1.5 h, and the resulting mixture was stirred for 9 h at 0° C. Aqueous NaOH (106 mL of a 3 N solution, 319.0 mmol, 6.0 equiv) was added, followed by aqueous H$_2$O$_2$ (32 mL, 30% w/w in water, 319.0 mmol, 6.0 equiv). Stirring was continued for 1 h at 0° C., after which time the reaction mixture was diluted with ether (500 mL) and water (500 mL). The organic layer was separated and the aqueous phase was extracted with ether (2×500 mL). The combined organic extracts were washed with brine (1 L), dried (MgSO$_4$) and concentrated under reduced pressure. Flash column chromatography (silica gel, 9 ⓑ 50% ether in hexanes) furnished primary alcohol 31 (34.6 g, 95%). R$_f$=0.54 (silica gel, 60% ether in hexanes); [a]$^{22}$D −3.5 (c 0.2, CHCl$_3$); IR (thin film) n$_{max}$ 3380, 3058, 3032, 2926, 2855, 1489, 1449, 1278, 1251, 1078, 835, 706, 632 cm$^{-1}$; $^1$H NMR (500 MHz, CDCl$_3$) d 7.47–7.45 (m, 5 H, Ph), 7.32–7.22 (m, 10 H, Ph), 6.22 (s, 1 H, CH=CCH$_3$), 5.58 (dd, J=7.1, 7.1 Hz, 1 H, C=CHCH$_2$), 4.22 (dd, J=6.8, 6.0 Hz, 1 H, CHOSi), 3.52 (bm, 2 H, CH$_2$OH), 3.50 (s, 2 H, CH$_2$OTr), 2.33 (dd, J=14.5, 6.8, 6.8 Hz, 1 H, CH$_2$CHOSi), 2.28 (ddd, J=14.5, 6.8, 6.8 Hz, 1 H, CH$_2$CHOSi), 2.14 (m, 2 H, CH$_2$CH$_2$CH$_2$OH), 1.82 (s, 3 H, CH=CCH$_3$), 1.46 (m, 2 H, CH$_2$CH$_2$OH), 0.90 (s, 9 H, SiC(CH$_3$)$_3$), 0.06 (s, 3 H, Si(CH$_3$)$_2$), 0.02 (s, 3 H, Si(CH$_3$)$_2$); $^{13}$C NMR (125.7 MHz, CDCl$_3$) d 150.2, 144.2, 137.9, 128.5, 127.8, 126.9, 122.2, 86.6, 77.5, 77.3, 67.1, 62.5, 34.6, 31.2, 25.7, 19.8, 18.2, −4.9, −5.0; HRMS (FAB), calcd for $C_{36}H_{47}IO_3Si$ (M+Cs$^+$), 815.1394 found 815.1430.

Iodide 32 as illustrated in FIG. 7. A solution of alcohol 31 (34.6 g, 50.73 mmol, 1.0 equiv) in a mixture of ether (380 mL) and MeCN (127 mL) was cooled to 0° C. Imidazole (17.3 g, 253.7 Immol, 5.0 equiv) and PPh$_3$ (33.3 g, 126.8 mmol, 2.5 equiv) were then added and the mixture was stirred until all the solids had dissolved. Iodine (33.5 g, 131.9 mol, 2.6 equiv) was added and the mixture was stirred for 45 min at 0° C. The reaction was quenched by the addition of saturated aqueous Na$_2$S$_2$O$_3$ (150 mL) and the layers were separated. The aqueous phase was then extracted with ether (2×250 mL) and the combined organic extracts were washed with brine (750 mL), dried (MgSO$_4$) and concentrated under reduced pressure. Flash column chromatography (silica gel, 5ⓑ 9% ether in hexanes) furnished iodide 32 (39.2 g, 97%). R$_f$=0.88 (silica gel, 60% ether in hexanes); [a]$^{22}$D −2.9 (c 2.6, CHCl$_3$); IR (thin film) n$_{max}$ 3057, 2926, 2855, 1481, 1448, 1251, 1083, 939, 836, 774, 706, 632 cm$^{-1}$; $^1$H NMR (500 MHz, CDCl$_3$) d 7.49–7.45 (m, 5 H, Ph), 7.33–7.23 (m, 10 H, Ph), 6.23 (s, 1 H, CH=CCH$_3$), 5.67 (dd, J=7.2, 7.1 Hz, 1 H, CH$_2$C=CH), 4.22 (dd, J=6.8, 6.8 Hz, 1 H, CHOSi), 3.51 (s, 2 H, CH$_2$OTr), 3.07 (dd, J=7.1, 7.0 Hz, 2 H, CH$_2$I), 2.34 (ddd, J=14.5, 6.8, 6.8 Hz, 1 H, CH$_2$CHOSi), 2.25 (ddd, J=14.5, 6.8, 6.8 Hz, CH$_2$CHOSi), 2.13 (m, 2 H, CH$_2$CH$_2$CH$_2$I), 1.84 (s, 3 H, CH=CCH$_3$), 1.75 (m, 2 H, CH$_2$CH$_2$CH$_2$I), 0.90 (s, 9 H, SiC(CH$_3$)$_3$), 0.07 (s, 3 H, Si(CH$_3$)$_2$), 0.02 (s, 3 H, Si(CH$_3$)$_2$); $^{13}$C NMR (125.7 MHz, CDCl$_3$) d 150.1, 144.1, 136.9, 128.6, 127.9, 126.9, 126.3, 86.7, 77.6, 77.2, 67.3, 34.7, 32.1, 25.8, 19.9, 18.2, 6.8, −4.9, −5.0; HRMS (FAB), calcd for $C_{36}H_{46}I_2O_2Si$ (M+Cs$^+$), 925.0411 found 925.0450.

Hydrazone 33 as illustrated in FIG. 7. The SAMP hydrazone of propionaldehyde (5.6 g, 32.76 mmol, 1.3 equiv) in THF (16 mL), was added to a freshly prepared solution of LDA at 0° C. [diisopropylamine (5.0 mL, 35.28 mmol, 1.4 equiv) was added to n-BuLi (22.0 mL, 1.6 M in hexanes, 35.28 mmol, 1.4 equiv) in 32 mL of THF at 0° C. After stirring at that temperature for 16 h, the resulting yellow solution was cooled to −100° C., and a solution of iodide 32 (20.0 g, 25.23 mmol, 1.0 equiv) in THF (32 mL) was added dropwise over a period of 2 h. The mixture was allowed to warm to −20° C. over 20 h, and then poured into saturated aqueous NH$_4$Cl (50 mL) and extracted with ether (3×100 mL). The combined organic extract was dried (MgSO$_4$), filtered and evaporated. Purification by flash column chromatography on silica gel (5 ® 50% ether in hexanes) provided hydrazone 33 (15.0 g, 71%) as a yellow oil. $R_f$=0.63 (silica gel, 40% ether in hexanes); $[a]^{22}$D −22.7 (c 0.2, $CHCl_3$); IR (thin film) $n_{max}$ 3057, 2927, 2854, 1489, 1448, 1251, 1078, 940, 836, 775, 706, 668, 632 cm$^{-1}$; $^1$H NMR (500 MHz, $CDCl_3$) d 7.46–7.44 (m, 5 H, Ph), 7.31–7.21 (m, 10 H, Ph), 6.40 (d, J=6.5 Hz, 1 H, N=CH), 6.21 (s, 1 H, CH=$CCH_3$), 5.50 (dd, J=7.0, 7.0 Hz, 1 H, $CH_2C$=CH), 4.20 (dd, J=6.0, 6.0 Hz, 1 H, CHOSi), 3.54 (dd, J=9.2, 3.5 Hz, 1 H, $CH_2OCH_3$), 3.45 (s, 2 H, $CH_2$OTr), 3.41 (dd, J=9.5, 7.0 Hz, 1 H, $CH_2OCH_3$), 3.37 (s, 3 H, $CH_2OCH_3$), 3.32–3.30 (m, 2 H, $CH_2$N), 2.60–2.55 (m, 1 H), 2.34–2.20 (m, 3 H), 2.04–1.95 (m, 1 H), 1.98–1.73 (m, 5 H), 1.82 (s, 3 H, CH=$CCH_3$), 1.38–1.21 (m, 4 H), 0.96 (d, J=6.9 Hz, 3 H, $CHCH_3$), 0.89 (s, 9 H, $SiC(CH_3)_3$), 0.06 (s, 3 H, $Si(CH_3)_2$), 0.01 (s, 3 H, $Si(CH_3)_2$); $^{13}$C NMR (125.7 MHz, $CDCl_3$) d 150.2, 144.3, 138.5, 128.6, 127.7, 126.8, 121.3, 86.5, 77.4, 74.7, 67.0, 63.5, 59.2, 50.4, 37.0, 35.5, 34.6, 28.8, 24.5, 25.9, 25.8, 22.1, 19.8, 18.9, 18.2, −4.9, −5.0; HRMS (FAB), calcd for $C_{45}H_{63}IN_2O_3Si$ (M+Cs$^+$), 967.2707 found 967.2740.

Nitrile 34 as illustrated in FIG. 7. Monoperoxyphthalic acid magnesium salt (MMPP.6$H_2$O, 80%, 52.4 g, 84.8 mmol, 2.5 equiv) was added portionwise over 10 min to a rapidly stirred solution of hydrazone 33 (28.3 g, 33.9 mmol, 1.0 equiv) in a mixture of MeOH (283 mL), THF (100 mL) and pH 7 phosphate buffer (283 mL) at 0° C. The mixture was stirred at 0° C. for 1.5 h and then more THF (120 mL) was added in two portions over 30 min to help dissolve the starting material. After stirring for a further 1.5 h the reaction mixture was poured into saturated aqueous solution of NaHCO$_3$ (750 mL) and the product was extracted with ether (750 mL) and then EtOAc (2×750 mL). The combined organic extracts were washed with brine (1 L), dried (MgSO$_4$) and concentrated under reduced pressure. Flash column chromatography (silica gel, 9® 20% ether in hexanes) furnished nitrile 34 as a colorless oil (21.8 g, 89%). $R_f$=0.44 (silica gel, 20% ether in hexanes); $[a]^{22}$D +2.9 (c 1.2, $CHCl_3$); IR (thin film) $n_{max}$ 3057, 2928, 2855, 2238, 1490, 1448, 1252, 1081, 836, 775, 707, 632 cm$^{-1}$; $^1$H NMR (500 MHz, $CDCl_3$) d 7.47–7.45 (m, 5 H, Ph), 7.33–7.23 (m, 10 H, Ph), 6.22 (s, 1 H, CH=$CCH_3$), 5.56 (dd, J=6.8, 6.8 Hz, 1 H, $CH_2C$=CH), 4.21 (dd, J=6.8, 6.8 Hz, 1 H, CHOSi), 3.49 (s, 2 H, $CH_2$OTr), 2.48 (m, 1 H, CH($CH_3$)), 2.29 (ddd, J=14.5, 6.8, 6.8 Hz, 1 H, $CH_2$CHOSi), 2.24 (ddd, J=14.5, 6.8, 6.8 Hz, 1 H, $CH_2$CHOSi), 2.07 (m, 2 H, $CH_2$(C)$CH_2$OTr)), 1.82 (s, 3 H, CH=$CCH_3$), 1.58–1.23 (m, 4 H), 1.24 (d, J=7.0 Hz, 3 H, $CHCH_3$), 0.90 (s, 9 H, $SiC(CH_3)_3$), 0.07 (s, 3 H, $Si(CH_3)_2$), 0.0 (s, 3 H, $Si(CH_3)_2$); $^{13}$C NMR (125.7 MHz, $CDCl_3$) d 150.0, 144.1, 137.6, 128.6, 127.8, 126.9, 122.7, 122.5, 86.5, 77.4, 76.7, 34.6, 33.7, 31.5, 27.8, 25.7, 25.5, 25.2, 22.6, 19.7, 18.1, 17.8, 14.1, −4.9, −5.0; HRMS (FAB), calcd for $C_{39}H_{50}INO_2Si$ (M+Cs$^+$), 852.1710 found 852.1738.

Aldehyde 35 as illustrated in FIG. 7. Nitrile 34 (7.01 g, 9.74 mmol, 1.0 equiv) was dissolved in toluene (195 mL, 0.05 M) and cooled to −78° C. DIBAL (29.2 mL, 1.0 M in toluene, 29.2 mmol, 3.0 equiv) was added dropwise at −78° C. over 10 min. The reaction mixture was stirred at −78° C. until completion was verified by TLC (1 h). Methanol (10 mL) and HCl (10 mL, 1.0 N in water) were sequentially added and the resulting mixture was brought up to 0° C. over 1 h. Ether (250 mL) and water (250 mL) were added and the layers were separated. The aqueous phase was extracted with ether (2×250 mL) and the combined organic extracts were washed with brine (500 mL), dried (MgSO$_4$) and concentrated under reduced pressure. Flash column chromatography (silica gel, 17 ® 33% ether in hexanes) afforded aldehyde 35 as an oil (6.18 g, 88%). $R_f$=0.51 (silica gel, 20% ether in hexanes); $[a]^{22}$D +2.0 (c 0.3, $CHCl_3$); IR (thin film) $n_{max}$ 3057, 2927, 2855, 1726, 1490, 1448, 1251, 1081, 836, 775, 707, 632 cm$^{-1}$; $^1$H NMR (500 MHz, $CDCl_3$) d 9.51 (d, J=1.9 Hz, 1 H, CHO), 7.46–7.45 (m, 5 H, Ph), 7.32–7.22 (m, 10 H, Ph), 6.20 (s, 1 H, CH=$CCH_3$), 5.54 (dd, J=7.0, 7.0 Hz, 1 H, $CH_2C$=CH), 4.20 (dd, J=6.5, 6.0 Hz, 1 H, CHOSi), 3.47 (s, 2 H, $CH_2$OTr), 2.34–2.20 (m, 3 H, $CH_2$CHOSi and CH($CH_3$)), 2.04 (m, 2 H, $CH_2$(C)$CH_2$OTr), 1.82 (s, 3 H, CH=$CCH_3$), 1.66 (m, 1 H), 1.30–1.19 (m, 3 H), 1.02 (d, J=7.0 Hz, 3 H, $CHCH_3$), 0.89 (s, 9 H, $SiC(CH_3)_3$), 0.06 (s, 3 H, $Si(CH_3)_2$), 0.00 (s, 3 H, $Si(CH_3)_2$); $^{13}$C NMR (125.7 MHz, $CDCl_3$) d 205.0, 150.1, 144.2, 138.0, 128.6, 127.8, 126.9, 122.1, 86.6, 77.5, 67.1, 46.1, 34.6, 30.3, 28.6, 25.8, 25.6, 19.8, 18.2, 13.2, −4.9, −5.0; HRMS (FAB), calcd for $C_{39}H_{51}IO_3Si$ (M+Cs$^+$), 855.1707 found 855.1672.

tris-(Silylethers) 37 and 38 as illustrated in FIG. 8. A solution of ketone 36$^{6e}$ (1.20 g, 2.99 mmol, 1.4 equiv) in THF (4.3 mL) was added dropwise over 5 min to a freshly prepared solution of LDA [diisopropylamine (424 mL, 3.03 mmol, 1.45 equiv) was added to n-BuLi (2.00 mL, 1.52 M in hexanes, 3.04 mmol, 1.45 equiv) at 0° C., and after 5 min THF (4.3 mL) was added] at −78° C. After stirring for 1.5 h at −78° C., the solution was allowed to warm up to −40° C. over a period of 30 min. The reaction mixture was then cooled to −78° C., and a solution of aldehyde 35 (1.51 g, 2.09 mmol, 1.0 equiv) in THF (12.5 mL) was added dropwise over 15 min. The resulting mixture was stirred for 1 h at −78° C., and then quenched by dropwise addition of saturated aqueous AcOH (3.1 mL of a 1 M solution in THF, 3.10 mmol, 1.5 equiv). The mixture was then warmed to 25° C. nad partitioned between ether (25 mL) and saturated aqueous NH$_4$Cl (25 mL). The aqueous phase was extracted with ether (3×25 mL) and the combined organic extracts were dried (MgSO$_4$) and concentrated under reduced pressure. Flash column chromatography (silica gel, 4 ® 20% ether in hexanes) provided unreacted ketone (502 mg, 42%), undesired aldol product 38 (705 mg, 27%) and a mixture of desired aldol product 37 and unreacted aldehyde 35 [1.136 g, (ca. 9:1 ratio of 37:35 by $^1$H NMR)] (i.e. 39% yield of 37). This mixture was used directly in the next step. 37: (major) (obtained as a colorless oil from a mixture containing 35, by flash column chromatography silica gel, (10® 17% EtOAc in hexanes). $R_f$=0.22 (silica gel, 10% ether in hexanes); $[a]^{22}$D −20.0 (c 0.3, $CHCl_3$); IR (thin film) $n_{max}$ 3486, 2954, 2928, 2856, 1682, 1472, 1448, 1253, 1090, 994, 836, 775, 706, 668, 632 cm$^{-1}$; $^1$H NMR (600 MHz, $CDCl_3$) d 7.45–7.43 (m, 5 H, Ph), 7.30–7.19 (m, H, Ph), 6.19 (s, 1 H, CH=$CCH_3$), 5.51 (dd, J=7.0, 6.9 Hz, 1 H, C=CH$CH_2$), 4.18 (dd, J=6.3, 6.2 Hz, 1 H, CHOSi), 3.88 (dd, J=7.5, 2.6 Hz, 1 H, CHOSi), 3.65 (m, 1 H, $CH_2$OSi), 3.59 (m, 1 H, $CH_2$OSi), 3.46 (d, J=11.2 Hz, 1 H, $CH_2$OTr), 3.43 (d, J=11.2 Hz, 1 H, $CH_2$OTr), 3.27 (m, 1 H, $CH_3$CH(C=O)), 3.22 (d, J=9.3 Hz, 1 H, CHOH), 2.32–2.18 (m, 2 H, C=CH$CH_2$CHOSi) 2.00 (m, 2 H, $CH_2$(C)$CH_2$OTr), 1.80 (s, 3 H, CH=C($CH_3$)), 1.66 (m, 2 H), 1.46 (m, 2 H), 1.27 (m, 1 H, CH($CH_3$)), 1.19 (S, 3 H, C($CH_3$)$_2$), 1.07 (s, 3 H, C($CH_3$)$_2$), 0.99 (d, J=6.8 Hz, 3 H, CH($CH_3$)), 0.89 (s, 9 H, $SiC(CH_3)_3$), 0.87 (s, 9 H, $SiC(CH_3)_3$), 0.86 (s, 9 H, $SiC(CH_3)_3$), 0.71 (d, J=6.7 Hz, 3 H, CH($CH_3$)), 0.10 (s, 3 H, $Si(CH_3)_2$), 0.07 (s, 3 H, $Si(CH_3)_2$), 0.04 (s, 3 H, $Si(CH_3)_2$), 0.3 (s, 6 H, $Si(CH_3)_2$), −0.01 (s, 3 H, $Si(CH_3)_2$); $^{13}$C NMR (150.9 MHz, $CDCl_3$) d 222.1, 150.1, 144.1, 138.6, 128.5, 127.6, 126.7, 121.1, 86.4, 77.4, 74.8, 74.1, 67.1, 60.4, 54.0, 41.2, 37.9, 35.4, 34.7, 33.0, 29.2, 26.2, 26.0, 25.9, 25.7, 23.0, 20.6, 19.8, 18.4, 18.3, 18.2, 15.4, 9.6, −3.5, −3.9, −4.7, −4.8, −5.1; HRMS (FAB), calcd for $C_{60}H_{97}IO_6Si_3$ (M+Cs$^+$), 1257.4692 found 1257.4639. 38: (minor) Colorless oil; $R_f$=0.38 (silica gel, 20% ether in hexanes); $[a]^{22}D$ −11.9 (c 2.9, CHCl$_3$); IR (thin film) n$_{max}$ 3501, 2954, 2930, 2856, 1682, 1469, 1254, 1088, 836, 776, 705, 670 cm$^{-1}$; $^1$H NMR (500 MHz, CDCl$_3$) d 7.46–7.44 (m, 5 H, Ph), 7.31–7.21 (m, 10 H, Ph), 6.21 (s, 1 H, CH=CCH$_3$), 5.52 (dd, J=7.0, 6.9Hz, 1 H, C=CHCH$_2$), 4.20 (dd, J=6.5, 6.5 Hz, 1 H, CHOSi), 3.88 (dd, J=7.5, 2.5 Hz, 1 H, CHOSi), 3.67 (m, 1 H, CH$_2$OSi), 3.60 (m, 1 H, CH$_2$OSi), 3.46 (s, 2 H, CH$_2$OTr), 3.30–3.21 (m, 2 H, CHOH, CH$_3$CH(C=O)), 2.30–2.25 (m, 2 H, C=CHCH$_2$CHOSi), 2.05–1.93 (m, 2 H, CH$_2$C(CH$_2$OTr)=CH), 1.81 (s, 3 H, CH=C(CH$_3$)), 1.63 (m, 1 H, CH(CH$_3$)), 1.45 (m, 2 H), 1.24 (m, 2 H), (s, 3 H, C(CH$_3$)$_2$), 1.05 (s, 3 H, C(CH$_3$)$_2$), 1.01 (d, J 6.9 Hz, 3 H, CH(CH$_3$)), 0.92 (s, 18 H, SiC(CH$_3$)$_3$), 0.89 (s, 9 H, SiC(CH$_3$)$_3$), 0.88 (obscured d, 3 H, CH(CH$_3$)), 0.88 (s, 18 H, SiC(CH$_3$)$_3$), 0.11 (s, 3 H, Si(CH$_3$)$_2$), 0.07 (s, 3 H, Si(CH$_3$)$_2$), 0.06 (s, 3 H, Si(CH$_3$)$_2$), 0.04 (s, 6 H, Si(CH$_3$)$_2$) 0.01 (s, 3 H, Si(CH$_3$)$_2$); $^{13}$C NMR (125.7 MHz, CDCl$_3$) d 221.8, 150.1, 144.2, 138.6, 128.7, 127.8, 126.9, 121.6, 86.5, 77.4, 77.3, 75.0, 74.0, 67.1, 60.5, 53.9, 53.4, 41.6, 37.8, 35.4, 34.7, 32.9, 29.0, 26.1, 25.9, 25.7, 23.2, 20.2, 19.8, 18.3, 18.2, 18.1, 15.4, 10.5, −3.7, −4.1, −4.9, −5.0, −5.3; HRMS (FAB), calcd for $C_{60}H_{97}IO_6Si_3$ (M+Cs$^+$), 1257.4692 found 1257.4749.

tetra-(Silylether) 39 as illustrated in FIG. 8. Alcohol 37 (1.136 g of a 9:1 mixture with aldehyde 35, 0.933 mmol, 1.0 equiv) was dissolved in CH$_2$Cl$_2$ (5.0 mL), cooled to −20° C. and treated with 2,6-lutidine (470 mL, 4.04 mmol, 4.3 equiv) and tert-butyldimethylsilyl trifluoromethanesulfonate (695 mL, 3.03 mmol, 3.2 equiv). The mixture was then stirred for 2.5 h with slow warming to 0° C. The reaction was then quenched with saturated aqueous NaHCO$_3$ (25 mL) and the aqueous phase was extracted with ether (3×25 mL). The combined organic extracts were washed with brine (250 mL), dried (MgSO$_4$) and concentrated under reduced pressure. Flash column chromatography (silica gel, 4® 9% ether in hexanes) furnished tetra-(silylether) 39 as a colorless oil (1.04 g, 90%). $R_f$=0.91 (silica gel, 20% ether in hexanes); $[a]^{22}D$ −16.8 (c 0.7, CHCl$_3$); IR (thin film) n$_{max}$ 3058, 2951, 2856, 1693, 1471, 1253, 1079, 1004, 836, 706 cm$^{-1}$; $^1$H NMR (600 MHz, CDCl$_3$) d 7.46–7.43 (m, 5 H, Ph), 7.29–7.19 (m, 10 H, Ph), 6.19 (s, 1 H, CH=CCH$_3$), 5.49 (dd, J=7.0, 7.0 Hz, 1 H, C=CHCH$_2$), 4.18 (dd, J=6.3, 6.1 Hz, 1 H, CHOSi), 3.85 (dd, J=7.6, 2.5 Hz, 1 H, CHOSi), 3.70 (dd, J=6.7, 2.0 Hz, 1 H, CHOSi), 3.67 (ddd, J=9.6, 4.8, 4.8 Hz, 1 H, CH$_2$OSi), 3.59 (ddd, J=9.7, 7.9. 7.9 Hz, 1 H, CH$_2$OSi), 3.45 (d, J=11.2 Hz, 1 H, CH$_2$OTr), 3.42 (d, J=11.2 Hz, 1 H, CH$_2$OTr), 3.08 (qd, J=6.8, 6.8 Hz, 1 H, CH$_3$CH (C=O)), 2.27 (ddd, J=14.4, 7.2, 7.2 Hz, 1 H, C=CHCH$_2$CHOSi), 2.23 (ddd, J=14.5, 6.2, 6.2 Hz, 1 H, C=CHCH$_2$CHOSi), 1.97 (m, 2 H, CH$_2$C(CH$_2$OTr)=CH), 1.79 (s, 3 H, CH=C(CH$_3$)), 1.57 (m, 1 H), 1.46 (m, 1 H), 1.25 (m, 3 H), 1.17 (s, 3 H, C(CH$_3$)$_2$), 1.01 (d, J=6.8 Hz, 3 H, CH(CH$_3$)), 0.95 (s, 3 H, C(CH$_3$)$_2$), 0.87 (s, 18 H, SiC(CH$_3$)$_3$), 0.86 (s, 18 H, SiC(CH$_3$)$_3$), 0.09–0.03 (m, 24 H, Si(CH$_3$)$_2$); $^{13}$C NMR (150.9 MHz, CDCl$_3$) d 218.2, 150.2, 144.3, 138.7, 128.6, 127.7, 126.8, 121.5, 86.5, 77.5, 77.4, 77.3, 74.0, 67.1, 60.9, 53.6, 45.1, 38.7, 38.0, 34.6, 31.0, 29.3, 26.5, 26.2, 26.1, 25.9, 25.8, 24.4, 19.7, 19.5, 18.5, 18.3, 18.2, 18.1, 17.5, 15.1, −3.6, −3.7, −3.8, −4.0, −4.9, −5.0, −5.2, −5.3; HRMS (FAB), calcd for $C_{66}H_{111}IO_6Si_4$ (M+Cs$^+$), 1371.5557 found 1371.5523.

Alcohol 40 as illustrated in FIG. 8. To a solution of tetra-silyl ether 39 (180 mg, 0.145 mmol) in THF (1.5 mL) at 0° C. was added HF.pyr. in pyridine/THF mixture (prepared from a stock solution containing 420 mL HF.pyridine, 1.14 mL pyridine and 300 mL THF) (1.5 mL) and the resulting solution was stirred for 2 h at 0° C. More HF.pyr. in pyridine/THF mixture (0.5 mL) was then added and stirring was continued for additional 1 h at 0° C. The reaction was quenched by careful addition of saturated aqueous NaHCO$_3$ and the product was extracted with EtOAc (3×25 mL). The combined organic extracts were then dried (MgSO$_4$) and concentrated under reduced pressure. Flash chromatography (silica gel 30% ether in hexanes) furnished alcohol 40 as a pale yellow oil (137 mg, 84%). $R_f$=0.36 (silica gel, 40% ether in hexanes); $[a]^{22}D$ −26.0 (c 0.3, CDCl$_3$); IR (thin film) n$_{max}$ 3422, 2928, 2855, 1690, 1490, 1471, 1448, 1360, 1252, 1086, 1004, 986, 836, 774, 706 cm$^{-1}$; $^1$H NMR (600 MHz, CDCl$_3$) d 7.44–7.42 (m, 5 H, Ph), 7.29–7.20 (m, 10 H, Ph), 6.19 (s, 1 H, CH=CCH$_3$), 5.49 (dd, J=7.1, 7.1 Hz, 1 H, C=CHCH$_2$), 4.17 (dd, J=6.2, 6.0 Hz, 1 H, CHOSi), 4.03 (dd, J=6.6, 3.7 Hz, 1 H, CHOSi), 3.73 (dd, J=7.2, 1.7 Hz, 1 H, CHOSi), 3.65 m, 2 H, CH$_2$OH), 3.45 (d, J=11.7 Hz, 1 H, CH$_2$OTr), 3.42 (d, J=11.7 Hz, 1 H, CH$_2$OTr), 3.06 (qd, J=6.9, 6.9 Hz, 1 H, CH$_3$CH(C=O)), 2.28 (ddd, J=14.7, 7.3, 7.3 Hz, 1 H, C=CHCH$_2$CHOSi), 2.22 (ddd, J=14.7, 6.3, 6.3 Hz, 1 H, C=CHCH$_2$CHOSi), 1.98 (m, 2 H, CH$_2$C(CH$_2$OTr)=CH), 1.79 (s, 3 H, CH=C (CH$_3$)), 1.56 (m, 2 H), 1.24 (m, 3 H), 1.18 (s, 3 H, C(CH$_3$)$_2$), 1.03 (d, J=6.9 Hz, 3 H, CH(CH$_3$)), 0.97 (s, 3 H, C(CH$_3$)$_2$), 0.87 (3 singlets, 27 H, SiC(CH$_3$)$_3$), 0.81 (d, J=6.7 Hz, 3 H, CH(CH$_3$)), 0.10 (s, 3 H, Si(CH$_3$)$_2$), 0.04 (s, 9 H, Si(CH$_3$)$_2$), 0.03 (s, 3 H, Si(CH$_3$)$_2$), 0.00 (s, 3 H, Si(CH$_3$)$_2$); $^{13}$C NMR (150.9 MHz, CDCl$_3$) d 219.2, 150.0, 144.1, 138.5, 128.5, 127.6, 126.7, 121.4, 86.4, 77.5, 77.4, 77.3, 73.1, 67.2, 60.2, 53.7, 45.2, 38.6, 38.4, 34.7, 30.9, 29.4, 26.6, 26.3, 26.1, 25.8, 25.0, 19.8, 30 18.6, 18.4, 17.9, 17.8, 15.7, −3.4, −3.6, −3.7, −3.8, −4.7, −4.8; HRMS (FAB), calcd for $C_{60}H_{97}IO_6Si_3$ (M+Cs$^+$), 1257.4692 found 1257.4780.

Aldehyde 41 as illustrated in FIG. 8. To a solution of oxalyl chloride (150 mL, 1.72 mmol, 2.0 equiv) in CH$_2$Cl$_2$ (10 mL) at −78° C. was added dropwise DMSO (247 mL, 3.48 mmol, 4.0 equiv). After stirring for 10 min at −78° C., a solution of alcohol 40 (960 mg, 0.853 mmol, 1.0 equiv) in CH$_2$Cl$_2$ (10 mL) was added dropwise. The resulting solution was stirred at −78° C. for 1 h, and then Et$_3$N (714 mL, 5.12 mmol, 6.0 equiv) was added and the reaction mixture was allowed to warm up to 25° C. over 30 min. Water (30 mL) was added, and the product was extracted with ether (3×40 mL). The combined organic extracts were dried (MgSO$_4$) and then concentrated under reduced pressure. Flash column chromatography (silica gel, 17 ® 50% ether in hexanes) furnished aldehyde 41 as a colorless oil (943 mg, 98%). $R_f$=0.74 (silica gel, 40% ether in hexanes); $[a]^{22}D$ −10.8 (c 0.1, CHCl$_3$); IR (thin film) n$_{max}$ 2928, 2855, 1728, 1690, 1471, 1448, 1260, 1252, 1085, 987, 836, 774, 706 cm$^{-1}$; $^1$H NMR (600 MHz, CDCl$_3$) d 9.74 (dd, J=2.4, 1.5 Hz, 1 H, CHO), 7.44–7.42 (m, 5 H, Ph), 7.29–7.20 (m, 10 H, Ph), 6.19 (s, 1 H, CH=CCH$_3$), 5.49 (dd, J=7.0, 6.8 Hz, 1 H, C=CHCH$_2$), 4.44 (dd, J=6.3, 5.0 Hz, 1 H, CHOSi), 4.18 (dd, J=6.9, 6.4 Hz, 1 H, CHOSi), 3.70 (dd, J=7.2, 1.8 Hz, 1 H, CHOSi), 3.45 (d, J=11.4 Hz, 1 H, CH$_2$OTr), 3.42 (d, J=11.4 Hz, 1 H, CH$_2$OTr), 3.05 (qd, J=7.0, 7.0 Hz, 1 H, CH$_3$CH(C=O)), 2.49 (ddd, J=17.0, 4.5, 1.4 Hz, CH$_2$CHO), 2.38 (ddd, J=17.0, 5.4, 2.8 Hz, 1 H, CH$_2$CHO), 2.27 (ddd, J=14.0, 7.1, 7.1 Hz, 1 H, C=CHCH$_2$CHOSi), 2.23 (ddd, J=14.5, 6.5, 6.5 Hz, 1 H, C=CHCH$_2$CHOSi), 1.98 (m, 2 H, CH$_2$C(CH$_2$OTr)=CH), 1.79 (s, 3 H, CH=C(CH$_3$)), 1.27 (m, 4 H), 1.19 (s, 3 H, C(CH$_3$)$_2$), 1.12 (m, 1 H), 1.00 (d, J=6.8 Hz, 3 H, CH(CH$_3$)), 0.98 (s, 3 H, C(CH$_3$)$_2$), 0.87 (s, 27 H, Si(CH$_3$)$_3$), 0.80 (d, J=6.7 Hz, 3 H, CH(CH$_3$)), 0.07 (s, 3 H, Si(CH$_3$)$_2$), 0.04 (s, 3 H, Si(CH$_3$)2), 0.03 (s, 3 H, Si(CH$_3$)2), 0.03 (s, 3 H, Si(CH$_3$)$_2$), 0.02 (s, 3 H, Si(CH$_3$)$_2$), 0.00 (s, 3 H, Si(CH$_3$)$_2$); $^{13}$C NMR (150.9 MHz, CDCl$_3$) d 218.4, 201.1, 150.2, 144.25, 138.6, 128.6, 127.7, 126.8, 121.5, 86.5, 77.5, 77.4, 77.3, 71.3, 67.1, 53.4, 49.5, 45.1, 38.6, 34.6, 30.8, 29.2, 26.2, 25.9, 25.7, 24.0, 19.7, 18.8, 18.4, 18.1, 18.0, 17.7, 15.4, −3.6, −3.7, −4.1, −4.4, −4.9, −5.0; HRMS (FAB), calcd for C$_{60}$H$_{95}$IO$_6$Si$_3$ (M+Cs$^+$), 1255.4536 found 1255.4561.

Carboxylic acid 42 as illustrated in FIG. 8. To a solution of aldehyde 41 (943 mg, 0.839 mmol, 1.0 equiv) in t-BuOH (38.5 mL) and H$_2$O (8.4 mL) was added 2-methyl-2-butene (31.5 mL, 2 M in THF, 63.0 mmol, 75 equiv), NaH$_2$PO$_4$ (250 mg, 2.08 mmol, 2.5 equiv) followed by NaClO$_2$ (380 mg, 4.20 mmol, 5.0 equiv) and the resulting mixture was stirred at 25° C. for 40 min. The volatiles were then removed under reduced pressure and the residue was partitioned between EtOAc (40 mL) and brine (40 mL) and the layers separated. The aqueous phase was then extracted with EtOAc (3×40 mL), and the combined organic extracts were dried (MgSO$_4$) and then concentrated under reduced pressure. Flash column chromatography (silica gel, 60% ether in hexanes) furnished carboxylic acid 42 as an oil (956 mg, 100%). R$_f$=0.47 (silica gel, 40% ether in hexanes); [a]$^{22}$D −19.6 (c 0.2, CHCl$_3$); IR (thin film) n$_{max}$ 3389, 2930, 2856, 1711, 1469, 1254, 1085, 988, 835, 775, 705 cm$^{-1}$; $^1$H NMR (600 MHz, CDCl$_3$) d 7.44–7.43 (m, 5 H, Ph), 7.29–7.20 (m, 10 H,Ph), 6.19 (s, 1 H, CH=CCH$_3$), 5.49 (dd, J=7.3, 7.1 Hz, 1 H, C=CHCH$_2$), 4.34 (dd, J=6.4, 3.3 Hz, 1 H, CHOSi), 4.18 (dd, J=6.2, 6.2 Hz, 1 H, CHOSi), 3.72 (dd, J=7.2, 1.7 Hz, 1 H, CHOSi), 3.45 (d, J=11.4 Hz, 1 H, CH$_2$OTr), 3.41 (d, J 11.4 Hz, 1 H, CH$_2$OTr), 3.07 (qd, J=7.0, 7.0 Hz, 1 H, CH$_3$CH(C=O)), 2.46 (dd, J=16.3, 3.1 Hz, 1 H, CH$_2$CO$_2$H), 2.32–2.18 (m, 3 H, CH$_2$CO$_2$H and C=CHCH$_2$CHOSi), 1.97 (m, 2 H, CH$_2$C(CH$_2$OTr)=CH), 1.80 (s, 3 H, CH=C(CH$_3$)), 1.31–1.19 (m, 5 H), 1.19 (s, 3 H, C(CH$_3$)$_2$), 1.02 (d, J=6.9 Hz, 3 H, CH(CH$_3$)), 0.99 (s, 3 H, C(CH$_3$)$_2$), 0.87 (s, 27 H, Si(CH$_3$)$_3$), 0.80 (d, J=6.8 Hz, 3 H, CH(CH$_3$)), 0.07, (s, 3 H, Si(CH$_3$)$_2$), 0.04 (s, 3 H, Si(CH$_3$)2), 0.04 (s, 3 H, Si(CH$_3$)2), 0.03 (s, 3 H, Si(CH$_3$)$_2$), 0.02 (s, 3 H, Si(CH$_3$)$_2$), 0.00 (s, 3 H, Si(CH$_3$)$_2$); $^{13}$C NMR (150.9 MHz, CDCl$_3$) d 218.2, 176.7, 150.2, 144.2, 138.6, 128.6, 127.7, 126.8, 121.5, 86.5, 77.6, 77.4, 77.3, 73.5, 67.1, 53.4, 45.2, 40.0, 38.5, 34.6, 30.8, 29.3, 26.2, 26.0, 25.8, 23.7, 19.7, 19.1, 18.5, 18.1, 17.7, 15.6, −3.6, −3.7, −4.3, −4.6, −4.9, −5.0; HRMS (FAB), calcd for C$_{60}$H$_{95}$IO$_7$Si$_3$ (M+Cs$^+$), 1271.4485 found 1271.4550.

Hydroxy acid 43 as illustrated in FIG. 8. A solution of carboxylic acid 42 (956 mg, 0.839 mmol, 1.0 equiv) in THF (17 mL) at 0° C. was treated with TBAF (5.0 mL, 1.0 M in THF, 5.00 mmol, 6.0 equiv) and the mixture was allowed to warm to 25° C. over 19 h. The reaction was then quenched by the addition of saturated aqueous NH$_4$Cl (40 mL) and the product was extracted with EtOAc (3×40 mL). The combined organic extracts were dried (MgSO$_4$) and concentrated under reduced pressure. Flash column chromatography (silica gel, 5% MeOH in CH$_2$Cl$_2$) furnished hydroxy acid 43 as a yellow oil (817 mg, 95%). R$_f$=0.27 (silica gel, 5% MeOH in CH$_2$Cl$_2$); [a]$^{22}$D −11.4 (c 0.2, CHCl$_3$); IR (thin film) n$_{max}$ 3364, 3057, 2938, 2856, 1712, 1694, 1469, 1254, 1086, 1053, 988, 836, 776, 734, 705 cm$^{-1}$; $^1$H NMR (600 MHz, CDCl$_3$) d 7.43–7.42 (m, 5 H, Ph), 7.30–7.21 (m, 10 H, Ph), 6.32 (s, 1 H, CH=CCH$_3$), 5.46 (dd, J=7.2, 7.2 Hz, 1 H, C=CHCH$_2$), 4.35 (dd, J=6.3, 3.2 Hz, 1 H, CHOH), 4.21 (dd, J=6.4, 6.3 Hz, 1 H, CHOSi), 3.73 (dd, J=7.3, 1.2 Hz, 1 H, CHOSi), 3.52 (d, J=12.1 Hz, 1 H, CH$_2$OTr), 3.48 (d, J=12.1 Hz, 1 H, CH$_2$OTr), 3.06 (m, 2 H, CH$_3$CH(C=O) and OH), 2.45 (dd, J=16.4, 3.0 Hz, 1 H, CH$_2$CO$_2$H), 2.35 (m, 2 H, C=CHCH$_2$CHOH), 2.29 (dd, J=16.4, 6.5 Hz, 1 H, CH$_2$CO$_2$H), 2.07–1.94 (m, 2 H, CH$_2$C(CH$_2$OTr)=CH), 1.85 (s, 3 H, CH=C(CH$_3$)), 1.71 (m, 1 H), 1.39 (m, 1 H, CH(CH$_3$)), 1.27 (m, 3 H), 1.18 (s, 3 H, C(CH$_3$)$_2$), 1.02 (obscured d, 3 H, CH(CH$_3$)), 1.02 (s, 3 H, C(CH$_3$)$_2$), 0.87 (s, 18 H, Si(CH$_3$)$_3$), 0.81 (d, J=6.8 Hz, 3 H, CH(CH$_3$)), 0.09 (s, 3 H, Si(CH$_3$)$_2$), 0.07 (s, 3 H, Si(CH$_3$)$_2$), 0.04 (s, 3 H, Si(CH$_3$)$_2$), 0.02 (s, 3 H, Si(CH$_3$)$_2$); $^{13}$C NMR (150.9 MHz, CDCl$_3$) d 218.1, 176.5, 149.1, 144.2, 140.7, 128.6, 127.7, 126.9, 120.3, 86.7, 78.5, 77.5, 76.1, 73.4, 67.1, 53.5, 53.0, 45.1, 40.0, 38.6, 33.4, 30.9, 29.2, 26.5, 26.2, 26.0, 25.6, 25.3, 23.7, 20.1, 19.9, 19.0, 18.5, 18.2, 17.6, 15.8, 13.5, −3.6, −3.7, −4.3, −4.6; HRMS (FAB), calcd for C$_{54}$H$_{81}$IO$_7$Si$_2$ (M+Cs$^+$), 1157.3620 found 1157.3669.

Macrolactone 44 as illustrated in FIG. 8. To a solution of hydroxy acid 43 (1.06 g, 1.04 mmol, 1.0 equiv) in THF (15 mL, 0.07 M) was added Et$_3$N (870 mL, 6.24 mmol, 6.0 equiv) and 2,4,6-trichlorobenzoyl chloride (390 mL, 2.50 mmol, 2.4 equiv). The reaction mixture was stirred at 0° C. for 1.5 h, and then added slowly over a period of 2 h via syringe pump to a solution of 4-DMAP (280 mg, 2.29 mmol, 2.2 equiv) in toluene (208 mL, 0.005 M based on 43) at 75° C. The mixture was stirred at that temperature for an additional 0.5 h and was then concentrated under reduced pressure. The resulting residue was filtered through a plug of silica gel eluting with 50% ether in hexanes. Flash column chromatography (silica gel, 17% ether in hexanes) furnished macrolactone 44 as a colorless foam (877 mg, 84%). R$_f$=0.19 (10% ether in hexanes); [a]$^{22}$D −7.4 (c 0.2, CDCl$_3$); IR (thin film) n$_{max}$ 2929, 2855, 1742, 1695, 1468, 1381, 1253, 1156, 1065, 985, 834, 774, 733, 706 cm$^{-1}$; $^1$H NMR (600 MHz, CDCl$_3$) d 7.44–7.42 (m, 5 H, Ph), 7.29–7.20 (m, 10 H, Ph), 6.39 (s, 1 H, CH=CCH$_3$), 5.51 (dd, J=9.5, 6.8 Hz, 1 H, C=CHCH$_2$), 5.07 (d, J=9.3 Hz, 1 H, CHOCO), 4.02 (d, J=9.2 Hz, 1 H, CHOSi), 3.82 (d, J=8.9 Hz, 1 H, CHOSi), 3.46 (d, J=11.5 Hz, 1 H, CH$_2$OTr), 3.42 (d, J=11.5 Hz, 1 H, CH$_2$OTr), 2.95 (dq, J=8.7, 7.0 Hz, 1 H, CH$_3$CH(C=O)), 2.72 (m, 2 H, C=CHCH$_2$CHO and CH$_2$COO), 2.54 (dd, J=16.2, 9.7 Hz, 1 H, CH$_2$COO), 2.29 (m, 1 H, C=CHCH$_2$CHO), 2.12 (dd, J=14.3, 5.1 Hz, 1 H, CH$_2$C(CH$_2$OTr)=CH), 1.98 (m, CH$_2$C(CH$_2$OTr)=CH), 1.88 (s, 3 H, CH=C(CH$_3$)), 1.44–1.23 (m, 5 H), 1.18 (s, 3 H, C(CH$_3$)$_2$), 1.10 (s, 3 H, C(CH$_3$)$_2$), 1.07 (d, J=6.8 Hz, 3 H, CH(CH$_3$)), 0.92 ((s, 9 H, Si(CH$_3$)$_3$), 0.82 (d, J=6.9 Hz, 3 H, CH(CH$_3$)), 0.72 (s, 9 H, Si(CH$_3$)$_3$), 0.08 (s, 3 H, Si(CH$_3$)$_2$), 0.05 (s, 3 H, Si(CH$_3$)$_2$), 0.05 (s, 3 H, Si(CH$_3$)$_2$), −0.32 (s, 3 H, Si(CH$_3$)$_2$); $^{13}$C NMR (150.9 MHz, CDCl$_3$) d 216.0, 171.7, 147.0, 145.0, 142.9, 129.5, 128.6, 127.8, 120.2, 87.3, 81.0, 78.8, 76.6, 67.5, 54.2, 48.8, 41.0, 40.1, 38.4, 33.6, 32.4, 32.2, 29.6, 28.0, 27.2, 26.9, 25.3, 23.5, 21.2, 19.5, 19.3, 18.6, 15.0, −2.5, −2.8, −3.0, −4.8; HRMS (FAB), calcd for C$_{54}$H$_{79}$IO$_6$Si$_2$ (M+Cs$^+$), 1139.3514 found 1139.3459.

Triol 24 as illustrated in FIG. 8. To a solution of macrolactone 44 (608 mg, 0.604 mmol, 1.0 equiv) in THF (45 mL) at 0° C. was added HF.pyr. (15 mL). The resulting mixture was allowed to warm up to 25° C. over 15 h and was then cooled to 0° C. and quenched by careful addition of saturated aqueous NaHCO$_3$ (50 mL). The product was then extracted with EtOAc (3×50 mL), and the combined organic extracts were dried (MgSO$_4$) and then concentrated under reduced pressure. Flash column chromatography (silica gel, 60% EtOAc in hexanes) furnished triol 24 as a colorless foam (280 mg, 86%). R$_f$=0.32 (silica gel, 60% EtOAc in hexanes); [a]$^{22}$D −32.1 (c 0.2, CHCl$_3$); IR (thin film) n$_{max}$ 3413, 2923, 2857, 1731, 1686, 1461, 1379, 1259, 1148, 1046, 737 cm$^{-1}$; $^1$H NMR (600 MHz, CDCl$_3$) d 6.43 (s, 1 H, CH=CCH$_3$), 5.38 (dd, J=9.7, 5.4 Hz, 1 H, C=CHCH$_2$), 5.29 (dd, J=8.8, 1.9 Hz, 1 H, CHOCO), 4.08 (m, 1 H, CHOH), 4.06 (d, J=13.0 Hz, 1 H, CH$_2$OH), 4.00 (d, J=13.0 Hz, 1 H, CH$_2$OH), 3.69 (dd, J=3.5, 3.4 Hz, 1 H, CHOH), 3.12 (qd, J=6.9, 3.1 Hz, 1 H, CH$_3$CH(C=O)), 2.76 (bs, 1 H, OH), 2.67 (ddd, J=15.0, 9.7, 9.7 Hz, 1 H, C=CHCH$_2$CHO), 2.45 (dd, J=15.4, 10.6 Hz, 1 H, CH$_2$COO), 2.38 (bs, 1 H, OH), 2.33 (dd, J=15.4, 3.0 Hz, 1 H, CH$_2$COO), 2.21 (m, 2 H, CH$_2$C(CH$_2$OH)=CH), 2.06 (m, 1 H, C=CHCH$_2$CHO), 1.87 (s, 3 H, CH=C(CH$_3$)), 1.71 (m, 1 H), 1.66 (m, 1 H), 1.32 (s, 3 H, C(CH$_3$)$_2$), 1.29–1.24 (m, 3 H), 1.17 (d, J=6.9 Hz, 3 H, CH(CH$_3$)), 1.08 (s, 3 H, C(CH$_3$)$_2$), 0.99 (d, J=7.0 Hz, 3 H, CH(CH$_3$)); $^{13}$C NMR (125.7 MHz, CDCl$_3$) d 220.1, 170.0, 145.3, 142.4, 120.7, 80.5, 77.6, 74.0, 72.9, 66.1, 53.0, 42.2, 39.3, 38.0, 31.8, 31.6, 28.0, 25.7, 22.5, 20.7, 19.2, 16.0, 13.6; HRMS (FAB), calcd for C$_{23}$H$_{37}$O$_6$ (M+Cs$^+$), 669.0689 found 669.0711.

Macrolactone 45 as illustrated in FIG. 9. A solution of vinyl iodide 24 (55 mg, 0.103 mmol, 1.0 equiv), stannane 8j (84 mg, 0.207 mmol, 2.0 equiv) and PdCl$_2$(MeCN)$_2$ (4 mg, 0.015 mmol, 0.15 equiv) in degassed DMF (1 mL, 0.1 M) was stirred at 25° C. for 33 h, according to the procedure described for the synthesis of macrolactone 18d, to yield, after preparative thin layer chromatography (250 mm silica gel plates, 80% EtOAc in hexanes), starting vinyl iodide 24 (21 mg, 39%) and acrolactone 45 (30 mg, 56%). R$_f$=0.48 (silica gel, 80% EtOAc in hexanes); [a]$^{22}$D −48.3 (c 0.2, CHCl$_3$); IR (thin film) n$_{max}$ 3372, 2924, 2860, 1731, 1682, 1454, 1384, 1252, 1148, 1040, 979, 735 cm$^{-1}$; $^1$H NMR (600 MHz, CDCl$_3$) d 7.21 (s, 1 H, ArH), 6.61 (s, 1 H, CH=CCH$_3$), 5.58 (d, J=47.0 Hz, 2 H, CH$_2$F), 5.45 (dd, J=9.8, 5.3 Hz, 1 H, C=CHCH$_2$), 5.26 (dd, J=9.4, 2.0 Hz, 1 H, CHOCO), 4.23 (dd, J=10.9, 2.4 Hz, 1 H, CHOH), 4.08 (d, J=13.1 Hz, 1 H, CH$_2$OH), 4.01 (d, J=13.1 Hz, 1 H, CH$_2$OH), 3.70 (dd, J=4.2, 2.7 Hz, 1 H, CHOH), 3.16 (qd, J=6.8, 2.6 Hz, 1 H, CH$_3$CH(C=O)), 2.94 (bs, 1 H, OH), 2.69 (ddd, J=15.2, 9.6, 9.6 Hz, 1 H, C=CHCH$_2$CHO), 2.46 (dd, J=14.8, 10.9 Hz, 1 H, CH$_2$COO), 2.36–2.24 (m, 2 H, CH$_2$C(CH$_2$OH)=CH), 2.30 (dd, J=14.8, 2.6 Hz, 1 H, CH$_2$COO), 2.09 (s, 3 H, CH=C(CH$_3$)), 2.07 (m, 1 H, C=CHCH$_2$CHO), 1.77–1.58 (m, 5 H), 1.33 (s, 3 H, C(CH$_3$)$_2$), 1.17 (d, J=6.9 Hz, 3 H, CH(CH$_3$)), 1.06 (s, 3 H, C(CH$_3$)$_2$), 1.00 (d, J=7.0 Hz, 3 H, CH(CH$_3$)); $^{13}$C NMR (150.9 MHz, CDCl$_3$) d 220.1, 170.1, 152.6, 141.9, 139.4, 121.4, 118.8, 117.7, 86.8, 81.0, 79.8, 78.7, 73.9, 72.4, 66.3, 53.4, 41.9, 39.6, 38.0, 32.0, 31.8, 28.1, 22.7, 18.4, 16.1, 15.8, 13.5; HRMS (FAB), calcd for C$_{22}$H$_{40}$FNO$_6$S (M+Cs$^+$), 658.1615 found 658.1644.

Macrolactone 46 as illustrated in FIG. 9. A solution of vinyl iodide 24 (32 mg, 0.060 mmol, 1.0 equiv), stannane 8p (28 mg, 0.101 mmol, 1.7 equiv) and PdCl$_2$(MeCN)$_2$ (1.7 mg, 0.07 mmol, 0.1 equiv) in degassed DMF (650 mL, 0.1 M) was stirred at 25° C. for 20 h, according to the procedure described for the synthesis of macrolactone 18d, to yield, after preparative thin layer chromatography (250 mm silica gel plates, 80% EtOAc in hexanes), starting vinyl iodide 24 (6 mg, 19%) and macrolactone 46 (17 mg, 54%). R$_f$=0.37 (silica gel, 80% EtOAc in hexanes); [a]$^{22}$D −48.7 (c 0.15, CDCl$_3$); IR (thin film) n$_{max}$ 3402, 2931, 2874, 1731, 1686, 1533, 1458, 1420, 1383, 1242, 1150, 1048, 1007, 979 cm$^{-1}$; $^1$H NMR (500 MHz, CDCl$_3$) d 6.50 (s, 1 H, ArH), 6.36 (s, 1 H, CH=CCH$_3$), 5.45 (dd, J=10.0, 5.0 Hz, 1 H, C=CHCH$_2$), 5.23 (dd, J=9.5, 1.5 Hz, 1 H, CHOCO), 4.24 (bd, J=11.0 Hz, 1 H, CHOH), 4.11–3.68 (m, 1 H, CH$_2$OH), 4.07 (s, 3 H, OCH$_3$), 4.01 (d, J=13.0 Hz, 1 H, CH$_2$OH), 3.71 (dd, J=4.0, 2.5 Hz, 1 H, CHOH), 3.30 (bs, 1 H, OH), 3.16 (qd, J=7.0, 2.5 Hz, 1 H, CH$_3$CH(C=O)), 3.00 (bs, 1 H, OH), 2.68 (ddd, J=15.0, 10.0, 9.5 Hz, 1 H, C=CHCH$_2$CHO), 2.46 (dd, J=15.0, 11.0 Hz, 1 H, CH$_2$COO), 2.30–2.20 (m, 2 H, CH$_2$C(CH$_2$OH)=CH), 2.29 (dd, J=15.0, 3.0 Hz, 1 H, CH$_2$COO), 2.11–2.04 (m, 1 H, C=CHCH$_2$CHO), 2.11 (s, 3 H, CH=C(CH$_3$)), 1.83–1.61 (m, 4 H), 1.41–1.25 (m, 1 H), 1.33 (s, 3 H, C(CH$_3$)$_2$), 1.18 (d, J=7.0 Hz, 3 H, CH(CH$_3$)), 1.07 (s, 3 H, C(CH$_3$)$_2$), 1.01 (d, J=7.0 Hz, 3 H, CH(CH$_3$)); $^{13}$C NMR (125.7 MHz, CDCl$_3$) d 220.4, 174.1, 170.3, 146.4, 141.9, 138.0, 121.8, 119.5, 109.2, 79.0, 73.8, 72.4, 66.2, 58.5, 53.5, 41.7, 39.6, 37.8, 32.0, 31.6, 28.0, 25.4, 22.8, 18.1, 15.9, 15.4, 13.2; HRMS (FAB), calcd for C$_{27}$H$_{41}$NO$_7$S (M+Cs$^+$), 656.1658 found 656.1675.

Macrolactone 47 as illustrated in FIG. 9. A solution of vinyl iodide 24 (41 mg, 0.076 mmol, 1.0 equiv), stannane 8r (61 mg, 0.151 mmol, 2.0 equiv) and PdCl$_2$(MeCN)$_2$ (4 mg, 0.015 mmol, 0.2 equiv) in degassed DMF (760 mL, 0.1 M) was stirred at 25° C. for 21 h, according to the procedure described for the synthesis of macrolactone 18d, to yield, after preparative thin layer chromatography (250 mm silica gel plates, 80% EtOAc in hexanes), starting vinyl iodide 24 (6 mg, 15%) and macrolactone 47 (20.5 mg, 51%). R$_f$=0.41 (silica gel, 80% EtOAc in hexanes); [a]$^{22}$D −86.0 (c 0.25, CHCl$_3$); IR (thin film) n$_{max}$ 3387, 2968, 2936, 2874, 1733, 1685, 1458, 1381, 1253, 1149, 1050, 1003, 912 cm$^{-1}$; $^1$H NMR (500 MHz, CDCl$_3$) d 6.97 (s, 1 H, ArH), 6.63 (s, 1 H, CH=CCH$_3$), 5.43 (dd, J=9.0, 5.5 Hz, 1 H, C=CHCH$_2$), 5.25 (dd, J=8.5, 2.0 Hz, 1 H, CHOCO), 4.32 (ddd, J=11.0, 5.5, 2.5 Hz, 1 H, CHOH), 4.12–4.07 (m, 2 H, CH$_2$OH and OH), 4.02 (d, J=11.0 Hz, 1 H, CH$_2$OH), 3.69 (dd, J=2.0, 2.0 Hz, 1 H, CHOH), 3.16 (qd, J=7.0, 2.5 Hz, 1 H, CH$_3$CH (C=O)), 3.08 (bs, 1 H, OH), 2.98 (q, J=7.0 Hz, 2 H, CH$_2$CH$_3$), 2.61 (ddd, J=15.0, 9.0, 9.0 Hz, 1 H, C=CHCH$_2$CHO), 2.46 (dd, J=14.5, 11.0 Hz, 1 H, CH$_2$COO), 2.38 (dd, J=15.0, 4.0 Hz, 1 H, CH$_2$C(CH$_2$OH)=CH), 2.31–2.25 (m, 1 H, CH$_2$C (CH$_2$OH)=CH), 2.23 (dd, J=14.5, 2.5 Hz, 1 H, CH$_2$COO), 2.17–2.07 (m, 1 H, C=CHCH$_2$CHO), 2.04 (s, 3 H, CH=C(CH$_3$)), 1.97 (bs, 1 H, OH), 1.78–1.61 (m, 3 H), 1.38–1.23 (m, 2 H), 1.37 (q, J=7.0 Hz, 3 H, CH$_2$CH$_3$), 1.35 (s, 3 H, C(CH$_3$)$_2$), 1.18 (d, J=7.0 Hz, 3 H, CH(CH$_3$)), 1.05 (s, 3 H, C(CH$_3$)$_2$), 1.01 (d, J=7.0 Hz, 3 H, CH(CH$_3$)); $^{13}$C NMR (125.7 MHz, CDCl$_3$) d 220.7, 172.0, 170.3, 151.7, 141.8, 138.7, 121.8, 119.2, 114.9, 78.1, 73.9, 71.8, 66.2, 53.8, 41.5, 39.6, 38.0, 31.8, 31.6, 27.8, 26.7, 25.2, 22.9, 17.4, 16.1, 15.7, 14.0, 13.2; HRMS (FAB), calcd for C$_{28}$H$_{43}$NO$_6$S (M+Na$^+$), 544.2709 found 544.2724.

Macrolactone 48 as illustrated in FIG. 9. A solution of vinyl iodide 24 (26 mg, 0.048 mmol, 1.0 equiv), stannane 8h (29 mg, 0.072 mmol, 1.5 equiv) and PdCl$_2$(MeCN)$_2$ (1.5 mg, 0.006 mmol, 0.1 equiv) in degassed DMF (480 mL, 0.1 M) was stirred at 25° C. for 15 h, according to the procedure described for the synthesis of macrolactone 18d, to yield, after preparative thin layer chromatography (250 mm silica gel plates, EtOAc), starting vinyl iodide 24 (10.5 mg, 40%) and macrolactone 48 (10.5 mg, 41%). R$_f$=0.27 (silica gel, EtOAc); [a]$^{22}$D −43.0 (c 0.14, CHCl$_3$); IR (thin film) n$_{max}$ 3388, 2924, 2851, 1732, 1682, 1462, 1384, 1251, 1185, 1150, 1067 cm$^{-1}$; $^1$H NMR (500 MHz, CDCl$_3$) d 7.13 (s, 1 H, ArH), 6.63 (s, 1 H, CH=CCH$_3$), 5.45 (dd, J=9.0, 6.0 Hz, 1 H, C=CHCH$_2$), 5.27 (bd, J=7.0 Hz, 1 H, CHOCO), 4.29 (dd, J=11.0, 2.5 Hz, 1 H, CHOH), 4.09 (d, J=13.0 Hz, 1 H, CH$_2$OH), 4.00 (d, J=13.0 Hz, 1 H, CH$_2$OH), 3.68 (dd, J=4.0, 2.5 Hz, 1 H, CHOH), 3.15 (qd, J=6.5, 2.5 Hz, 1 H, CH$_3$CH(C=O)), 2.99 (bs, 1 H, OH), 2.65 (ddd, J=15.0, 9.0, 9.0 Hz, 1 H, C=CHCH$_2$CHO), 2.46 (dd, J=14.5, 11.0 Hz, 1 H, CH$_2$COO), 2.39–2.33 (m, 1 H, CH$_2$C(CH$_2$OH)=CH), 2.26 (dd, J=14.5, 2.5 Hz, 1 H, CH$_2$COO), 2.26–2.20 (m, 1 H, CH$_2$C(CH$_2$OH)=CH), 2.14–2.10 (m, 1 H, C=CHCH$_2$CHO), 2.07 (s, 3 H, CH=C(CH$_3$)), 1.99–1.61 (m, 4 H), 1.42–1.24 (m, 2 H), 1.33 (s, 3 H, C(CH$_3$)$_2$), 1.16 (d, J=7.0 Hz, 3 H, CH(CH$_3$)), 1.04 (s, 3 H, C(CH$_3$)$_2$), 1.00 (d, J=7.0 Hz, 3 H, CH(CH$_3$)); $^{13}$C NMR (125.7 MHz, CHCl$_3$) d 220.5, 170.3, 170.2, 152.1, 141.9, 139.0, 121.5, 118.9, 116.4, 78.4, 73.9, 72.0, 66.2, 61.9, 53.6, 41.7, 39.6, 37.9, 31.8, 31.6, 29.7, 28.1, 25.4, 22.9, 17.7, 15.8, 13.2; HRMS (FAB), calcd for C$_{27}$H$_{41}$NO$_7$S (M+Cs$^+$), 656.1658 found 656.1677.

Macrolactone 49 as illustrated in FIG. 9. A solution of vinyl iodide 24 (37 mg, 0.069 mmol, 1.0 equiv), stannane 8q (47 mg, 0.117 mmol, 1.7 equiv) and Pd(PPh$_3$)$_4$ (10 mg, 0.009 mmol, 0.13 equiv) in degassed toluene (780 mL, 0.1 M) was heated at 100° C. for 2 h according to the procedure described for the synthesis of macrolactone 18h, to yield, after preparative thin layer chromatography (250 mm silica gel plates, 80% EtOAc in hexanes), macrolactone 49 (5.5 mg, 15%). R$_f$=0.35 (silica gel, 80% EtOAc in hexanes); [a]$^{22}$D −48.1 (c 0.27, CHCl$_3$); IR (thin film) n$_{max}$ 3403, 2930, 2873, 1732, 1686, 1462, 1381, 1291, 1266, 1250, 1149, 1004, 980, 937 cm$^{-1}$; $^1$H NMR (500 MHz, CHCl$_3$) d 7.04 (s, 1 H, ArH), 6.85 (dd, J=17.5, 11.0 Hz, 1 H, CH=CH$_2$), 6.61 (s, 1 H, CH=CCH$_3$), 6.05 (d, J=17.5 Hz, 1 H, CH=CH$_2$), 5.56 (d, J=11.0 Hz, 1 H, CH=CH$_2$), 5.45 (dd, J=10.0, 5.5 Hz, 1 H, C=CHCH$_2$), 5.26 (dd, J=9.5, 2.0 Hz, 1 H, CHOCO), 4.29 (ddd, J=11.0, 6.0, 2.5 Hz, 1 H, CHOH), 4.09 (dd, J=13.0, 6.5 Hz, 1 H, CH$_2$OH), 4.02 (dd, J=13.0, 6.0 Hz, 1 H, CH$_2$OH), 3.71 (ddd, J=4.5, 2.5, 2.5 Hz, 1 H, CHOH), 3.54 (d, J=6.0 Hz, 1 H, OH), 3.17 (qd, J=7.5, 2.0 Hz, 1 H, CH$_3$CH(C=O)), 3.02 (d, J=2.0 Hz, 1 H, OH), 2.68 (ddd, J=15.0, 10.0, 9.0 Hz, 1 H, C=CHCH$_2$CHO), 2.45 (dd, J=14.5, 11.0 Hz, 1 H, 3 H, CH$_2$COO), 2.37–2.31 (m, 1 H, CH$_2$C(CH$_2$OH)=CH), 2.30–2.24 (m, 1 H, CH$_2$C(CH$_2$OH)=CH), 2.28 (dd, J=15.0, 3.5 Hz, 1 H, CH$_2$COO), 2.14–2.07 (m, 1 H, C=CHCH$_2$CHO), 2.09 (d, J=1.0 Hz, 1 H, CH=C(CH$_3$)), 1.79–1.60 (m, 4 H), 1.39–1.25 (m, 2 H), 1.35 (s, 3 H, C(CH$_3$)$_2$), 1.18 (d, J=7.0 Hz, 3 H, CH(CH$_3$)), 1.07 (s, 3 H, C(CH$_3$)$_2$), 1.02 (d, J=7.0 Hz, 3 H, CH(CH$_3$)); $^{13}$C NMR (150.9 MHz, CDCl$_3$)d 221.4, 171.2, 166.9, 153.6, 142.8, 140.2, 130.9, 122.6, 121.1, 120.0, 116.7, 79.3, 74.7, 73.0, 67.1, 54.5, 42.5, 40.5, 38.7, 32.8, 32.5, 28.8, 26.2, 23.7, 18.7, 16.7, 14.1, 14.0; HRMS (FAB), calcd for C$_{28}$H$_{41}$NO$_6$S (M+Cs$^+$), 652.1709 found 652.1693.

Fluoride 50 as illustrated in FIG. 9. A solution of triol 45 (3.6 mg, 0.007 mmol, 1.0 equiv) in CH$_2$Cl$_2$ (10 mL, 0.07 M) at −78° C. was treated with DAST (11 mL of a 0.7 M solution in CH$_2$Cl$_2$, 0.08 mmol, 1.1 equiv) and the mixture was stirred at −78° C. for 10 min. The reaction was then quenched by the addition of saturated aqueous NaHCO$_3$ (500 mL) and the mixture was allowed to warm to 25° C. The product was then partitioned between saturated aqueous NaHCO$_3$ (5 mL) and CH$_2$Cl$_2$ (5 mL) and the layers were separated. The aqueous phase was extracted with CH$_2$Cl$_2$ (2×5 mL) and the combined organic extracts were dried (MgSO$_4$) and then concentrated under reduced pressure. Preparative thin layer chromatography (250 mm silica gel plate, 40% EtOAc in hexanes) furnished fluoride 50 (2.1 mg, 58%). R$_f$=0.39 (silica gel, 50% EtOAc in hexanes); [a]$^{22}$D −34.4 (c 0.09, CHCl$_3$); IR (thin film) n$_{max}$ 3413, 2919, 2849, 1725, 1684, 1465, 1381, 1290, 1250, 1150, 1041, 979, 872 cm$^{-1}$; $^1$H NMR (600 MHz, CHCl$_3$) d 7.22 (s, 1 H, ArH), 6.62 (s, 1 H, CH=CCH$_3$), 5.60 (d, J=47.0 Hz, 2 H, ArCH$_2$F), 5.56–5.52 (m, 1 H, C=CHCH$_2$), 5.27 (dd, J=9.5, 2.0 Hz, 1 H, CHOCO), 4.79 (dd, J=82.2, 10.8 Hz, 1 H, CH=CCH$_2$F), 4.71 (dd, J=81.8, 10.8 Hz, 1 H, CH=CCH$_2$F), 4.24 (dd, J=10.9, 2.6 Hz, 1 H, CHOH), 3.70 (dd, J=4.3, 2.5 Hz, 1 H, CHOH), 3.15 (qd, J=6.8, 2.5 Hz, 1 H, CH$_3$CH(C=O)), 3.00–2.85 (m, 1 H, OH), 2.71 (m, 1 H, C=CHCH$_2$CHO), 2.46 (dd, J=14.9, 11.0 Hz, 1 H, CH$_2$COO), 2.38–2.29 (m, 2 H, CH$_2$C(CH$_2$OH)=CH), 2.30 (dd, J=14.9, 2.8 Hz, 1 H, CH$_2$COO), 2.15–2.09 (m, 1 H, C=CHCH$_2$CHO), 2.11 (d, J=1.0 Hz, CH=C(CH$_3$)), 1.80–1.50 (m, 4 H), 1.37–1.29 (m, 2 H), 1.33 (s, 3 H, C(CH$_3$)$_2$), 1.18 (d, J=6.8 Hz, 3 H, CH(CH$_3$)), 1.06 (s, 3 H, C(CH$_3$)$_2$), 1.01 (d, J=7.1 Hz, 3 H, CH(CH$_3$)); HRMS (FAB), calcd for C$_{27}$H$_{39}$F$_2$NO$_5$S (M+H$^+$), 528.2595 found 528.2610.

Fluoride 51 as illustrated in FIG. 9. A solution of triol 46 (8.2 mg, 0.016 mmol, 1.0 equiv) in CH$_2$Cl$_2$ (200 mL, 0.04 M) at −78° C. was treated with DAST (2.5 mL, 0.019 mmol, 1.2 equiv) and the resulting mixture was stirred at −78° C. for 10 min according to the procedure described for the synthesis of fluoride 50, to yield, after preparative thin layer chromatography (250 mm silica gel plates, 30% EtOAc in hexanes), fluoride 51 (3.5 mg, 43%). R$_f$=0.57 (silica gel, 60% EtOAc in hexanes); [a]$^{22}$D −41.7 (c 0.11, CHCl$_3$); IR (thin film) n$_{max}$ 3418, 2925, 2852, 1734, 1686, 1535, 1461, 1415, 1383, 1334, 1241, 1150, 1045, 976 cm$^{-1}$; $^1$H NMR (400 MHz, CDCl$_3$) d 6.51 (s, 1 H, ArH), 6.37 (s, 1 H, CH=CCH$_3$), 5.55–5.51 (m, 1 H, C=CHCH$_2$), 5.22 (dd, J=10.0, 2.0 Hz, 1 H, CHOCO), 4.81 (dd, J=74.0, 11.0 Hz, 1 H, CH=CCH$_2$F), 4.71 (dd, J=73.0, 11.0 Hz, 1 H, CH=CCH$_2$F), 4.26 (dd, J=11.0, 2.5 Hz, 1 H, CHOH), 4.09 (s, 3 H, CH$_3$O), 3.71 (dd, J=4.5, 2.0 Hz, 1 H, CHOH), 3.17 (qd, J=7.0, 2.5 Hz, 1 H, CH$_3$CH(C=O)), 3.01–2.95 (m, 1 H, OH), 2.76–2.68 (m, 1 H, C=CHCH$_2$CHO), 2.47 (dd, J=14.5, 11.0 Hz, 1 H, CH$_2$COO), 2.37–2.27 (m, 2 H, CH$_2$C(CH$_2$OH)=CH), 2.29 (dd, J=14.5, 2.5 Hz, 1 H, CH$_2$COO), 2.17–2.11 (m, 1 H, C=CHCH$_2$CHO), 2.14 (s, 3 H, CH=C(CH$_3$)), 1.80–1.50 (m, 4 H), 1.40–1.22 (m, 2 H), 1.34 (s, 3 H, C(CH$_3$)$_2$), 1.19 (d, J=7.0 Hz, 3 H, CH(CH$_3$)), 1.08 (s, 3 H, C(CH$_3$)$_2$), 1.03 (d, J=7.0 Hz, 3 H, CH(CH$_3$)); $^{13}$C NMR (100.6 MHz, CDCl$_3$) d 220.3, 174.1, 170.1, 146.1, 138.1, 125.9, 125.8, 119.4, 109.1, 86.2 (d, J=660 Hz), 78.5, 73.7, 72.4, 58.5, 53.3, 41.6, 39.5, 37.8, 32.0, 31.6, 29.6, 27.6, 25.1, 22.8, 18.0, 15.7, 13.1; HRMS (FAB), calcd for C$_{27}$H$_{40}$FNO$_6$S (M+H$^+$), 526.2639 found 526.2625.

Fluoride 52 as illustrated in FIG. 9. A solution of triol 47 (12.5 mg, 0.024 mmol, 1.0 equiv) in CH$_2$Cl$_2$ (500 mL, 0.05 M) at −78° C. was treated with DAST (250 mL, 0.1 M in CH$_2$Cl$_2$ 0.025 mmol, 1.05 equiv) and the resulting mixture was stirred at −78 ° C. for 10 min according to the procedure described for the synthesis of fluoride 50, to yield, after preparative thin layer chromatography (250 mm silica gel plates, 60% EtOAc in hexanes), fluoride 52 (5.1 mg, 41%). R$_f$=0.19 (silica gel, 50% EtOAc in hexanes); [a]$^{22}$D −68.6 (c 0.22, CHCl$_3$); IR (thin film) n$_{max}$ 3504, 2969, 2935, 2877, 1736, 1687, 1461, 1369, 1290, 1250, 1148, 1068, 1044, 1008, 976 cm$^{-1}$; $^1$H NMR (500 MHz, CHCl$_3$) d 6.98 (s, 1 H, ArH), 6.60 (s, 1 H, CH=CCH$_3$), 5.56–5.52 (m, 1 H, C=CHCH$_2$), 5.23 (dd, J=10.0, 2.0 Hz, 1 H, CHOCO), 4.80 (dd, J=73.0, 10.5 Hz, 1 H, CH=CCH$_2$F), 4.71 (dd, J=72.5, 10.5 Hz, 1 H, CH=CCH$_2$F), 4.33 (ddd, J=11.0, 5.5, 2.5 Hz, 1 H, CHOH), 3.71 (ddd, J=5.0, 2.5, 2.0 Hz, 1 H, CHOH), 3.71 (d, J=6.0 Hz, 1 H, CHOH), 3.17 (qd, J=7.0, 2.0 Hz, 1 H, CH$_3$CH(C=O)), 3.07 (m, 1 H, OH), 4.51 (q, J=7.5 Hz, 2 H, CH$_2$CH$_3$), 2.70 (ddd, J=15.0, 10.0, 2.0 Hz, 1 H, C=CHCH$_2$CHO), 2.45 (dd, J=14.5, 11.0 Hz, 1 H, CH$_2$COO), 2.39–2.28 (m, 2 H, CH$_2$C(CH$_2$OH)=CH), 2.26 (dd, J=14.5, 2.5 Hz, 1 H, CH$_2$COO), 2.17–2.10 (m, 1 H, C=CHCH$_2$CHO), 2.08 (d, J=1.5 Hz, 3 H, CH=C(CH$_3$)), 1.80–1.67 (m, 3 H), 1.39 (t, J=7.5 Hz, 3 H, CH$_2$CH$_3$), 1.39–1.24 (m, 2 H), 1.35 (s, 3 H, C(CH$_3$)$_2$), 1.19 (d, J=7.0 Hz, 3 H, CH(CH$_3$)), 1.07 (s, 3 H, C(CH$_3$)$_2$), 1.03 (d, J=7.0

Hz, 3 H, CH(CH₃)); ¹³C NMR (100.6 MHz, CHCl₃) d 220.7, 172.0, 170.3, 151.6, 138.9, 138.1, 126.1 (d, J=46.2 Hz), 119.5, 115.2, 86.3 (d, J=658 Hz), 78.2, 73.8, 72.2, 53.7, 41.5, 39.7, 37.9, 32.3, 31.6, 27.7, 26.8, 25.1, 23.0, 17.6, 15.9, 15.8, 14.0, 13.1; HRMS (FAB), calcd for $C_{28}H_{42}FNO_5S$ (M+Cs⁺), 656.1822 found 656.1843.

Fluoride 53 as illustrated in FIG. 9. A solution of triol 49 (6.0 mg, 0.0115 mmol, 1.0 equiv) in CH₂Cl₂ (1.5 mL, 0.01 M) at −78° C. was treated with DAST (25 mL, 0.08 M in CH₂Cl₂, 0.016 mmol, 1.1 equiv) and the resulting mixture was stirred at −78° C. for 10 min according to the procedure described for the synthesis of fluoride 50, to yield, after preparative thin layer chromatography (250 mm silica gel plates, 50% EtOAc in hexanes), fluoride 53 (3.0 mg, 50%). $R_f$=0.50 (silica gel, 50% EtOAc in hexanes); $[α]^{22}D$ −12.4 (c 0.2, CHCl₃); IR (thin film) $n_{max}$ 3408, 2926, 2851, 1732, 1682, 1462, 1384, 1292, 1250, 1150, 1068, 974 cm⁻¹; ¹H NMR (600 MHz, CHCl₃) d 7.04 (s, 1 H, ArH), 6.86 (d, J=17.4, 10.8 Hz, 1 H, CH=CH₂), 6.59 (s, 1 H, CH=CCH₃), 6.05 (d, J=17.5 Hz, 1 H, CH=CH₂), 5.55 (d, J=11.0 Hz, 1 H, CH=CH₂) 5.57–5.51 (m, 1 H, C=CHCH₂), 5.25 (d, J=10.0 Hz, 1 H, CHOCO), 4.79 (dd, J=83.8, 10.7 Hz, 1 H, CH=CCH₂F), 4.71 (dd, J=83.6, 10.7 Hz, 1 H, CH=CCH₂F), 4.28 (dd, J=10.6, 1.6 Hz, 1 H, CHOH), 3.70 (m, 1 H, CHOH), 3.33–3.25 (m, 1 H, CHOH), 3.16 (qd, J=7.0, 2.1 Hz, 1 H, CH₃CH(C=O)), 2.98 (m, 1 H, OH), 2.75–2.66 (m, 1 H, C=CHCH₂CHO), 2.46 (dd, J=14.6, 11.0 Hz, 1 H, CH₂COO), 2.37–2.27 (m, 2 H, CH₂C(CH₂OH)=CH), 2.28 (dd, J=14.6, 2.6 Hz, 1 H, CH₂COO), 2.15–2.08 (m, 1 H, C=CHCH₂CHO), 2.11 (s, 3 H, CH=C(CH₃)), 1.80–1.64 (m, 3 H), 1.43–1.27 (m, 2 H), 1.34 (s, 3 H, C(CH₃)₂), 1.18 (d, J=6.8 Hz, 3 H, CH(CH₃)), 1.07 (s, 3 H, C(CH₃)₂), 1.03 (d, J=7.0 Hz, 3 H, CH(CH₃)); ¹³C NMR (150.9 MHz, CHCl₃) d 220.9, 170.5, 166.3, 152.9, 139.3, 138.7 (d, J=54 Hz), 130.2, 126.1 (d, J=43 Hz), 120.4, 119.4, 116.1, 86.3 (d, J=659 Hz), 78.3, 73.8, 72.3, 53.5, 41.5, 39.5, 37.8, 32.1, 31.6, 29.6, 27.5, 25.1, 22.8, 17.7, 15.7, 13.0; HRMS (FAB), calcd for $C_{28}H_{40}FNO_5S$ (M+H⁺), 522.2689 found 522.2704.

Epoxide 54 as illustrated in FIG. 9. To a solution of allylic alcohol 45 (25.4 mg, 0.049 mmol, 1.0 equiv) and 4 Å molecular sieves in CH₂Cl₂ (0.50 mL) at −40° C. was added dropwise (+)-diethyl-D-tartrate (41 mL, 0.59 M in CH₂Cl₂, 0.024 mmol, 0.5 equiv) followed by titanium isopropoxide (55 mL, 0.35 M in CH₂Cl₂, 0.019 mmol, 0.4 equiv). After 1 h at that temperature, t-butyl hydroperoxide (22 mL of a 5 M solution in decane, 0.110 mmol, 2.2 equiv) was added and the reaction mixture was stirred at −30° C. for 2 h. The reaction mixture was then filtered through celite into saturated aqueous Na₂SO₄ (10 mL), eluting with EtOAc (10 mL). The resulting biphasic mixture was then stirred for 1 h and the layers were separated. The aqueous phase was extracted with EtOAc (3×10 mL) and the combined organic extracts were dried (MgSO₄) and concentrated under reduced pressure. Preparative thin layer chromatography (250 mm silica gel plates, 80% EtOAc in hexanes) furnished epoxide 54 (13.5 mg, 52%). $R_f$=0.23 (silica gel, 80% EtOAc in hexanes); $[α]^{22}D$ −55.4 (c 0.06, CHCl₃); IR (thin film) $n_{max}$ 3425, 2929, 2862, 1732, 1688, 1456, 1367, 1292, 1258, 1195, 1149, 1040, 980 cm⁻¹; ¹H NMR (600 MHz, CHCl₃) d 7.22 (s, 1 H, ArH), 6.62 (s, 1 H, CH=CCH₃), 5.59 (d, J=47.0 Hz, 2 H, ArCH₂F), 5.46 (dd, J=6.7, 3.4 Hz, 1 H, CHOCO), 4.14–4.09 (m, 1 H, CHOH), 3.89 (d, J=6.4 Hz, 1 H, OH), 3.76 (bs, 1 H, CHOH), 3.72 (d, J=12.1 Hz, 1 H, CH₂OH), 3.56 (dd, J=12.1, 7.5 Hz, 1 H, CH₂OH), 3.33 (qd, J=6.8, 5.3 Hz, 1 H, CH₃CH(C=O)), 3.16 (dd, J=6.3, 6.1 Hz, 1 H, C(O)CHCH₂CHO), 2.55 (dd, J=14.1, 10.2 Hz, 1 H, CH₂COO), 2.50 (bs, 1 H, OH), 2.41 (dd, J=14.1, 3.1 Hz, 1 H, CH₂COO), 2.11 (s, 3 H, CH=C(CH₃)), 2.10–1.97 (m, 2 H, C(O)CHCH₂CHO), 1.91–1.81 (m, 2 H, CH₂C(CH₂OH)), 1.74–1.60 (m, 3 H), 1.50–1.30 (m, 2 H), 1.34 (s, 3 H, C(CH₃)₂), 1.18 (d, J=6.8 Hz, 3 H, CH(CH₃)), 1.06 (s, 3 H, C(CH₃)₂), 0.99 (d, J=7.0 Hz, 3 H, C(CH₃)₂); ¹³C NMR (150.9 MHz, CDCl₃) d 220.0, 170.3, 163.5 (d, J=93 Hz), 152.6, 137.5, 119.3, 118.2, 80.5 (d, J=675 Hz), 76.4, 74.6, 73.2, 63.8, 63.3, 56.9, 52.7, 39.1, 36.6, 31.2, 31.0, 28.1, 22.4, 20.9, 20.6, 17.5, 15.8, 14.2; HRMS (FAB), calcd for $C_{27}H_{40}FNO_7S$ (M+H⁺), 542.2588 found 542.2575.

Epoxide 55 as illustrated in FIG. 9. To a solution of allylic alcohol 46 (22 mg, 0.042 mmol, 1.0 equiv) and 4 Å molecular sieves in CH₂Cl₂ (420 mL) at −40° C. was added dropwise (+)-diethyl-D-tartrate (4 mL, 0.021 mmol, 0.5 equiv), followed by titanium isopropoxide (5 mL, 0.016 mmol, 0.4 equiv) and after 1 h at this temperature, t-butyl hydroperoxide (18 mL of a 5 M solution in decane, 0.092 mmol, 2.2 equiv) according to the procedure described for the synthesis of epoxide 54 to yield, after preparative thin layer chromatography (250 mm silica gel plates, 80% EtOAc in hexanes), epoxide 55 (16 mg, 70%). $R_f$=0.25 (silica gel, 80% EtOAc in hexanes); $[α]^{22}D$ −44.8 (c 1.4, CHCl₃); IR (thin film) $n_{max}$ 3435, 2959, 2935, 2877, 1732, 1689, 1534, 1459, 1421, 1371, 1338, 1241, 1174, 1039, 980 cm⁻¹; ¹H NMR (500 MHz, CHCl₃) d 6.51 (s, 1 H, ArH), 6.35 (s, 1 H, CH=CCH₃), 5.40 (dd, J=7.0, 3.0 Hz, 1 H, CHOCO), 4.11 (ddd, J=10.0, 6.5, 3.0 Hz, 1 H, CHOH), 4.07 (s, 3 H, CH₃O), 3.88 (d, J=6.0 Hz, 1 H, OH), 3.77–3.74 (m, 1 H, CHOH), 3.73 (dd, J=12.5, 4.0 Hz, 1 H, CH₂OH), 3.57 (dd, J=12.5, 8.0 Hz, 1 H, CH₂OH), 3.32 (qd, J=7.0, 5.0 Hz, 1 H, CH₃CH(C=O)), 3.16 (dd, J=7.0, 5.5 Hz, 1 H, C(O)CHCH₂CHO), 2.54 (dd, J=14.5, 10.0 Hz, 1 H, CH₂COO), 2.50 (bs, 1 H, OH), 2.40 (dd, J=14.5, 3.5 Hz, 1 H, CH₂COO), 2.13 (s, 3 H, CH=C(CH₃)), 2.12–2.05 (m, 1 H, C(O)CHCH₂CHO), 2.03–1.95 (m, 2 H), 1.90–1.82 (m, 1 H, CH₂C(CH₂OH)), 1.75–1.60 (m, 2 H), 1.50–1.20 (m, 3 H), 1.35 (s, 3 H, C(CH₃)₂), 1.16 (d, J=7.0 Hz, 3 H, CH(CH₃)), 1.07 (s, 3 H, C(CH₃)₂), 0.99 (d, J=7.0 Hz, 3 H, 74.5, 73.1, 63.8, 63.4, 60.4, 58.4, 57.1, 52.7, 43.4, 39.1, 36.4, 31.2, 30.9, 28.1, 22.2, 21.0, 20.3, 17.3, 15.4, 14.0; HRMS (FAB), calcd for $C_{27}H_{41}NO_8S$ (M+Cs⁺), 672.1607 found 672.1584.

Fluoride 58 as illustrated in FIG. 9. A solution of triol 54 (5.0 mg, 0.009 mmol, 1.0 equiv) in CH₂Cl₂ (1 mL, 0.01 M) at −78° C. was treated with DAST (20 mL of a 0.1 M solution in CH₂Cl₂, 0.025 mmol, 1.05 equiv) according to the procedure described for the synthesis of fluoride 50, to yield, after preparative thin layer chromatography (250 mm silica gel plates, 60% EtOAc in hexanes), fluoride 58 (2.0 mg, 41%). $R_f$=0.22 (silica gel, 50% EtOAc in hexanes); IR (thin film) $n_{max}$ 3402, 2954, 2923, 2853, 1732, 1688, 1462, 1378, 1262, 1185, 1149, 1082, 1031, 980 cm⁻¹; ¹H NMR (500 MHz, CDCl₃) d 7.23 (s, 1 H, ArH), 6.63 (s, 1 H, CH=CCH₃), 5.60 (d, J=47 Hz, 2 H, ArCH₂F), 5.47 (dd, J=7.0, 3.0 Hz, 1 H, CHOCO), 4.39 (dd, J=97.0, 10.5 Hz, 1 H, 8 C(O)CH₂F), 4.30 (dd, J=97.0, 10.5 Hz, 1 H, C(O)CH₂F), 4.13 (ddd, J=9.5, 6.5,. 3.0 Hz, 1 H, CHOH), 3.75 (dd, J=5.0, 5.0 Hz, 1 H, CHOH), 3.74 (d, J=7.0 Hz, 1 H, OH), 3.31 (qd, J=7.0, 6.0 Hz, 1 H, CH₃CH(C=O)), 3.02 (dd, J=6.0, 6.0 Hz, 1 H, CH(O)CH₂CHO), 2.56 (dd, J=14.0, 10.0 Hz, 1 H, CH₂COO), 2.46 (brs, 1 H, OH), 2.42 (dd, J=14.0, 4.0 Hz, 1 H, CH₂COO), 2.13 (s, 3 H, CH=C(CH₃)), 2.10–1.97 (m, 3 H), 1.95–1.87 (m, 1 H), 1.90–1.82 (m, 1 H), 1.75–1.63 (m, 2 H), 1.50–1.20 (m, 2 H), 1.36 (s, 3 H, C(CH₃)₂), 1.16 (d, J=7.0 Hz, 3 H, CH(CH₃)), 1.08 (s, 3 H, C(CH₃)₂), 1.01 (d, J=7.0 Hz, 3 H, C(CH₃)₂);¹³C NMR (125.7 MHz, CDCl₃) d 221.5, 170.4, 163.7, 152.7, 137.4, 119.5, 118.4, 85.2 (d, J=700 Hz), 80.6 (d, J=675 Hz), 76.3, 74.3, 73.4, 60.2, 52.6, 43.3, 38.9, 36.5, 31.0, 30.9, 27.1, 22.2, 20.8, 20.6, 17.2, 15.7, 13.9; MS (electrospray), calcd for $C_{27}H_{39}F_2NO_6S$ (M+H$^+$) 544, found 544.

Fluoride 59 as illustrated in FIG. 9. A solution of triol 55 (15 mg, 0.028 mmol, 1.0 equiv) in $CH_2Cl_2$ (280 mL, 0.1 M) at −78° C. was treated with DAST (5 mL, 0.038 mmol, 1.4 equiv) according to the procedure described for the synthesis of fluoride 50, to yield, after preparative thin layer chromatography (250 mm silica gel plates, 50% EtOAc in hexanes), fluoride 59 (4.0 mg, 26%). $R_f$=0.42 (silica gel, 80% EtOAc in hexanes); [a]$^{22}$D −29.4 (c 0.33, CHCl$_3$); IR (thin film) n$_{max}$ 3492, 2960, 2928, 2874, 2865, 1738, 1732, 1693, 1682, 1537, 1462, 1455, 1422, 1384, 1241, 1144, 980 cm$^{-1}$; $^1$H NMR (500 MHz, CDCl$_3$) d 6.52 (s, 1 H, ArH), 6.35 (s, 1 H, CH=CCH$_3$), 5.41 (dd, J=7.0, 3.5 Hz, 1 H, CHOCO), 4.40 (dd, J=111.5, 10.5 Hz, 1 H, CH$_2$F), 4.30 (dd, J=111.5, 10.5 Hz, 1 H, CH$_2$F), 4.14 (ddd, J=10.0, 7.0, 3.5 Hz, 1 H, CHOH), 4.08 (s, 3 H, CH$_3$O), 3.80 (d, J=7.0 Hz, 1 H, OH), 3.78 (dd, J=3.5, 3.5 Hz, 1 H, CHOH), 3.31 (qd, J=7.0, 5.0 Hz, 1 H, CH$_3$CH(C=O)), 3.01 (dd, J=7.0, 5.5 Hz, 1 H, C(O)CHCH$_2$CHO), 2.55 (dd, J=14.5, 10.0 Hz, 1 H, CH$_2$COO), 2.53 (bs, 1 H, OH), 2.40 (dd, J=14.5, 3.5 Hz, 1 H, CH$_2$COO), 2.14 (s, 3 H, CH=C(CH$_3$)), 2.12–2.15–1.90 (m, 3 H), 1.73–1.70 (m, 1 H), 1.55–1.24 (m, 5 H), 1.36 (s, 3 H, C(CH$_3$)$_2$), 1.17 (d, J=6.5 Hz, 3 H, CH(CH$_3$)), 1.09 (s, 3 H, C(CH$_3$)$_2$), 1.00 (d, J=7.0 Hz, 3 H, C(CH$_3$)$_2$); $^{13}$C NMR (150.9 MHz, CHCl$_3$) d 220.1, 173.9, 170.2, 146.3, 135.7, 120.0, 109.8, 85.8, 85.2 (d, J=695 Hz), 65.8, 61.5 (d, J=82 Hz), 58.4, 57.3 (d, J=27 Hz), 52.7, 43.3, 39.2, 36.5, 31.1, 31.0, 27.3, 22.2, 21.2, 20.4, 17.3, 15.4, 13.9; HRMS (FAB), calcd for $C_{27}H_{40}FNO_7S$ (M+Cs$^+$), 674.1564 found 674.1594.

Epoxide 57 as illustrated in FIG. 10. To a solution of allylic alcohol 24 (81 mg, 0.151 mmol, 1.0 equiv) and 4 Å molecular sieves in CH$_2$Cl$_2$ (1.25 mL) at −40° C. was added dropwise (+)-diethyl-D-tartrate (13 mL, 0.076 mmol, 0.5 equiv), followed by titanium isopropoxide (18 mL, 0.060 mmol, 0.4 equiv) and after 1 h at this temperature, t-butyl hydroperoxide (66 mL of a 5 M solution in decane, 0.330 mmol, 2.2 equiv) and the reaction conducted according to the procedure described for the synthesis of epoxide 54 to yield, after flash column chromatography (silica gel, 80% EtOAc in hexanes), epoxide 57 (74 mg, 89%). $R_f$=0.34 (silica gel, 80% EtOAc in hexanes); [a]$^{22}$D −32.5 (c 0.3, CHCl$_3$); IR (thin film) n$_{max}$ 3455, 2959, 2931, 2877, 1733, 1689, 1465, 1377, 1289, 1257, 1147, 1040, 979, 912 cm$^{-1}$; $^1$H NMR (600 MHz, CDCl$_3$) d 6.46 (s, 1 H, CH=CCH$_3$), 5.48 (dd, J=4.9, 4.7 Hz, 1 H, CHOCO), 4.00 (bm, 1 H, CHOH), 3.75 (dd, J=5.6, 3.4 Hz, 1 H, CHOH), 3.71 (d, J=12.5 Hz, 1 H, CH$_2$OH), 3.64 (bs, 1 H, OH), 3.56 (d, J=12.5 Hz, 1 H, CH$_2$OH), 3.32 (qd, J=6.7, 6.7 Hz, 1 H, CH$_3$CH(C=O)), 3;09 (dd, J=6.3, 6.2 Hz, 1 H, C(O)CHCH$_2$CHO), 2.52 (dd, J=14.3, 9.8 Hz, 1 H, CH$_2$COO), 2.43 (dd, J=14.3, 3.4 Hz, 1 H, CH$_2$COO), 2.28 (bs, 1 H, OH), 1.95 (m, 2 H, C(O)CHCH$_2$CHO), 1.86 (s, 3 H, CH=C (CH$_3$)), 1.79 (m, 1 H, CH$_2$C(CH$_2$OH)), 1.67 (m, 1 H), 1.61 (m, 1 H), 1.46 (m, 2 H), 1.33 (s, 3 H, C(CH$_3$)$_2$), 1.24 (m, 2 H), 1.15 (d, J=6.8 Hz, 3 H, CH(CH$_3$)), 1.06 (s, 3 H, C(CH$_3$)$_2$), 0.98 (d, J=7.0 Hz, 3 H, C(CH$_3$)$_2$); $^{13}$C NMR (125.7 MHz, CDCl$_3$) d 220.2, 170.2, 143.7, 80.4, 75.3, 75.1, 73.6, 63.8, 63.0, 56.2, 52.2, 44.1, 38.7, 36.7, 31.6, 30.8, 30.7, 27.6, 22.7, 21.5, 21.3, 17.5, 14.6; HRMS (FAB), calcd for $C_{23}H_{37}IO_7$ (M+Na$^+$), 575.1483 found 575.1462.

Epoxide 56 as illustrated in FIG. 10. A solution of vinyl iodide 57 (20 mg, 0.036 mmol, 1.0 equiv), stannane 8r (29 mg, 0.072 mmol, 1.5 equiv) and PdCl$_2$(MeCN)$_2$ (2.0 mg, 0.004 mmol, 0.1 equiv) in degassed DMF (360 mL, 0.1 M) was stirred at 25° C. for 20 h, according to the procedure described for the synthesis of lactone 18d, to yield, after preparative thin layer chromatography (250 mm silica gel plates, EtOAc), starting vinyl iodide 57 (6 mg, 30%) and macrolactone 56 (10 mg, 51%). $R_f$=0.23 (silica gel, 80% EtOAc in hexanes); [a]$^{22}$D −60.0 (c 0.14, CHCl$_3$); IR (thin film) n$_{max}$ 3414, 2969, 2933, 2872, 1736, 1687, 1458, 1373, 1293, 1258, 1150, 980, 914 cm$^{-1}$; $^1$H NMR (500 MHz, CDCl$_3$) d 6.99 (s, 1 H, ArH), 6.61 (s, 1 H, CH=CCH$_3$), 5.43 (dd, J=8.0, 3.0 Hz, 1 H, CHOCO), 4.20 (ddd, J=9.5, 6.5, 3.0 Hz, 1 H, CHOH), 4.04 (d, J=6.5 Hz, 1 H, OH), 3.77 (dd, J=4.0, 4.0 Hz, 1 H, CHOH), 3.74 (dd, J=12.5, 4.0 Hz, 1 H, CH$_2$OH), 3.57 (dd, J=12.5, 8.0 Hz, 1 H, CH$_2$OH), 3.32 (qd, J=7.0, 4.5 Hz, 1 H, CH$_3$CH(C=O)), 3.16 (dd, J=7.5, 5.0 Hz, 1 H, C(O)CHCH$_2$CHO), 3.03 (q, J=7.5 Hz, 2 H, CH$_2$CH$_3$), 2.56 (brs, 1 H, OH), 2.54 (dd, J=14.0, 10.0 Hz, 1 H, CH$_2$COO), 2.38 (dd, J=14.0, 3.0 Hz, 1 H, CH$_2$COO), 2.14 (ddd, J=15.0, 4.5, 3.0 Hz, 1 H, C(O)CHCH$_2$CHO) 2.11 (s, 3 H, CH=C(CH$_3$)), 2.02–1.96 (m, 1 H, C(O)CHCH$_2$CHO), 1.93–1.84 (m, 1 H), 1.74–1.71 (m, 1 H), 1.55–1.25 (m, 5 H), 1.40 (t, J=8.0 Hz, 3 H, CH$_3$CH$_2$), 1.37 (s, 3 H, C(CH$_3$)$_2$), 1.17 (d, J=7.0 Hz, 3 H, CH(CH$_3$)), 1.08 (s, 3 H, C(CH$_3$)$_2$), 1.01 (d, J=7.0 Hz, 3 H C(CH$_3$)$_2$); $^{13}$C NMR (125.7 MHz, CDCl$_3$) d 220.4, 172.0, 170.5, 151.5, 137.2, 119.7, 115.5, 76.4, 74.1, 72.7, 63.8, 63.5, 57.3, 53.1, 42.9, 39.2, 36.4, 31.4, 30.9, 28.3, 26.8, 21.9, 21.2, 19.5, 17.1, 15.9, 14.0, 13.6; HRMS (FAB), calcd for $C_{28}H_{43}NO_7S$ (M+Na$^+$), 560.2658 found 560.2640.

bis-Silylether 61 as illustrated in FIG. 10. To a solution of triol 57 (83 mg, 0.150 mmol, 1.0 equiv) in DMF (1.5 mL, 0.1 M) was added Et$_3$N (315 mL, 2.26 mmol, 15 equiv) followed by TMSCl (152 mL, 1.20 mmol, 8 equiv) and the mixture was stirred at 25° C. for 12 h. The mixture was then concentrated under reduced pressure and the resulting oil was partitioned between ether (10 mL) and water (10 mL) and the layers were separated. The aqueous layer was extracted with ether (3×10 mL) and the combined extracts were dried (MgSO$_4$), concentrated under reduced pressure and then filtered through a short plug of silica gel. The resulting filtrate was concentrated, dissloved in CH$_2$Cl$_2$ (5 ml) and silica gel (1 g) was added. The resulting slurry was stirred at 25° C. for 12 h, filtered, concentrated and finally passed through a short plug of silica gel to afford the bis-silylether 61 as a foam (103 mg, 98%). $R_f$=0.48 (silica gel, 60% Et$_2$O in hexanes); [a]$^{22}$D −19.1 (c 0.23, CHCl$_3$); IR (thin film) n$_{max}$ 3408, 2956, 1746, 1698, 1454, 1383, 1250, 1156, 1113, 1060, 1021, 985, 898, 841, 752 cm$^{-1}$; $^1$H NMR (500 MHz, CDCl$_3$) d 6.44 (s, 1 H, ArH), 5.37 (dd, J=9.0 Hz, 1 H, CHOCO), 4.01 (dd, J=10.5, 2.5 Hz, 1 H, CHOH), 3.86 (d, J=10.0 Hz, 1 H, CHOSi), 3.79 (dd, J=12.5, 4.5 Hz, 1 H, CH$_2$OH), 3.49 (ddd, J=12.5, 10.5, 8.5 Hz, 1 H, CH$_2$OH), 3.39 (m, 1 H, OH), 3.09 (dd, J=10.5, 3.5 Hz, 1 H, CH(O)CH$_2$CO), 2.97 (qd, J=6.5, 4.0 Hz, 1 H, CH$_3$CH(C=O)), 2.74 (dd, J=16.5, 10.5 Hz, 1 H, CH$_2$COO), 2.67 (dd, J=16.0, 2.5 Hz, 1 H, CH$_2$COO), 2.18–2.15 (m, 1 H, CH(O)CH$_2$CHO), 1.95–1.82 (m, 2 H), 1.82 (s, 3 H, CH$_3$C=C), 1.68–1.40 (m, 4 H), 1.24 (m, 2 H), 1.18 (s, 3 H, C(CH$_3$)$_2$), 1.11 (s, 3 H, C(CH$_3$)$_2$), 1.06 (d, J=6.5 Hz, 3 H, CH(CH$_3$)), 0.95 (d, J=7.0 Hz, 3 H, CH(CH$_3$)), 0.14 (s, 9 H, (CH$_3$)$_3$Si), 0.06 (s, 9 H, (CH$_3$)$_3$Si); $^{13}$C NMR (125.7 MHz, CHCl$_3$) d 214.8, 170.8, 145.4, 81.4, 80.6, 76.2, 74.5, 64.0, 63.4, 58.1, 53.2, 48.3, 40.0, 35.6, 32.9, 31.4, 28.7, 24.5, 23.4, 23.3, 19.6, 19.5, 17.9, 0.9, 0.3; HRMS (FAD), calcd for $C_{29}H_{53}IO_7Si_2$ (M+Cs$^+$), 829.1429 found 829.1459.

Aldehyde 62 as illustrated in FIG. 10. To a suspension of alcohol 61 (20 mg, 0.029 mmol, 1.0 equiv) and 4 Å molecular sieves in $CH_2Cl_2$ (0.25 mL) was added NMO (10 mg, 0.085 mmol, 3.0 equiv) followed by TPAP (1 mg, 0.003 mmol, 0.1 equiv). The resulting slurry was stirred at 25° C. for 40 min and then filtered through a short plug of silica to afford aldehyde 62 (18 mg, 90%). $R_f$=0.66 (silica gel, 60% $Et_2O$ in hexanes); IR (thin film) $n_{max}$ 2956, 2913, 2851, 1732, 1698, 1454, 1383, 1250, 1156, 1113, 1021, 987, 895, 841, 750 cm$^{-1}$; $^1$H NMR (600 MHz, $CDCl_3$) d 8.84 (s, 1 H, CH=O), 6.51 (s, 1 H, ArH), 5.46 (dd, J=7.9, 3.4 Hz, 1 H, CHOCO), 3.81 (d, J=8.3 Hz, 1 H, CHOSi), 3.32 (dd, J=8.5, 4.2 Hz, 1 H, CHOSi), 3.04 (qd, J=7.1, 7.1 Hz, 1 H $CH_3CH$(C=O)), 2.65 (dd, J=15.6, 8.3 Hz, 1 H, $CH_2COO$), 2.59 (dd, J=15.6, 4.1 Hz, 1 H, $CH_2COO$), 2.21 (ddd, J=15.2, 3.8, 3.8 Hz, 1 H, $CH(O)CH_2CHO$), 2.06–1.97 (m, 2 H), 1.87 (s, 3 H, $CH_3C$=CH), 1.87–1.80 (m, 1 H), 1.62–1.56 (m, 1 H), 1.51–1.41 (m, 2 H), 1.27–1.21 (obscured m, 2 H), 1.15 (s, 3H, $C(CH_3)_2$), 1.08 (s, 3H, $C(CH_3)_2$), 1.08 (d, J=6.2 Hz, 3 H, $CH(CH_3)$), 0.96 (d, J=6.9 Hz, 3 H, $CH(CH_3)$), 0.13 (s, 9 H, $(CH_3)_3Si$), 0.05 (s, 9 H, $(CH_3)_3Si$); $^{13}$C NMR (150.9 MHz, $CDCl_3$) d 216.2, 198.7, 170.7, 144.9, 81.7, 79.6, 75.0, 74.2, 64.1, 57.7, 53.3, 47.5, 40.0, 36.0, 31.8, 31.0, 29.5, 25.3, 22.9, 22.7, 21.9, 19.9, 19.2, 17.1, 0.4, 0.0; HRMS (FAB), calcd for $C_{29}H_{51}IO_7Si_2$ (M+Cs$^+$), 827.1272 found 827.1304.

Olefin 63 as illustrated in FIG. 10. Methyltriphenylphosphonium bromide (104 mg of a mixture with sodium amide (Aldrich), 0.250 mmol, 9.7 equiv) in THF (2.0 mL) was added portionwise to a solution of aldehyde 62 (18.0 mg, 0.026 mmol, 1.0 equiv) in THF (0.5 mL) at −5° C. until the completion of the reaction was established by TLC. Saturated aqueous $NH_4Cl$ (1 mL) was added and the product was extracted with ether (3×2 mL) dried ($MgSO_4$) and then concentrated under reduced pressure. Flash column chromatography (silica gel, 15% ether in hexanes) furnished olefin 63 (11.7 mg, 65%). $R_f$=0.50 (silica gel, 20% $Et_2O$ in hexanes); $[a]^{22}D$ −17.9 (c 0.2, $CHCl_3$); IR (thin film) $n_{max}$ 2954, 2923, 1747, 1698, 1456, 1382, 1250, 1156, 1113, 1021, 986, 889, 841, 750 cm$^{-1}$; $^1$H NMR (500 MHz, $CHCl_3$) d 6.44 (s, 1 H, ArH), 6.00 (dd, J=17.0, 10.0 Hz, 1 H, CH=$CH_2$), 5.36 (dd, J=9.0, 2.0 Hz, 1 H, CHOCO), 5.29 (dd, J=17.5, 1.5 Hz, 1 H, $CH_2$=CH), 5.14 (dd, J=10.5, 1.5 Hz, 1 H, $CH_2$=CH), 4.12 (dd, J=9.0, 5.0 Hz, 1 H, CHOSi), 3.85 (d, J=9.5 Hz, 1 H, CHOSi), 3.04 (qd, J=9.0, 7.0 Hz, 1 H, $CH_3CH$(C=O)), 2.85 (dd, J=9.5, 4.0 Hz, 1 H, CH(O)CCH=$CH_2$), 2.73 (dd, J=16.0, 10.0 Hz, 1 H, $CH_2COO$), 2.65 (dd, J=16.0, 2.5 Hz, 1 H, $CH_2COO$), 2.12 (ddd, J=15.0, 4.0, 2.0 Hz, 1 H, $CH_2CH(O)$), 1.93–1.78 (3 H, m), 1.84 (s, 3 H, CH=$CCH_3$), 1.65–1.20 (m, 5 H), 1.19 (s, 3 H, $C(CH_3)_2$), 1.11 (s, 3 H, $C(CH_3)_2$), 1.08 (d, J=6.5 Hz, 3 H, $CH(CH_3)$), 0.95 (d, J=7.0 Hz, 3 H, $CH(CH_3)$), 0.14 (s, 9 H, $(CH_3)_3Si$), 0.07 (9 H, s, $(CH_3)_3Si$), $^{13}$C NMR (150.9 MHz, $CDCl_3$) d 215.2, 170.6, 145.4, 136.7, 116.0, 81.2, 80.2, 75.7, 74.7, 63.6, 63.3, 53.3, 48.0, 39.4, 35.9, 33.4, 31.0, 30.3, 29.3, 24.3, 23.6, 22.7, 19.8, 19.5, 17.6, 0.7, 0.3; HRMS (FAB), calcd for $C_{30}H_{53}IO_6Si_2$ (M+Cs$^+$), 825.1480 found 825.1450.

Macrolactone 65 as illustrated in FIG. 10. A solution of olefin 63 (15 mg, 0.022 mmol, 1.0 equiv) in EtOH (1.0 mL) was treated with hydrazine (17 mL, 0.500 mmol, 25.0 equiv) and $H_2O_2$ (25 mL, 30% w/w in water, 0.370 mmol, 16.0 equiv) and the resulting mixture stirred at 0° C. for 3 h. The mixture was then partitioned between ether (4 mL) and water (2 mL) and the layers were separated. The aqueous layer was extracted with ether (3×4 mL) and the combined organic extracts were dried ($MgSO_4$) and concentrated under reduced pressure to give a foam (15.0 mg) which was dissolved in THF (1.5 mL) and treated with HF.pyr. in pyr./THF (600 mL) and the mixture was stirred at 0° C. for 2 h. The reaction mixture was then quenched with saturated aqueous $NaHCO_3$ (5 mL) and was extracted with EtOAc (3×3 mL). The combined organic extracts were dried ($MgSO_4$) and concentrated under reduced pressure. Flash column chromatography (silica gel, 80% ether in hexanes) furnished macrolactone 65 (9.4 mg, 75%). $R_f$=0.06 (silica gel, 60% $Et_2O$ in hexanes); $[a]^{22}D$ −19.3 (c 0.33, $CHCl_3$); IR (thin film) $n_{max}$ 3416, 2954, 2926, 2872, 1734, 1689, 1456, 1384, 1287, 1256, 1149, 1084, 978, 892 cm$^{-1}$; $^1$H NMR (500 MHz, $CHCl_3$) d 6.46 (s, 1 H, CH=$CCH_3$), 5.48 (dd, J=5.0, 5.0 Hz, 1 H, CHOCO), 4.03 (brm, 1 H, CHOH), 3.76 (brm, 2 H, CHOH and OH), 3.34 (qd, J=6.5, 6.5 Hz, 1 H, $CH_3CH$(C=O)), 2.73 (dd, J=6.5, 6.5 Hz, 1 H, CH(O)$CCH_2CH_3$), 2.54 (dd, J=14.5, 10.0 Hz, 1 H, $CH_2COO$), 2.44 (dd, J=14.5, 8.5 Hz, 1 H, $CH_2COO$), 2.29 (brs, 1 H, OH), 1.96–1.85 (m, 2H), 1.89 (s, 3 H, $CH_3C$=CH), 1.70–1.40 (m, 5 H), 1.31–1.24 (m, 4 H), 1.35 (s, 3 H, $C(CH_3)_2$), 1.19 (d, J=6.5 Hz, 3 H, $CH(CH_3)$), 1.07 (s, 3 H, $C(CH_3)_2$), 0.99 (d, J=7.0 Hz, 3 H, $CH(CH_3)$), 0.91 (t, J=7.5 Hz, 3 H, $CH_3CH_2$) $^{13}$C NMR (150.9 MHz, $CDCl_3$) d 220.5, 170.3, 143.8, 80.2, 75.4, 73.8, 63.8, 59.1, 52.1, 44.1, 38.6, 36.4, 31.0, 30.5, 29.7, 29.2, 28.8, 22.8, 21.7, 21.3, 20.1, 17.4, 14.6, 8.8; HRMS (FAB), calcd for $C_{24}H_{39}IO_6$ (M+Cs$^+$), 683.0846 found 683.0870.

Macrolactone 66 as illustrated in FIG. 10. A solution of vinyl iodide 65 (9.4 mg, 0.017 mmol, 1.0 equiv), stannane 8j (10 mg, 0.036 mmol, 2.1 equiv) and $PdCl_2(MeCN)_2$ (1.0 mg, 0.004 mmol, 0.2 equiv) in degassed DMF (250 mL, 0.07 M) was stirred at 25° C. for 15 h, according to the procedure described for the synthesis of macrolactone 18d, to yield, after preparative thin layer chromatography (250 mm silica gel plates, EtOAc) macrolactone 66 (4.6 mg, 52%). $R_f$=0.40 (silica gel, 80% EtOAc in hexanes); $[a]^{22}D$ −30.0 (c 0.17, $CHCl_3$); IR (thin film) $n_{max}$ 3432, 2967, 2933, 2872, 1736, 1689, 1458, 1384, 1256, 1151, 1067, 1038, 979, 905, 733 cm$^{-1}$; $^1$H NMR (500 MHz, $CDCl_3$) d 7.23 (s, 1 H, ArH), 6.62 (s, 1 H, CH=$CCH_3$), 5.59 (d, J=47.1 Hz, 2 H, $CH_2F$), 5.46 (dd, J=6.3, 3.7 Hz, 1 H, CHOCO), 4.15 (d, J=8.8 Hz, 1 H, CHOH), 3.98 (brs, 1 H, OH), 3.77 (brs, 1 H, CHOH), 3.35 (qd, J=6.6, 4.8 Hz, 1 H, $CH_3CH$(C=O)), 2.82 (dd, J=6.1, 6.1 Hz, 1 H, CH(O)$CCH_2CH_3$), 2.56 (dd, J=14.0, 9.9 Hz, 1 H, $CH_2COO$), 2.48 (brs, 1 H, OH), 2.41 (dd, J=14.0, 3.0 Hz, 1 H, $CH_2COO$), 2.13 (s, 3 H, CH=$C(CH_3)$), 2.04 (ddd, J=15.1, 5.9, 4.0 Hz, 1 H, $CH_2CH(O)CHCH_2$), 2.00–1.94 (m, 1 H, $CH_2CH(O)CHCH_2$), 1.78–1.24 (m, 7 H), 1.36 (s, 3 H, $C(CH_3)_2$), 1.17 (d, J=7.0 Hz, 3 H, $CH(CH_3)$), 1.07 (s, 3 H, $C(CH_3)_2$), 1.00 (d, J=7.0 Hz, 3 H, $CH(CH_3)$); $^{13}$C NMR (150.9 MHz, $CHCl_3$) d 220.5, 170.5, 163.7, 152.8, 137.8, 119.2, 118.2, 81.2, 79.8, 74.8, 73.3, 64.1, 59.9, 52.6, 43.5, 38.9, 36.4, 31.5, 30.7, 29.2, 28.9, 22.4, 20.7, 20.6, 17.3, 15.7, 14.1, 8.7; HRMS (FAB), calcd for $C_{28}H_{42}FNO_6S$ (M+Cs$^+$), 672.1771 found 672.1793.

Macrolactone 67 as illustrated in FIG. 10. A solution of vinyl iodide 65 (11 mg, 0.020 mmol, 1.0 equiv), stannane 8p (14 mg, 0.034 mmol, 1.7 equiv) and $PdCl_2(MeCN)_2$ (1.0 mg, 0.004 mmol, 0.2 equiv) in degassed DMF (250 mL, 0.08 M) was stirred at 25° C. for 20 h, according to the procedure described for the synthesis of macrolactone 18d, to yield, after preparative thin layer chromatography (250 mm silica gel plates, EtOAc) macrolactone 67 (8.5 mg, 79%). $R_f$=0.68 (silica gel, $Et_2O$); $[a]^{22}D$ −44.7 (c 0.08 $CHCl_3$); IR (thin film) $n_{max}$ 3442, 2964, 2934, 1732, 1683, 1536, 1461, 1422, 1384, 1241, 1150, 1070, 979, 906, 732 cm$^{-1}$; $^1$H NMR (500 MHz, $CHCl_3$) d 6.52 (s, 1 H, ArH), 6.36 (s, 1 H, CH=$CCH_3$), 5.41 (dd, J=7.0, 3.3 Hz, 1 H, CHOCO), 4.15 (ddd, J=10.3, 7.0, 3.7 Hz, 1 H, CHOH), 4.08 (s, 3 H, $OCH_3$), 3.99 (brd, J=6.3 Hz, 1 H, OH), 3.77 (brm, 1 H, CHOH), 3.34

(qd, J=6.6, 4.8 Hz, 1 H, CH$_3$CH(C=O)), 2.81 (dd, J=6.6, 5.9 Hz, 1 H, CH(O)CCH$_2$CH$_3$), 2.55 (dd, J=14.2, 10.1 Hz, 1 H, CH$_2$COO), 2.52 (brs, 1 H, OH), 2.39 (dd, J=14.0, 2.9 Hz, 1 H, CH$_2$COO), 2.14 (s, 3 H, CH=C(CH$_3$)), 2.05 (ddd, J=15.1, 5.5, 4.0 Hz, 1 H, CH$_2$CH(O)CHCH$_2$), 1.98–1.92 (m, 1 H, CH$_2$CH(O)CHCH$_2$), 1.80–1.70 (m, 2 H), 1.58–1.39 (m, 5 H), 1.30–1.24 (m, 2 H), 1.17 (d, J=7.0 Hz, 3 H, CH(CH$_3$)), 1.08 (s, 3 H, C(CH$_3$)$_2$), 1.00 (d, J=7.0 Hz, 3 H, CH(CH$_3$)), 0.91 (t, J=7.4 Hz, 3 H, CH$_3$CH$_2$); $^{13}$C NMR (150.9 MHz, CHCl$_3$) d 220.5, 174.1, 170.5, 146.5, 136.3, 119.8, 109.7, 74.6, 73.3, 64.2, 60.1, 58.4, 52.7, 43.4, 39.1, 36.4, 31.6, 30.8, 29.4, 28.9, 22.6, 22.4, 21.0, 20.4, 17.2, 15.5, 14.0, 8.7; HRMS (FAB), calcd for C$_{28}$H$_{43}$NO$_7$S (M+Cs$^+$), 670.1815 found 670.1837.

Macrolactone 68 as illustrated in FIG. 10. A solution of vinyl iodide 65 (5.8 mg, 0.011 mmol, 1.0 equiv), stannane 8r (10 mg, 0.025 mmol, 2.3 equiv) and PdCl$_2$(MeCN)$_2$ (1.0 mg, 0.004 mmol, 0.3 equiv) in degassed DMF (100 mL, 0.1 M) was stirred at 25° C. for 23 h, according to the procedure described for the synthesis of macrolactone 18d, to yield, after preparative thin layer chromatography (250 mm silica gel plates, EtOAc) macrolactone 68 (3.7 mg, 65%). R$_f$=0.45 (silica gel, Et$_2$O); [a]$^{22}$D –33.3 (c 0.09, CHCl$_3$); IR (thin film) n$_{max}$ 3406, 2954, 2924, 2872, 1736, 1692, 1454, 1384, 1254, 1150, 1071, 979 cm$^{-1}$; $^1$H NMR (500 MHz, CDCl$_3$) d 6.99 (s, 1 H, ArH), 6.60 (s, 1 H, CH=CCH$_3$), 5.42 (dd, J=7.9, 3.1 Hz, 1 H, CHOCO), 4.33 (brs, 1 H, CHOH), 4.24 (brd, J=9.6 Hz, 1 H, OH), 3.76 (brm, 1 H, CHOH), 3.32 (qd, J=6.8, 4.3 Hz, 1 H, CH$_3$CH(C=O)), 3.01 (q, J=7.6 Hz, 2 H, ArCH$_2$CH$_3$), 2.82 (dd, J=7.4, 4.8 Hz, 1 H, CH(O)CH$_2$), 2.60 (brs, 1 H, OH), 2.54 (dd, J=13.6, 10.3 Hz, 1 H, CH$_2$COO), 2.35 (dd, J=14.0, 2.9 Hz, 1 H, CH$_2$COO), 2.10–2.05 (obscured m, 1 H, CH$_2$CH(O)), 2.09 (s, 3 H, CH=C (CH$_3$)), 1.96–1.90 (m, 1 H, CH$_2$CH(O)CHCH$_2$), 1.80–1.67 (m, 2 H), 1.66–1.25 (m, 7 H), 11.38 (s, 3 H, C(CH$_3$)$_2$), 1.16 (d, J=7.0 Hz, 3 H CH(CH$_3$)), 1.07 (s, 3 H, C(CH$_3$)$_2$), 1.00 (d, J=7.0 Hz, 3 H CH(CH$_3$)), 0.92 (t, J=7.4 Hz, 3 H, CH$_3$CH$_2$), 0.91 (t, J=7.5 Hz, 3 H, CH$_3$CH$_2$); $^{13}$C NMR (125.7 MHz, CDCl$_3$) d 220.7. 170.6, 115.4, 74.1, 72.6, 64.4, 60.4, 53.2, 42.7, 39.2, 36.3, 31.8, 30.8, 29.7, 28.9, 28.7, 27.8, 26.8, 22.7, 22.0, 21.3, 19.4, 17.5, 17.0, 16.0, 14.1, 14.0, 13.6, 8.6; HRMS (FAB), calcd for C$_{29}$H$_{45}$NO$_6$S (M+Cs$^+$), 668.2022 found 668.2042.

Epoxide 600. Sharpless Epoxidation of Lactone 500 as illustrated in FIG. 12. To a solution of allylic alcohol 500 (500 mg, 0.679 mmol, 1.0 equiv.) and 4 Å molecular sieves (200 mg) in CH$_2$Cl$_2$ (4.0 mL) at –30° C. was added dropwise (–)-diethyl-D-tartrate (60 mL, 0.351 mmol, 0.5 equiv.) and titanium isopropoxide (81 mL, 0.294 mmol, 0.4 equiv.) in CH$_2$Cl$_2$ (4 mL). After 1 h, t-butyl hydroperoxide (300 mL, 1.36 mmol, 5 M in decane, 2.0 equiv.) was added and the reaction mixture was stirred at –30° C. for 2 h. The reaction mixture was then filtered through celite and the filtrate diluted with EtOAc (6 mL). Aqueous saturated sodium sulfate solution (6 mL) was added and the mixture stirred at 25° C. for 1 h. The layers were separated and the aqueous phase was extracted with EtOAc (2×6 mL). The combined organic extracts were dried (MgSO$_4$), filtered and concentrated in vacuo to give a crude oil which was subjected to column chromatography (silica gel, 60% Et$_2$O in hexanes) to give the epoxide 600 (472 mg, 92%): 600: R$_f$=0.33 (silica gel, 60% Et$_2$O in hexanes); [a]$^{22}$D –11.9 (c 0.3, CHCl$_3$); $^1$H NMR (600 MHz, CHCl$_3$) d 6.97 (s, 1 H, SCH=C), 6.56 (s, 1 H, CH=CCH$_3$), 5.13 (d, J=7.5 Hz, 1 H, CHOCO), 4.05 (bd, J=7.7 Hz, 1 H, CHOSi), 3.84 (d, J=9.1 Hz, CHOSi), 3.80 (d, J=12.1 Hz, 1 H, CH$_2$OH), 3.51 (d, J 12.1 Hz, 1 H, CH$_2$OH), 3.10 (dd, J=10.0, 3.4 Hz, 1 H, CHOCH$_2$), 2.98 (dq, J=8.9, 6.9 Hz, 1 H, C(O)CH(CH$_3$)), 2.73 (obscured m, 1 H, CH$_2$COO), 2.71 (s, 3 H, N=C(CH$_3$) S), 2.60 (dd, J=16.3, 9.2 Hz, 1 H, CH$_2$COO), 2.26 (ddd, J=14.8, 3.2, 3.2 Hz, 1 H, OCHCH$_2$CHO), 2.10 (s, 3 H, CH=C(CH$_3$)), 1.96 (ddd, J=14.7, 9.8, 9.8 Hz, OCHCH$_2$CHO), 1.89–1.78 (m, 3 H), 1.61 (m, 1 H, CH(CH$_3$)), 1.44–1.40 (m, 3 H), 1.19 (s, 3 H, C(CH$_3$)$_2$), 1.13 (s, 3 H, C (CH$_3$)$_2$) 1 1. 06 (d, J=6.8 Hz, CH(CH$_3$)), 0.96 (d, J=6.9 Hz, CH(CH$_3$)), 0.93 (s, 9 H, SiC(CH$_3$)$_3$), 0.84 (s, 9 H, SiC(CH$_3$)$_3$), 0.10 (s, 3 H, Si(CH$_3$)$_2$), 0.08 (s, 3 H, Si(CH$_3$)$_2$), 0.05 (s, 3 H, Si(CH$_3$)$_2$), –0.06 (s, 3 H, Si(CH$_3$)$_2$); $^{13}$C NMR (150.9 MHz, CDCl$_3$) d 214.8, 170.8, 164.6, 151.9, 137.3, 120.4, 116.5, 75.9, 64.2, 63.5, 60.4, 58.2, 53.3, 39.6, 33.2, 31.7, 29.9, 26.3, 26;1, 24.3, 23.7, 19.3, 18.7, 18.6, 17.9, 14.8, –3.2, –3.4, –3.5, –5.4; FAB HRMS (NBA/CsI) m/e 884.3418, M+Cs$^+$ calcd for C$_{39}$H$_{69}$NO$_7$SSi$_2$ 884.3388.

Allylic alcohol 900 as illustrated in FIG. 12. To a stirred solution of epoxy alcohol 600 (472 mg, 0.627 mmol, 1.0 equiv.) in CH$_2$Cl$_2$ (6.5 mL) at 0° C. was added Et$_3$N (270 mL, 1.89 mmol, 3.0 equiv.) followed by tosyl chloride (180 mg, 0.944 mmol, 1.5 equiv.) and 4-DMAP (7.0 mg, 0.057 mmol, 0.1 equiv.). The reaction mixture was warmed to 25° C. and stirred for 2.5 h before saturated aqueous NH$_4$Cl solution (5 mL) was added. The layers were separated and the aqueous phase was extracted with EtOAc (3×5 mL). The combined organic extracts were dried (MgSO$_4$), filtered and concentrated in vacuo. The residue was then filtered through a short plug of silica gel (60% Et$_2$O in hexanes) and concentrated in vacuo. The residue was then dissolved in acetone (13 mL) and treated with NaI (470 mg, 3.14 mmol, 5.0 equiv.). After refluxing for 2 h, the reaction mixture was cooled to 0° C. and diluted with DMF (2.3 mL). Triphenylphosphine (250 mg, 0.953 mmol, 1.5 equiv.) was then added, followed by iodine (16 mg, 0.063 mmol, 0.1 equiv.) and the reaction mixture was stirred for 3 h. The solvents were then removed in vacuo, and the residue purified by flash chromatography (50% Et$_2$O in hexanes) to give allylic alcohol 900 as a colorless oil (410 mg, 89% over 3 steps). 900: R$_f$=0.37 (silica gel, 60% Et$_2$O in hexanes); [a]$^{22}$D –5.0 (c 0.3, CHCl$_3$); IR (thin film) n$_{max}$ 3440, 2931, 2887, 2856, 1740, 1694, 1471, 1382, 1254, 1184, 1156, 1087, 987, 939, 874, 835, 756, 667 cm$^{-1}$; $^1$H NMR (600 MHz, CDCl$_3$) d 6.93 (s, 1 H, SCH=C), 6.59 (s, 1 H, CH=CCH$_3$), 5.60 (bs, 1 H, CHOCO), 5.05 (s, 1 H, C=CH$_2$), 4.83 (s, 1 H, C=CH$_2$), 4.35 (bs, 1 H, CHOSi), 4.22 (bs, 1 H, CHOSi), 3.99 (d, J=9.1 Hz, CHOH), 1.96 (dq, J=8.9, 7.0 Hz, 1 H, C(O)CH(CH$_3$)), 2.71 (obscured m, 1 H, CH$_2$COO), 2.68 (s, 3 H, N=C(CH$_3$)S), 2.47 (dd, J=16.7, 5.7 Hz, CH$_2$COO), 2.20 (ddd, J=12.5, 12.5, 5.6 Hz, 1 H, CH$_2$C=CH$_2$), 2.11 (obscured m, 1 H, CH$_2$C=CH$_2$), 2.10 (s, 3 H, CH=C (CH$_3$)), 1.90 (bs, 1 H, OH), 1.75–1.71 (m, 2 H), 1.60 (m, 1 H, CH(CH$_3$)), 1.27–1.24 (m, 2 H), 1.22 (s, 3 H, C(CH$_3$)$_2$), 1.16 (s, 3 H, C(CH$_3$)$_2$), 1.08 (d, J=6.8 Hz, CH(CH$_3$)), 0.91 (d, J=7.0 Hz, CH(CH$_3$)), 0.89 (s, 9 H, SiC(CH$_3$)$_3$), 0.85 (s, 9 H, SiC(CH$_3$)$_3$), 0.11 (s, 3 H, Si(CH$_3$)$_2$), 0.05 (s, 3 H, Si(CH$_3$)$_2$), 0.04 (s, 3 H, Si(CH$_3$)$_2$), 0.00 (s, 3 H, Si(CH$_3$)$_2$); $^{13}$C NMR (150.9 MHz, CDCl$_3$) d 215.6, 170.8, 164.4, 153.0, 152.3, 137.2, 120.8, 116.3, 107.9, 77.8, 69.2, 60.4, 53.9, 41.6, 35.1, 27.7, 26.1, 24.7, 21.1, 18.5, 18.4, 18.2, 15.4, 14.3, –3.2, –3.7, –3.8, –5.4; FAB HRMS (NBA/CsI) m/e 868.3408, M+Cs$^+$ calcd for C$_{39}$H$_{69}$NO$_6$SSi$_2$ 868.3439.

Stannanes 1000 and 1100 as illustrated in FIG. 12. To a stirred solution of allylic alcohol 900 (375 mg, 0.509 mmol, 1.0 equiv.) and 10% Pd(OH)$_2$/C (27.5 mg, 0.1 equiv.) in THF (2.5 mL) at 25° C. was added via syringe pump over 7 h, a solution of tri-n-butyltinhydride (161 mg, 0.553 mmol, 1.5 equiv.) in THF (1 mL). The reaction mixture was then filtered over celite and concentrated in vacuo. Flash chromatography (gradient elution, 20% E 60% Et$_2$O in hexanes) then gave starting material (182 mg, 48%), stannane 1000 (183 mg, 35%) and stannane 1100 (78 mg, 15%). 1000: R$_f$=0.44 (silica gel, 60% Et$_2$O in hexanes); [a]$^{22}$D −34.9 (c 0.2, CHCl$_3$); IR (thin film) n$_{max}$ 3464, 2955, 2928, 2855, 1742, 1696, 1461, 1381, 1253, 1157, 1101, 1020, 987, 874, 834, 775, 733 cm$^{-1}$; $^1$H NMR (500 MHz, CDCl$_3$) d 6.96 (s, 1 H, SCH═C), 6.57 (s, 1 H, CH═CCH$_3$), 5.31 (bs, 1 H, CHOCO), 4.06 (bd, J=9.2 Hz, CHOSi), 3.96 (d, J=9.5 Hz, CHOH), 3.88 (bs, 1 H, CHOSi), 3.01 (dq, J=8.1, 6.8 Hz, C(O)CH(CH$_3$)), 2.85 (d, J=16.6 Hz, 1 H, CH$_2$COO), 2.70 (s, 3 H, N═C(CH$_3$)S), 2.58 (dd, J=16.6, 9.1 Hz, CH$_2$COO), 2.10 (s, 3 H, CH═C(CH$_3$)), 1.95 (dd, J=14.9, 11.5 Hz, 1 H), 1.72–1.51 (m, 7 H), 1.45 (m, 8 H, SnCH$_2$CH$_2$CH$_2$CH$_3$ and CH$_2$), 1.31 (m, 12 H, SnCH$_2$CH$_2$CH$_2$CH$_3$), 1.23 (s, 3 H, C(CH$_3$)$_2$), 0.98 (s, 3 H, C(CH$_3$)$_2$), 1.07 (d, J=6.8 Hz, 3 H, CH(CH$_3$)), 0.78 (obscured d, 3 H, CH(CH$_3$)), 0.92 (s, 9 H, SiC(CH$_3$)$_3$), 0.88 (t, J=7.3 Hz, 27 H, SnCH$_2$CH$_2$CH$_2$CH$_3$), 0.87 (s, 9 H, SiC(CH$_3$)$_3$), 0.47 (dd, J=11.9 Hz, 1 H), 0.16 (s, 3 H, Si(CH$_3$)$_2$), 0.09 (s, 3 H, Si(CH$_3$)$_2$), 0.05 (s, 3 H, Si(CH$_3$)$_2$), −0.01 (s, 3 H, Si(CH$_3$)$_2$); $^{13}$C NMR (125.7 MHz, CDCl$_3$) d 214.9, 171.1, 164.6, 152.4, 138.3, 119.5, 116.0, 78.2, 75.9, 71.7, 53.3, 44.4, 36.5, 35.7, 29.2, 27.4, 26.2, 26.1, 24.3, 19.2, 18.6, 18.0, 15.5, 13.7, 9.3, −3.2, −3.4, −3.7, −5.8; FAB HRMS (NBA/CsI) m/e 1160.4710, M+Cs$^+$ calcd for C$_{51}$H$_{97}$NO$_6$SSi$_2$Sn 1160.4652; 1100: R$_f$=0.40 (silica gel, 60% Et$_2$O in hexanes); [a]$^{22}$D −5.35 (c 0.7, CHCl$_3$); IR (thin film) n$_{max}$ 3405, 2927, 2855, 1707, 1697, 1461, 1382, 1255, 1084, 836, 775 cm$^{-1}$; $^1$H NMR (500 MHz, CHCl$_3$) d 6.94 (s, 1 H, SCH═C), 6.59 (s, 1 H, CH═CCH$_3$), 5.60 (bd, J=9.7 Hz, 1 H, CHOCO), 4.06 (bd, J=9.2 Hz, CHOSi), 4.40 (dd, J=5.1 Hz, CHOSi), 3.95 (d, J=8.8 Hz, CHOH), 3.80 (bs, 1 H, CHOSi), 3.02 (dq, J=8.4, 7.1 Hz, C(O)CH(CH$_3$)), 2.71 (s, 3 H, N═C(CH$_3$)S), 2.67 (dd, J=16.5, 5.8 Hz, 1 H, CH$_2$COO), 2.52 (dd, J=16.5, 4.8 Hz, 1 H, CH$_2$COO), 2.14 (s, 3 H, CH═C(CH$_3$)), 1.93–1.82 (m, 2 H), 1.68–1.61 (bm, 4 H), 1.52 (m, 1 H, CH(CH$_3$)), 1.45 (m, 8 H, SnCH$_2$CH$_2$CH$_2$CH$_3$ and CH$_2$), 1.32 (m, 9 H, SnCH$_2$CH$_2$CH$_2$CH$_3$), 1.18 (s, 3 H, C(CH$_3$)$_2$), 1.14 (s, 3 H, C(CH$_3$)$_2$), 1.10 (d, J=6.9 Hz, CH(CH$_3$)), 0.95 (d, J=6.9 Hz, CH(CH$_3$)), 0.91 (s, 9 H, SiC(CH$_3$)$_3$), 0.88 (t, J 7.3 Hz, 27 H, SnCH$_2$CH$_2$CH$_2$CH$_3$), 0.13 (s, 3 H, Si(CH$_3$)$_2$), 0.08 (s, 3 H, Si(CH$_3$)$_2$), 0.07 (s, 3 H, Si(CH$_3$)$_2$), 0.06 (s, 3 H, Si(CH$_3$)$_2$); $^{13}$C NMR (125.7 MHz, CHCl$_3$) d 217.9, 170.8, 168.3, 152.3, 138.1, 120.2, 116.4, 77.8, 73.8, 69.4, 54.2, 41.4, 39.5, 29.2, 27.4, 26.2, 26.0, 19.2, 18.4, 18.3, 17.9, 15.1, 13.7, 9.47, −3.2, −3.8, −5.0; FAB HRMS (NBA/NaI) m/e 1050.5548, M+Na$^+$ calcd for C$_{51}$H$_{97}$NO$_6$SSi$_2$Sn 1050.5495.

cis-Cyclopropane 300 and elimination product 1500 as illustrated in FIG. 12. To a stirred solution of stannane 1000 (38.0 mg, 0.037 mmol, 1.0 equiv.) in CH$_2$Cl$_2$ (0.5 mL) at −78 ° C. was added pyridine (24 mL, 0.297 mmol, 8.0 equiv.) followed by thionyl chloride (11 mL, 0.151 mmol, 4 equiv.). The reaction mixture was then slowly warmed to 25° C. over 5 h. Saturated aqueous sodium bicarbonate solution (1.0 mL) was then added, and the layers were separated. The aqueous phase was extracted with CH$_2$Cl$_2$ (3×4 mL) and the combined organic extracts were dried (MgSO$_4$), filtered and concentrated in vacuo. The resulting residue was then dissolved in THF (1.3 mL) and HF.pyr. (0.45 mL) was added. After stirring for 24 h, the reaction mixture was diluted with EtOAc (2 mL) and quenched by addition to cold (0° C.) saturated sodium bicarbonate solution (4 mL). The layers were then separated and the aqueous phase was extracted with EtOAc (3×4 mL). The combined organic extracts were then dried (MgSO$_4$), filtered and concentrated in vacuo. Preparative thin layer chromatography (5% MeOH in CH$_2$Cl$_2$) then gave elimination product 1500 (10.8 mg, 62% over 2 steps) and cyclopropane 3 (3.6 mg, 20% over 2 steps). 300: R$_f$=0.29 (silica gel, 5% MeOH in CH$_2$Cl$_2$); [a]$^{22}$D −48.9 (c 0.2, CHCl$_3$); IR (thin film) n$_{max}$ 3398, 2925, 2853, 1732, 1688, 1456, 1384, 1292, 1260, 1190, 1153, 1083, 1041, 983, 736 cm$^{-1}$; $^1$H NMR (600 Mhz, C$_6$D$_6$) d 6.76 (s, 1 H, SCH═C), 6.46 (s, 1 H, CH═CCH$_3$), 5.43 (bm, 1 H, CHOCO), 4.16 (dd, J=8.4, 4.4 Hz, CHOH), 3.81 (dd, J=5.3, 4.4 Hz, CHOH), 3.13 (dq, J=6.4, 6.4 Hz, C(O)CH(CH$_3$)), 2.43 (s, 1 H, CH$_2$COO), 2.42 (dd, J=20.8, 15.11 Hz, 1 H, CH$_2$COO), 2.18 (s, 3 H, N═C(CH$_3$)S), 1.99 (s, 3 H, CH═C(CH$_3$)), 1.78 (ddd, J=15.5, 4.7, 4.7 Hz, 1 H), 1.65 (m, 1 H, CH(CH$_3$)), 1.52–1.19 (m, 7 H), 1.09 (s, 3 H, C(CH$_3$)$_2$), 1.05 (d, J=6.8 Hz, 3 H, CH(CH$_3$)), 0.98 (s, 3 H, C(CH$_3$)$_2$), 0.93 (d, J=6.9 Hz, 3 H, CH (CH$_3$)), 0.71 (m, 1 H, CH(CH$_2$) CH), 0.63 (m, 1 H, CH(CH$_2$)CH), 0.47 (ddd, J=8.6, 8. 6, 4.3 Hz, 1 H, CH(CH$_2$)CH), 0.31 (ddd, J=5.0, 5.0, 4.3 Hz, 1 H, CH(CH$_2$)CH); $^{13}$C NMR (125.7 MHz, CHCl$_3$) d 220.4, 170.3, 165.0, 132.1, 118.4, 115.3, 77.7, 74.9, 72.4, 52.4, 43.7, 39.0, 35.7, 30.3, 29.7, 29.5, 29.2, 25.7, 21.7, 20.6, 18.9, 17.0, 16.3, 15.5, 14.1, 14.0, 10.9, 10.2; FAB HRMS (NBA/CsI) m/e 624.1781, M+Cs$^+$ calcd for C$_{27}$H$_{41}$NO$_5$S 624.1760. 1500: R$_f$=0.31 (silica gel, 5% MeOH in CH$_2$Cl$_2$); [a]$^{22}$D −24.0 (c 0.1, CHCl$_3$); IR (thin film) n$_{max}$ 3425, 2936, 1732, 1688, 1457, 1382, 1258, 1184, 1150, 1072, 1013, 979, 888, 732 cm$^{-1}$; $^1$H NMR (600 Mhz, CDCl$_3$) d 6.93 (s, 1 H, SCH═C), 6.54 (s, 1 H, CH═CCH$_3$), 5.17 (d, J=9.4 Hz, 1 H, CHOCO), 4.73 (s, 1 H, C═CH$_2$), 4.69 (s, 1 H, C═CH$_2$), 4.32 (bd, J=9.5 Hz, 1 H, CHOH), 3.73 (bm, 1 H, CHOH), 3.29 (dq, J=6.7, 2.9 Hz, 1 H, C(O)CH(CH$_3$)), 3.24 (bs, 1 H, OH), 2.89 (bs, 1 H, OH), 2.67 (s, 3 H, N═C(CH$_3$)S), 2.48 (dd, J=14.8, 10.2 Hz, CH$_2$COO), 2.42 (dd, J=14.8, 3.1 Hz, CH$_2$COO), 2.15–2.04 (m, 4 H, CH$_2$(C═CH$_2$)CH$_2$), 2.04 (s, 3 H, CH═C(CH$_3$)), 1.91–1.72 (m, 4 H), 1.55 (m, 1 H, CH(CH$_3$)), 1.35 (s, 3 H, C(CH$_3$)$_2$), 1.10 (d, J=6.9 Hz, 3 H, CH(CH$_3$)), 1.05 (s, 3 H, C(CH$_3$)$_2$), 0.95 (d, J=7.0 Hz, CH(CH$_3$)); $^{13}$C NMR (125.7 MHz, CHCl$_3$) d 220.0, 170.1, 164.8, 151.9, 148.5, 138.6, 118.8, 115.7, 110.5, 79.0, 72.4, 71.8, 53.7, 41.9, 39.4, 37.4, 36.2, 32.8, 31.4, 31.0, 23.9, 21.1, 19.1, 18.5, 16.3, 15.7, 11.9; FAB HRMS (NBA/CsI) m/e 624.1735, M+Cs$^+$ calcd for C$_{27}$H$_{41}$NO$_5$S 624.1760.

trans-Cyclopropane-di-TBS ether 1300 as illustrated in FIG. 12. To a stirred solution of stannane 1100 (88 mg, 0.086 mmol, 1.0 equiv.) in CH$_2$Cl$_2$ (1.5 mL) at −10° C., was added Et$_3$N (50 mL, 0.359 mmol, 4.2 equiv.) followed by mesyl chloride (14 mL, 0.181 mmol, 2.1 equiv.). After stirring for 10 min, the reaction was quenched by the addition of saturated aqueous sodium bicarbonate solution (1 mL). The layers were separated and the aqueous phase was extracted with CH$_2$Cl$_2$ (3×2 mL). The combined organic extracts were then dried (MgSO$_4$), filtered and concentrated in vacuo. The residue was then dissolved in CH$_2$Cl$_2$ (1 mL) and silica gel (1.0 g) was added. The suspension was stirred at 25° C. for 12 h before it was filtered. The silica gel was rinsed with EtOAc (2 mL), and the combined organics were then evaporated. Flash chromatography (silica gel, 20% EtOAc in hexanes) then gave the cyclopropane 1300 as a colorless oil (55 mg, 89%). 1300: R$_f$=0.33 (silica gel, 20% EtOAc in hexanes); [a]$^{22}$D −4.8 (c 1.0, CHCl$_3$); IR (thin film) n$_{max}$ 3372, 2930, 2856, 1737, 1698, 1471, 1383, 1255, 1083, 988, 836, 776, 733 cm$^{-1}$; $^1$H NMR (600 MHz, CHCl$_3$) d 6.88 (s, 1 H, SCH═C), 6.53 (s, 1 H, CH═CCH$_3$), 5.38 (bs, 1 H, CHOCO), 4.40 (dd, J=5.0, 5.0 Hz, CHOSi), 3.86 (dd, J=6.1, 2.5 Hz, CHOSi), 3.03 (dq, J=6.6, 6.6 Hz, C(O)CH(CH$_3$)), 2.69 (s, 3 H, N═C(CH$_3$)S), 2.55 (dd, J=15.1, 5.6 Hz, CH$_2$COO), 2.49 (dd, J=15.1, 4.9 Hz, CH$_2$COO), 2.10 (s, 3 H, CH═C(CH$_3$)), 1.87 (m, 3 H), 1.71 (m, 1 H), 1.63–1.39

(m, 4 H), 1.24 (s, 3 H, C(CH$_3$)$_2$), 1.11 (s, 3 H, C(CH$_3$)$_2$), 1.11 (d, J 6.8 Hz, 3 H, CH(CH$_3$)), 0.92 (d, J=6.9 Hz, 3 H, CH(CH$_3$)), 0.88 (s, 18 H, SiC(CH$_3$)$_3$), 0.54 (bm, 1 H, CH(CH$_2$)CH), 0.36 (bm, 2 H, CH(CH$_2$)CH and CH), 0.17 (dd, J=6.5 Hz, 2 H, CH(CH$_2$)CH), 0.10 (s, 3 H, Si(CH$_3$)$_2$), 0.08 (s, 3 H, Si(CH$_3$)$_2$), 0.08 (s, 3 H, Si(CH$_3$)$_2$), 0.05 (S, 3 H, Si(CH$_3$)$_2$); $^{13}$C NMR (125.7 MHz, CHCl$_3$) d 216.4, 170.3, 164.4, 152.9, 138.1, 118.6, 115.6, 77.6, 73.5, 54.0, 43.9, 42.6, 39.6, 37.1, 34.9, 33.6, 31.6, 28.1, 26.0, 24.5, 22.6, 19.2, 18.7, 18.3, 18.2, 18.0, 17.3, 16.0, 15.0, 14.1, 11.3, −3.9, −4.2, −4.4, −4.8; FAB HRMS (NBA/CsI) m/e 852.3459, M+Cs$^+$ calcd for C$_{51}$H$_{97}$NO$_6$SSi$_2$Sn 852.3489.

trans-Cyclopropane 400 as illustrated in FIG. 12. To a stirred solution of di-TBS ether 1300 (34 mg, 0.047 mmol, 1.0 equiv.) in THF (2.1 mL) at 25° C., was added HF.pyr. (0.7 mL) and the resulting solution was stirred at that temperature for 24 h. The reaction mixture was then quenched by dilution with EtOAc (3 mL) and addition to cold (0° C.) saturated sodium bicarbonate solution (4 mL). The layers were then separated and the aqueous phase was extracted with EtOAc (3×4 mL). The combined organic extracts were then dried (MgSO$_4$), filtered and concentrated in vacuo. Flash chromatography (5% MeOH in CH$_2$Cl$_2$) then gave 4 as a colorless oil (21 mg, 90%). 400: R$_f$=0.54 (silica gel, 5% MeOH in CH$_2$Cl$_2$); [a]$^{22}$ −55.0 (c 0.1, CHCl$_3$); IR (thin film) n$_{max}$ 3397, 2928, 1728, 1686, 1464, 1382, 1258, 1154, 1071, 979 cm$^{-1}$; $^1$H NMR (600 MHz, C$_6$D$_6$) d 6.66 (s, 1 H, SCH=C), 6.47 (s, 1 H, CH=CCH$_3$), 5.33 (dd, J=7.7, 2.7 Hz, CHOCO), 4.18 (d, J=9.6 Hz, CHOH), 3.82 (bm, 1 H, CHOH), 3.44 (bs, 1 H, OH), 3.15 (dq, J=6.7, 5.1 Hz, 1 H, C(O)CH(CH$_3$)), 2.84 (bs, 1 H, OH), 2.42 (dd, J=15.5, 1.5 Hz, 1 H, CH$_2$COO), 2.32 (dd, J=15.5, 10.0 Hz, 1 H, CH$_2$COO), 2.21 (s, 3 H, N=C(CH$_3$)S), 2.02 (ddd, J=12.1, 7.9, 4.1 Hz, 1 H), 1.97 (s, 3 H, CH=C(CH$_3$)), 1.86 (m, 1 H), 1.72 (m, 1 H, CH(CH$_3$)), 1.49 (m, 1 H), 1.35–1.22 (m, 3 H), 1.20 (s, 3 H, C(CH$_3$)$_2$), 1.06 (d, J=6.8 Hz, 3 H, CH(CH$_3$)), 1.04 (s, 3 H, C(CH$_3$)$_2$), 0.98 (d, J=6.9 Hz, 3 H, CH(CH$_3$)), 0.81 (m, 1 H), 0.44 (m, 1 H, CH(CH$_2$)CH), 0.37 (m, 1 H, CH(CH$_2$)CH), 0.29 (m, 1 H), 0.18 (ddd, J=8.9, 4.6, 4.6 Hz, CH(CH$_2$)CH), 0.08 (ddd, J=8.9, 4.7, 4.7 Hz, CH(CH$_2$)CH); $^{13}$C NMR (150.9 MHz, C$_6$D$_6$) d 218.7, 170.4, 164.5, 153.3, 137.4, 119.4, 116.2, 79.2, 74.4, 70.9, 53.7, 49.5, 42.9, 40.0, 37.7, 37.3, 35.6, 33.0, 28.2, 22.4, 19.7, 18.9, 17.7, 17.5, 16.0, 14.9, 14.6, 13.3; FAB HRMS (NBA/CsI) m/e 624.1784, M+Cs$^+$ calcd for C$_{27}$H$_{41}$NO$_5$S 624.1760.

Tubulin Polymerization and Cytotoxicity Assays

Tubulin polymerization was determined by the filtration-colorimetric method, developed by Bollag et Cancer Res. 1995, 55, 2325–2333. Purified tubulin (1 mg/mL) was incubated at 37° C. for 30 minutes in the presence of each compound (20 mM) in MEM buffer [(100 mM 2-(N-morpholino)ethanesulfonic acid, pH 6.75, 1 mM ethylene glycol bis(b-aminoethyl ether), N,N,N',N'-tetraacetic acid, and 1 mM MgCl$_2$]; the mixture was then filtered to remove unpolymerized tubulin by using a 96-well Millipore Multi-screen Durapore hydrophillic 0.22 mm pore size filtration plate; the collected polymerized tubulin was stained with amido black solution and quantified by measuring absorbance of the dyed solution on a Molecular Devices Microplate Reader. The growth of all cell lines was evaluated by quantitation of the protein in 96-well plates as described previously. Briefly, 500 cells were seeded in each well of the plates and incubated with the various concentrations of the epothilones at 37° C. in a humidified 5% CO2 atmosphere for four days. After cell fixation with 50% trichloroacetic acid, the optical density corresponding to the quantity of proteins was measured in 25 mM NaOH solution (50% methanol: 50% water) at a wavelength of 564 nm. The IC50 was defined as the dose of drug required to inhibit cell growth by 50%.

Epoxide 600. Sharpless Epoxidation of Lactone 500 as illustrated in FIG. 12. To a solution of allylic alcohol 500 (500 mg, 0.679 mmol, 1.0 equiv.) and 4 Å molecular sieves (200 mg) in CH2Cl2 (4.0 mL) at −30° C. was added dropwise (−)-diethyl-D-tartrate (60 mL, 0.351 mmol, 0.5 equiv.) and titanium isopropoxide (81 mL, 0.294 mmol, 0.4 equiv.) in CH2Cl2 (4 mL). After 1 h, t-butyl hydroperoxide (300 mL, 1.36 mmol, 5 M in decane, 2.0 equiv.) was added and the reaction mixture was stirred at −30° C. for 2 h. The reaction mixture was then filtered through celite and the filtrate diluted with EtOAc (6 mL). Aqueous saturated sodium sulfate solution (6 mL) was added and the mixture stirred at 25° C. for 1 h. The layers were separated and the aqueous phase was extracted with EtOAc (2×6 mL). The combined organic extracts were dried (MgSO4), filtered and concentrated in vacuo to give a crude oil which was subjected to column chromatography (silica gel, 60% Et2O in hexanes) to give the epoxide 600 (472 mg, 92%): 600: Rf=0.33 (silica gel, 60% Et2O in hexanes); [a]22D −11.9 (c 0.3, CHCl3); 1H NMR (600 MHz, CDCl3) d 6.97 (s, 1 H, SCH=C), 6.56 (s, 1 H, CH=CCH3), 5.13 (d, J=7.5 Hz, 1 H, CHOCO), 4.05 (bd, J=7.7 Hz, 1 H, CHOSi), 3.84 (d, J=9.1 Hz, CHOSi), 3.80 (d, J=12.1 Hz, 1 H, CH2OH), 3.51 (d, J=12.1 Hz, 1 H, CH2OH), 3.10 (dd, J=10.0, 3.4 Hz, 1 H, CHOCH2), 2.98 (dq, J=8.9, 6.9 Hz, 1 H, C(O)CH(CH3)), 2.73 (obscured m, 1 H, CH2COO), 2.71 (s, 3 H, N=C(CH3) S), 2.60 (dd, J=16.3, 9.2 Hz, 1 H, CH2COO), 2.26 (ddd, J=14.8, 3.2, 3.2 Hz, 1 H, OCHCH2CHO), 2.10 (s, 3 H, CH=C(CH3)), 1.96 (ddd, J=14.7, 9.8, 9.8 Hz, OCHCH2CHO), 1.89–1.78 (m, 3 H), 1.61 (m, 1 H, CH(CH3)), 1.44–1.40 (m, 3 H), 1.19 (s, 3 H, C(CH3)2), 1.13 (s, 3 H, C(CH3)2), 1.06 (d, J=6.8 Hz, CH(CH3)), 0.96 (d, J=6.9 Hz, CH(CH3)), 0.93 (S, 9 H, SiC(CH3)3), 0.84 (s, 9 H, SiC(CH3)3), 0.10 (s, 3 H, Si(CH3)2), 0.08 (s, 3 H, Si(CH3)2), 0.05 (s, 3 H, Si(CH3)2), −0.06 (s, 3 H, Si(CH3) 2); 13C NMR (150.9 MHz, CDCl3) d 214.8; 170.8, 164.6, 151.9, 137.3, 120.4, 116.5, 75.9, 64.2, 63.5, 60.4, 58.2, 53.3, 39.6, 33.2, 31.7, 29.9, 26.3, 26.1, 24.3, 23.7, 19.3, 18.7, 18.6, 17.9, 14.8, −3.2, −3.4, −3.5, −5.4; FAB HRMS (NBA/CsI) m/e 884.3418, M+Cs+ calcd for C39H69NO7SSi2 884.3388.

Allylic alcohol 900 as illustrated in FIG. 12. To a stirred solution of epoxy alcohol 600 (472 mg, 0.627 mmol, 1.0 equiv.) in CH2Cl2 (6.5 mL) at 0° C. was added Et3N (270 mL, 1.89 mmol, 3.0 equiv.) followed by tosyl chloride (180 mg, 0.944 mmol, 1.5 equiv.) and 4-DMAP (7.0 mg, 0.057 mmol, 0.1 equiv.). The reaction mixture was warmed to 25° C. and stirred for 2.5 h before saturated aqueous NH4Cl solution (5 mL) was added. The layers were separated and the aqueous phase was extracted with EtOAc (3×5 mL). The combined organic extracts were dried (MgSO4), filtered and concentrated in vacuo. The residue was then filtered through a short plug of silica gel (60% Et2O in hexanes) and concentrated in vacuo. The residue was then dissolved in acetone (13 mL) and treated with NaI (470 mg, 3.14 mmol, 5.0 equiv.). After refluxing for 2 h, the reaction mixture was cooled to 0° C. and diluted with DMF (2.3 mL). Triphenylphosphine (250 mg, 0.953 mmol, 1.5 equiv.) was then added, followed by iodine (16 mg, 0.063 mmol, 0.1 equiv.) and the reaction mixture was stirred for 3 h. The solvents were then removed in vacuo, and the residue purified by flash chromatography (50 % Et2O in hexanes) to give allylic alcohol 900 as a colorless oil (410 mg, 89% over 3 steps).

900: Rf=0.37 (silica gel, 60% Et2O in hexanes); [a]22D −5.0 (c 0.3, CHCl3); IR (thin film) nmax 3440, 2931, 2887, 2856, 1740, 1694, 1471, 1382, 1254, 1184, 1156, 1087, 987, 939, 874, 835, 756, 667 cm−1; 1H NMR (600 MHz, CDCl3) d 6.93 (s, 1 H, SCH═C), 6.59 (s, 1 H, CH═CCH3), 5.60 (bs, 1 H, CHOCO), 5.05 (s, 1 H, C═CH2), 4.83 (s, 1 H, C═CH2), 4.35 (bs, 1 H, CHOSi), 4.22 (bs, 1 H, CHOSi), 3.99 (d, J=9.1 Hz, CHOH), 1.96 (dq, J=8.9, 7.0 Hz, 1 H, C(O)CH(CH3)), 2.71 (obscured m, 1 H, CH2COO), 2.68 (s, 3 H, N═C(CH3)S), 2.47 (dd, J=16.7, 5.7 Hz, CH2COO), 2.20 (ddd, J=12.5, 12.5, 5.6 Hz, 1 H, CH2C═CH2), 2.11 (obscured m, 1 H, CH2C═CH2), 2.10 (s, 3 H, CH═C (CH3)), 1.90 (bs, 1 H, OH), 1.75–1.71 (m, 2 H), 1.60 (m, 1 H, CH(CH3)), 1.27–1.24 (m, 1 H), 1.22 (s, 3 H, C(CH3)2), 1.16 (s, 3 H, C(CH3)2), 1.08 (d, J=6.8 Hz, CH(CH3)), 0.91 (d, J=7.0 Hz, CH(CH3)), 0.89 (s, 9 H, SiC(CH3)3), 0.85 (s, 9 H, SiC(CH3)3), 0.11 (s, 3 H, Si(CH3)2), 0.05 (s, 3 H, Si(CH3)2), 0.04 (s, 3 H, Si(CH3)2), 0.00 (s, 3 H, Si(CH3)2); 13C NMR (150.9 MHz, CDCl3) d 215.6, 170.8, 164.4, 153.0, 152.3, 137.2, 120.8, 116.3, 107.9, 77.8, 69.2, 60.4, 53.9, 41.6, 35.1, 27.7, 26.1, 24.7, 21.1, 18.5, 18.4, 18.2, 15.4, 14.3, −3.2, −3.7, −3.8, −5.4; FAB HRMS (NBA/CsI) m/e 868.3408, M+Cs+ calcd for C39H69NO6SSi2 868.3439.

Stannanes 1000 and 1100 as illustrated in FIG. 12. To a stirred solution of allylic alcohol 900 (375 mg, 0.509 mmol, 1.0 equiv.) and 10 % Pd(OH)2/C (27.5 mg, 0.1 equiv.) in THF (2.5 mL) at 25° C. was added via syringe pump over 7 h, a solution of tri-n-butyltinhydride (161 mg, 0.553 mmol, 1.5 equiv.) in THF (1 mL). The reaction mixture was then filtered over celite and concentrated in vacuo. Flash chromatography (gradient elution, 20% to 60% Et2O in hexanes) then gave starting material (182 mg, 48%), stannane 1000 (183 mg, 35%) and stannane 1100 (78 mg, 15%). 1000: Rf=0.44 (silica gel, 60% Et2O in hexanes); [a]22D −34.9 (c 0.2, CHCl3); IR (thin film) nmax 3464, 2955, 2928, 2855, 1742, 1696, 1461, 1381, 1253, 1157, 1101, 1020, 987, 874, 834, 775, 733 cm−1; 1H NMR (500 MHz, CDCl3) d 6.96 (s, 1 H, SCH═C), 6.57 (s, 1 H, CH═CCH3), 5.31 (bs, 1 H, CHOCO), 4.06 (bd, J=9.2 Hz, CHOSi), 3.96 (d, J=9.5 Hz, CHOH), 3.88 (bs, 1 H, CHOSi), 3.01 (dq, J=8.1, 6.8 Hz, C(O)CH(CH3)), 2.85 (d, J=16.6 Hz, 1 H, CH2COO), 2.70 (s, 3 H, N═C(CH3)S), 2.58 (dd, J=16.6, 9.1 Hz, CH2COO), 2.10 (s, 3 H, CH═C(CH3)), 1.95 (dd, J=14.9, 11.5 Hz, 1 H), 1.72–1.51 (m, 7 H), 1.45 (m, 8 H, SnCH2CH2CH2CH3 and CH2), 1.31 (m, 12 H, SnCH2CH2CH2CH3), 1.23 (s, 3 H, C(CH3)2), 0.98 (s, 3 H, C(CH3)2), 1.07 (d, J=6.8 Hz, 3 H, CH(CH3)), 0.78 (obscured d, 3 H, CH(CH3)), 0.92 (s, 9 H, SiC(CH3)3), 0.88 (t, J=7.3 Hz, 27 H, SnCH2CH2CH2CH3), 0.87 (s, 9 H, SiC(CH3)3), 0.47 (dd, J=11.9 Hz, 1 H), 0.16 (s, 3 H, Si(CH3)2), 0.09 (s, 3 H, Si(CH3)2), 0.05 (s, 3 H, Si(CH3)2), −0.01 (s, 3 H, Si(CH3)2); 13C NMR (125.7 MHz, CDCl3) d 214.9, 171.1, 164.6, 152.4, 138.3, 119.5, 116.0, 78.2, 75.9, 71.7, 53.3, 44.4, 36.5, 35.7, 29.2, 27.4, 26.2, 26.1, 24.3, 19.2, 18.6, 18.0, 15.5, 13.7, 9.3, −3.2, −3.4, −3.7, −5.8; FAB HRMS (NBA/CsI) m/e 1160.4710, M+Cs+ calcd for C51H97NO6SSi2Sn 1160.4652; 1100: Rf=0.40 (silica gel, 60% Et2O in hexanes); [a]22D −5.35 (c 0.7, CHCl3); IR (thin film) nmax 3405, 2927, 2855, 1707, 1697, 1461, 1382, 1255, 1084, 836, 775 cm−1; 1H NMR (500 MHz, CDCl3) d 6.94 (s, 1 H, SCH═C), 6.59 (s, 1 H, CH═CCH3), 5.60 (bd, J=9.7 Hz, 1 H, CHOCO), 4.06 (bd, J=9.2 Hz, CHOSi), 4.40 (dd, J=5.1 Hz, CHOSi), 3.95 (d, J=8.8 Hz, CHOH), 3.80 (bs, 1 H, CHOSi), 3.02 (dq, J=8.4, 7.1 Hz, C(O)CH(CH3)), 2.71 (s, 3 H, N═C(CH3)S), 2.67 (dd, J=16.5, 5.8 Hz, 1 H, CH2COO), 2.52 (dd, J=16.5, 4.8 Hz, 1 H, CH2COO), 2.14 (s, 3 H, CH═C(CH3)), 1.93–1.82 (m, 2 H), 1.68–1.61 (bm, 4 H), 1.52 (m, 1 H, CH(CH3)), 1.45 (m, 8 H, SnCH2CH2CH2CH3 and CH2), 1.32 (m, 9 H, SnCH2CH2CH2CH3), 1.18 (s, 3 H, C(CH3)2), 1.14 (s, 3 H, C(CH3)2), 1.10 (d, J=6.9 Hz, CH(CH3)), 0.95 (d, J=6.9 Hz, CH(CH3)), 0.91 (s, 9 H, SiC(CH3)3), 0.88 (t, J=7.3 Hz, 27 H, SnCH2CH2CH2CH3), 0.13 (s, 3 H, Si(CH3)2), 0.08 (s, 3 H, Si(CH3)2), 0.07 (s, 3 H, Si(CH3)2), 0.06 (s, 3 H, Si(CH3)2); 13C NMR (125.7 MHz, CDCl3) d 217.9, 170.8, 168.3, 152.3, 138.1, 120.2, 116.4, 77.8, 73.8, 69.4, 54.2, 41.4, 39.5, 29.2, 27.4, 26.2, 26.0, 19.2, 18.4, 18.3, 17.9, 15.1, 13.7, 9.47, −3.2, −3.8, −5.0; FAB HRMS (NBA/NaI) m/e 1050.5548, M+Na+ calcd for C51H97NO6SSi2Sn 1050.5495.

cis-Cyclopropane 300 and elimination product 1500 as illustrated in FIG. 12. To a stirred solution of stannane 1000 (38.0 mg, 0.037 mmol, 1.0 equiv.) in CH2Cl2 (0.5 mL) at −78° C. was added pyridine (24 mL, 0.297 mmol, 8.0 equiv.) followed by thionyl chloride (11 mL, 0.151 mmol, 4 equiv.). The reaction mixture was then slowly warmed to 25° C. over 5 h. Saturated aqueous sodium bicarbonate solution (1.0 mL) was then added, and the layers were separated. The aqueous phase was extracted with CH2Cl2 (3×4 mL) and the combined organic extracts were dried (MgSO4), filtered and concentrated in vacuo. The resulting residue was then dissolved in THF (1.3 mL) and HF.pyr. (0.45 mL) was added. After stirring for 24 h, the reaction mixture was diluted with EtOAc (2 mL) and quenched by addition to cold (0° C.) saturated sodium bicarbonate solution (4 mL). The layers were then separated and the aqueous phase was extracted with EtOAc (3×4 mL). The combined organic extracts were then dried (MgSO4), filtered and concentrated in vacuo. Preparative thin layer chromatography (5% MeOH in CH2Cl2) then gave elimination product 1500 (10.8 mg, 62% over 2 steps) and cyclopropane 300 (3.6 mg, 20% over 2 steps). 300: Rf=0.29 (silica gel, 5% MeOH in CH2Cl2); [a]22D −48.9 (c 0.2, CHCl3); IR (thin film) nmax 3398, 2925, 2853, 1732, 1688, 1456, 1384, 1292, 1260, 1190, 1153, 1083, 1041, 983, 736 cm−1; 1H NMR (600 Mhz, C6D6) d 6.76 (s, 1 H, SCH═C), 6.46 (s, 1 H; CH═CCH3), 5.43 (bm, 1 H, CHOCO), 4.16 (dd, J=8.4, 4.4 Hz, CHOH), 3.81 (dd, J=5.3, 4.4 Hz, CHOH), 3.13 (dq, J=6.4, 6.4 Hz, C(O)CH(CH3)), 2.43 (s, 1 H, CH2COO), 2.42 (dd, J=20.8, 15.11 Hz, 1 H, CH2COO), 2.18 (s, 3 H, N═C(CH3)S), 1.99 (s, 3 H, CH═C(CH3)), 1.78 (ddd, J=15.5, 4.7, 4.7 Hz, 1 H), 1.65 (m, 1 H, CH(CH3)), 1.52–1.19 (m, 7 H), 1.09 (s, 3 H, C(CH3)2), 1.05 (d, J=6.8 Hz, 3 H, CH(CH3)), 0.98 (s, 3 H, C(CH3)2), 0.93 (d, J=6.9 Hz, 3 H, CH(CH3)), 0.71 (m, 1 H, CH(CH2)CH), 0.63 (m, 1 H, CH(CH2)CH), 0.47 (ddd, J=8.6, 8.6, 4.3 Hz, 1 H, CH(CH2)CH), 0.31 (ddd, J=5.0, 5.0, 4.3 Hz, 1 H, CH(CH2)CH); 13C NMR (125.7 MHz, CDCl3) d 220.4, 170.3, 165.0, 132.1, 118.4, 115.3, 77.7, 74.9, 72.4, 52.4, 43.7, 39.0, 35.7, 30.3, 29.7, 29.5, 29.2, 25.7, 21.7, 20.6, 18.9, 17.0, 16.3, 15.5, 14.1, 14.0, 10.9, 10.2; FAB HRMS (NBA/CsI) m/e 624.1781, M+Cs+ calcd for C27H41NO5S 624.1760. 15: Rf=0.31 (silica gel, 5% MeOH in CH2Cl2); [a]22D −24.0 (c 0.1, CHCl3); IR (thin film) nmax 3425, 2936, 1732, 1688, 1457, 1382, 1258, 1184, 1150, 1072, 1013, 979, 888, 732 cm−1; 1H NMR (600 Mhz, CDCl3) d 6.93 (s, 1 H, SCH═C), 6.54 (s, 1 H, CH═CCH3), 5.17 (d, J=9.4 Hz, 1 H, CHOCO), 4.73 (s, 1 H, C═CH2), 4.69 (s, 1 H, C═CH2), 4.32 (bd, J=9.5 Hz, 1 H, CHOH), 3.73 (bm, 1 H, CHOH), 3.29 (dq, J=6.7, 2.9 Hz, 1 H, C(O)CH(CH3)), 3.24 (bs, 1 H, OH), 2.89 (bs, 1 H, OH), 2.67 (s, 3 H, N═C(CH3)S), 2.48 (dd, J=14.8, 10.2 Hz, CH2COO), 2.42 (dd, J=14.8, 3.1 Hz, CH2COO), 2.15–2.04 (m, 4 H, CH2(C═CH2)CH2), 2.04 (s, 3 H, CH═C(CH3)), 1.91–1.72 (m, 4 H), 1.55 (m, 1 H, CH(CH3)), 1.35 (s, 3 H, C(CH3)2), 1.10 (d, J=6.9 Hz, 3 H, CH(CH3)), 1.05 (s, 3 H, C(CH3)2), 0.95

(d, J=7.0 Hz, CH(CH3)); 13C NMR (125.7 MHz, CDCl3) d 220.0, 170.1, 164.8, 151.9, 148.5, 138.6, 118.8, 115.7, 110.5, 79.0, 72.4, 71.8, 53.7, 41.9, 39.4, 37.4, 36.2, 32.8, 31.4, 31.0, 23.9, 21.1, 19.1, 18.5, 16.3, 15.7, 11.9; FAB HRMS (NBA/CsI) m/e 624.1735, M+Cs+ calcd for C27H41NO5S 624.1760.

trans-Cyclopropane-di-TBS ether 1300 as illustrated in FIG. 12. To a stirred solution of stannane 1100 (88 mg, 0.086 mmol, 1.0 equiv.) in CH2Cl2 (1.5 mL) at −10° C., was added Et3N (50 mL, 0.359 mmol, 4.2 equiv.) followed by mesyl chloride (14 mL, 0.181 mmol, 2.1 equiv.). After stirring for 10 min, the reaction was quenched by the addition of saturated aqueous sodium bicarbonate solution (1 mL). The layers were separated and the aqueous phase was extracted with CH2Cl2 (3×2 mL). The combined organic extracts were then dried (MgSO4), filtered and concentrated in vacuo. The residue was then dissolved in CH2Cl2 (1 mL) and silica gel (1.0 g) was added. The suspension was stirred at 25° C. for 12 h before it was filtered. The silica gel was rinsed with EtOAc (2 mL), and the combined organics were then evaporated. Flash chromatography (silica gel, 20% EtOAc in hexanes) then gave the cyclopropane 1300 as a colorless oil (55 mg, 89%). 1300: Rf=0.33 (silica gel, 20% EtOAc in hexanes); [a]22D −4.8 (c 1.0, CHCl3); IR (thin film) nmax 3372, 2930, 2856, 1737, 1698, 1471, 1383, 1255, 1083, 988, 836, 776, 733 cm-1; 1H NMR (600 MHz, CDCl3) d 6.88 (s, 1 H, SCH═C), 6.53 (s, 1 H, CH═CCH3), 5.38 (bs, 1 H, CHOCO), 4.40 (dd, J=5.0, 5.0 Hz, CHOSi), 3.86 (dd, J=6.1, 2.5 Hz, CHOSi), 3.03 (dq, J=6.6, 6.6 Hz, C(O)CH(CH3)), 2.69 (s, 3 H, N═C(CH3)S), 2.55 (dd, J=15.1, 5.6 Hz, CH2COO), 2.49 (dd, J=15.1, 4.9 Hz, CH2COO), 2.10 (s, 3 H, CH═C(CH3)), 1.87 (m, 3 H), 1.71 (m, 1 H), 1.63–1.39 (m, 4 H), 1.24 (s, 3 H, C(CH3)2), 1.11 (s, 3 H, C(CH3)2), 1.11 (d, J=6.8 Hz, 3 H, CH(CH3)), 0.92 (d, J=6.9 Hz, 3 H, CH(CH3)), 0.88 (s, 18 H, SiC(CH3)3), 0.54 (bm, 1 H, CH(CH2)CH), 0.36 (bm, 2 H, CH(CH2)CH and CH), 0.17 (dd, J=6.5 Hz, 2 H, CH(CH2)CH), 0.10 (s, 3 H, Si(CH3)2), 0.08 (s, 3 H, Si(CH3)2), 0.08 (s, 3 H, Si(CH3)2), 0.05 (s, 3 H, Si(CH3)2); 13C NMR (125.7 MHz, CDCl3) d 216.4, 170.3, 164.4, 152.9, 138.1, 118.6, 115.6, 77.6, 73.5, 54.0, 43.9, 42.6, 39.6, 37.1, 34.9, 33.6, 31.6, 28.1, 26.0, 24.5, 22.6, 19.2, 18.7, 18.3, 18.2, 18.0, 17.3, 16.0, 15.0, 14.1, 11.3, −3.9, −4.2, −4.4, −4.8; FAB HRMS (NBA/CsI) m/e 852.3459, M+Cs+ calcd for C51H97NO6SSi2Sn 852.3489.

trans-Cyclopropane 400 as illustrated in FIG. 12. To a stirred solution of di-TBS ether 1300 (34 mg, 0.047 mmol, 1.0 equiv.) in THF (2.1 mL) at 25° C., was added HF.pyr. (0.7 mL) and the resulting solution was stirred at that temperature for 24 h. The reaction mixture was then quenched by dilution with EtOAc (3 mL) and addition to cold (0° C.) saturated sodium bicarbonate solution (4 mL). The layers were then separated and the aqueous phase was extracted with EtOAc (3×4 mL). The combined organic extracts were then dried (MgSO4), filtered and concentrated in vacuo. Flash chromatography (5% MeOH in CH2Cl2) then gave 400 as a colorless oil (21 mg, 90%). 400: Rf=0.54 (silica gel, 5% MeOH in CH2Cl2); [a]22D −55.0 (c 0.1, CHCl3); IR (thin film) nmax 3397, 2928, 1728, 1686, 1464, 1382, 1258, 1154, 1071, 979 cm-1; 1H NMR (600 MHz, C6D6) d 6.66 (s, 1 H, SCH═C), 6.47 (s, 1 H, CH═CCH3), 5.33 (dd, J=7.7, 2.7 Hz, CHOCO), 4.18 (d, J=9.6 Hz, CHOH), 3.82 (bm, 1 H, CHOH), 3.44 (bs, 1 H, OH), 3.15 (dq, J=6.7, 5.1 Hz, 1 H, C(O)CH(CH3)), 2.84 (bs, 1 H, OH), 2.42 (dd, J=15.5, 1.5 Hz, 1 H, CH2COO), 2.32 (dd, J=15.5, 10.0 Hz, 1 H, CH2COO), 2.21 (s, 3 H, N═C(CH3)S), 2.02 (ddd, J=12.1, 7.9, 4.1 Hz, 1 H), 1.97 (s, 3 H, CH═C(CH3)), 1.86 (m, 1 H), 1.72 (m, 1 H, CH(CH3)), 1.49 (m, 1 H), 1.35–1.22 (m, 3 H), 1.20 (s, 3 H, C(CH3)2), 1.06 (d, J=6.8 Hz, 3 H, CH(CH3)), 1.04 (s, 3 H, C(CH3)2), 0.98 (d, J=6.9 Hz, 3 H, CH(CH3)), 0.81 (m, 1 H), 0.44 (m, 1 H, CH(CH2)CH), 0.37 (m, 1 H, CH(CH2)CH), 0.29 (m, 1 H), 0.18 (ddd, J=8.9, 4.6, 4.6 Hz, CH(CH2)CH), 0.08 (ddd, J=8.9, 4.7, 4.7 Hz, CH(CH2)CH); 13C NMR (150.9 MHz, C6D6) d 218.7, 170.4, 164.5, 153.3, 137.4, 119.4, 116.2, 79.2, 74.4, 70.9, 53.7, 49.5, 42.9, 40.0, 37.7, 37.3, 35.6, 33.0, 28.2, 22.4, 19.7, 18.9, 17.7, 17.5, 16.0, 14.9, 14.6, 13.3; FAB HRMS (NBA/CsI) m/e 624.1784, M+Cs+ calcd for C27H41NO5S 624.1760.

FIGS. 16–18 are shown using conditions described in Nicolaou et al. *J. Am. Chem. Soc.,* 1997, 119, 7974–7991 and those as indicated in the description of figures above.

Vinyl iodide 7002 as illustrated in FIG. 16. Diiodide 7001 (1 equiv.; from 57) and sodium cyanoborohydride (10 equiv.) were dissolved in anhydrous HMPA (0.2 M) and the resulting mixture heated at 45–50° C. for 48 h. After cooling to room temperature, water was added and the aqueous phase extracted four times with ethyl acetate. The combined organic fractions were dried (Na2SO4) and passed through a short plug of silica gel to remove traces of HMPA (eluting with 50% ethyl acetate in hexanes). Following evaporation of solvents, the residue was purified by preparative thin layer chromatography (eluting with 50% ethyl acetate in hexanes) to provide pure vinyl iodide 7002 (84%).

Ylide 708 as illustrated in FIG. 17. Phosphonium salt 7007 (1.0 equiv.) was dissolved in THF (0.2 M) and the solution was cooled to 0° C. Potassium hexamethyldisilylamide (KHMDS, 2.0 equiv.) was slowly added and the resulting mixture was stirred for 30 min. The mixture was then cooled to −78° C. and methyl chloroformate was added dropwise. Stirring was continued for another 3 h at −78° C. and then the reaction mixture was quenched with saturated aqueous NH4Cl solution and the mixture allowed to warm to 25° C. Water and CH2Cl2 (250 mL each) were then added and the layers separated. The aqueous layer was extracted with CH2Cl2 (2×250 mL) and the combined organic layers were washed with brine (500 mL), dried (MgSO4) and concentrated in vacuo. The crude product was used directly in the next reaction without further purification.

Aldehyde 7011 as illustrated in FIG. 17. Ylide 7010 (1.15 equiv.) was added to a solution of aldehyde 7009 (1.0 equiv.) in CH2Cl2 (0.5 M) and the mixture heated at reflux for 12 h. The mixture was then filtered through silica gel washing with 2:1 ether:hexanes and the eluant reduced. The crude product was then purified by crystallization (hexanes) to afford aldehyde 7011 (82%).

Alcohol 7012. Aldehyde 7011 (1 equiv.) was dissolved in a mixture of anhydrous ether and CH2Cl2 (1:1) [0.2 M] and the solution was cooled to −100° C. (+)-Diisopinocampheylallyl borane (2.0 equiv. in pentane (prepared from (−)-Ipc2BOMe (1.0 equiv.) and 1.0 equiv. of allyl magnesium bromide according to the method described previously[1]) was added dropwise under vigorous stirring, and the reaction mixture was allowed to stir for 1 h at the same temperature. Methanol was added at −100° C., and the reaction mixture was allowed to warm up to room temperature. Amino ethanol (10.0 equiv.) was added and stirring was continued for 15 ether. The combined orgainc extracts were dried (MgSO4), filtered the required acid chloride (1.1 equiv.). After stirring for 1 h, the reaction was quenched with saturated aqueous sodium bicarbonate solution. The layers were separated and the aqueous phase extracted with ether. The combined orgainc extracts were dried (MgSO4), filtered and concentrated in vacuo. Flash chromatography afforded alcohol 7012 (99%).

What is claimed is:

1. An epothilone compound represented by the following structure:

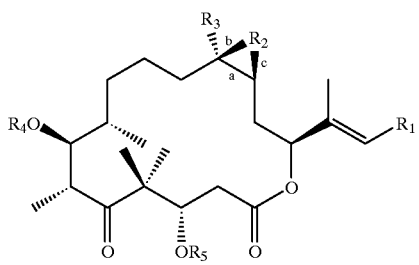

wherein:

R₂ is absent or oxygen;

"a" can be either a single or double bond;

"b" can be either absent or a single bond;

"c" can be either absent or a single bond; with the following provisos:
  if R₂ is oxygen, then "b" and "c" are both a single bonds and "a" is a single bond;
  if R₂ is absent, then "b" and "c" are absent and "a" is a double bond;
  if "a" is a double bond, then R₂, "b", and "c" are absent;

R₃ is a radical selected from the group consisting of hydrogen, methyl, —CHO, —COOH, —CO₂Me, —CO₂(tert-butyl), —CO₂(iso-propyl), —CO₂(phenyl), —CO₂(benzyl), —CONH(furfuryl), —CO₂(N-benzo-(2R,3S)-3-phenylisoserine), —CON(methyl)₂, —CON(ethyl)₂, —CONH(benzyl), —CH=CH₂, —C≡CH, and —CH₂R₁₁, wherein
  R₁₁ is a radical selected from the group consisting of —OH, —O-Trityl, —O—(C₁-C₆ alkyl), —(C₁-C₆ alkyl), —O-benzyl, —O-allyl, —O—COCH₃, —O—COCH₂Cl, —O—COCH₂CH₃, —O—COCF₃, —O—COCH(CH₃)₂, —O—COC(CH₃)₃, —O—CO(cyclopropane), —OCO(cyclohexane), —O—COCH=CH₂, —O—CO-Phenyl, —O-(2-furoyl), —O-(N-benzo-(2R,3S)-3-phenylisoserine), —O-cinnamoyl, —O—(acetyl-phenyl), —O-(2-thiophenesulfonyl), —S—(C₁-C₆ alkyl), —SH, —S-Phenyl, —S-Benzyl, —S-furfuryl, —NH₂, —N₃, —NHCOCH₃, —NHCOCH₂Cl, —NHCOCH₂CH₃, —NHCOCF₃, —NHCOCH(CH₃)₂, —NHCOC(CH₃)₃, —NHCO(cyclopropane), —NHCO(cyclohexane), —NHCOCH=CH₂, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, —I, and —CH₂CO₂H;

R₄ and R₅ are each independently selected from hydrogen, methyl or a TBS or TMS protecting group; and R₁ is a radical selected from the following structures:

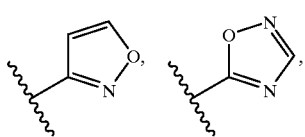

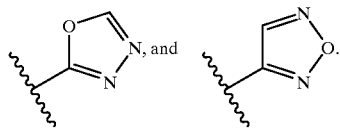

2. An epothilone compound according to claim 1 wherein R₁ is represented by the following structure:

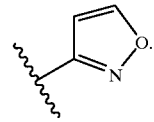

3. An epothilone compound according to claim 1 wherein R₁ is represented by the following structure:

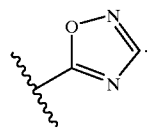

4. An epothilone compound according to claim 1 wherein R₁ is represented by the following structure:

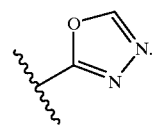

5. An epothilone compound according to claim 1 wherein R₁ is represented by the following structure:

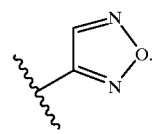

6. A process for synthesizing an epothilone compound, or a salt thereof, the method comprising the following steps:

Step A: providing an epothilone intermediate represented by the following structure:

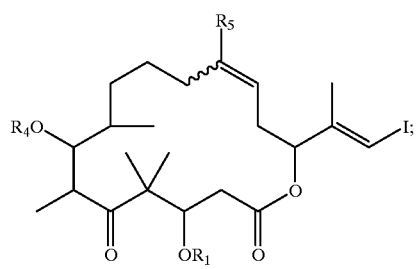

wherein
R₁ and R₄ are each independently selected from hydrogen, methyl or a TBS or TMS protecting group;

$R_5$ is —$CH_2R_x$ wherein $R_x$ is a radical selected from the group consisting of —OH, —O-Trityl, —O—($C_1$–$C_6$ alkyl), —($C_1$–$C_6$ alkyl), —O-benzyl, —O-allyl, —O—$COCH_3$, —O—$COCH_2Cl$, —O—$COCH_2CH_3$, —O—$COCF_3$, —O—$COCH(CH_3)_2$, —O—$COC(CH_3)_3$, —O—CO(cyclopropane), —OCO(cyclohexane), —O—$COCH=CH_2$, —O—CO-Phenyl, —O-(2-furoyl), —O-(N-benzo-(2R,3S)-3-phenylisoserine), —O-cinnamoyl, —O-(acetyl-phenyl), —O-(2-thiophenesulfonyl), —S—($C_1$–$C_6$ alkyl), —SH, —S-Phenyl, —S-Benzyl, —S-furfuryl, —$NH_2$, —$N_3$, —$NHCOCH_3$, —$NHCOCH_2Cl$, —$NHCOCH_2CH_3$, —$NHCOCF_3$, —$NHCOCH(CH_3)_2$, —$NHCOC(CH_3)_3$, —NHCO(cyclopropane), —NHCO(cyclohexane), —$NHCOCH=CH_2$, —NHCO-Phenyl, —NH(2-furoyl), —NH—(N-benzo-(2R,3S)-3-phenylisoserine), —NH-(cinnamoyl), —NH-(acetyl-phenyl), —NH-(2-thiophenesulfonyl), —F, —Cl, —I, and —$CH_2CO_2H$ and methyl; and then Step B: coupling said epothilone intermediate and an aromatic stannane by means of a Stille coupling reaction for producing the epothilone compound, said epothilone compound being represented by the following structure:

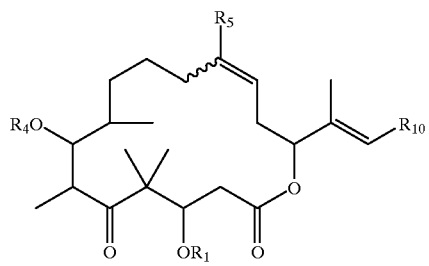

and the aromatic stannane being a compound represented as $(R_y)_3Sn$—$R_{10}$ wherein $R_y$ is either n-butyl or methyl; $R_{10}$ is a radical selected from a group consisting of one of the following structures:

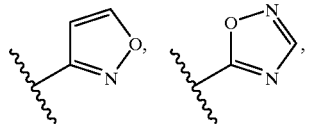

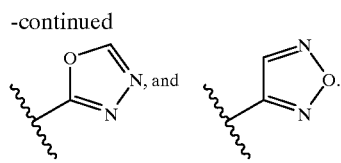

7. A process for synthesizing an epothilone compound according to claim 6 wherein $R_{10}$ is represented by the following structure:

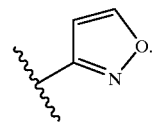

8. A process for synthesizing an epothilone compound according to claim 6 wherein $R_{10}$ is represented by the following structure:

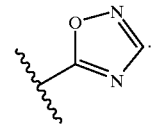

9. A process for synthesizing an epothilone compound according to claim 6 wherein $R_{10}$ is represented by the following structure:

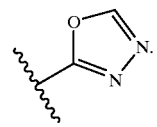

10. A process for synthesizing an epothilone compound according to claim 6 wherein $R_{10}$ is represented by the following structure:

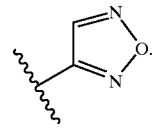

* * * * *